(12) United States Patent
Spetzler et al.

(10) Patent No.: US 9,067,977 B2
(45) Date of Patent: *Jun. 30, 2015

(54) PEPTIDES DERIVATIZED WITH A-B-C-D- AND THEIR THERAPEUTICAL USE

(71) Applicant: Novo Nordisk A/S, Bagsvaerd (DK)

(72) Inventors: Jane Spetzler, Broenshoej (DK); Lauge Schaeffer, Lyngby (DK); Jesper Lau, Farum (DK); Thomas Kruse, Herlev (DK); Patrick William Garibay, Holte (DK); Soeren Oestergaard, Broenshoej (DK); Steffen Reedtz-Runge, Frederiksberg (DK); Henning Thoegersen, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/930,079

(22) Filed: Jun. 28, 2013

(65) Prior Publication Data

US 2014/0011732 A1    Jan. 9, 2014

Related U.S. Application Data

(63) Continuation of application No. 12/676,310, filed as application No. PCT/EP2008/061830 on Sep. 5, 2008.

(60) Provisional application No. 60/971,931, filed on Sep. 13, 2007, provisional application No. 61/024,622, filed on Jan. 30, 2008.

(30) Foreign Application Priority Data

Sep. 5, 2007  (EP) .................................. 07115741
Jan. 28, 2008 (EP) .................................. 08101011

(51) Int. Cl.
| | |
|---|---|
| *C07K 1/107* | (2006.01) |
| *C07K 14/00* | (2006.01) |
| *C07K 14/575* | (2006.01) |
| *C07K 14/605* | (2006.01) |
| *A61K 38/16* | (2006.01) |
| *A61K 38/22* | (2006.01) |
| *A61K 38/26* | (2006.01) |
| *A61K 38/17* | (2006.01) |
| *A61K 47/48* | (2006.01) |
| *A61K 38/00* | (2006.01) |

(52) U.S. Cl.
CPC .............. *C07K 14/001* (2013.01); *C07K 14/00* (2013.01); *C07K 14/575* (2013.01); *A61K 38/16* (2013.01); *A61K 38/17* (2013.01); *A61K 38/22* (2013.01); *A61K 38/26* (2013.01); *A61K 47/48* (2013.01); *A61K 47/48007* (2013.01); *A61K 47/48023* (2013.01); *A61K 47/48169* (2013.01); *A61K 38/00* (2013.01); *A61K 47/48038* (2013.01); *A61K 47/48046* (2013.01); *A61K 47/48061* (2013.01); *A61K 47/48215* (2013.01); *C07K 14/57563* (2013.01); *C07K 14/605* (2013.01)

(58) Field of Classification Search
CPC ....... A61K 38/00; A61K 38/16; A61K 38/17; A61K 38/22; A61K 38/26; A61K 47/48046; A61K 47/48601; A61K 47/48215; A61K 47/48; A61K 47/48007; A61K 47/48023; A61K 47/48038; A61K 47/48169; C07K 14/00; C07K 14/001; C07K 14/605; C07K 14/575
USPC ........................................................... 514/1.9
See application file for complete search history.

(56) References Cited

U.S. PATENT DOCUMENTS

| | | | | |
|---|---|---|---|---|
| 5,968,899 | A | * | 10/1999 | Sekine et al. ................ 424/85.2 |
| 6,268,343 | B1 | | 7/2001 | Knudsen et al. |
| 6,458,924 | B2 | * | 10/2002 | Knudsen et al. ............. 530/324 |
| 7,235,627 | B2 | | 6/2007 | Knudson et al. |
| 7,271,149 | B2 | | 9/2007 | Glaesner et al. |
| 8,097,698 | B2 | | 1/2012 | Knudsen et al. |
| 2001/0011071 | A1 | | 8/2001 | Knudsen et al. |
| 2007/0203058 | A1 | | 8/2007 | Lau et al. |

FOREIGN PATENT DOCUMENTS

| | | |
|---|---|---|
| JP | 2006-520818 A | 9/2006 |
| WO | 96/29342 | 9/1996 |
| WO | 99/43708 A1 | 9/1999 |

(Continued)

OTHER PUBLICATIONS

The Medical Dictionary Online. http://cancerweb.ncl.ac.uklomd/about.html. 2005.

Nauck, M A. Regulatory Peptides. "Glucagon-Like Peptide 1 and its Derivatives in the Treatment od Diabetes." 2005. vol. 128(2). pp. 135-148.

(Continued)

*Primary Examiner* — Karlheinz R Skowronek
*Assistant Examiner* — Catherine Mader
(74) *Attorney, Agent, or Firm* — Richard W. Bork

(57) ABSTRACT

The invention relates to protracted peptide derivatives such as Glucagon-Like Peptide-1 (GLP-1), exendin-4, and analogs thereof, as well as therapeutic uses thereof. The peptide derivative of the invention comprises a peptide wherein at least one amino acid residue is derivatized with A-B-C-, or A-B-C-D-. These compounds are useful in the treatment or prevention of diabetes type 2 and related diseases. The compounds are potent, have a low ratio of binding affinity to the GLP-1 receptor in the presence of high/low albumin concentrations, have long half-lives, and have a high affinity of binding to albumin, all of which is of potential relevance for the overall aim of achieving long-acting, stable and active GLP-1 derivatives with a potential for once weekly administration.

22 Claims, No Drawings

(56) References Cited

FOREIGN PATENT DOCUMENTS

| WO | 00/34331 | | 6/2000 | |
|---|---|---|---|---|
| WO | 00/69911 | | 11/2000 | |
| WO | 02/46227 | A2 | 6/2002 | |
| WO | 2005/058954 | A1 | 6/2005 | |
| WO | WO/2006/097537 | * | 9/2006 | ........... C07K 14/605 |

OTHER PUBLICATIONS

Pan, 2006 Journal of Biological Chemistry vol. 281 pp. 12506-12515.

David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.

* cited by examiner

SEQUENCE LISTING

```
<160> NUMBER OF SEQ ID NOS: 7

<210> SEQ ID NO 1
<211> LENGTH: 31
<212> TYPE: PRT
<213> ORGANISM: Homo sapiens
<220> FEATURE:
<221> NAME/KEY: PEPTIDE
<222> LOCATION: (1)..(31)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(39)
<220> FEATURE:
<221> NAME/KEY: MISC_FEATURE
<222> LOCATION: (1)..(1)
<223> OTHER INFORMATION: X = L-his, D-his, desamino-his, 2-amino-his,
      beta-hydroxy-his, homo-his, Nalpha-acetyl-his, alpha-fluoroethyl-
      his, alhpa-methyl-his,2 (3H-imidazol-4-yl)acetyl, 3-pyridyl-ala,
      2-pyridyl-ala
```

```
<220> FEATURE:
<221> NAME/KEY: MISC_FEATURE
<222> LOCATION: (2)..(2)
<223> OTHER INFORMATION: X = Ala, Gly, Val, Leu, Ile, Lys, Aib,
      (1-aminocyclopropyl-, -butyl-, -pentyl-, -hexyl-, -heptyl-, or
      -octyl) carboxylic acid
<220> FEATURE:
<221> NAME/KEY: MISC_FEATURE
<222> LOCATION: (10)..(10)
<223> OTHER INFORMATION: X = is Val or Leu
<220> FEATURE:
<221> NAME/KEY: MISC_FEATURE
<222> LOCATION: (12)..(12)
<223> OTHER INFORMATION: X = Ser, Lys, or Arg
<220> FEATURE:
<221> NAME/KEY: MISC_FEATURE
<222> LOCATION: (13)..(13)
<223> OTHER INFORMATION: X = Tyr, or Gln
<220> FEATURE:
<221> NAME/KEY: MISC_FEATURE
<222> LOCATION: (14)..(14)
<223> OTHER INFORMATION: X = Leu, Met, or Lys
<220> FEATURE:
<221> NAME/KEY: MISC_FEATURE
<222> LOCATION: (16)..(16)
<223> OTHER INFORMATION: X = Gly, Glu, or Aib
<220> FEATURE:
<221> NAME/KEY: MISC_FEATURE
<222> LOCATION: (17)..(17)
<223> OTHER INFORMATION: X = Gln, Glu, Lys, or Arg
<220> FEATURE:
<221> NAME/KEY: MISC_FEATURE
<222> LOCATION: (19)..(19)
<223> OTHER INFORMATION: X = Ala, or Val
<220> FEATURE:
<221> NAME/KEY: MISC_FEATURE
<222> LOCATION: (20)..(20)
<223> OTHER INFORMATION: X = Lys, Glu, or Arg
<220> FEATURE:
<221> NAME/KEY: MISC_FEATURE
<222> LOCATION: (21)..(21)
<223> OTHER INFORMATION: X = Glu, or Leu
<220> FEATURE:
<221> NAME/KEY: MISC_FEATURE
<222> LOCATION: (24)..(24)
<223> OTHER INFORMATION: X = Ala, Glu, Lys, or Arg
<220> FEATURE:
<221> NAME/KEY: MISC_FEATURE
<222> LOCATION: (27)..(27)
<223> OTHER INFORMATION: X = Val, Thr(O-benzyl), or Lys
<220> FEATURE:
<221> NAME/KEY: MISC_FEATURE
<222> LOCATION: (28)..(28)
<223> OTHER INFORMATION: X = Lys, Glu, Gln, Asn, or Arg
<220> FEATURE:
<221> NAME/KEY: MISC_FEATURE
<222> LOCATION: (29)..(29)
<223> OTHER INFORMATION: X = Gly, Aib, or absent
<220> FEATURE:
<221> NAME/KEY: MISC_FEATURE
<222> LOCATION: (30)..(30)
<223> OTHER INFORMATION: X = Arg, Gly, Lys, or absent
<220> FEATURE:
<221> NAME/KEY: MISC_FEATURE
<222> LOCATION: (31)..(31)
<223> OTHER INFORMATION: X = Gly, Ala, Glu, Pro, Lys, epsilon-amino-Lys,
      amide, or absent
<220> FEATURE:
<221> NAME/KEY: MISC_FEATURE
<222> LOCATION: (32)..(32)
<223> OTHER INFORMATION: X = is Lys, Ser, amide, or absent
<220> FEATURE:
<221> NAME/KEY: MISC_FEATURE
<222> LOCATION: (33)..(33)
<223> OTHER INFORMATION: X = Lys, Ser, amide, or absent
<220> FEATURE:
<221> NAME/KEY: MISC_FEATURE
<222> LOCATION: (34)..(34)
<223> OTHER INFORMATION: X = Gly, amide, or absent
```

```
<220> FEATURE:
<221> NAME/KEY: MISC_FEATURE
<222> LOCATION: (35)..(35)
<223> OTHER INFORMATION: X = Ala, amide, or absent
<220> FEATURE:
<221> NAME/KEY: MISC_FEATURE
<222> LOCATION: (36)..(36)
<223> OTHER INFORMATION: X = Pro, amide, or absent
<220> FEATURE:
<221> NAME/KEY: MISC_FEATURE
<222> LOCATION: (37)..(37)
<223> OTHER INFORMATION: X = Pro, amide, or absent
<220> FEATURE:
<221> NAME/KEY: MISC_FEATURE
<222> LOCATION: (38)..(38)
<223> OTHER INFORMATION: X = Pro, amide, or absent
<220> FEATURE:
<221> NAME/KEY: MISC_FEATURE
<222> LOCATION: (39)..(39)
<223> OTHER INFORMATION: X = Ser, amide, or absent

<400> SEQUENCE: 2

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa
        35

<210> SEQ ID NO 3
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(32)
<220> FEATURE:
<221> NAME/KEY: MISC_FEATURE
<222> LOCATION: (1)..(1)
<223> OTHER INFORMATION: X = L-his, D-his, desamino-his, 2-amino-his,
      beta-hydroxy-his, homohis, Nalpha-acetyl-his, alpha-fluoromethyl-
      his, alpha-methyl-his, 2(3H-imidazol-4-yl)acetyl,
      3-pyridylalanine, 2-pyridylalanine
<220> FEATURE:
<221> NAME/KEY: MISC_FEATURE
<222> LOCATION: (2)..(2)
<223> OTHER INFORMATION: X = Ala, Gly, Val, Leu, Ile, Lys, Aib,
      (1-aminocyclopropyl-, -butyl-, -pentyl-, -hexyl-, -heptyl-,
      or -octyl) carboxylic acid
<220> FEATURE:
<221> NAME/KEY: MISC_FEATURE
<222> LOCATION: (12)..(12)
<223> OTHER INFORMATION: X = Ser, Lys, or Arg
<220> FEATURE:
<221> NAME/KEY: MISC_FEATURE
<222> LOCATION: (16)..(16)
<223> OTHER INFORMATION: X = Gly, Glu, or Aib
<220> FEATURE:
<221> NAME/KEY: MISC_FEATURE
<222> LOCATION: (17)..(17)
<223> OTHER INFORMATION: X = Gln, Glu, Lys, or Arg
<220> FEATURE:
<221> NAME/KEY: MISC_FEATURE
<222> LOCATION: (20)..(20)
<223> OTHER INFORMATION: X = Lys, Glu, or Arg
<220> FEATURE:
<221> NAME/KEY: MISC_FEATURE
<222> LOCATION: (24)..(24)
<223> OTHER INFORMATION: X = Ala, Glu, Lys, or Arg
<220> FEATURE:
<221> NAME/KEY: MISC_FEATURE
<222> LOCATION: (28)..(28)
<223> OTHER INFORMATION: X = Lys, Glu, Gln, or Arg
```

```
<220> FEATURE:
<221> NAME/KEY: MISC_FEATURE
<222> LOCATION: (29)..(29)
<223> OTHER INFORMATION: X = Gly, Aib, or absent
<220> FEATURE:
<221> NAME/KEY: MISC_FEATURE
<222> LOCATION: (30)..(30)
<223> OTHER INFORMATION: X = Arg, Lys, or absent
<220> FEATURE:
<221> NAME/KEY: MISC_FEATURE
<222> LOCATION: (31)..(31)
<223> OTHER INFORMATION: X = Gly, Ala, Glu, Pro, Lys, or epsilon-aminol-
      Lys
<220> FEATURE:
<221> NAME/KEY: MISC_FEATURE
<222> LOCATION: (32)..(32)
<223> OTHER INFORMATION: X = Lys, amide, or is absent

<400> SEQUENCE: 3

Xaa Xaa Glu Gly Thr Phe Thr Ser Asp Val Ser Xaa Tyr Leu Glu Xaa
1               5                   10                  15

Xaa Ala Ala Xaa Glu Phe Ile Xaa Trp Leu Val Xaa Xaa Xaa Xaa Xaa
            20                  25                  30

<210> SEQ ID NO 4
<211> LENGTH: 39
<212> TYPE: PRT
<213> ORGANISM: Heloderma suspectum
<220> FEATURE:
<221> NAME/KEY: PEPTIDE
<222> LOCATION: (1)..(39)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 5
<211> LENGTH: 44
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(44)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
            35                  40

<210> SEQ ID NO 6
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(32)
<220> FEATURE:
```

```
<221> NAME/KEY: MISC_FEATURE
<222> LOCATION: (1)..(2)
<223> OTHER INFORMATION: X =  2(3H-imidazol-4-yl)acetyl-alanine,
      L-histidine-Aib, desamino-histidine-alanine, or desamino-
      histidine-Aib
<220> FEATURE:
<221> NAME/KEY: MISC_FEATURE
<222> LOCATION: (1)..(2)
<223> OTHER INFORMATION: X =  2(3H-imidazol-4-yl)acetyl-alanine,
      L-histidine-Aib, desamino-histidine-alanine, or desamino-
      histidine-Aib
<220> FEATURE:
<221> NAME/KEY: MISC_FEATURE
<222> LOCATION: (3)..(3)
<223> OTHER INFORMATION: X = Glu or Glu derivative such as alpha,
      alpha dimethyl-Glu
<220> FEATURE:
<221> NAME/KEY: MISC_FEATURE
<222> LOCATION: (10)..(10)
<223> OTHER INFORMATION: X = Val, or Leu
<220> FEATURE:
<221> NAME/KEY: MISC_FEATURE
<222> LOCATION: (12)..(12)
<223> OTHER INFORMATION: X = Ser, Lys, or Arg
<220> FEATURE:
<221> NAME/KEY: MISC_FEATURE
<222> LOCATION: (13)..(13)
<223> OTHER INFORMATION: X = Tyr, or Gln
<220> FEATURE:
<221> NAME/KEY: MISC_FEATURE
<222> LOCATION: (17)..(17)
<223> OTHER INFORMATION: X = Gln, Glu, Lys, or Arg
<220> FEATURE:
<221> NAME/KEY: MISC_FEATURE
<222> LOCATION: (19)..(19)
<223> OTHER INFORMATION: X = Ala, or Val
<220> FEATURE:
<221> NAME/KEY: MISC_FEATURE
<222> LOCATION: (21)..(21)
<223> OTHER INFORMATION: X = Glu, or Leu
<220> FEATURE:
<221> NAME/KEY: MISC_FEATURE
<222> LOCATION: (24)..(24)
<223> OTHER INFORMATION: X = Ala, Glu, Lys, Arg, or absent
<220> FEATURE:
<221> NAME/KEY: MISC_FEATURE
<222> LOCATION: (27)..(27)
<223> OTHER INFORMATION: X = Val, Thr(O-benzyl), or Lys
<220> FEATURE:
<221> NAME/KEY: MISC_FEATURE
<222> LOCATION: (28)..(28)
<223> OTHER INFORMATION: X = Lys, Glu, Gln, Asn, or Arg
<220> FEATURE:
<221> NAME/KEY: MISC_FEATURE
<222> LOCATION: (29)..(29)
<223> OTHER INFORMATION: X = Gly, Aib, or absent
<220> FEATURE:
<221> NAME/KEY: MISC_FEATURE
<222> LOCATION: (30)..(30)
<223> OTHER INFORMATION: X = Arg, Lys, or absent
<220> FEATURE:
<221> NAME/KEY: MISC_FEATURE
<222> LOCATION: (31)..(31)
<223> OTHER INFORMATION: X = Gly, Aib, Pro, epsilon-amino-Lys, or absent
<220> FEATURE:
<221> NAME/KEY: MISC_FEATURE
<222> LOCATION: (32)..(32)
<223> OTHER INFORMATION: X = Lys, Glu, or absent

<400> SEQUENCE: 6

Xaa Xaa Xaa Gly Thr Phe Thr Ser Asp Xaa Ser Xaa Xaa Leu Glu Glu
1               5                   10                  15

Xaa Ala Xaa Arg Xaa Phe Ile Xaa Trp Leu Xaa Xaa Xaa Xaa Xaa Xaa
            20                  25                  30

<210> SEQ ID NO 7
<211> LENGTH: 31
```

```
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(31)
<220> FEATURE:
<221> NAME/KEY: MISC_FEATURE
<222> LOCATION: (1)..(1)
<223> OTHER INFORMATION: X = L-his, D-his, desamino-his, 2-amino-his,
      beta-hydroxy-his, homohis, Nalpha-acetyl-his, alpha-fluoromethyl-
      his, alpha-methyl-his, 2(3H-imidazol-4-yl)acetyl,
      3-pyridylalanine, 2-pyridylalanine
<220> FEATURE:
<221> NAME/KEY: MISC_FEATURE
<222> LOCATION: (2)..(2)
<223> OTHER INFORMATION: X = Ala, Gly, Val, Leu, Ile, Lys, Aib,
      (1-aminocyclopropyl-, -butyl-, -pentyl-, -hexyl-, -heptyl-, or
      -octyl) carboxylic acid
<220> FEATURE:
<221> NAME/KEY: MISC_FEATURE
<222> LOCATION: (12)..(12)
<223> OTHER INFORMATION: X = Ser, Lys, or Arg
<220> FEATURE:
<221> NAME/KEY: MISC_FEATURE
<222> LOCATION: (24)..(24)
<223> OTHER INFORMATION: X = Ala, Glu, Lys, or Arg
<220> FEATURE:
<221> NAME/KEY: MISC_FEATURE
<222> LOCATION: (27)..(27)
<223> OTHER INFORMATION: X = Val, or Lys
<220> FEATURE:
<221> NAME/KEY: MISC_FEATURE
<222> LOCATION: (28)..(28)
<223> OTHER INFORMATION: X = Lys, Glu, Gln, or Arg
<220> FEATURE:
<221> NAME/KEY: MISC_FEATURE
<222> LOCATION: (29)..(29)
<223> OTHER INFORMATION: X = Gly, Aib, or absent
<220> FEATURE:
<221> NAME/KEY: MISC_FEATURE
<222> LOCATION: (30)..(30)
<223> OTHER INFORMATION: X = Gly, Aib, Pro, epsilon-amino-Lys, or
      absent
<220> FEATURE:
<221> NAME/KEY: MISC_FEATURE
<222> LOCATION: (31)..(31)
<223> OTHER INFORMATION: X = Lys, or absent

<400> SEQUENCE: 7

Xaa Xaa Glu Gly Thr Phe Thr Ser Asp Val Ser Xaa Tyr Leu Glu Glu
1               5                  10                  15

Gln Ala Ala Arg Glu Phe Ile Xaa Trp Leu Xaa Xaa Xaa Xaa Xaa
            20                  25                  30
```

PEPTIDES DERIVATIZED WITH A-B-C-D- AND THEIR THERAPEUTICAL USE

CROSS-REFERENCE TO RELATED APPLICATIONS

This application is a Continuation of copending U.S. application Ser. No. 12/676,310, filed Mar. 3, 2010, which is a 35 U.S.C. §371 national stage application of International Patent Application PCT/EP2008/061830 (published as WO 2009/030771), filed Sep. 5, 2008, which claimed priority of European Patent Application 07115741.6, filed Sep. 5, 2007 and European Patent Application 08101011.8, filed Jan. 28, 2008; this application further claims priority under 35 U.S.C. §119 of U.S. Provisional Application 60/971,931, filed Sep. 13, 2007 and U.S. Provisional Application 61/024,622, filed Jan. 30, 2008, the contents of which are incorporated herein.

FIELD OF THE INVENTION

This invention relates to the field of therapeutic peptides, i.e. to new protracted peptides derivatized with A-B-C-D, and their therapeutical use. Examples of therapeutic peptides of particular relevance for the present invention are Glucagon-Like Peptide-1 (GLP-1) and exendin-4, as well as analogues thereof.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Feb. 25, 2010. The Sequence Listing is made up of 10 kilobytes, and the information contained in the attached "SEQUENCE LISTING" is identical to the information in the specification as originally filed. No new matter is added.

BACKGROUND OF THE INVENTION

A range of different approaches have been used for modifying the structure of therapeutical peptides such as GLP-1 and exendin-4 in order to provide a longer duration of action in vivo. For example, WO 2006/097538, WO 2006/097536, WO 2006/037810, WO2006005667, WO 2005/027978. WO 98/08871 and US 2001/0011071 describe various GLP-1 analogues and derivatives thereof.

Many diabetes patients particularly in the type 2 diabetes segment are subject to so-called "needle-phobia", i.e. a substantial fear of injecting themselves. In the type 2 diabetes segment most patients are treated with oral hypoglycaemic agents, and since GLP-1 compounds are expected to be an injectable pharmaceutical product these patients will be administered, the fear of injections may become a serious obstacle for the widespread use of the clinically very promising compounds. Thus, there is a need to develop new compounds which can be administered less than once daily, e.g. once every second or third day preferably once weekly, while retaining an acceptable clinical profile or optionally via non invasive administration such as pulmonary, nasal, sublingual, bucal or oral administration.

One object of the invention is to provide long acting, i.e. having an administration regimen as described above, peptide derivatives, such as derivatives of GLP-1, exendin-4, or analogues thereof.

Another object of this invention is to provide peptide derivatives such as derivatives of GLP-1, exendin-4, or analogues thereof with high potency (receptor affinity) in order to reduce the therapeutic dose used for example for once weekly s.c. dosing or alternatively for non-invasive delivery.

A further object is to provide derivatives of GLP-1 or analogues thereof for which the affinity to the GLP-1 receptor is only partly decreased when comparing the affinity in the presence of very low concentration of human albumin to the affinity in the presence of a higher concentration of human albumin. The shift in binding affinity is preferably low.

Another object of this invention is to provide peptide derivatives such as derivatives of GLP-1 or analogues thereof with high albumin binding affinity which protects the peptide for proteolytic degradation and reduce renal clearance of the peptide.

Potency, in particular the ratio of binding affinity to the GLP-1 receptor in the presence of low and high albumin concentrations, half-life, and binding affinity to albumin are properties of potential relevance for an overall object of achieving long-acting, stable and of course therapeutically active peptide derivatives such as GLP-1 derivatives with a potential for once weekly administration.

The peptide derivatives of the invention are preferably chemically, physically and enzymatically stable.

SUMMARY OF THE INVENTION

The present invention relates to a peptide derivative comprising a peptide wherein at least one amino acid residue is derivatized with A-B-C-D-, wherein A- is

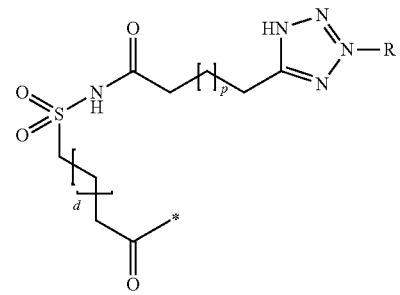

wherein R is lower linear or branched alkyl such as isobutyl, p is selected from the group consisting of 10, 11, 12, 13 and 14, and d is selected from the group consisting of 0, 1, 2, 3, 4 and 5, and
-B- is selected from the group consisting of

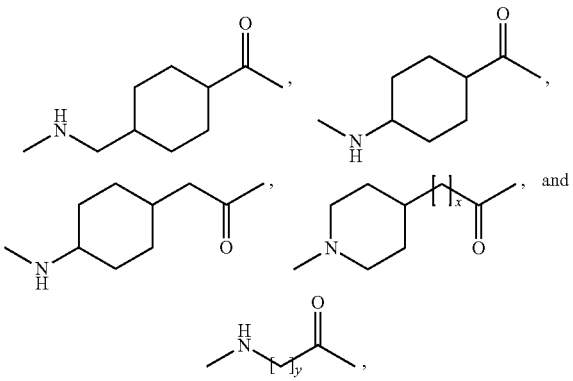

wherein x is selected from the group consisting of 0, 1, 2, 3 and 4, and y is selected from the group consisting of 1, 2, 3, 4, 5, 6, 7, 8, 9, 10, 11 and 12, or A is

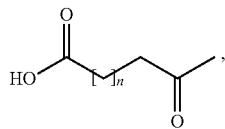

wherein n is selected from the group consisting of 14, 15, 16 17, 18 and 19, and B is selected from the group consisting of

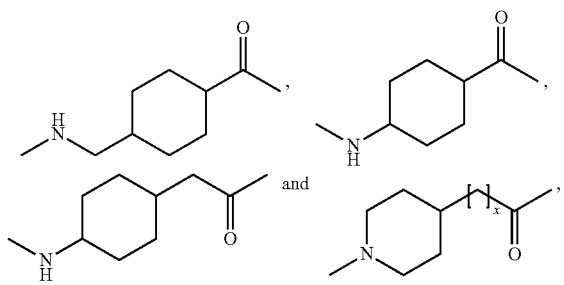

wherein x is selected from the group consisting of 0, 1, 2, 3 and 4, and
-C- is selected from the group consisting of

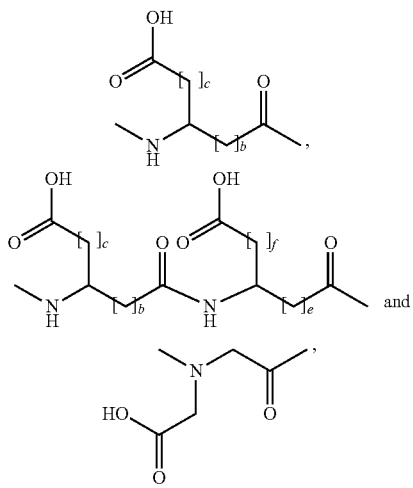

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker, represents a bond, or is absent.

The invention also relates to compositions and uses of these peptide derivatives.

DESCRIPTION OF THE INVENTION

Definitions and Particular Embodiments

In the present specification, the following terms have the indicated meaning: The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib α-aminoisobutyric acid), Abu (α-aminobutyric acid), Tle (tert-butylglycine), β-alanine, 3-aminomethyl benzoic acid, anthranilic acid.

The 22 proteogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteogenic amino acid (which may also be designated a non-natural amino acid) is a moiety which can be incorporated into a peptide via peptide bonds but is not a proteogenic amino acid. Examples are γ-carboxyglutamate, ornithine, phosphoserine, the D-amino acids such as D-alanine and D-glutamine, Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), 3-aminomethyl benzoic acid, anthranilic acid, des-amino-histidine (abbreviated DesaminoHis, alternative name imidazopropionic acid, abbreviated Impr), the beta analogs of amino acids such as β-alanine etc., D-histidine, 2-amino-histidine, β-hydroxy-histidine, homohistidine, $N^\alpha$-acetyl-histidine, α-fluoromethyl-histidine, α-methyl-histidine, α,α-dimethyl-glutamic acid, m-CF3-phenylalanine (abbreviated m-CF3-Phe), alpha,alpha-diaminopropionic acid (abbreviated Dap), 2-naphthyl-threonine (abbreviated 2-naphthyl-Thr or -T), 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid.

The term epsilon-amino-Lys (or epsilon-Lys) is intended to indicate that a lysine residue is bound to a peptide such as GLP-1(7-37) peptide or an analogue thereof via its epsilon amino group, not (as is usually the case) via its alpha amino group (see e.g. the compound of Example 53).

The term "analogue" as used herein referring to a polypeptide means a modified peptide wherein one or more amino acid residues of the peptide have been substituted by other amino acid residues and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide.

A simple system is often used to describe analogues: For example [$Arg^{34}$]GLP-1(7-37)Lys designates a GLP-1(7-37) analogue wherein the naturally occurring lysine at position 34 has been substituted with arginine and wherein a lysine has been added to the terminal amino acid residue, i.e. to the $Gly^{37}$.

All amino acids for which the optical isomer is not stated is to be understood to mean the L-isomer.

In a particular embodiment of the peptide derivative of the invention, the linker D is absent, meaning the peptide is derivatized with A-B-C- only.

In another particular embodiment, the linker D is included and comprises at least 5, 8, 10, 19, 20, 29, 41, or at least 60 non-hydrogen atoms.

In a still further particular embodiment, 30-50% (such as 34, 38, 40, 41, or 42%) of the non-hydrogen atoms of the linker are constituted by N or O atoms.

Functional Properties

A number of peptide derivatives of the invention have been synthesized and tested as described in the experimental part.

The peptide derivatives of the invention have several advantageous and beneficial properties as explained in the following, by reference to the Examples.

In a first aspect, the peptide derivative of the invention has a protracted profile of action, which makes it potentially suitable for less-frequently-than-once-daily administration, preferably with a potential for once-weekly, or even less frequent, administration. The profile of action can be evaluated in pharmacokinetic experiments with laboratory animals such as mice or pigs. Suitable experiments are found in Example 73 (minipigs) and Example 77 (mice) of the present application.

As described in minipig Example 73, (i) the peptide derivative may be administered s.c. or i.v., preferably s.c.; (ii) the pigs are preferably Göttingen minipigs, preferably about 5 months old and weighing 8-10 kg; (iii) the animals are preferably fasting before administration, preferably as described; (iv) the injection is preferably given as indicated; (v) the number of animals tested is preferably as indicated; (vi) the dosage is preferably as indicated; and/or (vii) blood samples are also preferably taken, collected, and assayed as indicated in this Example.

Pharmacokinetic experiments like the one in Example 73 result in a plasma concentration profile of the compound in question versus time, on the basis of which the half-life, T½, may be determined.

In a first particular embodiment, the half-life of a peptide, such as a GLP-1, derivative of the invention, after s.c. administration in minipigs, is above 18 hours, preferably above 24 hours, more preferably above 28 hours, even more preferably above 30 hours, most preferably above 32 hours.

In a second particular embodiment, the half-life of the peptide derivative of the invention, after s.c. administration in minipigs, is above 32 hours, preferably above 34 hours, more preferably above 36 hours, even more preferably above 38 hours, most preferably above 40 hours.

In a third particular embodiment, the half-life of the peptide derivative of the invention, after s.c. administration in minipigs, is above 45 hours, preferably above 50 hours, more preferably above 55 hours, even more preferably above 60 hours, most preferably above 65 hours.

In a fourth particular embodiment, the half-life of the peptide derivative of the invention, after s.c. administration in minipigs, is above 45 hours, preferably above 50 hours, more preferably above 55 hours, even more preferably above 60 hours, most preferably above 65 hours.

In a fifth particular embodiment, the half-life of the peptide derivative of the invention, after s.c. administration in minipigs, is above 70 hours, preferably above 75 hours, more preferably above 80 hours, even more preferably above 85 hours, most preferably above 90 hours.

In a sixth particular embodiment, the half-life of the peptide derivative of the invention, after s.c. administration in minipigs, is above 92 hours, preferably above 94 hours, more preferably above 96 hours, even more preferably above 98 hours, most preferably above 100 hours.

Accordingly, exemplary half-life intervals (time indicated in hours, h) of the peptide derivative of the invention, determined in minipigs by s.c. administration, are: 20-100, 30-100, 40-100, 50-100, 60-100, 70-100, 80-100, or 90-100 (hours).

The half-life of a peptide derivative such as a GLP-1 derivative of the invention may also be determined in a dose-response study in db/db mice, e.g. as described in Example 77. As described in this Example, (i) the mice are preferably from Taconic; (ii) of 10-12 weeks of age; (iii) have free access to standard feed such as Altromin 1324 and tap water; (iv) are kept at 24 dgC; (v) being acclimatised for 1 week; (vi) allocated into 7 groups (preferably n=6) based on matching mean blood glucose values; (vii) receive treatment as described in the example; (viii) being dosed as described; (ix) blood glucose is assessed according to a scheme as described, preferably assayed as described; and/or (x) the half-life determined based on the blood glucose vs. time determinations, preferably as described in the example.

In a first particular embodiment, the half-life of a peptide derivative such as a GLP-1 derivative of the invention, after s.c. administration in db/db mice, is above 10 hours, preferably above 11 hours, more preferably above 12 hours, even more preferably above 13 hours, most preferably above 14 hours.

In a second particular embodiment, the half-life of a peptide derivative of the invention, after s.c. administration in db/db mice, is above 15 hours, preferably above 16 hours, more preferably above 17 hours, even more preferably above 18 hours, most preferably above 19 hours.

In a third particular embodiment, the half-life of a peptide derivative of the invention, after s.c. administration in db/db mice, is above 20 hours, preferably above 21 hours, more preferably above 22 hours, even more preferably above 23 hours, most preferably above 24 hours.

In a fourth particular embodiment, the half-life of a peptide derivative of the invention, after s.c. administration in db/db mice, is above 25 hours, preferably above 26 hours, more preferably above 27 hours, even more preferably above 28 hours, most preferably above 29 hours.

In a fifth particular embodiment, the half-life of a peptide derivative of the invention, after s.c. administration in db/db mice, is above 30 hours, preferably above 31 hours, more preferably above 32 hours, even more preferably above 33 hours, most preferably above 34 hours.

Accordingly, exemplary half-life intervals (time indicated in hours, h) of the peptide derivative of the invention, assayed in db/db mice by s.c. administration, are: 5-35, 10-35, 15-35, 20-35, or 25-35 (hours).

In a second aspect, the peptide derivative of the invention has an acceptable, preferably a high potency (at its receptor). The potency of an insulinotropic agent such as the GLP-1 derivative of the invention may be determined by calculating the $EC_{50}$ value from the dose-response curve as described in Example 74.

The term "insulinotropic agent" as used herein means a derivative which is an agonist of the human GLP-1 receptor, i.e. a derivative which stimulates the formation of cAMP in a suitable medium containing the human GLP-1 receptor (one such medium disclosed below).

In particular embodiments, (i) baby hamster kidney (BHK) cells expressing the cloned human GLP-1 receptor are used, preferably BHK-467-12A, more preferably BHK-467-12A (tk-ts13); (ii) the cells are grown in DMEM media with the addition of 100 IU/mL penicillin, 100 μg/mL streptomycin (1% Pen/Strep), 5% fetal calf serum (FCS) and 0.5 mg/mL Geneticin G-418 (Life Technologies), preferably at 5% $CO_2$; (iii) the cells, preferably at approximately 80% confluence, are washed twice in phosphate buffered saline (PBS); (iv) the cells are harvested with an aqueous solution of the tetrasodium salt of ethylenediaminetetraacetic acid, such as Versene; (v) plasma membranes are prepared from the cells by homogenisation, preferably in buffer 1; (vi) the homogenate is centrifuged, e.g. at 48,000×g for 15 min at 4° C.; and/or (vii) the pellet is suspended by homogenization in buffer 2; Steps (vi) and (viii) are preferably repeated, e.g. one or two times more.

The functional receptor assay may be carried out as described in Example 74 by measuring cyclic AMP (cAMP) as a response to stimulation by the insulinotropic agent. cAMP formed is preferably quantified by the AlphaScreen™ cAMP Kit (Perkin Elmer Life Sciences). Incubations may be carried out in half-area 96-well microtiter plates in a total volume of 50 μL buffer 3 (50 mM Tris-HCl, 5 mM HEPES, 10 mM $MgCl_2$, pH 7.4) and with the following additions: 1 mM ATP, 1 μM GTP, 0.5 mM 3-isobutyl-1-methylxanthine (IBMX), 0.01% Tween-20, 0.1% BSA, 6 μg membrane preparation, 15 μg/mL acceptor beads, 20 μg/mL donor beads preincubated with 6 nM biotinyl-cAMP. Derivatives to be tested for agonist activity are preferably dissolved and diluted in buffer 3. GTP is freshly prepared for each experiment. The plate is incubated in the dark with slow agitation for three hours at room temperature followed by counting in the Fusion™ instrument (Perkin Elmer Life Sciences). Concentration-response curves are plotted for the individual derivatives and $EC_{50}$ values estimated using a four-parameter logistic model with Prism, preferably in version 4.0, or 5.0, (GraphPad, Carlsbad, Calif.).

In a first particular embodiment, the GLP-1 derivative of the invention has a potency ($EC_{50}$ in nM), as determined using the cAMP assay, below 4.00, preferably below 3.50, more preferably below 3.00, even more preferably below 2.50, and most preferably below 2.00 (nM).

In a second particular embodiment, the GLP-1 derivative of the invention has a potency ($EC_{50}$ in nM), as determined using the cAMP assay, below 1.80, preferably below 1.60, more preferably below 1.40, even more preferably below 1.20, and most preferably below 1.00 (nM).

In a third particular embodiment, the GLP-1 derivative of the invention has a potency ($EC_{50}$ in nM), as determined using the cAMP assay, below 0.80, preferably below 0.60, more preferably below 0.40, even more preferably below 0.20, and most preferably below 0.10 (nM).

In a fourth particular embodiment, the GLP-1 derivative of the invention has a potency ($EC_{50}$ in nM), as determined using the cAMP assay, below 0.090, preferably below 0.080, more preferably below 0.070, even more preferably below 0.060, and most preferably below 0.050 (nM).

In a fifth particular embodiment, the GLP-1 derivative of the invention has a potency ($EC_{50}$ in nM), as determined using the cAMP assay, below 0.040, preferably below 0.030, more preferably below 0.020, and most preferably below 0.010 (nM).

Accordingly, exemplary ranges of potency ($EC_{50}$ in nM, as determined using the cAMP assay) of GLP-1 derivatives of the invention are 0.010-2.00, 0.010-1.80, 0.010-1.60, 0.010-1.40, 0.010-1.20, 0.010-1.00, 0.010-0.80, 0.010-0.60, 0.010-0.40, 0.010-0.30, 0.010-0.20, 0.010-0.10, and 0.010-0.90 (nM), preferably 0.010-0.40, 0.010-0.30, 0.010-0.20, 0.010-0.10, and 0.010-0.90 (nM).

In a sixth particular embodiment, the GLP-1 derivative of the invention can bind to albumin and the GLP-1 receptor simultaneously. For example, the GLP-1 derivative of the invention may bind to the GLP-1 receptor with an affinity below 100 nM, preferable below 30 nM in the presence of 2% albumin.

In a third aspect, the GLP-1 derivative of the invention has an affinity to the GLP-1 receptor which is only partly decreased when comparing the affinity in the presence of very low concentration (e.g. 0.005% to 0.2%) of human albumin to the affinity in the presence of 2% human albumin (high/low). The shift in binding affinity under these conditions is preferably less than 100 fold, more preferably below 50 fold, even more preferably below 30 fold and most preferably below 10 fold. The binding affinity at the receptor in a high and low concentration of human albumin may be determined as described in Example 75.

In a first particular embodiment, the GLP-1 derivative of the invention has a ratio of [($IC_{50}$/nM) high HSA]/[($IC_{50}$/nM) ultralow HSA] of below 500, preferably below 400, more preferably below 300, even more preferably below 200, and most preferably below 100.

In a second particular embodiment, the GLP-1 derivative of the invention has a ratio of [($IC_{50}$/nM) high HSA]/[($IC_{50}$/nM) ultralow HSA] of below 90, preferably below 80, more preferably below 70, even more preferably below 69, and most preferably below 50.

In a third particular embodiment, the GLP-1 derivative of the invention has a ratio of [($IC_{50}$/nM) high HSA]/[($IC_{50}$/nM) ultralow HSA] of below 40, preferably below 35, more preferably below 30, even more preferably below 25, and most preferably below 20.

In a fourth particular embodiment, the GLP-1 derivative of the invention has a ratio of [($IC_{50}$/nM) high HSA]/[($IC_{50}$/nM) ultralow HSA] of below 15, preferably below 10, more preferably below 8, even more preferably below 5, and most preferably below 4.

Accordingly, exemplary ranges for the ratio of [($IC_{50}$/nM) high HSA]/[($IC_{50}$/nM) ultralow HSA] are 2-500, 2-300, 2-100, 2-50, 2-30, 2-20, and 2-10.

In a fourth aspect, the peptide derivative of the invention has a high albumin binding affinity. The albumin refers to human serum albumin (HSA), and the affinity may be determined as described in Example 76.

The affinities of the GLP-1 derivatives for human serum albumin (HSA) may be measured by a competition scintillation proximity assay (SPA), preferably by (i) incubating streptavidin-SPA beads (such as GE Healthcare RPNQ0009) with biotinylated HSA, e.g. for 5 hours; (ii) washing the beads with buffer; (iii) mixing the beads mixed with an $^{125}$I-labeled acylated GLP-1 analogue, such as N-epsilon26-[2-(2-{2-[2-(2-{2-[(S)-4-Carboxy-4-(17-carboxy-heptadecanoylamino) butyrylamino]ethoxy}ethoxy)acetylamino]ethoxy}ethoxy) acetyl][Aib8, $^{125}$I-Tyr19,Arg34]GLP-1(7-37) or N-epsilon37-[2-(2-[2-((S)-4-((S)-4-(12-[4-(16-(1H-tetrazol-5-yl)hexadecanoylsulfamoyl)butyrylamino]dodecanoylamino)-4-carboxybutyrylamino)-4-carboxybutyrylamino) ethoxy]ethoxy)acetyl][Aib8,$^{125}$I-Tyr19,Glu22,Arg26,34, Lys37] GLP-1(7-37)-$NH_2$, preferably in a buffer containing 100 mM Hepes, 100 mM NaCl, 10 mM $MgSO_4$, 0.025% Tween-20, pH 7.4; (iv) transferring the mixture into the wells of a scintillation counter such as Perkin Elmer Optiplate-96 6005290 (100 μl per well), using suitable volumes such as 100 μl of a suitable dilution series of the GLP-1 derivative to be measured, preferably in the same buffer; (v) centrifuging the plates after a suitable incubation time such as 20 hours, preferably with gentle rocking, more preferably at room temperature; (vi) counting the plates, e.g. on a TopCounter; and/or (vii) plotting bound cpm as a function of GLP-1 derivative concentration. The $EC_{50}$ value of the competition curve is preferably used as a measure of the affinity of the derivative for HSA. The HSA binding affinity may also be expressed as $K_d$ apparent ($K_d$ for Dissociation Equilibrium Constant).

In a first particular embodiment, the albumin binding affinity (i.e. the $EC_{50}$ value (in nM) of the competition curve, as measured using the assay of Example 76), is below 3000, preferably below 2500, more preferably below 2000, even more preferably below 800, and most preferably below 600 (nM).

In a second particular embodiment, the albumin binding affinity (i.e. the $EC_{50}$ value (in nM) of the competition curve, as measured using the assay of Example 76), is below 500, preferably below 400, more preferably below 300, even more preferably below 200, and most preferably below 100 (nM).

Accordingly, exemplary ranges of albumin binding affinity (EC50 in nM) of the GLP-1 derivative of the invention are: 1-3000, 1-2500, 1-2000, 100-2000, 200-2000, 400-1500, 600-1500, and 800-1500 (nM).

Additional Definitions and Particular Embodiments

Examples of other peptides which may be derivatised according to the invention is a therapeutic peptide with a molar weight of less than 100 kDa, less than 50 kDa, or less than 10 kDa.

Examples of other peptides which can be derivatised according to the invention is Exendine 4, human growth hormone, human insulin, coagulation factors including factor VII, factor VIII, factor IX, factor X, factor XIII, parathyroid hormone, human follicle stimulating hormone, platelet-derived growth factor (PDGF), transforming growth factor α (TGF-α), transforming growth factor β (TGF-β), epidermal growth factor (EGF), vascular endothelial growth factor (VEGF), a somatomedin such as insulin growth factor I (IGF-I), insulin growth factor II (IFG-II), erythropoietin (EPO), thrombopoietin (TPO) or angiopoietin, interferon, pro-urokinase, urokinase, tissue plasminogen activator (t-PA), plasminogen activator inhibitor 1, plasminogen activator inhibitor 2, von Willebrandt factor, a cytokine, e.g. an interleukin such as interleukin (IL) 1, IL-1Ra, IL-2, IL-4, IL-5, IL-6, IL-9, IL-11, IL-12, IL-13, IL-15, IL-16, IL-17, IL-18, IL-20 or IL-21, a colony stimulating factor (CFS) such as GM-CSF, stem cell factor, a tumor necrosis factor such as TNF-α, lymphotoxin-α, lymphotoxin-β, CD40L, or CD30L, a protease inhibitor e.g. aprotinin, an enzyme such as superoxide dismutase, asparaginase, arginase, arginine deaminase, adenosine deaminase, ribonuclease, catalase, uricase, bilirubin oxidase, trypsin, papain, alkaline phosphatase, β-glucoronidase, purine nucleoside phosphorylase or batroxobin, an opioid, e.g. endorphins, enkephalins or non-natural opioids, a hormone or neuropeptide, e.g. calcitonin, glucagon, gastrins, adrenocorticotropic hormone (ACTH), cholecystokinins, lutenizing hormone, gonadotropin-releasing hormone, chorionic gonadotropin, corticotrophin-releasing factor, vasopressin, oxytocin, antidiuretic hormones, thyroid-stimulating hormone, thyrotropin-releasing hormone, relaxin, prolactin, peptide YY, Y2 receptor agonists, Y4 receptor agonists, mixed Y2/Y4 receptor agonists, neuropeptide Y, pancreatic polypeptide, leptin, CART (cocaine and amphetamine regulated transcript), a CART related peptide, perilipin, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins and analogs thereof, hematide and analogs thereof.

The term "each amino acid residue downstream" as used herein refers to each amino acids positioned towards the C-terminal relative to a specific amino acid. As an example Lys34, Gly35 and Arg36 and Gly37 are each amino acid residues downstream of Val33 in GLP-1 (7-37).

In one aspect of the invention, the C-terminal of the derivative according to the invention may be terminated as either an acid or amide. In a preferred aspect, the C-terminal of the derivative of the invention is an amide. In another preferred aspect, the C-terminal of the derivative of the invention is an acid.

In embodiments of the invention a maximum of 17 amino acids have been modified. In embodiments of the invention a maximum of 15 amino acids have been modified. In embodiments of the invention a maximum of 10 amino acids have been modified. In embodiments of the invention a maximum of 8 amino acids have been modified. In embodiments of the invention a maximum of 7 amino acids have been modified. In embodiments of the invention a maximum of 6 amino acids have been modified. In embodiments of the invention a maximum of 5 amino acids have been modified. In embodiments of the invention a maximum of 4 amino acids have been modified. In embodiments of the invention a maximum of 3 amino acids have been modified. In embodiments of the invention a maximum of 2 amino acids have been modified. In embodiments of the invention 1 amino acid has been modified.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. An example of a derivative of an analogue of GLP-1(7-37) according to the invention is N-epsilon37{2-[2-(2-{2-[2-((R)-3-carboxy-3-{[1-(19-carboxynonadecanoyl)piperidine-4-carbon yl]amino}propionylamino)ethoxy]ethoxy}acetylamino)ethoxy]ethoxy}acetyl [desaminoHis7, Glu22,Arg26,Arg34,Lys37]GLP-1(7-37)amide wherein the naturally occurring Gly in position 37 has been substituted with lysine which has been derivatised at N-epsilon37 with {2-[2-(2-{2-[2-((R)-3-carboxy-3-{[1-(19-carboxynonadecanoyl)piperidine-4-carbon yl]amino}propionylamino) ethoxy]ethoxy}acetylamino)ethoxy]ethoxy}acetyl (structure 1)

Structure 1

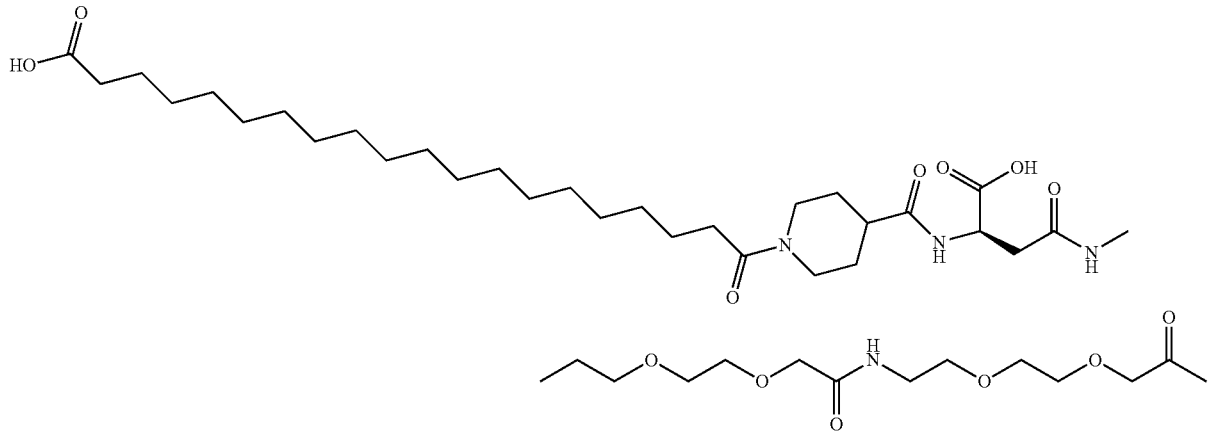

and wherein the naturally occurring histidine in position 7 has been substituted with desaminoHis and the naturally occurring glycine in pos 22 has been substituted with glutamate and lysine in position 26 and 34 has been substituted with arginine.

The term "GLP-1 peptide" as used herein means GLP-1(7-37) (SEQ ID No 1) or a GLP-1(7-37) analogue thereof.

In one aspect of the invention, the GLP-1 peptide is selected from the group consisting of
[desaminoHis7,Glu22,Arg26,Arg34,Lys37]GLP-1(7-37) amide,
[desaminoHis7,Arg34]GLP-1-(7-37), [Aib8,Glu22,Arg26, Arg34,Lys37]GLP-1-(7-37)amide,
[DesaminoHis7, Glu22 Arg26, Arg 34, Phe(m-CF3)28]GLP-1-(7-37)amide,
[DesaminoHis7,Glu22,Arg26,Arg34]GLP-1-(7-37)-Lys,
[DesaminoHis7, Glu22,Arg26,Arg34]GLP-1-(7-37)-Lys,
[desaminoHis7,Arg26,Arg34]GLP-1-(7-37)-Lys,
[DesaminoHis7,Glu22,Arg26,Arg34,Lys37]GLP-1-(7-37) amide,
[DesaminoHis7,Arg26,Arg34,Lys37]GLP-1-(7-37)amide,
[DesaminoHis7,Glu22,Arg26,Arg34,Lys37]GLP-1-(7-37),
[DesaminoHis7,Arg26,Arg34,Lys37]GLP-1-(7-37),
[DesaminoHis7,Glu22,Arg26,Glu30,Arg34,Lys37]GLP-1-(7-37),
[Aib8,Lys20,Arg26,Glu30,Thr(O-benzyl)33]GLP-1-(7-37) amide,
[Aib8,Glu22,Arg26,Lys30]GLP-1-(7-37), [Aib8, Glu22, Arg26,Lys 31]GLP-1-(7-37),
[Aib8,Lys20,Arg26, 2-Naphtylalanine28, Glu30]GLP-1 (7-37)amide,
[Aib8, Glu22, Arg26, Arg34]GLP-1-(7-37)-Lys,
[Aib8,Lys20,Arg 26, 2-Naphtylalanine12, Glu30]GLP-1-(7-37)amide,
[Aib8,Glu22,Arg26,Lys31,Arg34]GLP-1-(7-37),
[Aib8,Arg34]GLP-1-(7-37),
[Aib8,Arg34]GLP-1-(7-37)-amide,
[Aib8,Lys18,Arg26,Arg34]GLP-1(7-37),
[Aib8,Glu22,Arg26,Arg34,Lys37]GLP-1-(7-37)amide,
[Aib8, Lys 26] GLP-1 (7-37)amide,
[Aib8,Arg34]GLP-1-(7-34),
[Aib8,Arg34]GLP-1-(7-35),
[Aib8,Lys33,Arg34]GLP-1-(7-34),
[Aib8,Arg34]GLP-1-(7-36)amide,
[Aib8,Lys26,Arg34]GLP-1-(7-36)amide,
[Aib8,Glu22,Arg26,Arg34]GLP-1-(7-37)Lys,
[Aib8,Lys20,Glu22,Arg26,Glu30,Pro37]GLP-1-(7-37) amide,
[Aib8,Glu22,Arg26,Arg34,Lys37]GLP-1-(7-37)amide,
[DesaminoHis7,Glu22,Arg26,Arg34,Lys37]GLP-1-(7-37) amide,
[DesaminoHis7,Arg26,Arg34,Lys37]GLP-1-(7-37)amide,
[Aib8,Glu22,Arg26,Glu30,Pro37]GLP-1-(7-37)Lys,
[Aib8,Glu22,Arg26,Glu30,Pro37]GLP-1-((7-37)Lys, and
[Aib8,Arg26,Arg34]GLP-1-(7-37).

In one aspect of the invention, the GLP-1 peptide is Arg18, Leu20, Gln34, Lys33 (Nε-(γ-aminobutyroyl(Nα-hexadecanoyl))) Exendin-4-(7-45)-amide or Arg33, Leu20, Gln34, Lys18 (Nε-(γ-aminobutyroyl(Nα-hexadecanoyl))) Exendin-4-(7-45)-amide.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like.

Any amino acid position in the peptide e.g. the GLP-1 peptide may be derivatised. In one aspect of the invention, the amino acid residue which is derivatised comprises an amino group. In one aspect, the derivatised amino acid residue comprises an amino group. In a further aspect, the derivatised amino acid residue comprises a primary amino group in a side chain. In a further aspect, the derivatised amino acid residue is lysine. In one aspect of the invention, the derivatised amino acid residue is cysteine. In one aspect of the invention, one amino acid residue is derivatised. In yet a further aspect of the invention, the derivative according to the invention is only derivatised in one position, e.g. only one amino acid residue is derivatised.

Examples of amino acid residues comprising an amino group is lysine, ornithine, Epsilon-N-alkylated lysine such as Epsilon-N methylLysine, O-aminoethylserine, O-aminopropylserine or longer O alkylated serines containing a primary or secondary amino group in the side chain. In a further aspect of the invention, the derivatised amino acid residue comprises a primary amino group in a side chain. Examples of amino acid residues comprising a primary amino group is lysine ornithine, O-aminoethylserine, O-aminopropylserine or longer O alkylated serines containing a primary amino group in the side chain.

In one embodiment the derivative of the GLP-1 peptide according to the invention is an insulinotropic agent.

The term "insulinotropic agent" as used herein means a derivative which is an agonist of the human GLP-1 receptor, i.e. a derivative which stimulates the formation of cAMP in a suitable medium containing the human GLP-1 receptor (one such medium disclosed below). The potency of an insulinotropic agent is determined by calculating the $EC_{50}$ value from the dose-response curve as described below.

Baby hamster kidney (BHK) cells expressing the cloned human GLP-1 receptor (BHK-467-12A) arere grown in DMEM media with the addition of 100 IU/mL penicillin, 100 μg/mL streptomycin, 5% fetal calf serum and 0.5 mg/mL Geneticin G-418 (Life Technologies). The cells are washed twice in phosphate buffered saline and harvested with Versene. Plasma membranes are prepared from the cells by homogenisation with an Ultraturrax in buffer 1 (20 mM HEPES-Na, 10 mM EDTA, pH 7.4). The homogenate is centrifuged at 48,000×g for 15 min at 4° C. The pellet is suspended by homogenization in buffer 2 (20 mM HEPES-Na, 0.1 mM EDTA, pH 7.4), then centrifuged at 48,000×g for 15 min at 4° C. The washing procedure is repeated one more time. The final pellet is suspended in buffer 2 and used immediately for assays or stored at −80° C.

The functional receptor assay is carried out by measuring cyclic AMP (cAMP) as a response to stimulation by the insulinotropic agent. cAMP formed is quantified by the AlphaScreen™ cAMP Kit (Perkin Elmer Life Sciences). Incubations are carried out in half-area 96-well microtiter plates in a total volume of 50 μL buffer 3 (50 mM Tris-HCl, 5 mM HEPES, 10 mM $MgCl_2$, pH 7.4) and with the following additions: 1 mM ATP, 1 μM GTP, 0.5 mM 3-isobutyl-1-methylxanthine (IBMX), 0.01% Tween-20, 0.1% BSA, 6 μg membrane preparation, 15 μg/mL acceptor beads, 20 μg/mL donor beads preincubated with 6 nM biotinyl-cAMP. Derivatives to be tested for agonist activity are dissolved and diluted in buffer 3. GTP is freshly prepared for each experiment. The plate is incubated in the dark with slow agitation for three hours at room temperature followed by counting in the Fusion™ instrument (Perkin Elmer Life Sciences). Concentration-response curves are plotted for the individual derivatives and $EC_{50}$ values estimated using a four-parameter logistic model with Prism v. 4.0 (GraphPad, Carlsbad, Calif.).

The term "DPP-IV protected" as used herein referring to a polypeptide means a polypeptide which has been chemically modified in order to render said derivative resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV.

In one aspect of the invention, the GLP-1 peptide is a DPPIV protected GLP-1 peptide.

In one aspect of the invention, the said GLP-1 peptide is stabilised against DPP-IV degradation relatively to the stability of liraglutide In one embodiment a derivative according to the invention is a DPP-IV protected derivative which is more resistant to DPP-IV than liraglutide.

Resistance of a peptide to degradation by dipeptidyl aminopeptidase IV is determined by the following degradation assay:

Aliquots of the peptide (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

Alternatively, the resistance of a peptide to degradation by dipeptidyl aminopeptidase IV is determined by the following degradation assay:

Aliquots of the peptide (4 nmol) are incubated at 37° C. with 10.9 mU of purified dipeptidyl aminopeptidase IV for 22 hours in 40 μL of 0.085 M Tris-HCl buffer, pH 8.0, in presence or absence of 1.6% human serum albumin. After 0, 4, and 22 hours samples of 10 μl are taken and enzymatic reactions are terminated by mixing with 100 μl of 1% trifluoroacetic acid. The peptide degradation products are separated and quantified using HPLC analysis. One method for performing this analysis is: The mixtures are applied onto an Agilent Zorbax 300SB-C18 (5 μm particles) 150×2.1 mm column and eluted at a flow rate of 0.5 ml/min with a linear gradient from 0.1% trifluoroacetic acid to 100% acetonitrile with 0.07% TFA in 30 minutes. Peptides and their degradation products are monitored by their absorbance at 214 nm, and are quantified by integration of their peak areas. The stability of a peptide against dipeptidyl aminopeptidase IV is determined as the peak area of the intact peptide relative to the sum of the peak areas of the intact peptide and the degradation product lacking the two aminoterminal amino acids after cleavage.

The term "pharmaceutically acceptable" as used herein means suited for normal pharmaceutical applications, i.e. giving rise to no serious adverse events in patients etc.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active derivative according to the invention together with pharmaceutical excipients such as buffer, preservative, and optionally a tonicity modifier and/or a stabilizer. Thus a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active derivative according to the invention to eliminate or control the disease, condition or disorder as well as to alleviate the symptoms or complications associated with the disease, condition or disorder.

In another aspect, the present invention relates to a derivative of a GLP-1 peptide that can bind to albumin and the GLP-1 receptor simultaneously.

In another aspect the present invention relates to a derivative of a GLP-1 peptide that bind to the GLP-1 receptor with an affinity below 100 nM, preferable below 30 nM in the presence of 2% albumin.

In another aspect, the present invention relates to a derivative of a GLP-1 peptide which affinity to the GLP-1 receptor is only partly decreased when comparing the affinity in the presence of very low concentration (e.g. 0.005% to 0.2%) of human albumin to the affinity in the presence of 2% human albumin. The shift in binding affinity under these conditions is less than 50 fold, preferable below 30 fold and more preferable below 10 fold.

In another aspect the present invention relates to a derivative of a GLP-1 peptide which is stable against the chemical degradation normally seen with exendin-4—especially oxidation and deamidation.

In another aspect, the present invention relates to a derivative of a GLP-1 peptide which has a high potency at the receptor. For very strong albumin binding analogues with albumin binding affinity below 100 nM, the GLP-1 potency is better than 3 micro molar and preferable the potency is better than 1 micromolar in the cAMP assay.

For strong albumin binding derivatives with albumin binding affinity below 500 nM, the GLP-1 potency is better than 1 micro molar and preferable the potency is better than 0.2 micromolar in the cAMP assay.

In another aspect, the present invention relates to a derivative of a GLP-1 peptide which has high albumin binding affinity. The derivatives of this invention have an albumin binding affinity that is below 1 micromolar. More preferable the derivatives of this invention has an albumin binding affinity that is below 500 nM and even more preferable below 200 nM or even below 100 nM.

The albumin binding affinity can be measured using the following assay:

Albumin Binding Assay:

The affinities of the GLP-1 derivatives for human serum albumin (HSA) are measured by a competition scintillation proximity assay (SPA). Streptavidin-SPA beads (GE Healthcare RPNQ0009) are incubated with biotinylated HSA for 5 hours. The beads are washed with buffer to remove unbound HSA. The beads are mixed with an $^{125}$I-labeled acylated GLP-1 analogue such as N-epsilon26-[2-(2-{2-[2-(2-{2-[(S)-4-Carboxy-4-(17-carboxy-heptadecanoylamino)butyrylamino]ethoxy}ethoxy)acetylamino]ethoxy}ethoxy)acetyl][Aib8, $^{125}$I-Tyr19,Arg34]GLP-1(7-37) or N-epsilon37-[2-(2-[2-((S)-4-((S)-4-(12-[4-(16-(1H-tetrazol-5-yl)hexadecanoylsulfamoyl)butyrylamino]dodecanoylamino)-4-carboxybutyrylamino)-4-carboxybutyrylamino)ethoxy]ethoxy)acetyl][Aib8,$^{125}$I-Tyr19,Glu22,Arg26,34, Lys37] GLP-1(7-37)-NH2 in a buffer containing 100 mM Hepes, 100 mM NaCl, 10 mM MgSO$_4$, 0.025% Tween-20, pH 7.4. The mixture is pipetted into the wells of a Perkin Elmer Optiplate-96 6005290 (100 µl per well) and 100 µl of a dilution series of the GLP-1 derivative to be measured is added in the same buffer. After 20 hours of gentle rocking at room temperature the plates are centrifuged and counted on a TopCounter. Bound cpm are plotted as a function of GLP-1 derivative concentration end the EC50 value of the competition curve is used as a measure of the affinity of the derivative for HSA.

In another aspect, the present invention relates to a GLP-1 peptide derivative with high affinity binding to the isolated N-terminal extracellular domain of the GLP-1R receptor (nGLP-1R). The affinity is measured by the ability to displace $^{125}$I-Exendin-4(9-39) from binding to nGLP-1R. In this assay Exendin-4 binds nGLP-1R with an IC$_{50}$ value of 5 nM, GLP-1(7-37) binds nGLP-1R with an IC$_{50}$ value of 1120 nM and liraglutide binds nGLP-1R with an IC$_{50}$ value of 1000 nM. In one aspect, the derivatives of this invention binds nGLP-1R with an IC$_{50}$ value lower than that of liraglutide. More preferable the derivatives of this invention binds nGLP-1R with an IC$_{50}$ value lower than 100 nM and even more preferable below 10 nM or even below 5 nM.

The binding to nGLP-1R is measured in the following assay: the protein nGLP-1R is prepared as described previously (Runge et al 2007), biotinylated and immobilized on streptavidin-coated SPA beads. The nGLP1R in 0.1M NaHCO$_3$ is biotinylated using 75 µg BNHS (Sigma H1759) to 1 mg protein. The biotinylated nGLP1R is subsequently dialyzed against PBS. All reagents and derivatives are diluted in PBS with 0.05% v/v Tween 20. The binding assay is carried out in 96 well OptiPlates (PerkinElmer 6005290) in a final volume of 200 µl. Each well contains 2 mg streptavidin coated SPA beads (PerkinElmer RPNQ007), 0.1 pmol biotinylated nGLP1R, 50 pCi $^{125}$I-Exendin (9-39) and test peptide in final concentrations ranging from 1000 nM to 0.064 nM.

The plates are incubated on a shaker at RT for 3 hours. The SPA particles are spun down by centrifugation for 10 min at 1500 rpm and the plates are counted in a TopCount-NXT (Perkin Elmer).

In another aspect, the present invention relates to a derivative of a GLP-1 peptide which has substantially improved terminal half-life in rodent and in a non-rodent model relative to liraglutide.

In one aspect of this invention, the terminal half-life in rodent or in a non-rodent model is improved at least 3 fold relative to liraglutide.

In another aspect of this invention, the terminal half-life in a non-rodent model is improved at least 6 fold relative to liraglutide.

In another aspect, the present invention relates to a derivative of a GLP-1 peptide which has an in vivo half-life of at least 10 hrs after i.v. administration to rats.

In another aspect, the present invention relates to a derivative of a GLP-1 peptide which has an in vivo half-life of at least 50 hrs after s.c. administration to mini pigs, and preferable an in vivo half-life of at least 80 hrs after s.c. administration to mini pigs.

In another aspect, the present invention relates to a derivative of a GLP-1 peptide which can be formulated into particles suitable for pulmonary administration.

In another aspect, the present invention relates to a derivative of a GLP-1 peptide which is chemically and physically stable at neutral pH, most preferably in the range 6-8.

In another aspect, the present invention relates to a derivative of a GLP-1 peptide which has little or no tendency to aggregate. In one aspect the aggregation tendency is significantly improved relatively to the aggregation tendency of liraglutide when tested in a thioflavin assay.

In another aspect, the present invention relates to a derivative of a GLP-1 peptide which is suitable for pulmonal delivery. This may be with regard to physical or chemical aspects which are useful for a pulmonal formulation. Alternatively, the derivatives are stable against degradation by enzymes in the airways and lungs.

In embodiments of the invention a combination of the above features is achieved.

The term "albumin binding moiety" as used herein means a residue which binds non-covalently to human serum albumin. The albumin binding residue attached to the therapeutic polypeptide typically has an albumin binding affinity that is below 1 micromolar, preferable below 500 nM and even more preferable below 200 nM or even below 100 nM.

A range of albumin binding residues are known among linear and branched lipohophillic moieties containing 4-40 carbon atoms having a distal acidic group.

The term "hydrophilic linker" as used herein means a spacer that separates a peptide and an albumin binding residue with a chemical moiety which comprises at least 5 non-hydrogen atoms where 30-50% of these are either N or O.

In the formulas below the terminal bonds from the attached groups are to be regarded as attachment bonds and not ending in methylene groups unless stated.

Compositions and Pharmaceutical Uses

Another object of the present invention is to provide a pharmaceutical formulation comprising a derivative according to the present invention which is present in a concentration from 0.1 mg/ml to 25 mg/ml, and wherein said formulation has a pH from 3.0 to 9.0. The formulation may further comprise a buffer system, preservative(s), tonicity agent(s), chelating agent(s), stabilizers and surfactants.

In one embodiment of the invention, the pharmaceutical formulation is an aqueous formulation, i.e. formulation comprising water. Such formulation is typically a solution or a suspension.

In a further embodiment of the invention, the pharmaceutical formulation is an aqueous solution.

The term "aqueous formulation" is defined as a formulation comprising at least 50% w/w water. Likewise, the term "aqueous solution" is defined as a solution comprising at least 50 w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the invention relates to a pharmaceutical formulation comprising an aqueous solution of a derivative according to the present invention, and a buffer, wherein said derivative is present in a concentration from 0.1 mg/ml or above, and wherein said formulation has a pH from about 3.0 to 9.0.

In another embodiment of the invention, the pH of the formulation is from about 7.0 to about 9.5. In another embodiment of the invention, the pH of the formulation is from about 3.0 to about 7.0. In another embodiment of the invention, the pH of the formulation is from about 5.0 to about 7.5. In another embodiment of the invention, the pH of the formulation is from about 7.5 to about 9.0. In another embodiment of the invention, the pH of the formulation is from about 7.5 to about 8.5. In another embodiment of the invention, the pH of the formulation is from about 6.0 to about 7.5. In another embodiment of the invention, the pH of the formulation is from about 6.0 to about 7.0. In another embodiment, the pharmaceutical formulation is from 8.0 to 8.5.

In an embodiment of the invention, each administered dose contains from 0.01 mg-10 mg of active derivative. In an embodiment, the dose administered contains more than 0.05 mg active derivative. In an embodiment, the dose administered contains more than 0.1 mg active derivative. In an embodiment, the dose administered contains up to 10 mg active derivative. In an embodiment, the dose administered contains up to 9 mg active derivative. In an embodiment, the dose administered contains up to 8 mg active derivative. In an embodiment, the dose administered contains up to 7 mg active derivative. In an embodiment, the dose administered contains up to 6 mg active derivative. In an embodiment, the dose administered contains up to 5 mg active derivative. In an embodiment, the dose administered contains from 0.2 mg to 5 mg active derivative.

In a further embodiment of the invention, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention, the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In an embodiment, the preservative is phenol or m-cresol. In a further embodiment of the invention, the preservative is present in a concentration from 0.1 mg/ml to 20 mg/ml. In a further embodiment of the invention, the preservative is present in a concentration from 0.1 mg/ml to 5 mg/ml. In a further embodiment of the invention, the preservative is present in a concentration from 5 mg/ml to 10 mg/ml. In a further embodiment of the invention, the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy,* 19$^{th}$ edition, 1995.

In a further embodiment of the invention, the formulation further comprises an isotonic agent. In a further embodiment of the invention, the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. In an embodiment, the isotoncity agent is propyleneglycol. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention, the isotonic agent is present in a concentration from 1 mg/ml to 50 mg/ml. In a further embodiment of the invention, the isotonic agent is present in a concentration from 1 mg/ml to 7 mg/ml. In an embodiment of the invention, the isotonic agent is present in a concentration from 5 mg/ml to 7 mg/ml. In a further embodiment of the invention, the isotonic agent is present in a concentration from 8 mg/ml to 24 mg/ml. In a further embodiment of the invention, the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention, the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention, the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations.

By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention, methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention, the formulation further comprises a stabilizer selected from the group of high molecular weight polymers or low molecular compounds.

In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein.

Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention, the formulation further comprises a surfactant. In another embodiment of the invention, the pharmaceutical composition comprises two different surfactants. The term "Surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general.

Anionic surfactants may be selected from the group of: Chenodeoxycholic acid, Chenodeoxycholic acid sodium salt, Cholic acid, Dehydrocholic acid, Deoxycholic acid, Deoxycholic acid methyl ester, Digitonin, Digitoxigenin, N,N-Dimethyldodecylamine N-oxide, Docusate sodium, Glycochenodeoxycholic acid sodium, Glycocholic acid hydrate, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine sodium salt, N-Lauroylsarcosine, N-Lauroylsarcosine, Lithium dodecyl sulfate, Lugol, 1-Octanesulfonic acid sodium salt, 1-Octanesulfonic acid sodium salt, Sodium 1-butanesulfonate, Sodium 1-decanesulfonate, Sodium 1-dodecanesulfonate, Sodium 1-heptanesulfonate, Sodium 1-heptanesulfonate, Sodium 1-nonanesulfonate, Sodium 1-propanesulfonate monohydrate, Sodium 2-bromoethanesulfonate, Sodium cholate hydrate, ox or sheep bile, Sodium cholate hydrate, Sodium choleate, Sodium deoxycholate, Sodium dodecyl sulfate, Sodium dodecyl sulfate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurolithocholic acid 3-sulfate disodium salt, Tauroursodeoxycholic acid sodium salt, Trizma® dodecyl sulfate, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), Dodecylphosphocholine (FOS-Choline-12), Decylphosphocholine (FOS-Choline-10), Nonylphosphocholine (FOS-Choline-9), dipalmitoyl phosphatidic acid, sodium caprylate, and/or Ursodeoxycholic acid.

Cationic surfactants may be selected from the group of: Alkyltrimethylammonium bromide Benzalkonium chloride, Benzalkonium chloride, Benzyldimethylhexadecylammonium chloride, Benzyldimethyltetradecylammonium chloride, Benzyltrimethyl tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Hexadecyltrimethylammonium bromide, Hexadecyltrimethylammonium bromide, Polyoxyethylene (10)-N-tallow-1,3-diaminopropane, Thonzonium bromide, and/or Trimethyl(tetradecyl)ammonium bromide.

Nonionic surfactants may be selected from the group of: BigCHAP, Bis(polyethylene glycol bis[imidazoyl carbonyl]), block copolymers as polyethyleneoxide/polypropyleneoxide block copolymers such as poloxamers, poloxamer 188 and poloxamer 407, Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Dodecanoyl-N-methylglucamide, alkyl-polyglucosides, ethoxylated castor oil, Heptaethylene glycol monodecyl ether, Heptaethylene glycol monododecyl ether, Heptaethylene glycol monotetradecyl ether, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O-(N-heptylcarbamoyl)-beta-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from *Quillaja* bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tetradecyl-3-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165 solution, Triton® X-305 solution, Triton® X-405, Triton® X-45, Triton® X-705-70, TWEEN® 20, TWEEN® 40, TWEEN® 60, TWEEN® 6, TWEEN® 65, TWEEN® 80, TWEEN® 81, TWEEN® 85, Tyloxapol, sphingophospholipids (sphingomyelin), and sphingoglycolipids (ceramides, gangliosides), phospholipids, and/or n-Undecyl β-D-glucopyranoside.

Zwitterionic surfactants may be selected from the group of: CHAPS, CHAPSO, 3-(Decyldimethylammonio)propanesulfonate inner salt, 3-(Dodecyldimethylammonio)-propanesulfonate inner salt, 3-(Dodecyldimethylammonio)propanesulfonate inner salt, 3-(N,N-Dimethylmyristylammonio) propanesulfonate, 3-(N,N-Dimethyloctadecylammonio)-propanesulfonate, 3-(N,N-Dimethyloctylammonio)

propanesulfonate inner salt, 3-(N,N-Dimethylpalmitylammonio)propanesulfonate, N-alkyl-N,N-dimethylammonio-1-propanesulfonates, 3-cholamido-1-propyldimethylammonio-1-propanesulfonate, Dodecylphosphocholine, myristoyl lysophosphatidylcholine, Zwittergent 3-12 (N-dodecyl-N,N-dimethyl-3-ammonio-1-propanesulfonate), Zwittergent 3-10 (3-(Decyldimethyl-ammonio)propanesulfonate inner salt), Zwittergent 3-08 (3-(Octyldimethylammonio)propanesulfonate), glycerophospholipids (lecithins, kephalins, phosphatidyl serine), glyceroglycolipids (galactopyranoside), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, lysophosphatidylserine and lysophosphatidylthreonine, acylcarnitines and derivatives, $N^{beta}$-acylated derivatives of lysine, arginine or histidine, or side-chain acylated derivatives of lysine or arginine, $N^{beta}$-acylated derivatives of dipeptides comprising any combination of lysine, arginine or histidine and a neutral or acidic amino acid, $N^{beta}$-acylated derivative of a tripeptide comprising any combination of a neutral amino acid and two charged amino acids, or the surfactant may be selected from the group of imidazoline derivatives, long-chain fatty acids and salts thereof $C_6$-$C_{12}$ (eg. oleic acid and caprylic acid), N-Hexadecyl-N,N-dimethyl-3-ammonio-1-propane-sulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), or mixtures thereof.

The term "alkyl-polyglucosides" as used herein in relates to an straight or branched $C_{5-20}$-alkyl, -alkenyl or -alkynyl chain which is substituted by one or more glucoside moieties such as maltoside, saccharide etc. Embodiments of these alkyl-polyglucosides include $C_{6-18}$-alkyl-polyglucosides. Specific embodiments of these alkyl-polyglucosides includes the even numbered carbon-chains such as $C_6$, $C_8$, $C_{10}$, $C_{12}$, $C_{14}$, $C_{16}$, $C_{18}$ and $C_{20}$ alkyl chain. Specific embodiments of the glucoside moieties include pyranoside, glucopyranoside, maltoside, maltotrioside and sucrose. In embodiments of the invention, less than 6 glucosid moieties are attached to the alkyl group. In embodiments of the invention, less than 5 glucosid moieties are attached to the alkyl group. In embodiments of the invention, less than 4 glucosid moieties are attached to the alkyl group. In embodiments of the invention, less than 3 glucosid moieties are attached to the alkyl group. In embodiments of the invention, less than 2 glucosid moieties are attached to the alkyl group. Specific embodiments of alkyl-polyglucosides are alkyl glucosides such n-decyl β-D-glucopyranoside, decyl β-D-maltopyranoside, dodecyl β-D-glucopyranoside, n-dodecyl β-D-maltoside, n-dodecyl β-D-maltoside, n-dodecyl β-D-maltoside, tetradecyl β-D-glucopyranoside, decyl β-D-maltoside, hexadecyl β-D-maltoside, decyl β-D-maltotrioside, dodecyl β-D-maltotrioside, tetradecyl β-D-maltotrioside, hexadecyl β-D-maltotrioside, n-dodecyl-sucrose, n-decyl-sucrose, sucrose monocaprate, sucrose monolaurate, sucrose monomyristate, and sucrose monopalmitate.

The use of a surfactant in pharmaceutical compositions is well-known to the skilled person. For convenience reference is made to Remington: *The Science and Practice of Pharmacy*, 19$^{th}$ edition, 1995.

In a further embodiment of the invention, the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a derivative according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, chewing gum, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the derivative of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block copolymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions thereof, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of derivatives of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension or a powder for the administration of the derivative of the present invention in the form of a nasal or pulmonal liquid or powder spray. As a still further option, the pharmaceutical compositions containing the derivative of the invention can also be adapted to transdermal administration, e.g. by needle-free injection or from a patch, optionally an iontophoretic patch, or transmucosal, e.g. buccal, administration.

The derivatives of the present invention can be administered via the pulmonary route in a vehicle, as a solution, suspension or dry powder using any of known types of devices suitable for pulmonary drug delivery. Examples of these comprise, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air. In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the derivative of the present invention may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention, the pharmaceutical formulation comprising the derivative of the present invention is stable for more than 6 weeks of usage and for more than 3 years of storage.

In another embodiment of the invention, the pharmaceutical formulation comprising the derivative of the present invention is stable for more than 4 weeks of usage and for more than 3 years of storage.

In a further embodiment of the invention, the pharmaceutical formulation comprising the derivative of the present invention is stable for more than 4 weeks of usage and for more than two years of storage.

In an even further embodiment of the invention, the pharmaceutical formulation comprising the derivative of the present invention is stable for more than 2 weeks of usage and for more than two years of storage.

In another aspect, the present invention relates to the use of a derivative according to the invention for the preparation of a medicament.

In one embodiment, a derivative according to the invention is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, stroke, coronary heart disease and other cardiovascular disorders, inflammatory bowel syndrome, dyspepsia and gastric ulcers.

In another embodiment, a derivative according to the invention is used for the preparation of a medicament for delaying or preventing disease progression in type 2 diabetes.

In another embodiment, a derivative according to the invention is used for the preparation of a medicament for decreasing food intake, decreasing β-cell apoptosis, increasing β-cell function and β-cell mass, and/or for restoring glucose sensitivity to β-cells.

In one aspect of the invention, a method for increasing the time of action in a patient of a peptide, such as a GLP-1 peptide, characterised in that said peptide such as a GLP-1(7-37) peptide is derivatised with A-B-C-D- as disclosed herein, is provided.

In one aspect of the invention, a method for increasing the time of action in a patient of a peptide, such as a GLP-1 peptide to more than about 40 hours, characterised in that said peptide such as a GLP-1(7-37) peptide is derivatised with A-B-C-D- as disclosed herein, is provided.

In one aspect of the invention, a pharmaceutical composition comprising a derivative according to the invention, and a pharmaceutically acceptable excipient, is provided.

In one aspect of the invention, the pharmaceutical composition according to the invention is suited for parenteral administration.

In a further aspect of the invention, the use of a derivative according to the invention for the preparation of a medicament, is provided.

In yet a further aspect of the invention, the use of a derivative according to the invention for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers, is provided.

In yet a further aspect of the invention, the use of a derivative according to the invention for the preparation of a medicament for delaying or preventing disease progression in type 2 diabetes, is provided.

The treatment with a derivative according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with surgery—a surgery that influence the glucose levels and/or lipid homeostasis such as gastric banding or gastric bypass.

It should be understood that any suitable combination of the derivatives according to the invention with one or more of the above-mentioned compounds and optionally one or more further pharmacologically active substances are considered to be within the scope of the present invention.

Method of Manufacturing Peptides and Analogues Thereof.

Depending on the sequence the analogues of this invention can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the therapeutic polypeptide may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well-known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well-known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well-known and used in the art are, without limitation, *E. coli, Saccharomyces cerevisiae*, or mammalian BHK or CHO cell lines.

Embodiments According to the Invention

1. A peptide derivative comprising a peptide wherein at least one amino acid residue is derivatized with A-B-C-D- wherein A- is

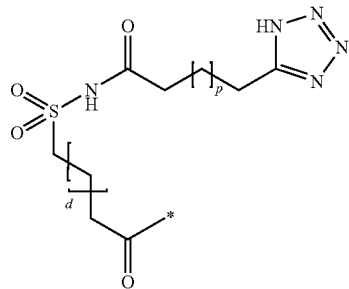

wherein p is selected from the group consisting of 10, 11, 12, 13 and 14, and d is selected from the group consisting of 0, 1, 2, 3, 4 and 5, and -B- is selected from the group consisting of

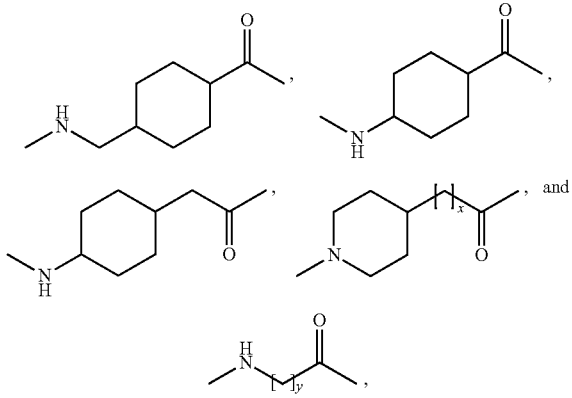

wherein x is selected from the group consisting of 0, 1, 2, 3 and 4, and y is selected from the group consisting of 1, 2, 3, 4, 5, 6, 7, 8, 9, 10, 11 and 12, or A is

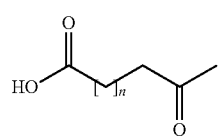

wherein n is selected from the group consisting of 14, 15, 16 17, 18 and 19, and B is selected from the group consisting of

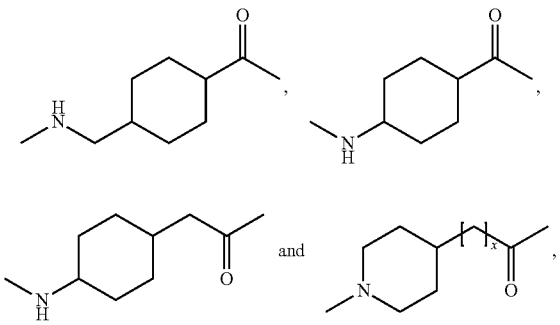

wherein x is selected from the group consisting of 0, 1, 2, 3 and 4, and

-C- is selected from the group consisting of

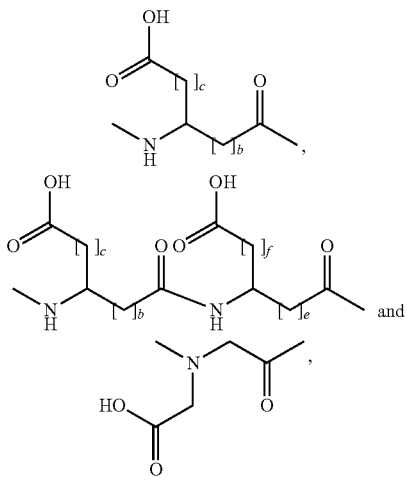

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

2. The derivative according to embodiment 1, wherein said peptide is a GLP-1 peptide selected from GLP-1(7-37) and an analogue of GLP-1(7-37), wherein, in said peptide, at least one amino acid residue is derivatised with A-B-C-D-.

3. The derivative according to any one of embodiments 1-2, wherein the derivatised amino acid residue comprises an amino group.

4. The derivative according to any one of embodiments 1-4, wherein the derivatised amino acid residue is lysine.

5. The derivative according to any of the embodiments 1-4, wherein D is selected from the group consisting of

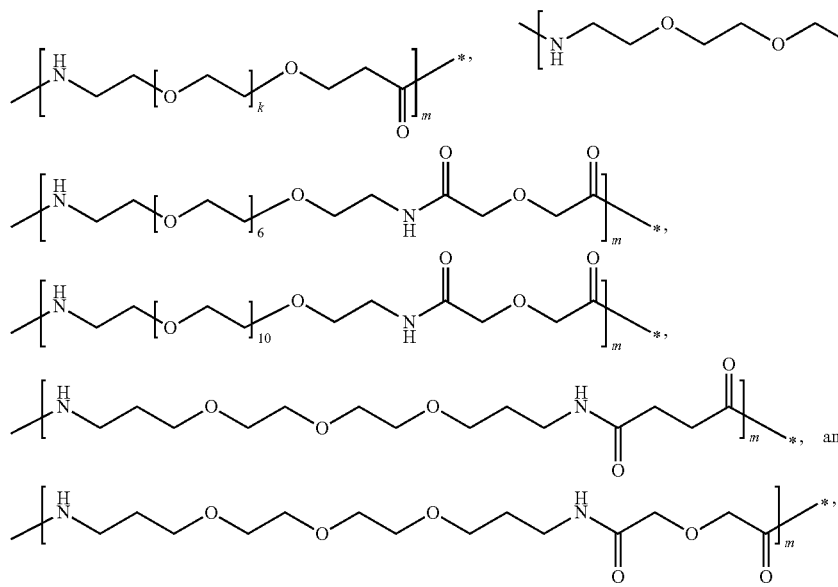

(preferably no. 1, 3, 4, 5, and 6 of these structures, i.e. excluding no. 2),
   wherein k is selected from the group consisting of 0, 1, 2, 3, 4, 5, 11 and 27, and m is selected from the group consisting of 0, 1, 2, 3, 4, 5 and 6, and D is attached to the amino acid residue in the end depicted with *.

6. The derivative according to any one of the embodiments 1-5, wherein said GLP-1 analogue comprises the amino acid sequence of the formula (I):

Formula (I) (SEQ ID No: 2)
$Xaa_7$-$Xaa_8$-Glu-Gly-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-

Ala-$Xaa_{25}$-$Xaa_{26}$-$Xaa_{27}$-Phe-Ile-$Xaa_{30}$-Trp-Leu-$Xaa_{33}$-$Xaa_{34}$-$Xaa_{35}$-$Xaa_{36}$-$Xaa_{37}$-$Xaa_{38}$-

$Xaa_{39}$-$Xaa_{40}$-$Xaa_{41}$-$Xaa_{42}$-$Xaa_{43}$-$Xaa_{44}$-$Xaa_{45}$-$Xaa_{46}$ wherein
   $Xaa_7$ is L-histidine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine or 4-pyridylalanine;
   $Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
   $Xaa_{16}$ is Val or Leu;
   $Xaa_{18}$ is Ser, Lys or Arg;
   $Xaa_{19}$ is Tyr or Gln;
   $Xaa_{20}$ is Leu, Met, or Lys, preferably Leu or Met;
   $Xaa_{22}$ is Gly, Glu or Aib;
   $Xaa_{23}$ is Gln, Glu, Lys or Arg;
   $Xaa_{25}$ is Ala or Val;
   $Xaa_{26}$ is Lys, Glu or Arg;
   $Xaa_{27}$ is Glu or Leu;
   $Xaa_{30}$ is Ala, Glu, Lys, or Arg, preferably Ala, Glu, or Arg;
   $Xaa_{33}$ is Val or Lys;
   $Xaa_{34}$ is Lys, Glu, Asn or Arg;
   $Xaa_{35}$ is Gly or Aib;
   $Xaa_{36}$ is Arg, Gly or Lys;
   $Xaa_{37}$ is Gly, Ala, Glu, Pro, Lys, amide or is absent;
   $Xaa_{38}$ is Lys, Ser, amide or is absent.
   $Xaa_{39}$ is Ser, Lys, amide or is absent;
   $Xaa_{40}$ is Gly, amide or is absent;
   $Xaa_{41}$ is Ala, amide or is absent;
   $Xaa_{42}$ is Pro, amide or is absent;
   $Xaa_{43}$ is Pro, amide or is absent;
   $Xaa_{44}$ is Pro, amide or is absent;
   $Xaa_{45}$ is Ser, amide or is absent;
   $Xaa_{46}$ is amide or is absent;
   provided that if $Xaa_{38}$, $Xaa_{39}$, $Xaa_{40}$, $Xaa_{41}$, $Xaa_{42}$, $Xaa_{43}$, $Xaa_{44}$, $Xaa_{45}$ or $Xaa_{46}$ is absent then each amino acid residue downstream is also absent.

7. The derivative according to any one of the embodiments 1-5, wherein said GLP-1 analogue comprises the amino acid sequence of the formula (II):

Formula (II) (SEQ ID No: 3)
$Xaa_7$-$Xaa_8$-Glu-Gly-Thr-Phe-Thr-Ser-Asp-Val-Ser- $Xaa_{18}$-Tyr-Leu-Glu-$Xaa_{22}$-$Xaa_{23}$-Ala-Ala-$Xaa_{26}$-Glu- Phe-Ile-$Xaa_{30}$-Trp-Leu-Val-$Xaa_{34}$-$Xaa_{35}$-$Xaa_{36}$-

$Xaa_{37}$-$Xaa_{38}$ wherein
   $Xaa_7$ is L-histidine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine or 4-pyridylalanine;

Xaa₈ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa₁₈ is Ser, Lys or Arg;
Xaa₂₂ is Gly, Glu or Aib;
Xaa₂₃ is Gln, Glu, Lys or Arg;
Xaa₂₆ is Lys, Glu or Arg;
Xaa₃₀ is Ala, Glu, Lys, or Arg, preferably Ala, Glu, or Arg;
Xaa₃₄ is Lys, Glu or Arg;
Xaa₃₅ is Gly or Aib;
Xaa₃₆ is Arg or Lys;
Xaa₃₇ is Gly, Ala, Glu or Lys;
Xaa₃₈ is Lys, amide or is absent.

8. The derivative according to any one of the embodiments 1-5, wherein said GLP-1 analogue comprises the amino acid sequence of the formula (III) which is derivatised in position 18, 23, 34, 36, 37 or 38:

```
                            Formula (III) (SEQ ID No: 6)
Xaa₇-Xaa₈-Xaa₉-Gly-Thr-Phe-Thr-Ser-Asp-Xaa₁₆-Ser- Xaa₁₈-Tyr-Leu-Glu-Glu-Xaa₂₃-Ala-Xaa₂₅-Arg-Xaa₂₇-

Phe-Ile-Xaa₃₀-Trp-Leu-Xaa₃₃-Xaa₃₄-Xaa₃₅-Xaa₃₆-

Xaa₃₇-Xaa₃₈-Xaa₃₉
``` wherein
Xaa₇-Xaa₈ is L-histidine-Aib, desamino-histidine-alanine or desamino-histidine-Aib
Xaa₉ is Glu or a Glu derivative such as alpha, alpha dimethyl-Glu
Xaa₁₆ is Val or Leu;
Xaa₁₈ is Ser, Lys, or Arg;
Xaa₁₉ is Tyr or Gln;
Xaa₂₃ is Gln, Glu, Lys or Arg;
Xaa₂₅ is Ala or Val;
Xaa₂₇ is Glu or Leu;
Xaa₃₀ is Ala, Glu, Arg or absent;
Xaa₃₃ is Val, or Lys;
Xaa₃₄ is Lys, Glu, Asn or Arg;
Xaa₃₅ is Gly or Aib;
Xaa₃₆ is Arg or Lys,
Xaa₃₇ is Gly, Aib or absent
Xaa₃₈ is Lys, Glu or absent
Xaa₃₉ is amide or is absent;
provided that if Xaa₃₇ is absent then Xaa₃₈ is also absent.

9. The derivative according to any one of the embodiments 1-5, wherein the GLP-1 peptide comprises the amino acid sequence of formula (IV) which is derivatised with an albumin binding residue in position 18, 23, 34, 36, 37 or 38:

```
                            Formula (IV) (SEQ ID No: 7)
Xaa₇-Xaa₈-Glu-Gly-Thr-Phe-Thr-Ser-Asp-Val-Ser- Xaa₁₈-Tyr-Leu-Glu-Glu-Gln-Ala-Ala-Arg-Glu- Phe-Ile-Xaa₃₀-Trp-Leu-Xaa₃₃-Xaa₃₄-Xaa₃₅-Xaa₃₆-

Xaa₃₇-Xaa₃₈-Xaa₃₉
``` wherein
Xaa₇ is L-histidine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine or 4-pyridylalanine;
Xaa₈ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa₁₈ is Ser, Lys or Arg;
Xaa₃₀ is Ala, Glu, Lys, Arg or absent, preferably Ala, Glu, or Arg;
Xaa₃₃ is Val or Lys;
Xaa₃₄ is Lys, Glu or Arg;
Xaa₃₅ is Gly or Aib;
Xaa₃₆ is Arg or Lys,
Xaa₃₇ is Gly, Aib or absent,
Xaa₃₈ is Lys or absent, and
Xaa₃₉ is amide or is absent.

10. The derivative according to any one of the embodiments 1-9, wherein Xaa₃₈ is absent.
11. The derivative according to any one of the embodiments 1-10, wherein Xaa₃₇ and Xaa₃₈ are both absent.
12. The derivative according to any one of the embodiments 1-11, wherein Xaa₇ is desamino-histidine.
13. The derivative according to any one of the embodiments 1-12, wherein Xaa₈ is Aib
14. A pharmaceutical composition comprising a derivative according to any one of embodiments 1-13, and a pharmaceutically acceptable excipient.
15. A derivative according to any one of the embodiments 1-13 for use in the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers.

The amino acid sequence of human GLP-1(7-37) is included in the Sequence Listing as SEQ ID No 1, and SEQ ID Nos 2-3 and 6-7 are examples of GLP-1(7-37) analogues for use in derivatives according to the invention. In the Sequence Listing the numbering of GLP-1(7-37) and the analogues thereof starts with amino acid residue no. 1. Accordingly, e.g., position 1 of SEQ ID No 1 is equivalent to position 7 of GLP-1(7-37) (His), position 16 of SEQ ID No 1 is equivalent to position 22 of GLP-1(7-37) (Gly), and position 20 of SEQ ID No 1 is equivalent to position 26 of GLP-1(7-37) (Lys)- and vice versa for the other positions and the other sequences.

Accordingly, the invention also provides, e.g. in above embodiment 6, a peptide derivative wherein the GLP-1(7-37) analogue comprises the amino acid sequence of the formula (I) (SEQ ID NO: 2) wherein:
Xaa₇ (position no. 1 in SEQ ID NO: 2) is L-histidine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine or 4-pyridylalanine;
Xaa₈ (position no. 2 in SEQ ID NO: 2) is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa₁₆ (position no. 10 in SEQ ID NO: 2) is Val or Leu;
Xaa₁₈ (position no. 12 in SEQ ID NO: 2) is Ser, Lys or Arg;

Xaa$_{19}$ (position no. 13 in SEQ ID NO: 2) is Tyr or Gln;
Xaa$_{20}$ (position no. 14 in SEQ ID NO: 2) is Leu, Met or Lys;
Xaa$_{22}$ (position no. 16 in SEQ ID NO: 2) is Gly, Glu or Aib;
Xaa$_{23}$ (position no. 17 in SEQ ID NO: 2) is Gln, Glu, Lys or Arg;
Xaa$_{25}$ (position no. 19 in SEQ ID NO: 2) is Ala or Val;
Xaa$_{26}$ (position no. 20 in SEQ ID NO: 2) is Lys, Glu or Arg;
Xaa$_{27}$ (position no. 21 in SEQ ID NO: 2) is Glu or Leu;
Xaa$_{30}$ (position no. 24 in SEQ ID NO: 2) is Ala, Glu, Lys or Arg;
Xaa$_{33}$ (position no. 27 in SEQ ID NO: 2) is Val or Lys;
Xaa$_{34}$ (position no. 28 in SEQ ID NO: 2) is Lys, Glu, Asn or Arg;
Xaa$_{35}$ (position no. 29 in SEQ ID NO: 2) is Gly or Aib;
Xaa$_{36}$ (position no. 30 in SEQ ID NO: 2) is Arg, Gly or Lys;
Xaa$_{37}$ (position no. 31 in SEQ ID NO: 2) is Gly, Ala, Glu, Pro, Lys, amide or is absent;
Xaa$_{38}$ (position no. 32 in SEQ ID NO: 2) is Lys, Ser, amide or is absent.
Xaa$_{39}$ (position no. 33 in SEQ ID NO: 2) is Ser, Lys, amide or is absent;
Xaa$_{40}$ (position no. 34 in SEQ ID NO: 2) is Gly, amide or is absent;
Xaa$_{41}$ (position no. 35 in SEQ ID NO: 2) is Ala, amide or is absent;
Xaa$_{42}$ (position no. 36 in SEQ ID NO: 2) is Pro, amide or is absent;
Xaa$_{43}$ (position no. 37 in SEQ ID NO: 2) is Pro, amide or is absent;
Xaa$_{44}$ (position no. 38 in SEQ ID NO: 2) is Pro, amide or is absent;
Xaa$_{45}$ (position no. 39 in SEQ ID NO: 2) is Ser, amide or is absent;
Xaa$_{46}$ (position no. 40 in SEQ ID NO: 2) is amide or is absent; provided that if Xaa$_{38}$, Xaa$_{39}$, Xaa$_{40}$, Xaa$_{41}$, Xaa$_{42}$, Xaa$_{43}$, Xaa$_{44}$, Xaa$_{45}$ or Xaa$_{46}$ (position no. 32 to 40 in SEQ ID NO: 2, respectively) is absent then each amino acid residue downstream is also absent.

The invention furthermore provides additional derivatives, methods and uses thereof, and pharmaceutical compositions with a content thereof corresponding to any of the claims and particular embodiments according to the invention, in which corresponding position numbering amendments have been made as explained above, and shown above for the derivative of embodiment 6. For example, in claims 7-13 of the priority application (above embodiments 7-13) relating to particular derivatives of the invention in which the GLP-1 analogue comprises the amino acid sequence of formulas (II, III, and IV) (SEQ ID NOs. 3, 6, and 7, respectively), the position numbering may be amended as explained above to refer to the respective SEQ ID NOs instead of to the formulas.

Additional embodiments of the invention are:

8a. A GLP-1 derivative which comprises the amino acid sequence of the formula (I):

Formula (I) (SEQ ID No: 2)
Xaa$_7$-Xaa$_8$-Glu-Gly-Thr-Phe-Thr-Ser-Asp-Xaa$_{16}$-Ser- Xaa$_{18}$-Xaa$_{19}$-Xaa$_{20}$-Glu-Xaa$_{22}$-Xaa$_{23}$-Ala-Xaa$_{25}$-Xaa$_{26}$-

Xaa$_{27}$-Phe-Ile-Xaa$_{30}$-Trp-Leu-Xaa$_{33}$-Xaa$_{34}$-Xaa$_{35}$-

Xaa$_{36}$-Xaa$_{37}$-Xaa$_{38}$-Xaa$_{39}$-Xaa$_{40}$-Xaa$_{41}$-Xaa$_{42}$-Xaa$_{43}$-

Xaa$_{44}$-Xaa$_{45}$-Xaa$_{46}$ wherein
Xaa$_7$ is L-histidine, D-histidine, desamino-histidine, 2-amino-histidine, β-hydroxy-histidine, homohistidine, Nα-acetyl-histidine, α-fluoromethyl-histidine, α-methyl-histidine, 2(3H-imidazol-4-yl)acetyl, 3-pyridylalanine, 2-pyridylalanine or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{16}$ is Val, or Leu;
Xaa$_{18}$ is Ser, Lys, or Arg;
Xaa$_{19}$ is Tyr, or Gln;
Xaa$_{20}$ is Leu, Met, or Lys;
Xaa$_{22}$ is Gly, Glu, or Aib;
Xaa$_{23}$ is Gln, Glu, Lys, or Arg;
Xaa$_{25}$ is Ala, or Val;
Xaa$_{26}$ is Lys, Glu, or Arg;
Xaa$_{27}$ is Glu, or Leu;
Xaa$_{30}$ is Ala, Glu, Lys, or Arg;
Xaa$_{33}$ is Val, Thr(O-benzyl), or Lys;
Xaa$_{34}$ is Lys, Glu, Gln, Asn, or Arg;
Xaa$_{35}$ is Gly, Aib, or absent;
Xaa$_{36}$ is Arg, Gly, Lys, or absent;
Xaa$_{37}$ is Gly, Ala, Glu, Pro, Lys, epsilon-amino-Lys, amide or is absent;
Xaa$_{38}$ is Lys, Ser, amide, or is absent;
Xaa$_{39}$ is Ser, Lys, amide, or is absent;
Xaa$_{40}$ is Gly, amide, or is absent;
Xaa$_{41}$ is Ala, amide, or is absent;
Xaa$_{42}$ is Pro, amide, or is absent;
Xaa$_{43}$ is Pro, amide, or is absent;
Xaa$_{44}$ is Pro, amide, or is absent;
Xaa$_{45}$ is Ser, amide, or is absent;
Xaa$_{46}$ is amide, or is absent;
provided that if Xaa$_{38}$, Xaa$_{39}$, Xaa$_{40}$, Xaa$_{41}$, Xaa$_{42}$, Xaa$_{43}$, Xaa$_{44}$, Xaa$_{45}$ or Xaa$_{46}$ is absent then each amino acid residue downstream is also absent.

9a. A GLP-1 derivative which comprises the amino acid sequence of the formula (II):

Formula (II) (SEQ ID No: 3)
Xaa$_7$-Xaa$_8$-Glu-Gly-Thr-Phe-Thr-Ser-Asp-Val-Ser- Xaa$_{18}$-Tyr-Leu-Glu-Xaa$_{22}$-Xaa$_{23}$-Ala-Ala-Xaa$_{26}$-Glu- Phe-Ile-Xaa$_{30}$-Trp-Leu-Val-Xaa$_{34}$-Xaa$_{35}$-Xaa$_{36}$-

Xaa$_{37}$-Xaa$_{38}$ wherein
Xaa$_7$ is L-histidine, D-histidine, desamino-histidine, 2-amino-histidine, β-hydroxy-histidine, homohistidine, Nα-acetyl-histidine, α-fluoromethyl-histidine, α-methyl-histidine, 2(3H-imidazol-4-yl)acetyl, 3-pyridylalanine, 2-pyridylalanine or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{18}$ is Ser, Lys, or Arg;
Xaa$_{22}$ is Gly, Glu, or Aib;
Xaa$_{23}$ is Gln, Glu, Lys, or Arg;
Xaa$_{26}$ is Lys, Glu, or Arg;

Xaa$_{30}$ is Ala, Glu, Lys, or Arg;
Xaa$_{34}$ is Lys, Glu, Gln, or Arg;
Xaa$_{35}$ is Gly, Aib, or absent;
Xaa$_{36}$ is Arg, Lys, or absent;
Xaa$_{37}$ is Gly, Ala, Glu, Pro, Lys, or epsilon-amino-Lys;
Xaa$_{38}$ is Lys, amide, or is absent.

10a. The GLP-1 derivative, preferably according to any one of the embodiments 8a-9a, wherein said GLP-1 analogue comprises the amino acid sequence of the formula (III) which is derivatised in position 18, 23, 26, 30, 31, 34, 36, 37 or 38:

```
                        Formula (III) (SEQ ID No: 6)
Xaa7-Xaa8-Xaa9-Gly-Thr-Phe-Thr-Ser-Asp-Xaa16-

Ser-Xaa18-Tyr-Leu-Glu-Glu-Xaa23-Ala-Xaa25-

Arg-Xaa27-Phe-Ile-Xaa30-Trp-Leu-Xaa33-Xaa34-

Xaa35-Xaa36-Xaa37-Xaa38-Xaa39
``` wherein
Xaa$_7$-Xaa$_8$ is 2(3H-imidazol-4-yl)acetyl-alanine, L-histidine-Aib, desamino-histidine-alanine, or desamino-histidine-Aib;
Xaa$_9$ is Glu or a Glu derivative such as alpha, alpha dimethyl-Glu;
Xaa$_{16}$ is Val, or Leu;
Xaa$_{18}$ is Ser, Lys, or Arg;
Xaa$_{19}$ is Tyr, or Gln;
Xaa$_{23}$ is Gln, Glu, Lys, or Arg;
Xaa$_{25}$ is Ala, or Val;
Xaa$_{27}$ is Glu, or Leu;
Xaa$_{30}$ is Ala, Glu, Lys, Arg, or absent;
Xaa$_{33}$ is Val, Thr(O-benzyl), or Lys;
Xaa$_{34}$ is Lys, Glu, Gln, Asn, or Arg;
Xaa$_{35}$ is Gly, Aib, or absent;
Xaa$_{36}$ is Arg, Lys, or absent;
Xaa$_{37}$ is Gly, Aib, Pro, epsilon-amino-Lys, or absent
Xaa$_{38}$ is Lys, Glu, or absent
Xaa$_{39}$ is amide, or is absent;
provided that if Xaa$_{37}$ is absent then Xaa$_{38}$ is also absent.

11a. A GLP-1 derivative which comprises the amino acid sequence of formula (IV) which is derivatised with an albumin binding residue in position 18, 23, 26, 30, 31, 34, 36, 37, or 38:

```
                        Formula (IV) (SEQ ID No: 7)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu-Phe- Ile-Xaa30-Trp-Leu-Xaa33-Xaa34-Xaa35-Xaa36-Xaa37-

Xaa38-Xaa39
``` wherein
Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 2(3H-imidazol-4-yl)acetyl, 3-pyridylalanine, 2-pyridylalanine or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{18}$ is Ser, Lys or Arg;
Xaa$_{30}$ is Ala, Glu, Lys or Arg;
Xaa$_{33}$ is Val or Lys;
Xaa$_{34}$ is Lys, Glu, Gln, or Arg;
Xaa$_{35}$ is Gly, Aib, or absent;
Xaa$_{36}$ is Arg, Lys, or absent;
Xaa$_{37}$ is Gly, Aib, Pro, epsilon-amino-Lys, or absent;
Xaa$_{38}$ is Lys, or absent; and
Xaa$_{39}$ is amide or is absent.

12a. The derivative according to any one of the embodiments 8a-11a, wherein Xaa$_{38}$ is absent.

13a. The derivative according to any one of the embodiments 8a-12a, wherein Xaa$_{37}$ and Xaa$_{38}$ are both absent.

14a. The derivative according to any one of the embodiments 8a-13a, wherein Xaa$_7$ is desamino-histidine.

15a. The derivative according to any one of the embodiments 8a-14a, wherein Xaa$_8$ is Aib.

16a. A GLP-1 derivative, which is selected from the following:
N-ε$^{37}${2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis$^7$,Glu$^{22}$,Arg$^{26}$,Arg$^{34}$, Lys$^{37}$]GLP-1(7-37)amide;
N-ε$^{20}$-{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib$^2$,Leu$^{14}$,Lys$^{20}$,Gln$^{28}$,Ser(O-benzyl)$^{39}$] exendin-4 (1-39)amide:
N-ε$^{26}${2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis$^7$,Arg$^{34}$]GLP-1-(7-37);
N-epsilon37{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Arg34,Lys37]GLP-1-(7-37)amide;
N-epsilon23-[2-(2-[2-(2-[2-(2-((R)-3-[1-(17-Carboxyheptadecanoylamino)piperidin-4-ylcarbonylamino]-3-(carboxypropionylamino)ethoxy)ethoxy]acetylamino)ethoxy]ethoxy)acetyl][Aib8,Arg26,Arg 34]GLP-1-(7-37);
N-epsilon37-[2-(2-[2-(2-[2-(2-((R)-3-[1-(17-Carboxyheptadecanoyl)piperidin-4-ylcarbonylamino]3-carboxypropionylamino)ethoxy)ethoxy]acetylamino)ethoxy]ethoxy)acetyl][DesaminoHis7, Glu22 Arg26, Arg 34, Phe(m-CF3) 28]GLP-1-(7-37)amide;
[DesaminoHis7,Glu22,Arg26,Arg34]GLP-1-(7-37)-Lys(2-{2-[2-(2-{2-[2-((S)-4-Carboxy-4-{[1-(19-carboxynonadecanoyl)piperidine-4-carbonyl]amino}butyrylamino)ethoxy]ethoxy}acetylamino)ethoxy]ethoxy}acetyl);
N-ε$^{20}$({2-[2-(2-{2-[2-((R)-3-carboxy-3-{[1-(17-carboxyheptadecanoyl)piperidine-4-carbonyl]amino}propionylamino)ethoxy]ethoxy}acetylamino)ethoxy]ethoxy}acetyl) [Aib$^8$,Lys$^{20}$,Arg$^{26}$,Glu$^{30}$,Thr(O-benzyl)$^{33}$]GLP-1-(7-37)amide;
N-epsilon30{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Lys30]GLP-1-(7-37);
N-epsilon31{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8, Glu22, Arg26,Lys 31]GLP-1-(7-37);
N-ε$^{20}$({2-[2-(2-{2-[2-((R)-3-carboxy-3-{[1-(17-carboxyheptadecanoyl)piperidine-4-carbon yl]amino}propionylamino)ethoxy]ethoxy}acetylamino)ethoxy]ethoxy}acetyl) [Aib$^8$,Lys$^{20}$,Arg$^{26}$,2-Naphtylalanine$^{28}$, Glu$^{30}$]GLP-1 (7-37)amide;

[Aib8, Glu22, Arg26, Arg34]GLP-1-(7-37)Lys[2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl]amide;

N-ε$^{20}$({2-[2-(2-{2-[2-((R)-3-carboxy-3-{[1-(17-carboxy-heptadecanoyl)piperidine-4-carbon yl]amino}propionylamino)ethoxy]ethoxy}acetylamino)ethoxy]ethoxy}acetyl) [Aib$^8$,Lys$^{20}$,Arg$^{26}$, 2-Naphtylalanine$^{12}$, Glu$^{30}$]GLP-1-(7-37)amide;

[DesaminoHis7,Glu22,Arg26,Arg34]GLP-1-(7-37)Lys[2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl]amide N-epsilon31-(2-{2-[2-(2-{2-[2-((S)-3-Carboxy-3-{[1-(19-carboxy-nonadecanoyl)piperidine-4-carbonyl]amino}propionylamino)ethoxy]ethoxy}acetylamino)ethoxy]ethoxy}acetyl)[Aib8,Glu22,Arg26,Lys31,Arg34]GLP-1-(7-37);

N-epsilon26-[(S)-4-Carboxy-4-({trans-4-[(19-carboxynonadecanoylamino)methyl]cyclohexanecarbonyl}amino)butyryl][Aib8,Arg34]GLP-1-(7-37);

N-epsilon26-{4-[(S)-4-Carboxy-4-({trans-4-[(19-carboxynonadecanoylamino)methyl]cyclohexanecarbonyl}amino)butyrylamino]butyryl}[Aib8,Arg34]GLP-1-(7-37);

N-epsilon26-[2-(2-{2-[(S)-4-Carboxy-4-({trans-4-[(19-carboxy-nonadecanoylamino)methyl]cyclohexanecarbonyl}amino)butyrylamino]ethoxy}ethoxy) acetyl][Aib8,Arg34]GLP-1-(7-37);

N-epsilon26-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Arg34]GLP-1-(7-37)-amide;

N-epsilon18-{2-(2-(2-(2-[2-(2-[(S)-4-Carboxy-4-({4-[(19-carboxynonadecanoylamino)methyl]cyclohexanecarbonyl}amino)butanoylamino]ethoxy)ethoxy]acetyl)ethoxy)ethoxy)acetyl}[Aib8,Lys18,Arg26,Arg34]GLP-1(7-37)

N-ε$^{20}$-[2-(2-[2-(2-[2-(2-((S)-4-[trans-4-([19-Carboxynonadecanoylamino]methyl)cyclohexylcarbonylamino]-4-carboxybutanoylamino)ethoxy)ethoxy]acetylamino)ethoxy]ethoxy)acetyl][desaminoHis$^1$, Lys$^{20}$, Ser(O-benzyl)$^{33}$, Ser (O-benzyl)$^{39}$] exendin (1-39);

[Aib8,Glu22,Arg26,Arg34]GLP-1-(7-37)Lys[2-(2-[2-(2-[2-(2-((S)-3-[4-([19-Carboxynonadecanoylamino]methyl)cyclohexylcarbonylamino]-3-carboxypropionylamino)ethoxy)ethoxy]acetylamino)ethoxy]ethoxy)acetyl]amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37)amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37)amide;

N-epsilon37-[2-(2-{2-[2-(2-{2-[(S)-4-Carboxy-4-({4-[(trans-19-carboxy-nonadecanoylamino)methyl]cyclohexanecarbonyl}amino)butyrylamino]ethoxy}ethoxy)acetylamino]ethoxy}ethoxy)acetyl][DesaminoHis7,Arg26,Arg34,Lys37]GLP-1-(7-37) amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37);

[DesaminoHis7,Glu22,Arg26,Arg34]GLP-1-(7-37)Lys[2-(2-{2-[2-(2-{2-[4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl]-amide;

[desaminoHis$^7$,Arg$^{26}$,Arg$^{34}$]GLP-1-(7-37)Lys[2-(2-[2-(242-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl]amide;

N-epsilon26[2-(2-{2-[2-(2-{2-[(S)-4-Carboxy-4-({4-[(19-carboxy-nonadecanoylamino)methyl]cyclohexanecarbonyl}amino)butyrylamino]ethoxy}ethoxy)acetylamino]ethoxy}ethoxy)acetyl[Aib8, Lys 26] GLP-1 (7-37)amide;

N-epsilon26 [2-(2-[2-(2-[2-(2-((S)-2-[trans-4-((9-Carboxynonadecanoylamino]methyl)cyclohexylcarbonylamino]-4-carboxybutanoylamino)ethoxy)ethoxy]acetylamino)ethoxy]ethoxy)acetyl][Aib8, Lys26] GLP-1 (7-37)amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Arg26,Arg34,Lys37]GLP-1-(7-37);

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Glu30,Arg34,Lys37]GLP-1-(7-37);

N-epsilon26-[2-(2-{2-[(S)-4-Carboxy-4-((S)-4-carboxy-4-{4-[4-(16-(1H-tetrazol-5-yl)-hexadecanoylsulfamoyl)butyrylamino]-butyrylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{4-[4-(16-(1H-tetrazol-5-yl)hexadecanoylsulfamoyl)butyrylamino]butyrylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]-dodecanoylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-36)amide;

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys33,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-36)amide;

N-epsilon26-[2-(2-{2-[2-(2-{2-[2-(2-{2-[2-(2-{2-[2-(2-{2-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetylamino]ethoxy}ethoxy)acetylamino]ethoxy}ethoxy)acetylamino]ethoxy}ethoxy)acetylamino]ethoxy}ethoxy)acetylamino]ethoxy}ethoxy)acetyl][Aib8,Lys26,Arg34]GLP-1-(7-36)amide;

[Aib8,Glu22,Arg26,Arg34]GLP-1-(7-37)Lys[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}-butyrylamino)butyrylamino]ethoxy}ethoxy)acetyl]amide;

N-epsilon20-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys20,Glu22,Arg26,Glu30,Pro37]GLP-1-(7-37)amide;

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Glu22,Arg26,Arg34,Lys37]GLP-1-(7-37)amide;

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Glu22,Arg26,Arg34,Lys37]GLP-1-(7-37)amide;

N-epsilon37-[[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Arg26,Arg34,Lys37]GLP-1-(7-37)amide;

[Aib8,Glu22,Arg26,Glu30,Pro37]GLP-1-(7-37)Lys [2-(2-{2-[4-Carboxy-4-(4-carboxy-4-{4-[4-(16-1H-tetrazol-5-yl-hexadecanoylsulfamoyl)butyrylamino]butyrylamino}butyrylamino)butyrylamino]ethoxy}ethoxy)acetyl];

[Aib8,Glu22,Arg26,Glu30,Pro37]GLP-1-((7-37)Lys (2-(2-(3-(2-(2-(2-(2-(2-(2-(2-(2-(2-(2-[4-(S)-carboxy-4-(4-(S)-carboxy-4-(4-{4-[16-(Tetrazol-5-yl)hexadecanoylsulfamoyl]butanoylamino}butanoylamino) butyrylamino) butyrylamino];
ethoxy)ethoxy)ethoxy)ethoxy)ethoxy)ethoxy)ethoxy)ethoxy)ethoxy)ethoxy)ethoxy)ethoxy)ethoxy) propionylamino) ethoxy)ethoxy) peptide;

N-alpha37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,epsilon-Lys37]GLP-1-(7-37);

N-alpha8-[2-(4-imidazolyl)acetyl] N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][Glu22,Arg26,Arg34,Lys37]GLP-1-(8-37);

[DesaminoHis7,Glu22,Arg26,34]-GLP-1 (7-37)-Lys-(2-{2-[2-((S)-4-carboxy-4-{[1-(19-carboxynonadecanoyl)piperidine-4-carbonyl]amino}butyrylamino)ethoxy]ethoxy}acetyl) peptide;

[DesaminoHis7,Glu22,Arg26,34]-GLP-1 (7-37)-Lys-[2-(2-{2-[2-(2-{2-[4-Carboxy-4-({4-[(19-carboxynonadecanoylamino)methyl]cyclohexanecarbonyl}amino)butyrylamino]ethoxy}ethoxy)acetylamino]ethoxy}ethoxy)acetyl] peptide;

[DesaminoHis7,Glu22,Arg26,34]-GLP-1 (7-37)-Lys((S)-4-carboxy-4-(2-{2-[2-((S)-4-carboxy-4-{[1-(19-carboxynonadecanoyl)piperidine-4-carbonyl]amino}butyrylamino)ethoxy]ethoxy}acetylamino)butyryl) peptide;

[DesaminoHis7,Glu22,Arg26,34]-GLP-1 (7-37)-Lys-(2-(2-{2-[(S)-4-carboxy-4-(2-{2-[2-((S)-4-carboxy-4-{[1-(19-carboxynonadecanoyl)piperidine-4-carbonyl]amino}butyrylamino)ethoxy]ethoxy}acetylamino)butyrylamino]ethoxy}ethoxy)acetyl) peptide;

[DesaminoHis7,Arg26,34]-GLP-1 (7-37)-Lys(2-{2-[2-(2-{2-[2-((S)-4-Carboxy-4-{[1-(19-carboxynonadecanoyl)piperidine-4-carbonyl]amino}butyrylamino)ethoxy]ethoxy}acetylamino)ethoxy]ethoxy}acetyl) peptide;

N-epsilon37-(2-{2-[2-(2-{2-[2-((S)-4-Carboxy-4-{[1-(19-carboxynonadecanoyl)piperidine-4-carbonyl]amino}butyrylamino)ethoxy]ethoxy}acetylamino)ethoxy]ethoxy}acetyl) [DesaminoHis7,Arg26,Arg34,Lys37]GLP-1-(7-37);

N-epsilon37-((S)-4-Carboxy-4-{[1-(19-carboxy-nonadecanoyl)-piperidine-4-carbonyl]-amino}-butyryl) [DesaminoHis7,Arg26,Arg34,Lys37]GLP-1-(7-37);

[DesaminoHis7,Glu22,Arg26,34]-GLP-1 (7-37)-Lys-((S)-4-Carboxy-4-{[1-(19-carboxy-nonadecanoyl)-piperidine-4-carbonyl]-amino}-butyryl) peptide;

N-epsilon26-[2-(2-{2-[(R)-4-Carboxy-4-((R)-4-carboxy-4-{12-[4-(16-1H-tetrazol-5-yl-hexadecanoylsulfamoyl)butyrylamino]dodecanoylamino}butyrylamino)butyrylamino]ethoxy}ethoxy)acetyl]-[Aib8,Arg34]GLP-1 (7-37);

N-epsilon37-{2-[2-(2-{(S)-4-[(S)-4-(12-{4-[16-(2-tert-Butyl-2H-tetrazol-5-yl)-hexadecanoylsulfamoyl]butyrylamino}dodecanoylamino)-4-carboxybutyrylamino]-4-carboxybutyrylamino}ethoxy)ethoxy]acetyl} [DesaminoHis7,Glu22,Arg26,Arg34,Lys37] GLP-1 (7-37);

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Arg26,Arg34,Lys37]GLP-1-(7-37);

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37);

[ImPr7,Arg26,34,Glu22]GLP-1-(7-37)Lys[2-(2-[2-((S)-4-((S)-4-(12-[4-(16-1H-tetrazol-5-ylhexadecanoylsulfamoyl)butyrylamino]dodecanoylamino)-4-carboxybutyrylamino)-4-carboxybutyrylamino)ethoxy]ethoxy)acetyl]-amid;

N-epsilon36-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Glu22, Gln34]GLP-1-(7-37);

N-epsilon26-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Glu22, Gln34]GLP-1-(7-37);

N-epsilon18-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, 22,35, Lys18, Arg26,34]GLP-1-(7-37); and N-epsilon18-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Lys18, Glu22, Gln34]GLP-1-(7-37).

Additional Embodiments According to the Invention

1. A peptide derivative comprising a peptide wherein at least one amino acid residue is derivatized with A-B-C-D- wherein A- is

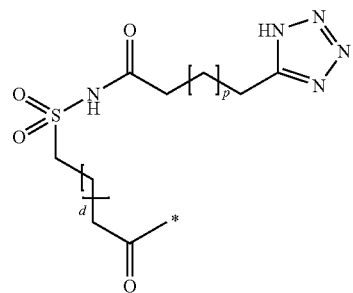

wherein p is selected from the group consisting of 10, 11, 12, 13 and 14, and d is selected from the group consisting of 0, 1, 2, 3, 4 and 5, and -B- is selected from the group consisting of

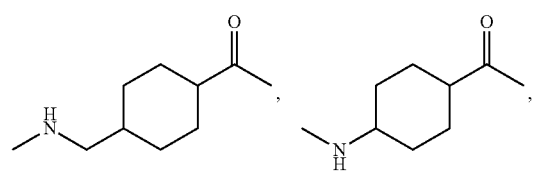

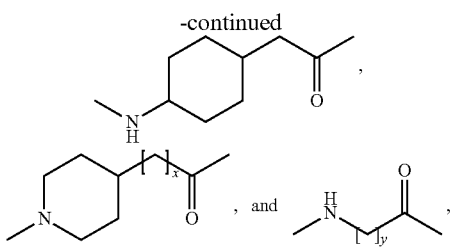

wherein x is selected from the group consisting of 0, 1, 2, 3 and 4, and y is selected from the group consisting of 1, 2, 3, 4, 5, 6, 7, 8, 9, 10, 11 and 12, or A is

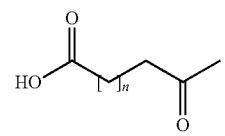

wherein n is selected from the group consisting of 14, 15, 16, 17, 18 and 19, and B is selected from the group consisting of

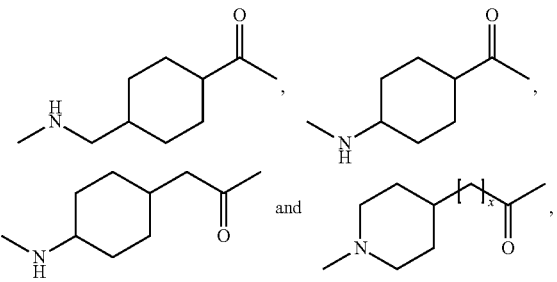

wherein x is selected from the group consisting of 0, 1, 2, 3 and 4, and

-C- is selected from the group consisting of

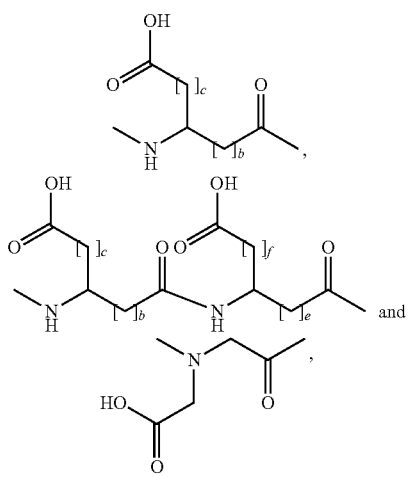

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

2. The derivative according to embodiment 1, wherein said peptide is a GLP-1 peptide selected from GLP-1(7-37) and an analogue of GLP-1(7-37), wherein, in said peptide, at least one amino acid residue is derivatised with A-B-C-D-.

3. The derivative according to any one of embodiments 1-2, wherein the derivatised amino acid residue comprises an amino group.

4. The derivative according to any one of embodiments 1-3, wherein the derivatised amino acid residue comprises a primary amino group in a side chain.

5. The derivative according to any one of embodiments 1-4, wherein the derivatised amino acid residue is lysine.

6. The derivative according to any one of embodiments 1-5, wherein only one amino acid residue is derivatised.

7. The derivative according to any one of embodiments 1-6, wherein A- is

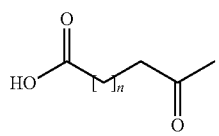

8. The derivative according to any of the embodiments 1-7, wherein n is selected from the group consisting of 15 and 17, and more preferred is 17.

9. The derivative according to any one of the embodiments 1-6, wherein A- is

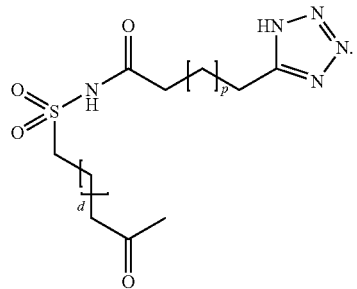

10. The derivative according to any of the embodiments 1-6 and 9, wherein p is selected from the group consisting of 12, 13, and 14 and more preferred is 13.

11. The derivative according to any of the embodiments 1-6 and 9-10, wherein d is selected from the group consisting of 0, 1, 2, 3 and 4, more preferred 0, 1 and 2 and most preferred 1.

12. The derivative according to any of the embodiments 1-6 and 9-11, wherein d is selected from the group consisting of 0, 1 and 2 and p is selected from the group consisting of 12, 13 or 14, more preferred d is selected from the group consisting of 1 and 2 and p is selected from the group consisting of 13 and 14, and most preferred d is 1 and p is 13.

13. The derivative according to any of the embodiments 1-12, wherein -B- is

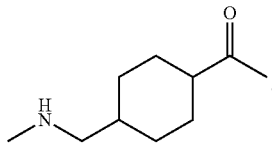

14. The derivative according to any of the embodiments 1-12, wherein -B- is

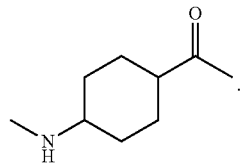

15. The derivative according to any of the embodiments 1-12, wherein -B- is

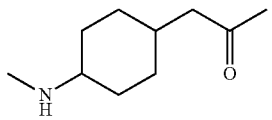

16. The derivative according to any of the embodiments 1-12, wherein -B- is

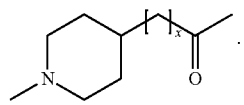

17. The derivative according to any of the embodiments 1-12 and 16, wherein x is selected from the group consisting of 0, 1 and 2, more preferred x is selected from the group consisting of 0 and 1 and most preferred x is 1.

18. The derivative according to any of the embodiments 1-6 and 9-12, wherein -B- is

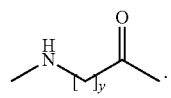

19. The derivative according to any of the embodiments 1-6 and 9-13, wherein y is selected from the group consisting of 2, 3, 4, 5, 6, 7, 8, 9 and 10 and more preferred y is selected from the group consisting of 2, 3, 4, 5, 6, 7, and 8.

20. The derivative according to any of the embodiments 1-19, wherein -C- is

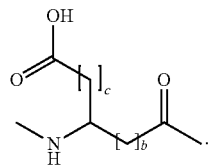

21. The derivative according to embodiment 20, wherein c is selected from the group consisting of 0 and 1 and b is selected from the group consisting of 1 and 2, more preferred b is 1 and c is 0.
22. The derivative according to any of the embodiments 1-19, wherein -C- is

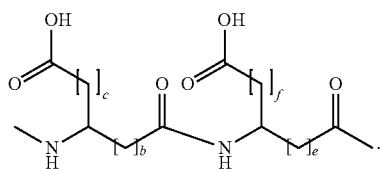

23. The derivative according to embodiment 22, wherein f is selected from the group consisting of 0 and 1 and e is selected from the group consisting of 1 and 2, more preferred e is 1 and f is 0.
24. The derivative according to any of the embodiments 1-19, wherein -C- is

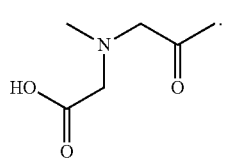

25. The derivative according to any of the embodiments 1-24, wherein D is selected from the group consisting of

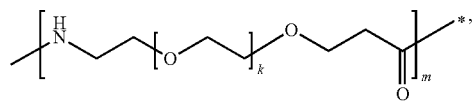

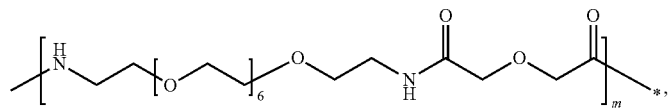

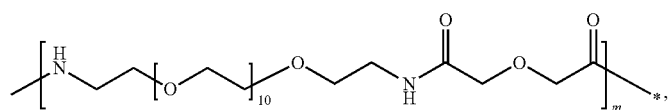

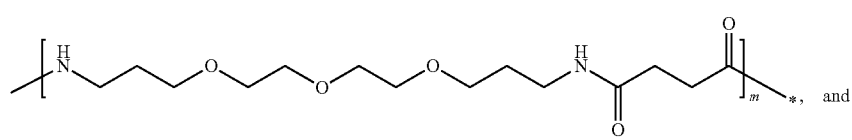, and

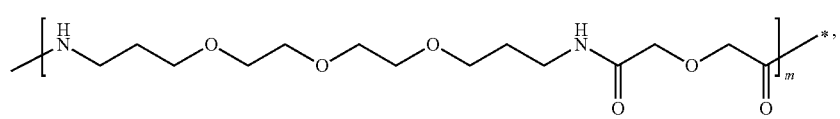

wherein k is selected from the group consisting of 0, 1, 2, 3, 4, 5, 11 and 27, and m is selected from the group consisting of 0, 1, 2, 3, 4, 5 and 6, and D is attached to the amino acid residue in the end depicted with *.
26. The derivative according to any of the embodiments 1-25, wherein -D- is

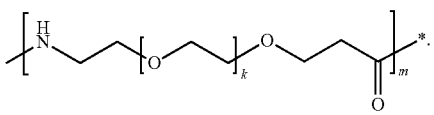

27. The derivative according to any of the embodiments 25-26, wherein k is selected from the group consisting of 1, 2, 3, 11 and 27 and more preferred k is 1.
28. The derivative according to any of the embodiments 25-27, wherein m is selected from the group consisting of 0, 1, 2, 3, and 4 and more preferred m is selected from the group consisting of 0, 1 and 2.
29. The derivative according to embodiment 29, wherein m is selected from the group consisting of 0, 1, 2, 3, and 4 and more preferred m is selected from the group consisting of 0, 1 and 2.
30. The derivative according to any of the embodiments 1-25, wherein -D- is

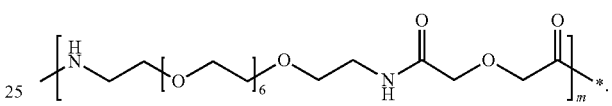

31. The derivative according to embodiment 31, wherein m is selected from the group consisting of 0, 1, 2, 3, and 4 and more preferred m is selected from the group consisting of 0, 1 and 2.
32. The derivative according to any of the embodiments 1-25, wherein -D- is

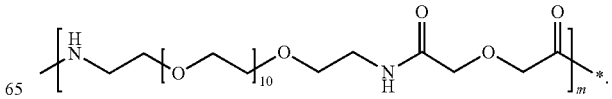

33. The derivative according to embodiment 33, wherein m is selected from the group consisting of 0, 1, 2, 3, and 4 and more preferred m is selected from the group consisting of 0, 1 and 2.

34. The derivative according to any of the embodiments 1-25, wherein -D- is

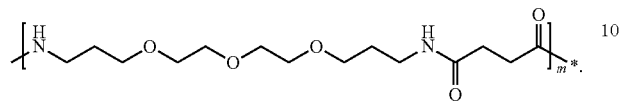

35. The derivative according to embodiment 35, wherein m is selected from the group consisting of 0, 1, 2, 3, and 4 and more preferred m is selected from the group consisting of 0, 1 and 2.

36. A derivative according to any of the embodiments 1-25, wherein -D- is

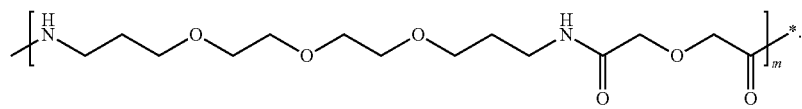

37. The derivative according to embodiment 37, wherein m is selected from the group consisting of 0, 1, 2, 3, and 4 and more preferred m is selected from the group consisting of 0, 1 and 2.

38. The derivative according to any of the embodiments 1-38, wherein A-B-C-D- is selected and combined from

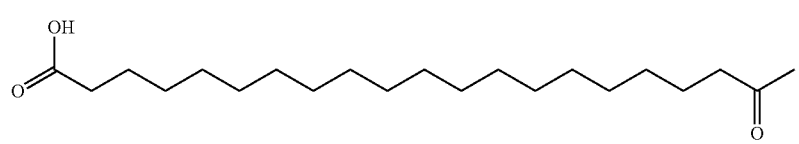

A-

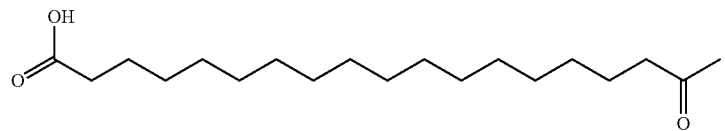

-B-

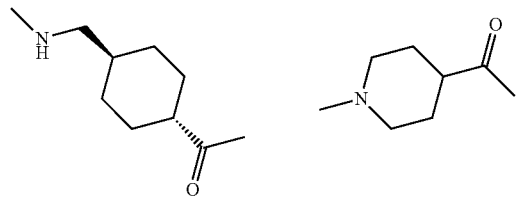

-C-

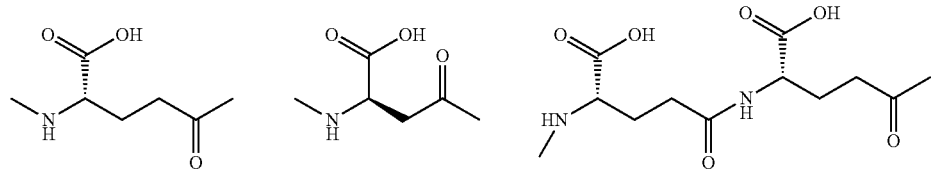

-continued
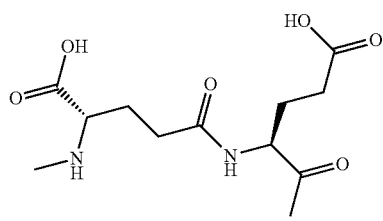
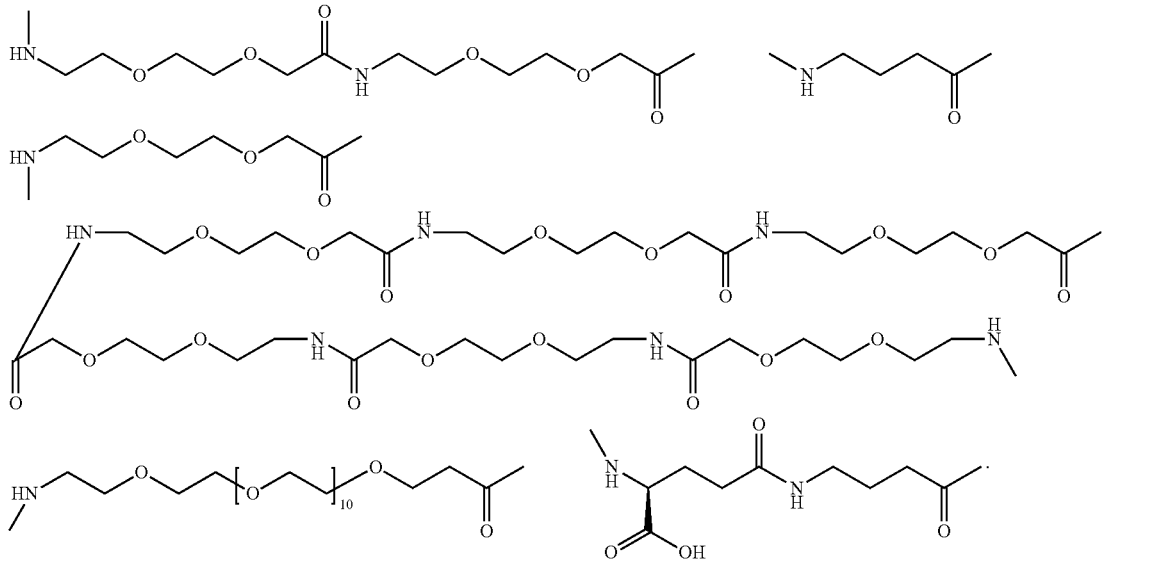
-D-
39. The derivative according to any of the embodiments 1-38, wherein A-B-C-D- is selected and combined from
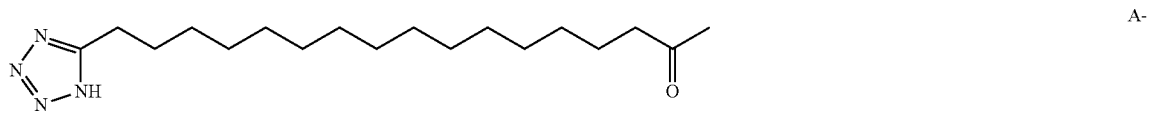
A-
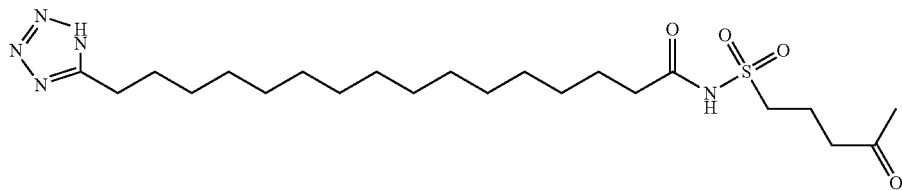
-B-
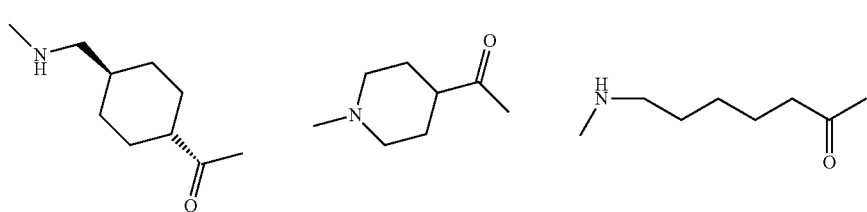
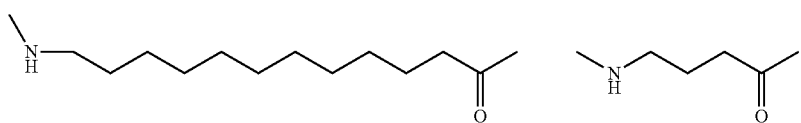

-continued
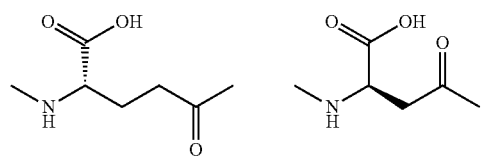
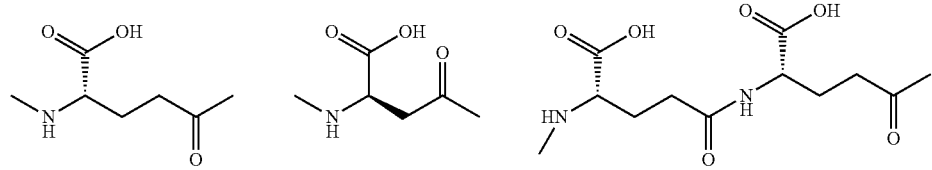
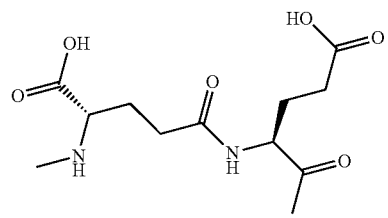
-C-
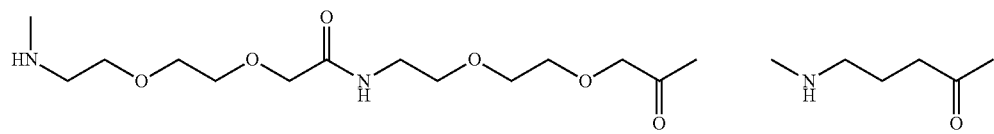
-D-
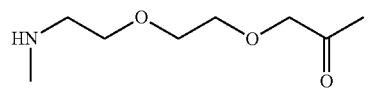
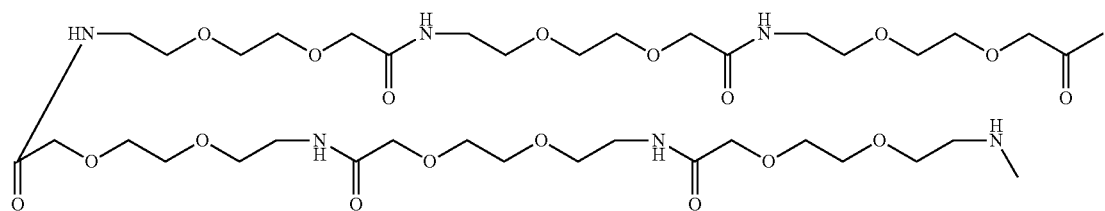
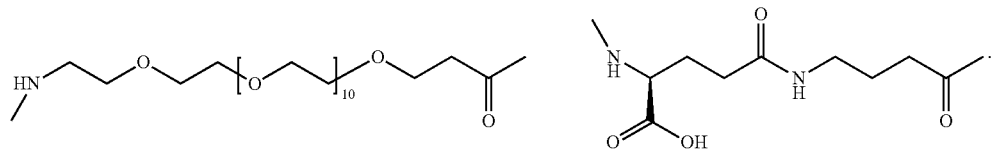
40. The derivative according to any of the embodiments 1-40, wherein A-B-C-D- is selected from the group consisting of
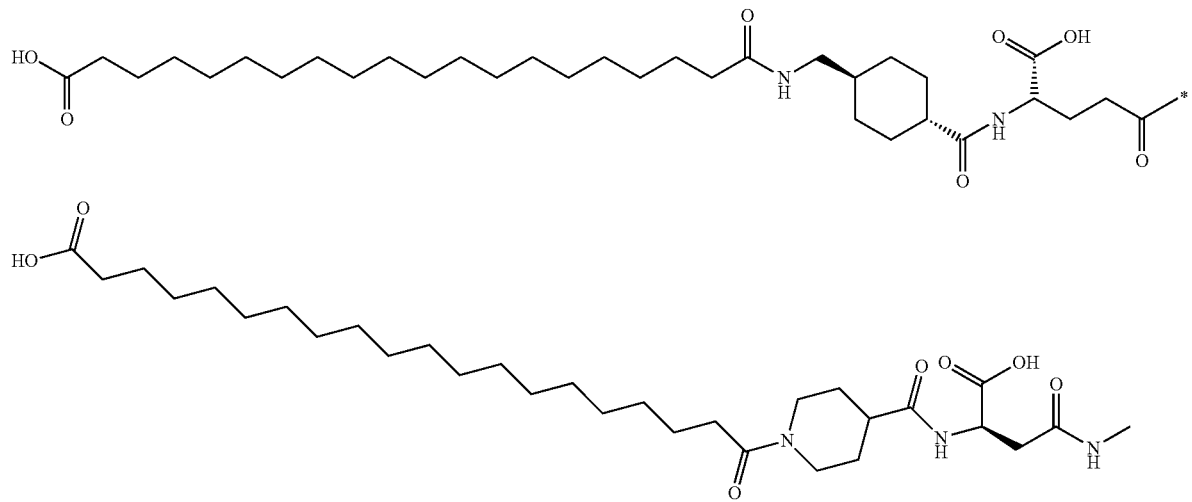

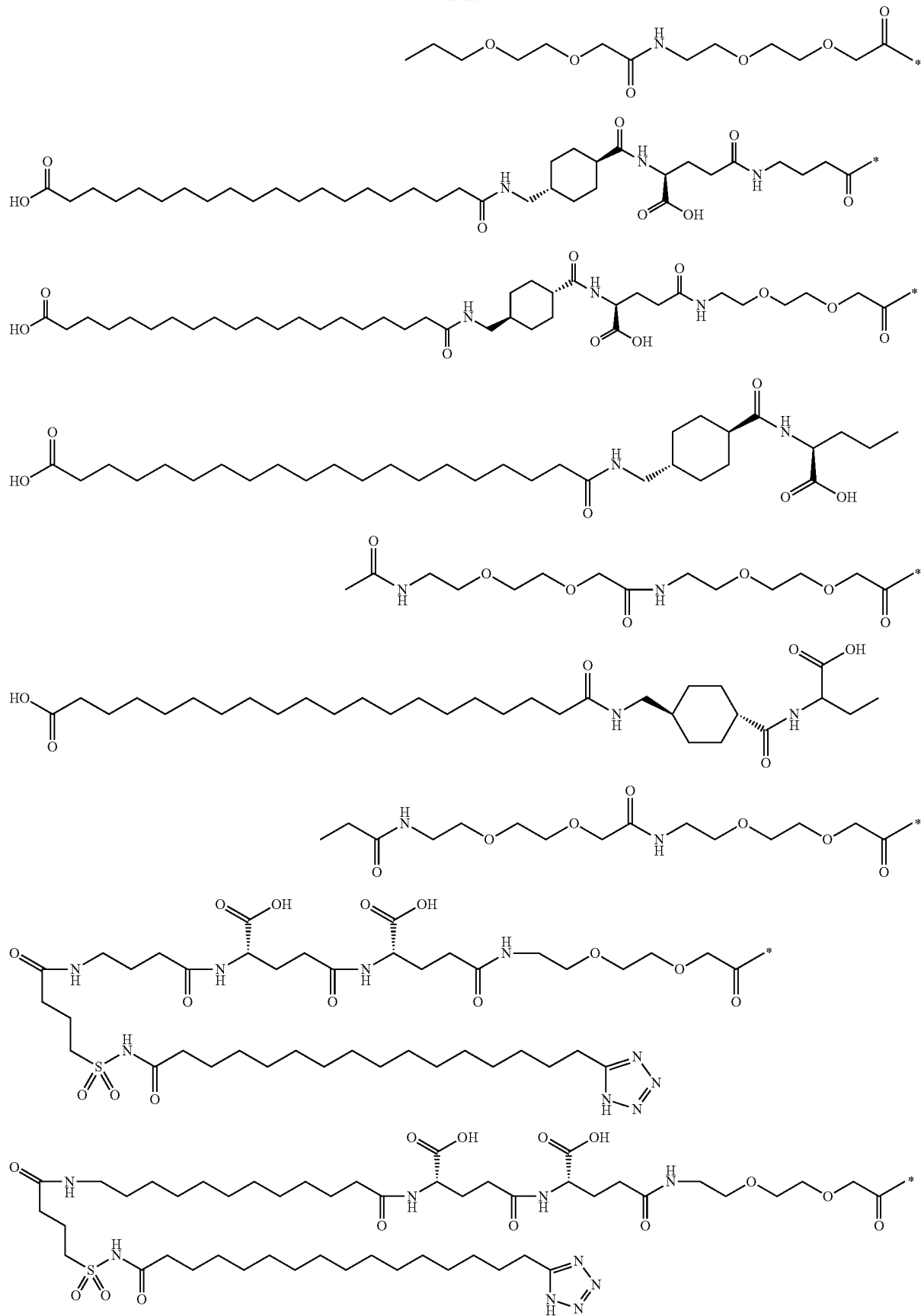

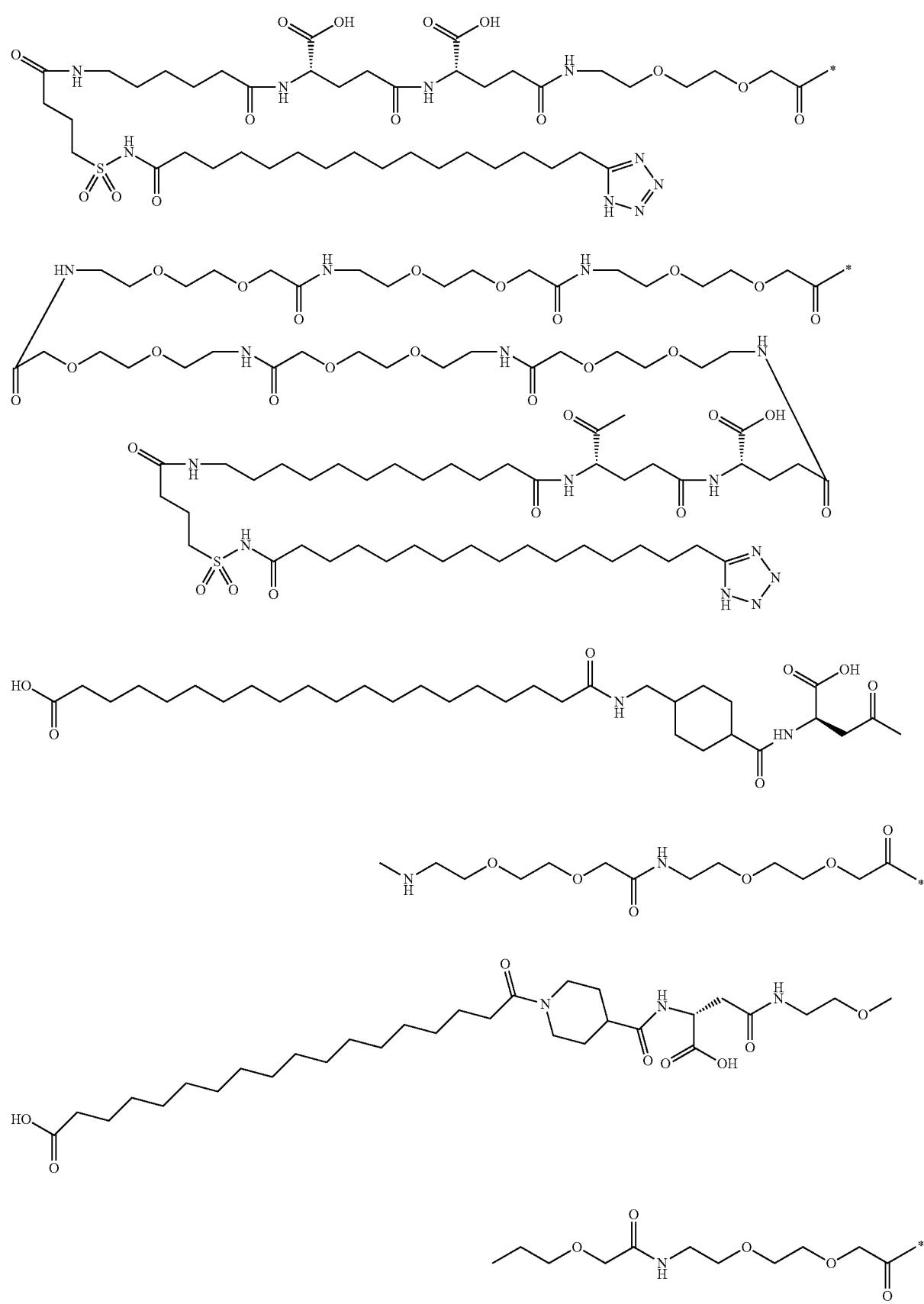

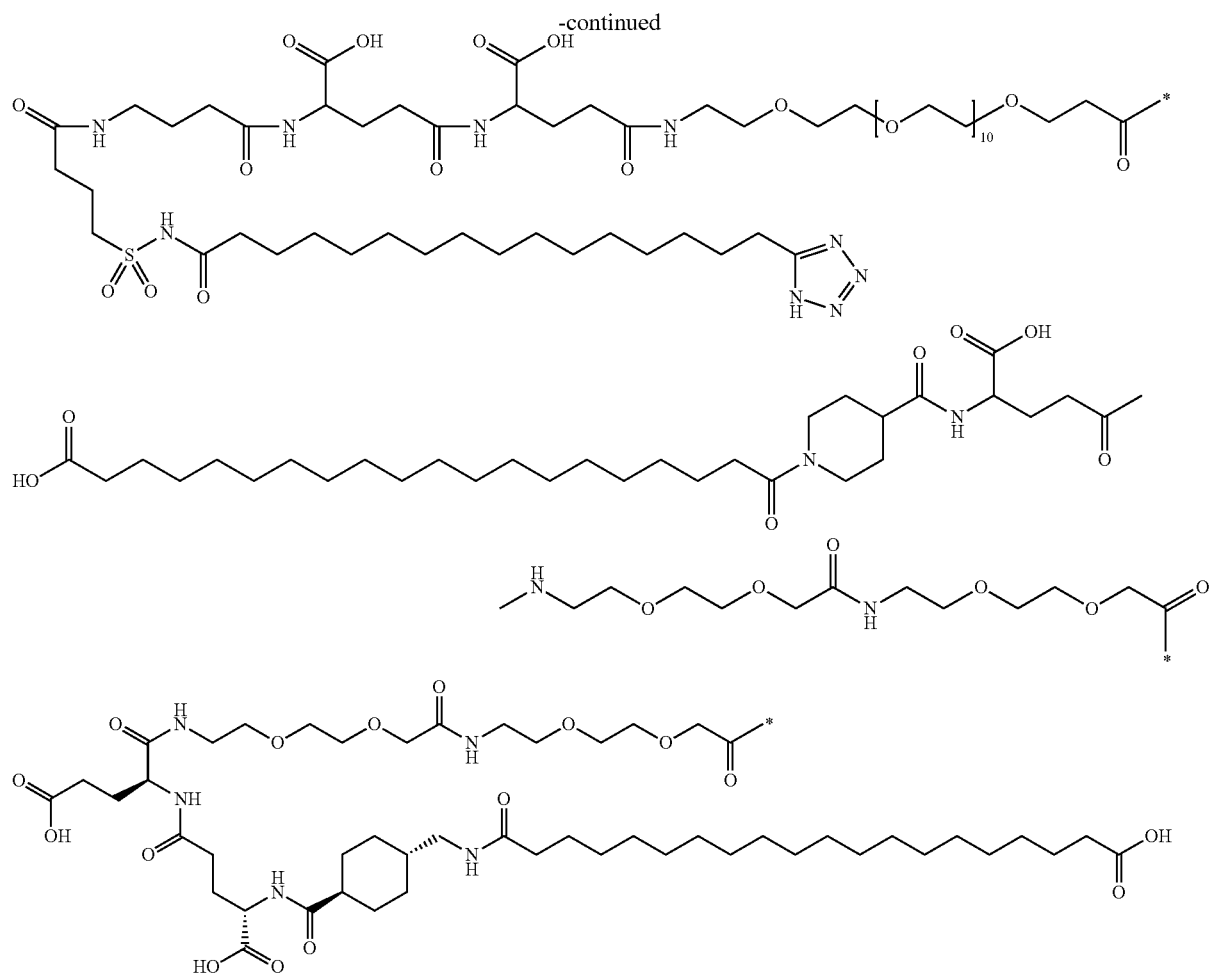

41. The derivative according to any one of the above embodiments, wherein said GLP-1 analogue comprises the amino acid sequence of the formula (I):

```
                              Formula (I) (SEQ ID No: 2)
Xaa7-Xaa8-Glu-Gly-Thr-Phe-Thr-Ser-Asp-Xaa16-

Ser-Xaa18-Xaa19-Xaa20-Glu-Xaa22-Xaa23-Ala-

Xaa25-Xaa26-Xaa27-Phe-Ile-Xaa30-Trp-Leu-

Xaa33-Xaa34-Xaa35-Xaa36-Xaa37-Xaa38-Xaa39-

Xaa40-Xaa41-Xaa42-Xaa43-Xaa44-Xaa45-Xaa46
``` wherein $Xaa_7$ is L-histidine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{16}$ is Val or Leu;

$Xaa_{18}$ is Ser, Lys or Arg;

$Xaa_{19}$ is Tyr or Gln;

$Xaa_{20}$ is Leu, Met or Lys;

$Xaa_{22}$ is Gly, Glu or Aib;

$Xaa_{23}$ is Gln, Glu, Lys or Arg;

$Xaa_{25}$ is Ala or Val;

$Xaa_{26}$ is Lys, Glu or Arg;

$Xaa_{27}$ is Glu or Leu;

$Xaa_{30}$ is Ala, Glu, Lys or Arg;

$Xaa_{33}$ is Val or Lys;

$Xaa_{34}$ is Lys, Glu, Asn or Arg;

$Xaa_{35}$ is Gly or Aib;

$Xaa_{36}$ is Arg, Gly or Lys;

$Xaa_{37}$ is Gly, Ala, Glu, Pro, Lys, amide or is absent;

$Xaa_{38}$ is Lys, Ser, amide or is absent.

$Xaa_{39}$ is Ser, Lys, amide or is absent;

$Xaa_{40}$ is Gly, amide or is absent;

$Xaa_{41}$ is Ala, amide or is absent;

$Xaa_{42}$ is Pro, amide or is absent;

$Xaa_{43}$ is Pro, amide or is absent;

$Xaa_{44}$ is Pro, amide or is absent;

$Xaa_{45}$ is Ser, amide or is absent;

$Xaa_{46}$ is amide or is absent;

provided that if $Xaa_{38}$, $Xaa_{39}$, $Xaa_{40}$, $Xaa_{41}$, $Xaa_{42}$, $Xaa_{43}$, $Xaa_{44}$, $Xaa_{45}$ or $Xaa_{46}$ is absent then each amino acid residue downstream is also absent.

42. The derivative according to any one of the above embodiments, wherein said GLP-1 analogue comprises the amino acid sequence of the formula (II):

Formula (II) (SEQ ID No: 3)

Xaa₇-Xaa₈-Glu-Gly-Thr-Phe-Thr-Ser-Asp-Val-Ser-Xaa₁₈-Tyr-Leu-Glu-Xaa₂₂-Xaa₂₃-Ala-Ala-Xaa₂₆-Glu-Phe-Ile-Xaa₃₀-Trp-Leu-Val-Xaa₃₄-Xaa₃₅-Xaa₃₆-Xaa₃₇-Xaa₃₈ wherein
- Xaa₇ is L-histidine, D-histidine, desamino-histidine, 2-amino-histidine, β-hydroxy-histidine, homohistidine, Nᵅ-acetyl-histidine, α-fluoromethyl-histidine, α-methyl-histidine, 3-pyridylalanine, 2-pyridylalanine or 4-pyridylalanine;
- Xaa₈ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
- Xaa₁₈ is Ser, Lys or Arg;
- Xaa₂₂ is Gly, Glu or Aib;
- Xaa₂₃ is Gln, Glu, Lys or Arg;
- Xaa₂₆ is Lys, Glu or Arg;
- Xaa₃₀ is Ala, Glu, Lys or Arg;
- Xaa₃₄ is Lys, Glu or Arg;
- Xaa₃₅ is Gly or Aib;
- Xaa₃₆ is Arg or Lys;
- Xaa₃₇ is Gly, Ala, Glu or Lys;
- Xaa₃₈ is Lys, amide or is absent.

43. The derivative according to any one of the above embodiments, wherein said GLP-1 peptide is GLP-1(A-B) wherein A is an integer from 1 to 7 and B is an integer from 38 to 45, and optionally have one or more substitutions, which GLP-1 peptide is derivatised via a hydrophilic spacer to the C-terminal amino acid residue and, optionally, also derivatised to one of the other amino acid residues.

44. The derivative to any one of the above embodiments, wherein said GLP-1 peptide is selected from GLP-1(7-35), GLP-1(7-36), GLP-1(7-36)-amide, GLP-1(7-37), GLP-1(7-38), GLP-1(7-39), GLP-1(7-40), and GLP-1(7-41), and optionally have one or more substitutions.

45. The derivative according to any one of the embodiments 1-45, which is a derivative of GLP-1(7-37) (SEQ ID No 1).

46. The derivative according to any one of the embodiments 1-45, which is a derivative of an analogue of GLP-1(7-37) (SEQ ID No 1).

47. The derivative according embodiment 47, wherein said GLP-1 analogue comprises no more than fifteen amino acid residues which have been substituted, added or deleted as compared to GLP-1(7-37) (SEQ ID No. 1).

48. The derivative according to embodiment 47, wherein said GLP-1 analogue comprises no more than ten amino acid residues which have been substituted, added or deleted as compared to GLP-1(7-37) (SEQ ID No. 1).

49. The derivative according to embodiment 47, wherein said GLP-1 analogue comprises no more than six amino acid residues which have been substituted, added or deleted as compared to GLP-1(7-37) (SEQ ID No. 1).

50. The derivative according to embodiment 47, wherein said GLP-1 analogue comprises no more than four amino acid residues which have been substituted, added or deleted as compared to GLP-1(7-37) (SEQ ID No. 1).

51. The derivative according to embodiment 51, wherein said GLP-1 analogue comprises no more than 4 amino acid residues which are not encoded by the genetic code.

52. The derivative according to embodiment 47, wherein said GLP-1 analogue comprises no more than 3 amino acid residues which have been substituted, added or deleted as compared to GLP-1(7-37) (SEQ ID No. 1).

53. The derivative according to embodiment 53, wherein said GLP-1 analogue comprises no more than 3 amino acid residues which are not encoded by the genetic code.

54. The derivative according to any one of the above embodiments, wherein said GLP-1 peptide comprises only one lysine residue which has been derivatised.

55. The derivative according to any one of the above embodiments, wherein said GLP-1 peptide is a DPPIV protected GLP-1 peptide.

56. The derivative according to any one of the above embodiments, wherein said GLP-1 peptide is DPPIV stabilised.

57. The derivative according to any one of the above embodiments, wherein said GLP-1 peptide comprises an Aib residue in position 8.

58. The derivative according to any one of the above embodiments, wherein the amino acid residue in position 7 of said GLP-1 peptide is selected from the group consisting of D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine and 4-pyridylalanine.

59. The derivative according to any one of the above embodiments, wherein said GLP-1 peptide is selected from the group consisting of
Arg³⁴GLP-1(7-37), Lys³⁸Arg²⁶,³⁴GLP-1(7-38), Lys³⁸Arg²⁶,³⁴GLP-1(7-38)-OH, Lys³⁶Arg²⁶,³⁴GLP-1(7-36), Aib⁸,²²,³⁵ GLP-1(7-37), Aib⁸,³⁵ GLP-1(7-37), Aib⁸,²² GLP-1(7-37), Aib⁸,²²,³⁵ Arg²⁶,³⁴Lys³⁸GLP-1(7-38), Aib⁸,³⁵ Arg²⁶,³⁴Lys³⁸GLP-1(7-38), Aib⁸,²² Arg²⁶,³⁴Lys³⁸GLP-1(7-38), Aib⁸,²²,³⁵ Arg²⁶,³⁴Lys³⁸GLP-1(7-38), Aib⁸,³⁵ Arg²⁶,³⁴Lys³⁸GLP-1(7-38), Aib⁸,²²,³⁵ Arg²⁶Lys³⁸GLP-1(7-38), Aib⁸,³⁵ Arg²⁶Lys³⁸GLP-1(7-38), Aib⁸,²² Arg²⁶Lys³⁸GLP-1(7-38), Aib⁸,²²,³⁵ Arg³⁴Lys³⁸GLP-1(7-38), Aib⁸,³⁵Arg³⁴Lys³⁸GLP-1(7-38), Aib⁸,²²Arg³⁴Lys³⁸GLP-1(7-38), Aib⁸,²²,³⁵ Ala³⁷Lys³⁸GLP-1(7-38), Aib⁸,³⁵Ala³⁷Lys³⁸GLP-1(7-38), Aib⁸,²²Ala³⁷Lys³⁸GLP-1(7-38), Aib⁸,²²,³⁵ Lys³⁷GLP-1(7-37), Aib⁸,³⁵Lys³⁷GLP-1(7-37) and Aib⁸,²²Lys³⁷GLP-1(7-38).

60. The derivative according to any one of the above embodiments, wherein said GLP-1 peptide is exendin-4 (SEQ ID NO 4).

61. The derivative according to any one of the above embodiments, wherein said GLP-1 peptide is ZP-10, i.e. HGEGTFTSDLSKQMEEEAVRLFIEWLKNGGPSSGAPPSKKKKKK-amide (SEQ ID NO 5).

62. The derivative according to any one of the above embodiments, wherein said GLP-1 peptide is HGEGTFTSDLSKQMEEEAVRLFIEWLKNGGX, wherein X=P or Y, or a fragment or an analogue thereof.

63. The derivative according to any one of the above embodiments, wherein said GLP-1 peptide is Arg18, Leu20, Gln34, Lys33 (Nε-(γ-aminobutyroyl(Nα-hexadecanoyl))) Exendin-4-(7-45)-amide or Arg33, Leu20, Gln34, Lys18 (Nε-(γ-aminobutyroyl(Nα-hexadecanoyl))) Exendin-4-(7-45)-amide.

64. The derivative according to any one of the above embodiments, wherein said GLP-1 analogue comprises the amino acid sequence of the formula (III) which is derivatised in position 18, 23, 34, 36, 37 or 38:

Formula (III) (SEQ ID No: 6)
Xaa$_7$-Xaa$_8$-Xaa$_9$-Gly-Thr-Phe-Thr-Ser-Asp-Xaa$_{16}$-

Ser-Xaa$_{18}$-Tyr-Leu-Glu-Glu-Xaa$_{23}$-Ala-Xaa$_{25}$-

Arg-Xaa$_{27}$-Phe-Ile-Xaa$_{30}$-Trp-Leu-Xaa$_{33}$-Xaa$_{34}$-

Xaa$_{35}$-Xaa$_{36}$-Xaa$_{37}$-Xaa$_{38}$-Xaa$_{39}$ wherein

Xaa$_7$-Xaa$_8$ is L-histidine-Aib, desamino-histidine-alanine or desamino-histidine-Aib Xaa$_9$ is Glu or a Glu derivative such as alpha, alpha dimethyl-Glu Xaa$_{16}$ is Val or Leu;

Xaa$_{18}$ is Ser, Lys, or Arg;

Xaa$_{19}$ is Tyr or Gln;

Xaa$_{23}$ is Gln, Glu, Lys or Arg;

Xaa$_{25}$ is Ala or Val;

Xaa$_{27}$ is Glu or Leu;

Xaa$_{30}$ is Ala, Glu, Lys, Arg or absent;

Xaa$_{33}$ is Val, or Lys;

Xaa$_{34}$ is Lys, Glu, Asn or Arg;

Xaa$_{35}$ is Gly or Aib;

Xaa$_{36}$ is Arg or Lys,

Xaa$_{37}$ is Gly, Aib or absent

Xaa$_{38}$ is Lys, Glu or absent

Xaa$_{39}$ is amide or is absent;

provided that if Xaa$_{37}$ is absent then Xaa$_{38}$ is also absent.

65. The derivative according to any one of the above embodiments, wherein the GLP-1 peptide comprises the amino acid sequence of formula (IV) which is derivatised with an albumin binding residue in position 18, 23, 34, 36, 37 or 38:

Formula (IV) (SEQ ID No: 7)
Xaa$_7$-Xaa$_8$-Glu-Gly-Thr-Phe-Thr-Ser-Asp-Val-Ser- Xaa$_{18}$-Tyr-Leu-Glu-Glu-Gln-Ala-Ala-Arg-Glu-Phe- Ile-Xaa$_{30}$-Trp-Leu-Xaa$_{33}$-Xaa$_{34}$-Xaa$_{35}$-Xaa$_{36}$-Xaa$_{37}$-

Xaa$_{38}$-Xaa$_{39}$ wherein

Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;

Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa$_{18}$ is Ser, Lys or Arg;

Xaa$_{30}$ is Ala, Glu, Lys or Arg;

Xaa33 is Val or Lys;

Xaa34 is Lys, Glu or Arg;

Xaa35 is Gly or Aib;

Xaa36 is Arg or Lys,

Xaa37 is Gly, Aib or absent,

Xaa38 is Lys or absent, and

Xaa39 is amide or is absent.

66. The derivative according to any one of the above embodiments 65-66, wherein Xaa$_{38}$ is absent.

67. The derivative according to any one of the above embodiments 65-67, wherein Xaa$_{37}$ and Xaa$_{38}$ are both absent.

68. The derivative according to any one of the above embodiments 65-68, wherein 2 amino acids are substituted compared to GLP-1 (7-37).

69. The derivative according to any one of the above embodiments 65-68, wherein 3 amino acids are substituted compared to GLP-1 (7-37).

70. The derivative according to any one of the above embodiments 65-68, wherein 4 amino acids are substituted compared to GLP-1 (7-37).

71. The derivative according to any one of the above embodiments 65-68, wherein 5 amino acids are substituted compared to GLP-1 (7-37).

72. The derivative according to any one of the above embodiments 65-68, wherein 6 amino acids are substituted compared to GLP-1 (7-37).

73. The derivative according to any one of the above embodiments 65-73, wherein Xaa$_7$ is desamino-histidine.

74. The derivative according to any one of the above embodiments 65-74, wherein Xaa$_8$ is Aib 75. The derivative according to any of the above embodiments, which is selected from the group consisting of N-epsilon37{2-[2-(2-{2-[2-((R)-3-carboxy-3-{[1-(19-carboxynonadecanoyl)piperidine-4-carbon yl]amino}propionylamino)ethoxy]ethoxy}acetylamino) ethoxy]ethoxy}acetyl [desaminoHis7,Glu22,Arg26,Arg34,Lys37]GLP-1(7-37)amide;

N-epsilon20-{2-[2-(2-{2-[2-((R)-3-carboxy-3-{[1-(19-carboxynonadecanoyl)piperidine-4-carbonyl] amino}propionylamino)ethoxy]ethoxy}acetylamino) ethoxy]ethoxy}acetyl [Aib2,Leu14,Lys20,Gln28,Ser(O-Benzyl)39] exendin-4 (1-39)amide;

N-epsilon26{2-[2-(2-{2-[2-((R)-3-carboxy-3-{[1-(19-carboxynonadecanoyl)piperidine-4-carbonyl] amino}propionylamino)ethoxy]ethoxy}acetylamino) ethoxy]ethoxy}acetyl [desaminoHis7,Arg34]GLP-1-(7-37);

N-epsilon37{2-[2-(2-{2-[2-((S)-3-carboxy-3-{[1-(19-carboxynonadecanoyl)piperidine-4-carbonyl] amino}propionylamino)ethoxy]ethoxy}acetylamino) ethoxy]ethoxy}acetyl [Aib8,Glu22,Arg26,Arg34,Lys37] GLP-1-(7-37)amide;

N-epsilon23-[2-(2-[2-(2-[2-(2-((R)-3-[1-(17-Carboxyheptadecanoyl)piperidin-4-ylcarbonylamino]-3-(carboxypropionylamino)ethoxy)ethoxy]acetylamino)ethoxy] ethoxy)acetyl][Aib8,Arg26, Arg34]GLP-1-(7-37);

N-epsilon37-[2-(2-[2-(2-[2-(2-((R)-3-[1-(17-Carboxyheptadecanoyl)piperidin-4-ylcarbonylamino]3-carboxypropionylamino)ethoxy)ethoxy]acetylamino)ethoxy]ethoxy) acetyl][,DesaminoHis 7, Glu22 Arg26, Arg 34, Phe(m-CF3)28]GLP-1-(7-37)amide;

[DesaminoHis7,Glu22,Arg26,Arg34]GLP-1-(7-37)-Lys(2-{2-[2-(2-{2-[2-((S)-4-Carboxy-4-{[1-(19-carboxynonadecanoyl)piperidine-4-carbonyl]amino}butyrylamino) ethoxy]ethoxy}acetylamino)ethoxy]ethoxy}acetyl);

N-epsilon20({2-[2-(2-{2-[2-((R)-3-carboxy-3-{[1-(17-carboxyheptadecanoyl)piperidine-4-carbon yl]amino}propionylamino)ethoxy]ethoxy}acetylamino) ethoxy]ethoxy}acetyl) [Aib8,Lys20,Arg26,Glu30,Thr(O-benzyl)33]GLP-1-(7-37) amide N-epsilon30{2-[2-(2-{2-[2-((S)-3-carboxy-3-{[1-(19-carboxynonadecanoyl)piperidine-4-carbonyl] amino}propionylamino)ethoxy]ethoxy}acetylamino) ethoxy]ethoxy}acetyl [Aib8,Glu22,Arg26,Lys30]GLP-1-(7-37);

N-epsilon31{2-[2-(2-{2-[2-((S)-3-carboxy-3-{[1-(19-carboxynonadecanoyl)piperidine-4-carbonyl]

amino}propionylamino)ethoxy]ethoxy}acetylamino)ethoxy]ethoxy}acetyl [Aib8, Glu22, Arg26,Lys 31]GLP-1-(7-37);

N-epsilon20({2-[2-(2-{2-[2-((R)-3-carboxy-3-{[1-(17-carboxyheptadecanoyl)piperidine-4-carbon yl]amino}propionylamino)ethoxy]ethoxy}acetylamino)ethoxy]ethoxy}acetyl) [Aib8,Lys20,Arg26,2-Naphtylalanine28, Glu30]GLP-1 (7-37)amide; [Aib8, Glu22, Arg26, Arg34]GLP-1-(7-37)Lys[2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl]amide;

N-epsilon20({2-[2-(2-{2-[2-((R)-3-carboxy-3-{[1-(17-carboxyheptadecanoyl)piperidine-4-carbon yl]amino}propionylamino)ethoxy]ethoxy}acetylamino)ethoxy]ethoxy}acetyl) [Aib8,Lys20,Arg 26, 2-Naphtylalanine12, Glu30]GLP-1-(7-37)amide;

[DesaminoHis7,Glu22,Arg26,Arg34]GLP-1-(7-37)Lys[2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl]amide;

N-epsilon31-(2-{2-[2-(2-{2-[2-((S)-3-Carboxy-3-{[1-(19-carboxy-nonadecanoyl)piperidine-4-carbonyl]amino}propionylamino)ethoxy]ethoxy}acetylamino)ethoxy]ethoxy}acetyl)[Aib 8,Glu22,Arg26,Lys31,Arg34]GLP-1-(7-37);

N-epsilon26-[(S)-4-Carboxy-4-({trans-4-[(19-carboxynonadecanoylamino)methyl]cyclohexanecarbonyl}amino)butyryl][Aib8,Arg34]GLP-1-(7-37);

N-epsilon26-{4-[(S)-4-Carboxy-4-({trans-4-[(19-carboxynonadecanoylamino)methyl]cyclohexanecarbonyl}amino)butyrylamino]butyryl}[Aib8,Arg34]GLP-1-(7-37);

N-epsilon26-[2-(2-{2-[(S)-4-Carboxy-4-({trans-4-[(19-carboxy-nonadecanoylamino)methyl]cyclohexanecarbonyl}amino)butyrylamino]ethoxy}ethoxy) acetyl][Aib8,Arg34]GLP-1-(7-37);

N-epsilon26-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Arg34]GLP-1-(7-37)amide;

N-epsilon18-{2-(2-(2-(2-[2-(2-[(S)-4-Carboxy-4-({4-[(19-carboxynonadecanoylamino)methyl]cyclohexanecarbonyl}amino)butanoylamino]ethoxy)ethoxy]acetyl)ethoxy)ethoxy)acetyl}[Aib8,Lys18,Arg26,Arg34]GLP-1(7-37);

N-epsilon20-[2-(2-[2-(2-[2-(2-((S)-4-[trans-4-([19-Carboxynonadecanoylamino]methyl)cyclohexylcarbonylamino]-4-carboxybutanoylamino)ethoxy)ethoxy]acetylamino)ethoxy]ethoxy)acetyl][desaminoHis1, Lys20, Ser(O-benzyl)33, Ser(O-benzyl)33] exendin (1-39);

[Aib8,Glu22,Arg26,Arg34]GLP-1-(7-37)Lys[2-(2-[2-(2-[2-(2-((S)-3-[4-([19-Carboxynonadecanoylamino]methyl)cyclohexylcarbonylamino]-3-carboxypropionylamino)ethoxy)ethoxy]acetylamino)ethoxy]ethoxy)acetyl]amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37)amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37)amide;

N-epsilon37-[2-(2-{2-[2-(2-{2-[(S)-4-Carboxy-4-({4-[(trans-19-carboxy-nonadecanoylamino)methyl]cyclohexanecarbonyl}amino)butyrylamino]ethoxy}ethoxy)acetylamino]ethoxy}ethoxy)acetyl][DesaminoHis7,Arg26,Arg34,Lys37]GLP-1-(7-37) amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37);

[DesaminoHis7,Glu22,Arg26,Arg34]GLP-1-(7-37)Lys[2-(2-{2-[2-(2-{2-[4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl]-amide;

[desaminoHis7,Arg26,Arg34]GLP-1-(7-37)Lys[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl]amide;

N-epsilon26[2-(2-{2-[2-(2-{2-[(S)-4-Carboxy-4-({4-[(19-carboxy-nonadecanoylamino)methyl]cyclohexanecarbonyl}amino)butyrylamino]ethoxy}ethoxy)acetylamino]ethoxy}ethoxy)acetyl[Aib8, Lys 26] GLP-1 (7-37)amide;

N-epsilon26 [2-(2-[2-(2-[2-(2-((S)-2-[trans-4-((9-Carboxynonadecanoylamino]methyl)cyclohexylcarbonylamino]-4-carboxybutanoylamino)ethoxy)ethoxy]acetylamino)ethoxy]ethoxy)acetyl][Aib8, Lys26] GLP-1 (7-37)amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Arg26,Arg34,Lys37]GLP-1-(7-37);

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Glu30,Arg34,Lys37]GLP-1-(7-37);

N-epsilon26-[2-(2-{2-[(S)-4-Carboxy-4-((S)-4-carboxy-4-{4-[4-(16-(1H-tetrazol-5-yl)-hexadecanoylsulfamoyl)butyrylamino]-butyrylamino}butyrylamino)butyrylamino]ethoxy}ethoxy)acetyl][Aib8,Arg34]GLP-1(7-37);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{4-[4-(16-(1H-tetrazol-5-yl)hexadecanoylsulfamoyl)butyrylamino]butyrylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]-dodecanoylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-36)amide;

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys33,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-36)amide;

N-epsilon26-[2-(2-{2-[2-(2-{2-[2-(2-{2-[2-(2-{2-[2-(2-{2-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetylamino]ethoxy}ethoxy)acetylamino]ethoxy}ethoxy)acetylamino]ethoxy}ethoxy)acetylamino]ethoxy}ethoxy)acetyl][Aib8,Lys26,Arg34]GLP-1-(7-36)amide;

[Aib8,Glu22,Arg26,Arg34]GLP-1-(7-37)Lys[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}-butyrylamino)butyrylamino]ethoxy}ethoxy)acetyl]amide;

N-epsilon20-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys20,Glu22,Arg26,Glu30,Pro37]GLP-1-(7-37)amide;

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Glu22,Arg26,Arg34,Lys37]GLP-1-(7-37)amide;

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Glu22,Arg26,Arg34,Lys37]GLP-1-(7-37)amide;

N-epsilon37-[[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Arg26,Arg34,Lys37]GLP-1-(7-37)amide;

[Aib8,Glu22,Arg26,Glu30,Pro37]GLP-1-(7-37)Lys [2-(2-{2-[4-Carboxy-4-(4-carboxy-4-{4-[4-(16-1H-tetrazol-5-yl-hexadecanoylsulfamoyl)butyrylamino]butyrylamino}butyrylamino)butyrylamino]ethoxy}ethoxy)acetyl]; and

[Aib8,Glu22,Arg26,Glu30,Pro37]GLP-1-((7-37)Lys (2-(2-(3-(2-(2-(2-(2-(2-(2-(2-(2-(2-(2-[4-(S)-carboxy-4-(4-(S)-carboxy-4-(4-{4-[16-(Tetrazol-5-yl)hexadecanoylsulfamoyl]butanoylamino}butanoylamino) butyrylamino) butyrylamino]ethoxy)ethoxy)ethoxy)ethoxy)ethoxy) ethoxy)ethoxy)ethoxy)ethoxy)ethoxy)ethoxy) propionylamino)ethoxy)ethoxy) peptide.

76. A method for increasing the time of action in a patient of a GLP-1 peptide, characterised in that a GLP-1(7-37) peptide or an analogue thereof is derivatised with A-B-C-D- as disclosed in any of the preceding embodiments.

77. A method for increasing the time of action in a patient of a GLP-1 peptide to more than about 40 hours, characterised in that a GLP-1(7-37) peptide or an analogue thereof is derivatised with A-B-C-D- as disclosed in any of the preceding embodiments.

78. A pharmaceutical composition comprising a derivative according to any one of embodiments 1-76, and a pharmaceutically acceptable excipient.

79. The pharmaceutical composition according to embodiment 1-76, which is suited for parenteral administration.

80. Use of a derivative according to any one of the embodiments 1-76 for the preparation of a medicament.

81. Use of a derivative according to any one of the embodiments 1-76 for the preparation of a medicament for the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers.

82. Use of a derivative according to any one of the embodiments 1-76 for the preparation of a medicament for delaying or preventing disease progression in type 2 diabetes.

83. Use of a derivative according to any one of the embodiments 1-76 for the preparation of a medicament for decreasing food intake, decreasing β-cell apoptosis, increasing β-cell function and β-cell mass, and/or for restoring glucose sensitivity to β-cells.

84. A derivative according to any one of the claims 1-76 for use in the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a formulation described herein as comprising a particular element should be understood as also describing a formulation consisting of that element, unless otherwise stated or clearly contradicted by context).

This invention includes all modifications and equivalents of the subject matter recited in the aspects or claims presented herein to the maximum extent permitted by applicable law.

The present invention is further illustrated in the following representative methods and examples which are, however, not intended to limit the scope of the invention in any way.

The features disclosed in the foregoing description and in the following examples may, both separately and in any combination thereof, be material for realising the invention in diverse forms thereof.

EXAMPLES

Abbreviations Used r.t: Room temperature
DIPEA: diisopropylethylamine
$H_2O$: water
$CH_3CN$: acetonitrile
DMF: NN dimethylformamide
HBTU: 2-(1H-Benzotriazol-1-yl-)-1,1,3,3 tetramethyluronium hexafluorophosphate
Fmoc: 9H-fluoren-9-ylmethoxycarbonyl
Boc: tert butyloxycarbonyl
OtBu: tert butyl ester
tBu: tert butyl
Trt: triphenylmethyl
Pmc: 2,2,5,7,8-Pentamethyl-chroman-6-sulfonyl
Dde: 1-(4,4-Dimethyl-2,6-dioxocyclohexylidene)ethyl
ivDde: 1-(4,4-Dimethyl-2,6-dioxocyclohexylidene)-3-methylbutyl
Mtt: 4-methyltrityl
Mmt: 4-methoxytrityl
DCM: dichloromethane
TIS: triisopropylsilane)
TFA: trifluoroacetic acid
$Et_2O$: diethylether
NMP: 1-Methyl-pyrrolidin-2-one
DIPEA: Diisopropylethylamine
HOAt: 1-Hydroxy-7-azabenzotriazole
HOBt: 1-Hydroxybenzotriazole
DIC: Diisopropylcarbodiimide
DBU: 1,8-diazabicycli-[5,4,0]undecene-7
MW: Molecular weight
A: Synthesis of Resin Bound Peptide
SPPS Method A.

The protected peptidyl resin was synthesized according to the Fmoc strategy on an Applied Biosystems 433 peptide synthesizer in 0.25 mmol or 1.0 mmol scale using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methyl pyrrolidone), and UV monitoring of the deprotection of the Fmoc protection group. The starting resin used for the synthesis of the peptide amides was Rink-Amide resin and either Wang or chlorotrityl resin was used for peptides with a carboxy C-terminal. The protected amino acid derivatives used were standard Fmoc-amino acids (supplied from e.g. Anaspec, or Novabiochem) supplied in preweighed cartridges suitable for the ABI433A synthesizer with the exception of unnatural aminoacids such as Fmoc-Aib-OH (Fmoc-aminoisobutyric acid). The N terminal amino acid was Boc protected at the alpha amino group (e.g. Boc-His(Boc)OH was used for peptides with His at the N-terminal). The epsilon amino group of lysine in position 26 was either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2002/2003 or newer version, or W. R. Sampson (1999), J. Pep. Sci. 5, 403.
SPPS Method B:

One alternative method (method B) of peptide synthesis was by Fmoc chemistry on a microwave-based Liberty peptide synthesizer (CEM Corp., North Carolina). The resin was Tentagel S RAM with a loading of 0.24 mmol/g. The coupling chemistry was DIC/HOAt in NMP using amino acid solutions of 0.3 M in NMP and a molar excess of 8-10 fold. Coupling conditions was 5 minutes at up to 70° C. Deprotection was with 5% piperidine in NMP at up to 70° C. When a chemical modification of a lysine side chain was desired, the lysine was incorporated as Lys(Mtt). The Mtt group was removed by suspending the resin in neat hexafluoroisopropanol for 20 minutes followed by washing with DCM and NMP. The chemical modification of the lysine was performed either by manual synthesis or by one or more automated steps on the Liberty followed by a manual coupling. Another method of peptide synthesis was by Fmoc chemistry on an ABI 433 with HBTU coupling. After synthesis the resin was washed with DCM and dried, and the peptide was cleaved from the resin by a 2 hour treatment with TFA/TIS/water (92.5/5/2.5) followed by precipitation with diethylether. the peptide was redissolved in 30% acetic acid or similar solvent and purified by standard RP-HPLC on a C18 column using acetonitrile/TFA. The identity of the peptide was confirmed by MALDI-MS.

SPPS Method C

The protected peptidyl resin was synthesized according to the Fmoc strategy on an Advanced ChemTech Synthesiser (APEX 348) 0.25 mmol scale using the manufacturer supplied protocols which employ DIC (dicyclohexylcarbodiimide) and HOBt (1-Hydroxybenzotriazole) mediated couplings in NMP (N-methylpyrrolidone. The starting resin used for the synthesis of the peptide amides was Rink-Amide resin and either Wang or chlorotrityl resin was used for peptides with a carboxy C-terminal. The protected amino acid derivatives used were standard Fmoc-amino acids (supplied from e.g. Anaspec, or Novabiochem. The N terminal amino acid was Boc protected at the alpha amino group (e.g. Boc-His (Boc)OH was used for peptides with His at the N-terminal). The epsilon amino group of lysine in position 26 was either protected with Mtt, Mmt, Dde, ivDde, or Boc, depending on the route for attachment of the albumin binding moiety and spacer. The synthesis of the peptides may in some cases be improved by the use of dipeptides, e.g., pseudoprolines from Nova biochem, Fmoc-Ser(tbu)-ΨSer(Me,Me)-OH, see e.g. catalogue from Novobiochem 2002/2003 or newer version, or W. R. Sampson (1999), J. Pep. Sci. 5, 403

Procedure for Removal of ivDde or Dde-Protection.

The resin (0.25 mmol) was placed in a manual shaker/filtration apparatus and treated with 2% hydrazine in N-methylpyrrolidone (20 ml, 2×12 min) to remove the Dde or ivDde group and wash with N-methylpyrrolidone (4×20 ml).

Procedure for Removal of Mtt or Mmt-Protection.

The resin (0.25 mmol) was placed in a manual shaker/filtration apparatus and treated with 2% TFA and 2-3% TIS in DCM (20 ml, 5-10 min repeated 6-12 times) to remove the Mtt or Mmt group and wash with DCM (2×20 ml), 10% MeOH and 5% DIPEA in DCM (2×20 ml) and N-methylpyrrolidone (4×20 ml).

Alternative Procedure for Removal of Mtt-Protection:

The resin was placed in a syringe and treated with hexafluoroisopropanol for 2×10 min to remove the Mtt group. The resin was then washed with DCM and NMP as described above.

Procedure for Attachment of Sidechains to Lysine Residue.

The albumin binding residue (B—U— sidechain of formula I) can be attached to the peptide either by acylation to resin bound peptide or acylation in solution to the unprotected peptide using standard acylating reagent such as but not limited to DIC, HOBt/DIC, HOAt/DIC, or HBTU.

Attachment to Resin Bound Peptide:

Route I

Activated (active ester or symmetric anhydride) albumin binding residue (A-B)— sidechain of formula I) such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, dichloromethane, 2-propanol, methanol and diethyl ether.

Route II

The albumin binding residue (A-(B)— sidechain of formula I) was dissolved in N-methyl pyrrolidone/methylene chloride (1:1, 10 ml). The activating reagent such as hydroxybenzotriazole (HOBt) (4 molar equivalents relative to resin) and diisopropylcarbodiimide (4 molar equivalents relative to resin) was added and the solution was stirred for 15 min. The solution was added to the resin and diisopropyethylamine (4 molar equivalents relative to resin) was added. The resin was shaken 2 to 24 hours at room temperature. The resin was washed with N-methylpyrrolidone (2×20 ml), N-methyl pyrrolidone/Methylene chloride (1:1) (2×20 ml) and methylene chloride (2×20 ml).

Route III

Activated (active ester or symmetric anhydride) albumin binding residue (A-B— sidechain of formula I) such as octadecanedioic acid mono-(2,5-dioxo-pyrrolidin-1-yl) ester (Ebashi et al. EP511600, 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the albumin binding residue such as tert.-butyl, the reaction mixture was lyophilized 0/N and the isolated crude peptide deprotected afterwards—in case of a tert-butyl group the peptide was dissolved in a mixture of trifluoroacetic acid, water and triisopropylsilane (90:5:5). After for 30 min the mixture was, evaporated in vacuo and the finale peptide purified by preparative HPLC.

Procedure for Removal of Fmoc-Protection:

The resin (0.25 mmol) was placed in a filter flask in a manual shaking apparatus and treated with N-methylpyrrolidone/methylene chloride (1:1) (2×20 ml) and with N-methylpyrrolidone (1×20 ml), a solution of 20% piperidine in N-methylpyrrolidone (3×20 ml, 10 min each). The resin was washed with N-methyl pyrrolidone (2×20 ml), N-methylpyrrolidone/Methylene chloride (1:1) (2×20 ml) and methylene chloride (2×20 ml).

Procedure for Cleaving the Peptide Off the Resin:

The peptide was cleaved from the resin by stirring for 180 min at room temperature with a mixture of trifluoroacetic acid, water and triisopropylsilane (95:2.5:2.5 to 92:4:4). The cleavage mixture was filtered and the filtrate was concentrated to an oil by a stream of nitrogen. The crude peptide was precipitated from this oil with 45 ml diethyl ether and washed 1 to 3 times with 45 ml diethyl ether.

Purification:

The crude peptide was purified by semipreparative HPLC on a 20 mm×250 mm column packed with either 5μ or 7μ C-18 silica. Depending on the peptide one or two purification systems were used.

TFA: After drying the crude peptide was dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The peptide containing fractions were collected. The purified peptide was lyophilized after dilution of the eluate with water.

Ammonium sulphate: The column was equilibrated with 40% $CH_3CN$ in 0.05M $(NH_4)_2SO_4$, which was adjusted to pH 2.5 with concentrated $H_2SO_4$. After drying the crude peptide was dissolved in 5 ml 50% acetic acid $H_2O$ and diluted to 20 ml with $H_2O$ and injected on the column which then was eluted with a gradient of 40%-60% $CH_3CN$ in 0.05M $(NH_4)_2SO_4$, pH 2.5 at 10 ml/min during 50 min at 40° C. The peptide containing fractions were collected and diluted with 3 volumes of $H_2O$ and passed through a Sep-Pak® C18 cartridge (Waters part. #:51910) which has been equilibrated with 0.1% TFA. It was then eluted with 70% $CH_3CN$ containing 0.1% TFA and the purified peptide was isolated by lyophilisation after dilution of the eluate with water.

The final product obtained was characterised by analytical RP-HPLC (retention time) and by LCMS The RP-HPLC analysis may be performed using UV detection at 214 nm and e.g. a Vydac 218TP54 4.6 mm×250 mm 5μ C-18 silica column (The Separations Group, Hesperia, USA) and eluted at e.g. 1 ml/min at 42° C. Most often one of following specific conditions were used:

Method 03_A1_1

HPLC (Method 03_A1_1): The RP-analysis was performed using a Waters 2690 systems fitted with a Waters 996 diode array detector. UV detections were collected at 214, 254, 276, and 301 nm on a 218TP54 4.6 mm×250 mm 5μ C-18 silica column (The Seperations Group, Hesperia), which was eluted at 1 ml/min at 42° C. The column was equilibrated with 10% of a 0.5 M ammonium sulfate, which was adjusted to pH 2.5 with 4M sulfuric acid. After injection, the sample was eluted by a gradient of 0% to 60% acetonitrile in the same aqueous buffer during 50 min.

Method 03_B1_2

HPLC (Method 03_B1_2): The RP-analysis was performed using a Waters 2690 systems fitted with a Waters 996 diode array detector. UV detections were collected at 214, 254, 276, and 301 nm on a Zorbax 300SB C-18 (4.5×150 mm, 50, which was eluted at 0.5 ml/min at 42° C. The column was equilibrated with an aqueous solution of TFA in water (0.1%). After injection, the sample was eluted by a gradient of 0% to 60% acetonitrile (+0.1% TFA) in an aqueous solution of TFA in water (0.1%) during 50 min.

Method 02_B1_1

HPLC (Method 02_B1_1): The RP-analyses was performed using a Alliance Waters 2695 system fitted with a Waters 2487 dualband detector. UV detections at 214 nm and 254 nm were collected using a Vydac 218TP53, C18, 300 Å, 5 um, 3.2 mm×250 mm column, 42° C. Eluted with a linear gradient of 0-60% acetonitrile, 95-35% water and 5% trifluoroacetic acid (1.0%) in water over 50 minutes at a flow-rate of 0.50 ml/min.

Method 01_B4_2

HPLC (Method 01_B4_2): RP-analyses was performed using a Waters 600S system fitted with a Waters 996 diode array detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Method 02_B4_4

HPLC (Method 02_B4_4): The RP-analyses was performed using a Alliance Waters 2695 system fitted with a Waters 2487 dualband detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Method 02_B6_1

HPLC (Method 02_B6_1): The RP-analyses was performed using a Alliance Waters 2695 system fitted with a Waters 2487 dualband detector. UV detections at 214 nm and 254 nm were collected using a Vydac 218TP53, C18, 300 Å, 5 um, 3.2 mm×250 mm column, 42° C. Eluted with a linear gradient of 0-90% acetonitrile, 95-5% water, and 5% trifluoroacetic acid (1.0%) in water over 50 minutes at a flow-rate of 0.50 ml/min.

Method 03_B6_1

HPLC (Method 03_B1_1): The RP-analysis was performed using a Waters 2690 systems fitted with a Waters 996 diode array detector. UV detections were collected at 214, 254, 276, and 301 nm on a 218TP54 4.6 mm×250 mm 5μ C-18 silica column (The Seperations Group, Hesperia), which was eluted at 1 ml/min at 42° C. The column was equilibrated with 5% acetonitrile (+0.1% TFA) in an aqueous solution of TFA in water (0.1%). After injection, the sample was eluted by a gradient of 0% to 90% acetonitrile (+0.1% TFA) in an aqueous solution of TFA in water (0.1%) during 50 min.

Alternatively a preparative gradient elution can be performed as indicated above and the percentage of acetonitrile where the compound elutes is noted. Identity is confirmed by MALDI.

The following instrumentation was used:

LCMS was performed on a setup consisting of Sciex API 100 Single quadropole mass spectrometer, Perkin Elmer Series 200 Quard pump, Perkin Elmer Series 200 autosampler, Applied Biosystems 785A UV detector, Sedex 75 evaporative light scattering detector The instrument control and data acquisition were done by the Sciex Sample control software running on a Windows 2000 computer.

The HPLC pump is connected to two eluent reservoirs containing:

A: 0.05% Trifluoro acetic acid in water

B: 0.05% Trifluoro acetic acid in acetonitrile

The analysis is performed at room temperature by injecting an appropriate volume of the sample (preferably 20 μl) onto the column which is eluted with a gradient of acetonitrile.

The HPLC conditions, detector settings and mass spectrometer settings used are giving in the following table.

Column: Waters Xterra MS C-18×3 mm id 5 μm

Gradient: 5%-90% acetonitrile linear during 7.5 min at 1.5 ml/min

Detection: 210 nm (analogue output from DAD)

ELS (analogue output from ELS), 40° C.

MS ionisation mode API-ES

Alternatively LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detector controlled by HP Chemstation software. The HPLC pump is connected to two eluent reservoirs containing:

A: 10 mM $NH_4OH$ in water

B: 10 mM $NH_4OH$ in 90% acetonitrile

The analysis was performed at 23° C. by injecting an appropriate volume of the sample (preferably 20 μl) onto the column which is eluted with a gradient of A and B.

The HPLC conditions, detector settings and mass spectrometer settings used are giving in the following table.

| | |
|---|---|
| Column | Waters Xterra MS C-18 × 3 mm id 5 μm |
| Gradient | 5%-100% acetonitrile linear during 6.5 min at 1.5 ml/min |
| Detection | 210 nm (analogue output from DAD) |
| | ELS (analogue output from ELS) |
| | MS ionisation mode API-ES. Scan 100-1000 amu step 0.1 amu |

MALDI-MS:

Molecular weights of the peptides were determined using matrix-assisted laser desorption time of flight mass spectroscopy (MALDI-MS), recorded on a Microflex (Bruker). A matrix of α-cyano-4-hydroxy cinnamic acid was used.

Analytical HPLC Conditions (Method I):

Equilibration of the column (Xterra™ MS C18, 5 um, 4.6×150 mm Column, P7N 186 000490) with 0.1% TFA/$H_2O$ and elution by a gradient of 0% $CH_3CN$/0.1% TFA/$H_2O$ to 60% $CH_3CN$/0.1% TFA/$H_2O$ during 25 min followed by a gradient from 60% to 100% over 5 min.

In the examples of this invention the nomenclature and structurally graphics is meant as: One letter symbols for the natural amino acids is used, e.g. His L-histidine, A is L-alanine ect. Three letter abbreviations for amino acids may also be uses, e.g. His is L-histidine, Ala is L-alanine ect. For non natural amino acids three letter abbreviations are used, such as Aib for aminoisobutyric acid. The position of the amino acids may either be indicated with a number in superscript after the amino acid symbols such as $Lys^{37}$, or as Lys37. The N-terminal amino group may be symbolised either as $NH_2$ or as H. The C-terminal carboxylic group may be symbolised either as —OH or as —COOH. The C-terminal amide group is symbolised as —$NH_2$ The epsilon amino group of Lysine may be described either as the greek symbol ε or spelled "epsilon".

The structures in the examples below are in several cases a combination of one letter symbols for the naturally amino acids combined with the three letter abbreviation Aib for aminoisobutyric acid. In several cases some of the amino acids are shown in expanded full structure. Thus lysine that has been derivatised may be shown as the expanded full structures in example 1 where the lysine in position 38 is expanded. The nitrogen (with indicated H) between arginine in position 37 and the expanded lysine in position 38 is thus the nitrogen of the peptide bond connecting the two amino acids in example 1 According to the procedure above, the following derivatives were prepared as non-limiting examples of the invention:

Example 1

N-ε$^{37}$\{2-[2-(2-\{2-[2-((R)-3-carboxy-3-\{[1-(19-carboxynonadecanoyl)piperidine-4-carbon yl]amino\}propionylamino)ethoxy] ethoxy\}acetylamino)ethoxy]ethoxy\}acetyl [desamino$His^7$,$Glu^{22}$,$Arg^{26}$,$Arg^{34}$,$Lys^{37}$]GLP-1(7-37)amide

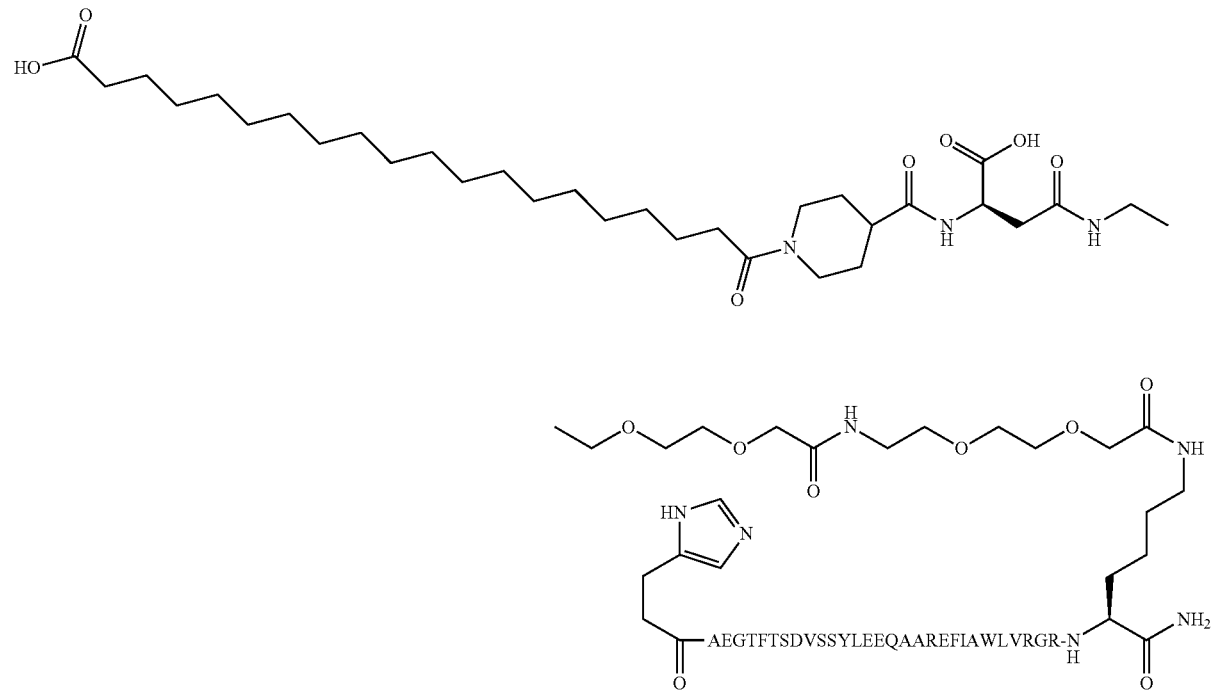

The Sub-Structures

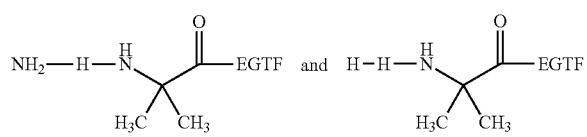

both means His-Aib-Glu-Gly-Thr-Phe.

Preparation method: A

HPLC method B6

RT=35.49 min

LCMS: m/z=1096.2 $(M+3H)^{3+}$

Calculated MW=4380.0

Example 2

N-ε$^{20}$-{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib$^2$,Leu$^{14}$,Lys$^{20}$,Gln$^{28}$,Ser(O-benzyl)$^{39}$] exendin-4 (1-39)amide

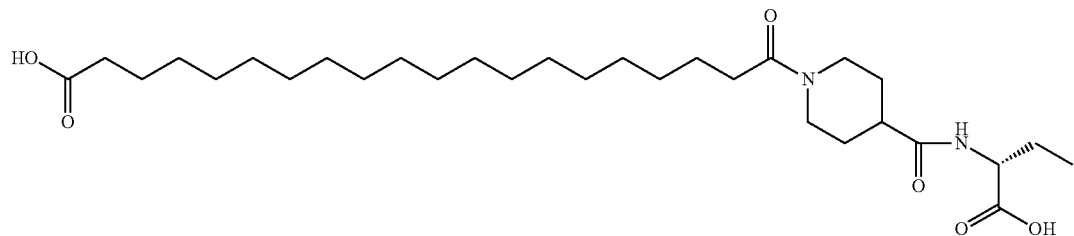

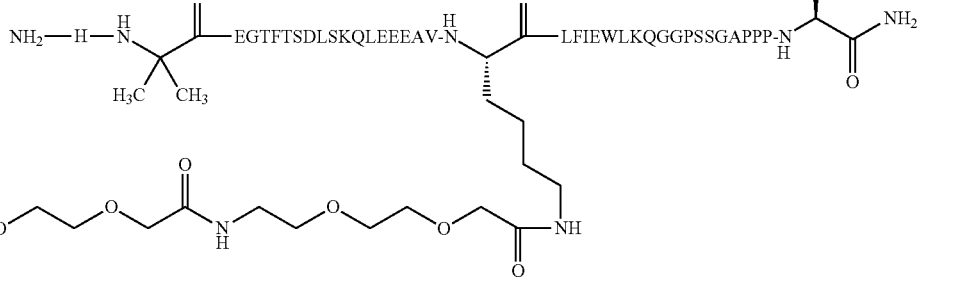

Preparation method: A
HPLC method B6:
RT=37.63 min
LCMS: m/z=1705.9 (M+3H)$^{3+}$
Calculated MW=5113.9

Example 3

N-ε$^{26}${2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis$^7$,Arg$^{34}$]GLP-1-(7-37)

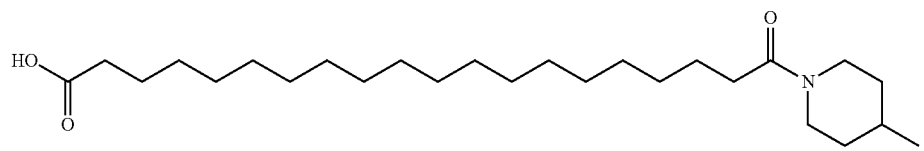

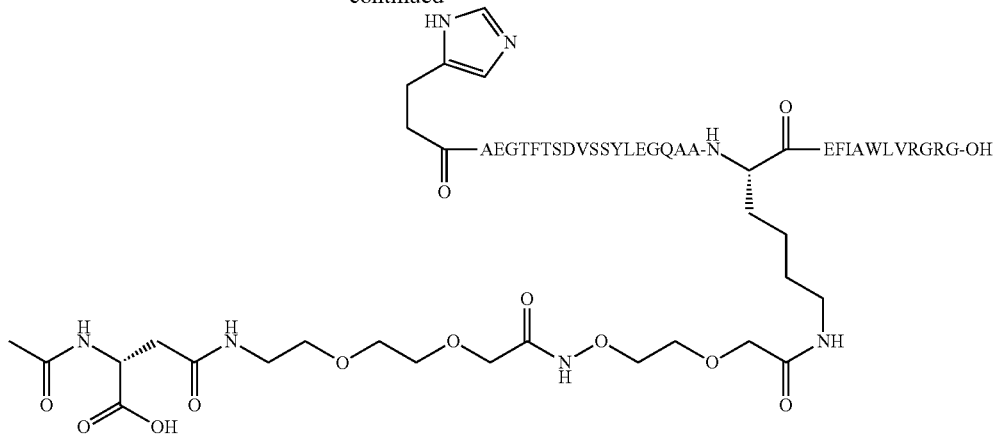
Preparation method: A
HPLC method B6:
RT=36.45 min
LCMS: m/z=1404.3 (M+3H)$^{3+}$
Calculated MW=4209.8
Example 4
N-epsilon37{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Arg34,Lys37]GLP-1-(7-37)amide
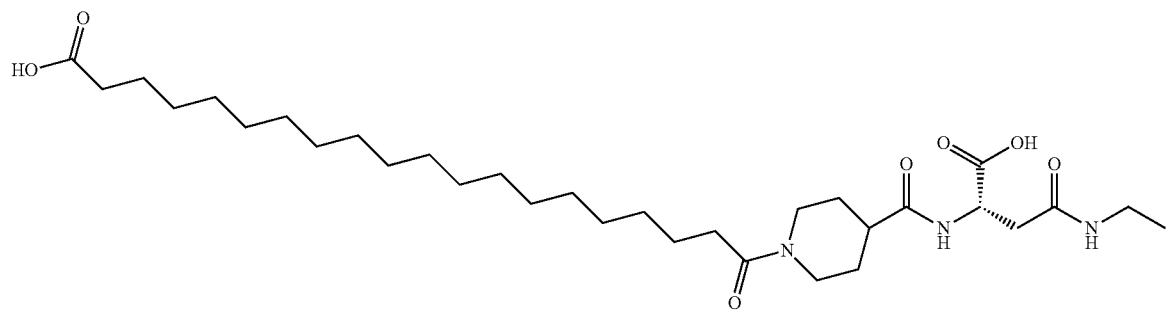
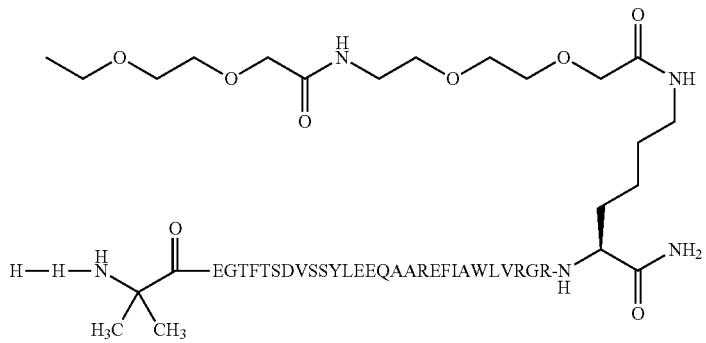
Preparation method: B
The peptide was eluted at 66% acetonitrile.
Structure confirmed by MALDI-MS
Calculated MW=4409.1

Example 5

N-epsilon23-[2-(2-[2-(2-[2-(2-((R)-3-[1-(17-Carboxyheptadecanoylamino)piperidin-4-ylcarbonylamino]-3-(carboxypropionylamino)ethoxy)ethoxy]acetylamino)ethoxy]ethoxy)acetyl][Aib8,Arg26,Arg34]GLP-1-(7-37)

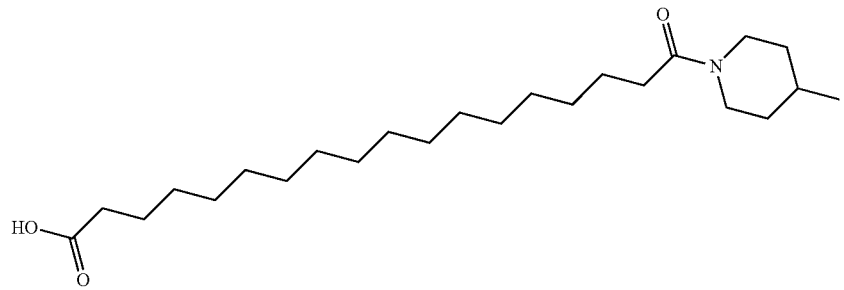

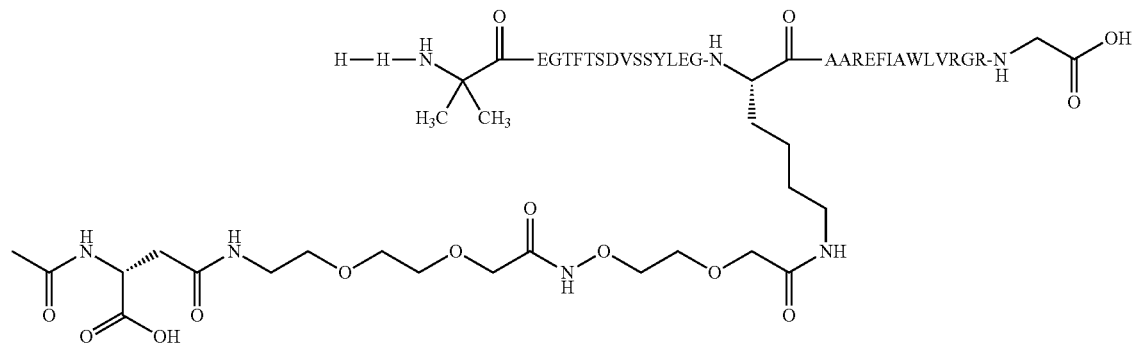

Preparation method: A
HPLC method 02_B6_4:
RT=9.32 min
LCMS: m/z=(M+3H)$^{3+}$1413.8
Calculated MW=4238.8

Example 6

N-epsilon37-[2-(2-[2-(2-[2-(2-((R)-3-[1-(17-Carboxyheptadecanoyl)piperidin-4-ylcarbonylamino]3-carboxypropionylamino)ethoxy)ethoxy]acetylamino)ethoxy]ethoxy)acetyl][DesaminoHis7, Glu22 Arg26, Arg 34, Phe(m-CF3)28]GLP-1-(7-37)amide

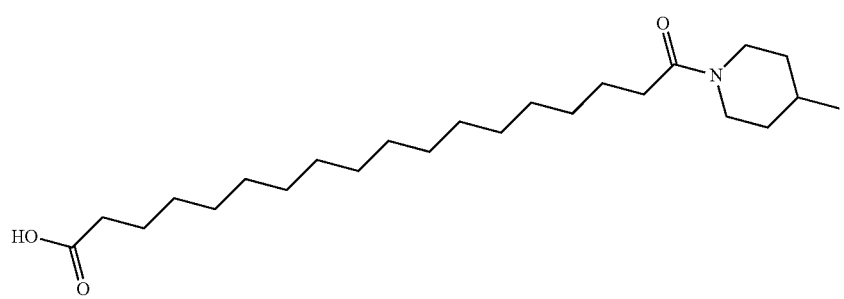

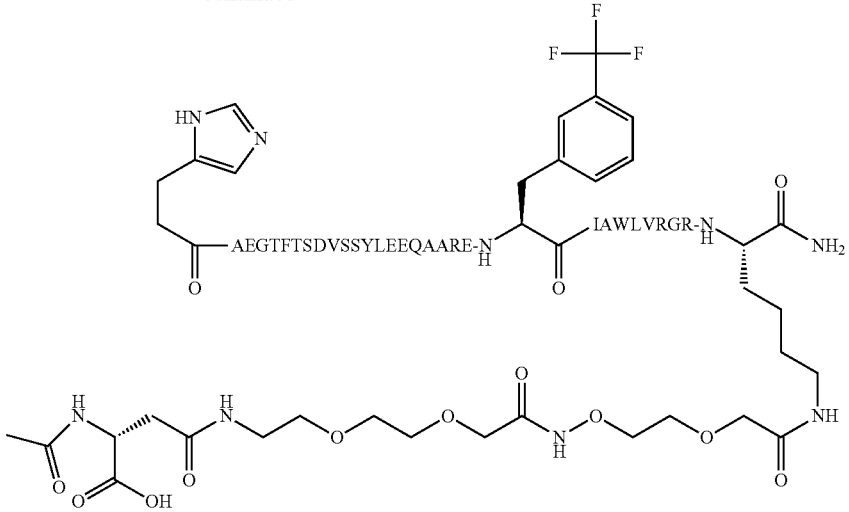
Preparation method: A
HPLC method 01_B6_2:
RT=11.92 min
LCMS: m/z=1474.8 $(M+3H)^{3+}$
Calculated MW=4420.0
Example 7
[DesaminoHis7,Glu22,Arg26,Arg34]GLP-1-(7-37)-
Lys(2-{2-[2-(2-{2-[2-((S)-4-Carboxy-4-{[1-(19-
carboxynonadecanoyl)piperidine-4-carbonyl]
amino}butyrylamino)ethoxy]ethoxy}acetylamino)
ethoxy]ethoxy}acetyl)
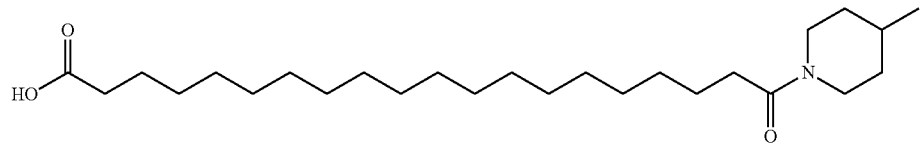
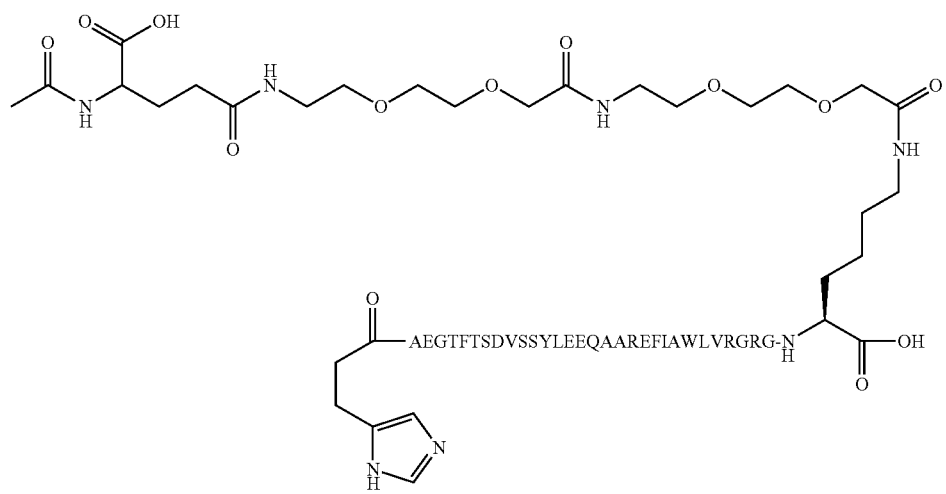

Preparation method: B
The peptide was prepared similar to method A, though using a CEM Liberty peptide synthesizer, and starting with fmoc-Lys(mtt)-wang resin. The N-terminal amine was protected with a Boc group. Mtt was removed from the lysine using hexafluoro-2-propanol, and the side chain was prepared using fmoc-chemistry on a CEM Liberty peptide synthesizer.
HPLC method 03_B6_1:
RT=35.50 min
LCMS: m/z=1114.0 $(M+4H)^{4+}$
Calculated (M)=4452.1

Example 8

N-$\epsilon^{20}$({2-[2-(2-{2-[2-((R)-3-carboxy-3-{[1-(17-carboxyheptadecanoyl)piperidine-4-carbonyl]amino}propionylamino)ethoxy]ethoxy}acetylamino)ethoxy]ethoxy}acetyl) [Aib$^8$,Lys$^{20}$,Arg$^{28}$,Glu$^{30}$,Thr(O-benzyl)$^{33}$]GLP-1-(7-37)amide

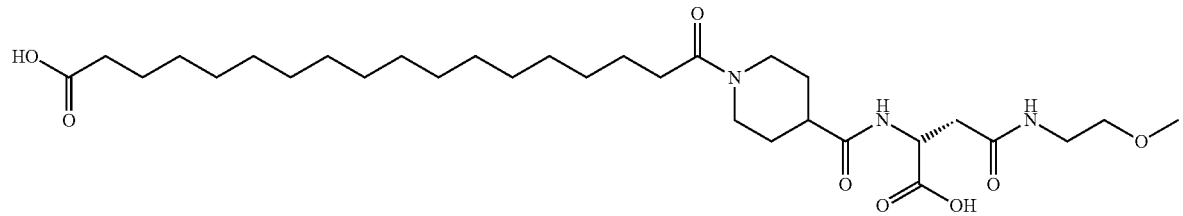

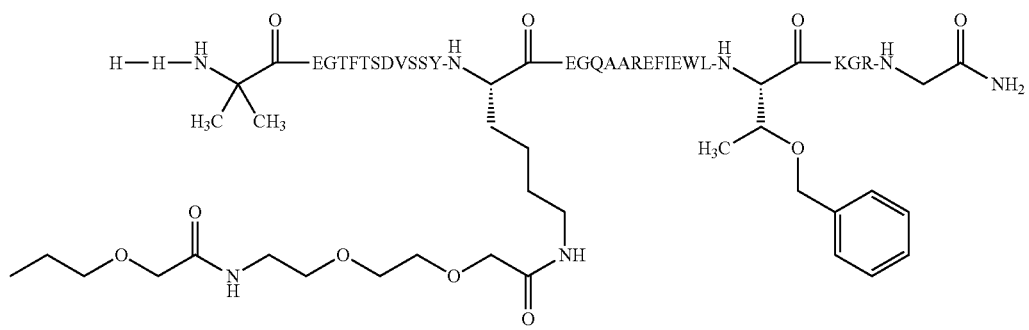

Preparation method: A
HPLC method B6:
RT=32.49 min
LCMS: m/z=1459.0 $(M+3H)^{3+}$
Calculated MW=4375.0

Example 9

N-epsilon30{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Lys30]GLP-1-(7-37)

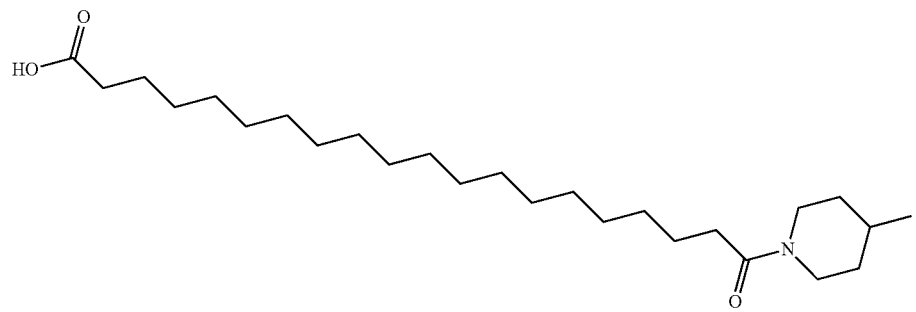

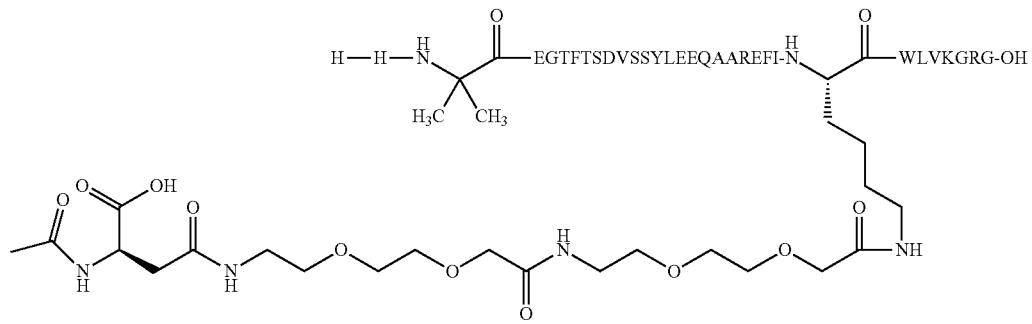

Preparation method: The peptide was prepared on an Apex396 from Advanced Chemtech and the final product was characterized by analytical HPLC and MALDI-MS.
HPLC (method I): see the description above
RT=27.6 min
MALDI-MS: 4367.9

Example 10

N-epsilon31{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8, Glu22, Arg26,Lys 31]GLP-1-(7-37)

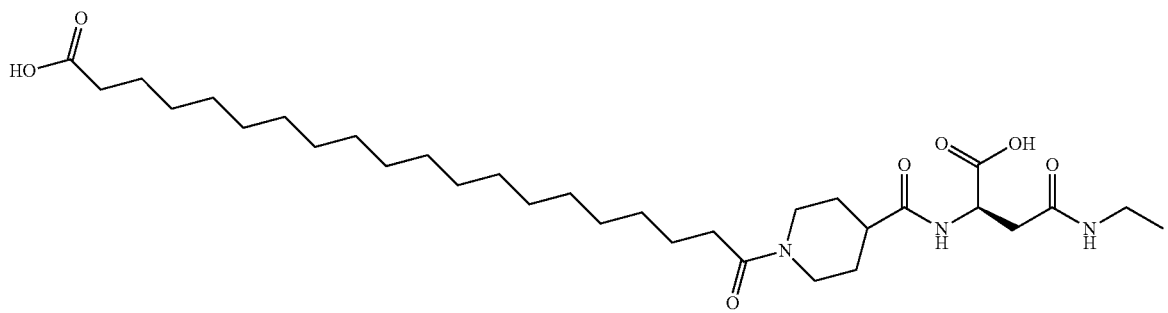

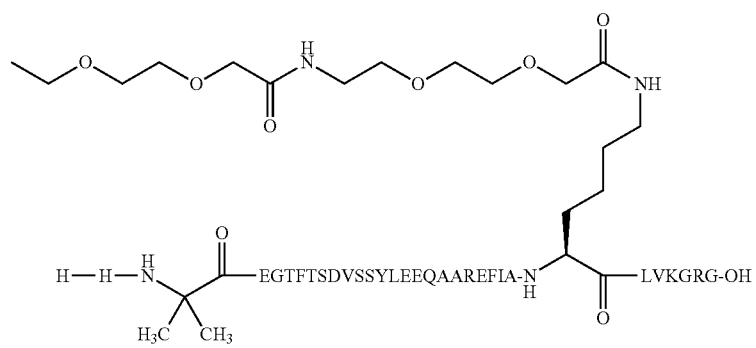

Preparation method: The peptide was prepared on an Apex396 from Advanced Chemtech and the final product was characterized by analytical HPLC and MALDI-MS.

HPLC (method A): see the description above
RT=28.4 min
MALDI-MS: 4252.5

Example 11

N-ε[20]({2-[2-(2-{2-[2-((R)-3-carboxy-3-{[1-(17-carboxyheptadecanoyl)piperidine-4-carbonyl]amino}propionylamino)ethoxy]ethoxy}acetylamino)ethoxy]ethoxy}acetyl) [Aib[8], Lys[20], Arg[26], 2-Naphtylalanine[28], Glu[30]]GLP-1(7-37)amide

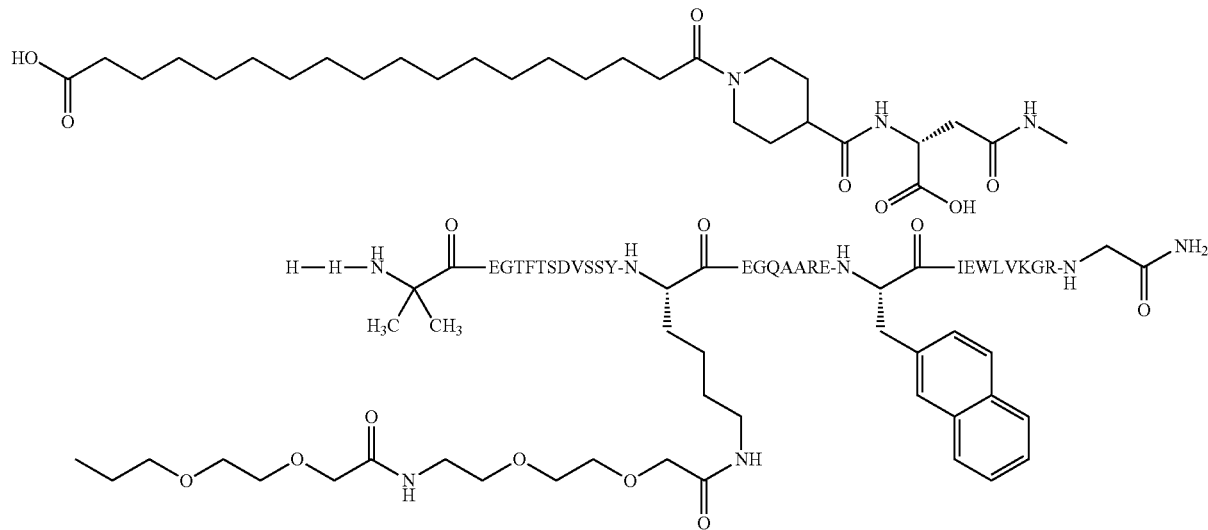

Preparation method: A
HPLC method B6:
RT=32.31 min
LCMS: m/z=1445.0 (M+3H)$^{3+}$
Calculated MW=4332.9

Example 12

[Aib8, Glu22, Arg26, Arg34]GLP-1-(7-37)Lys[2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl]amide

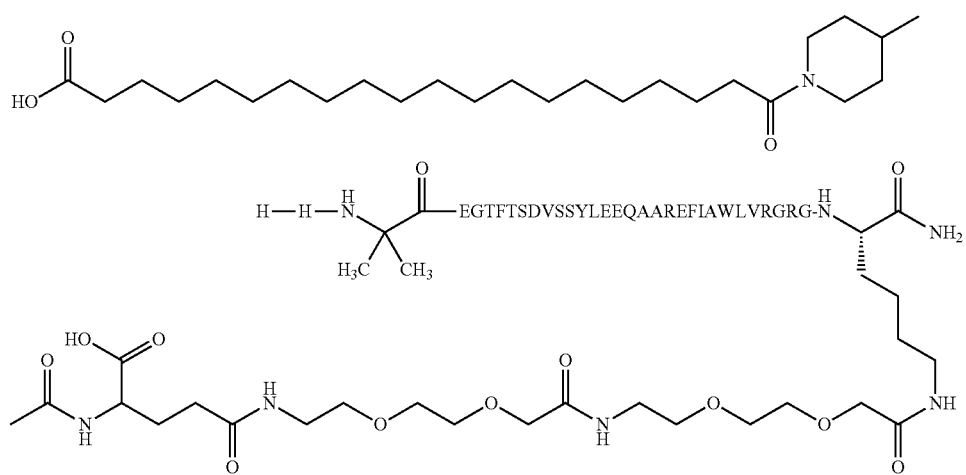

Preparation method: A
HPLC method 02_B4_4:
RT=9.73 min
LCMS: m/z=(M/3)+1=1494.9 and (M/4)+1=1120.9; (Sciex100 API)
Calculated MW=4480.1

Example 13

N-$\epsilon^{20}$({2-[2-(2-{2-[2-((R)-3-carboxy-3-{[1-(17-carboxyheptadecanoyl)piperidine-4-carbonyl]amino}propionylamino)ethoxy]ethoxy}acetylamino)ethoxy]ethoxy}acetyl) [Aib$^8$, Lys$^{20}$,Arg$^{26}$, 2-Naphtylalanine$^{12}$, Glu$^{30}$]GLP-1-(7-37)amide

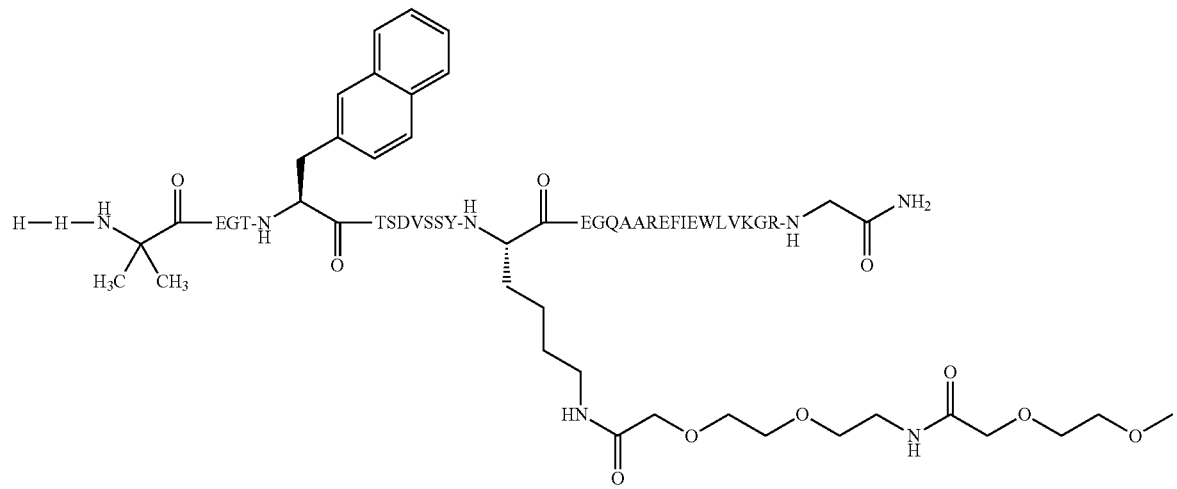

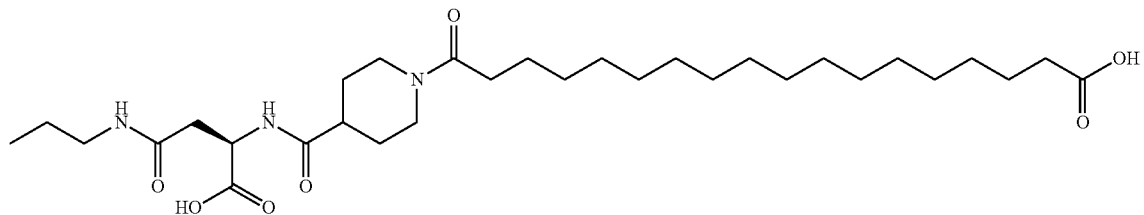

Preparation method: A
HPLC method B6:
RT=30.70 min
LCMS: m/z=1084.0 (M+4H)$^{4+}$
Calculated MW=4332.9

Example 14

[DesaminoHis7,Glu22,Arg26,Arg34]GLP-1-(7-37)
Lys[2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl]amide

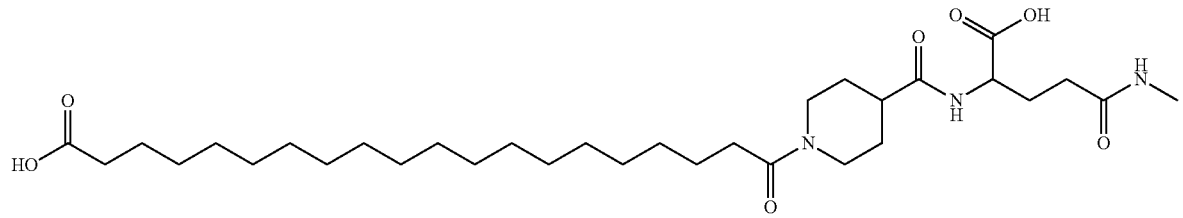

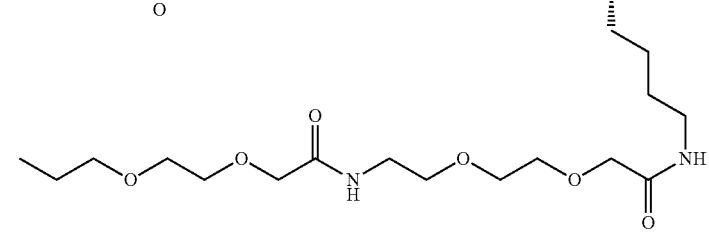

Preparation method: A, and Example 72
HPLC method 02_B6__4:
RT=9.95 min
LCMS: m/z=1484. (M+3H)$^{3+}$
Calculated MW=4451.1

Example 15

N-epsilon31-(2-{2-[2-(2-{2-[2-((S)-3-Carboxy-3-{[1-(19-carboxy-nonadecanoyl)piperidine-4-carbonyl]amino}propionylamino)ethoxy]ethoxy}acetylamino)ethoxy]ethoxy}acetyl)[Aib8,Glu22,Arg26,Lys31,Arg34]GLP-1-(7-37)

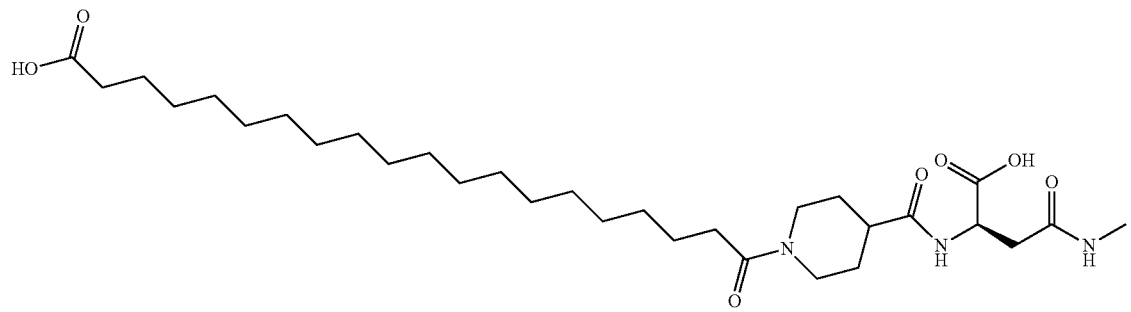

-continued

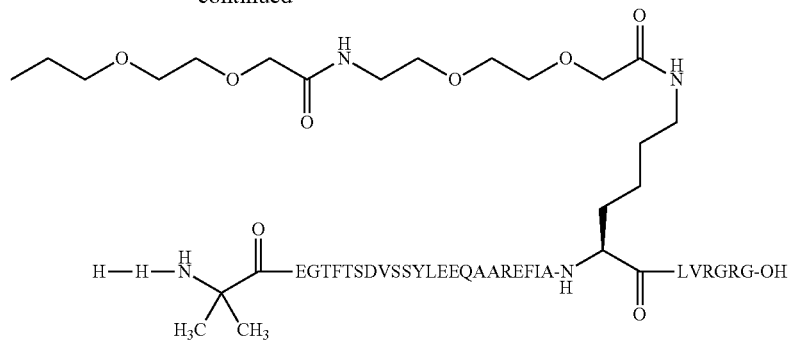

Preparation method: B, and Example 72
The peptide was eluted at 66% acetonitrile.
Structure confirmed by MALDI-MS
Calculated MW=4280.9

Example 16

N-epsilon26-[(S)-4-Carboxy-4-({trans-4-[(19-carboxynonadecanoylamino)methyl]cyclohexanecarbonyl}amino)butyryl][Aib8,Arg34] GLP-1-(7-37)

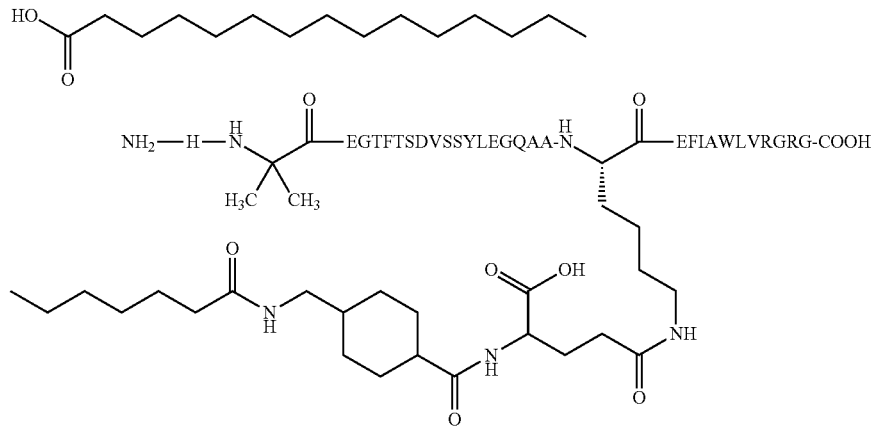

Preparation method: B, and Example 72
The peptide was eluted at 69% acetonitrile.
Structure confirmed by MALDI-MS
Calculated MW=3990.6

Example 17

N-epsilon26-{4-[(S)-4-Carboxy-4-({trans-4-[(19-carboxynonadecanoylamino)methyl]cyclohexanecarbonyl}amino)butyrylamino]butyryl}[Aib 8,Arg34]GLP-1-(7-37)

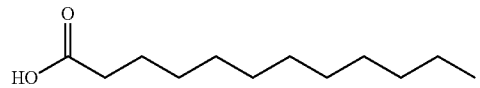

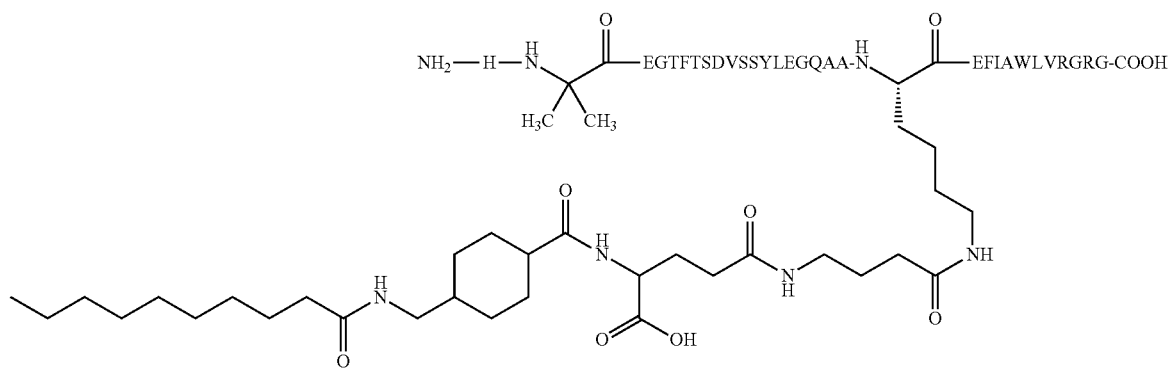

Preparation method: B
The peptide was eluted at 70% acetonitrile.
Structure confirmed by MALDI-MS
Calculated MW=4075.7

Example 18

N-epsilon26-[2-(2-{2-[(S)-4-Carboxy-4-({trans-4-[(19-carboxy-nonadecanoylamino)methyl]cyclohexanecarbonyl}amino)butyrylamino]ethoxy}ethoxy) acetyl][Aib8,Arg34]GLP-1-(7-37)

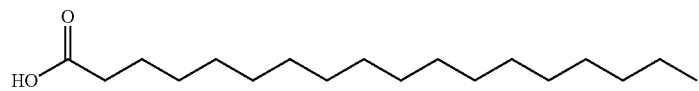

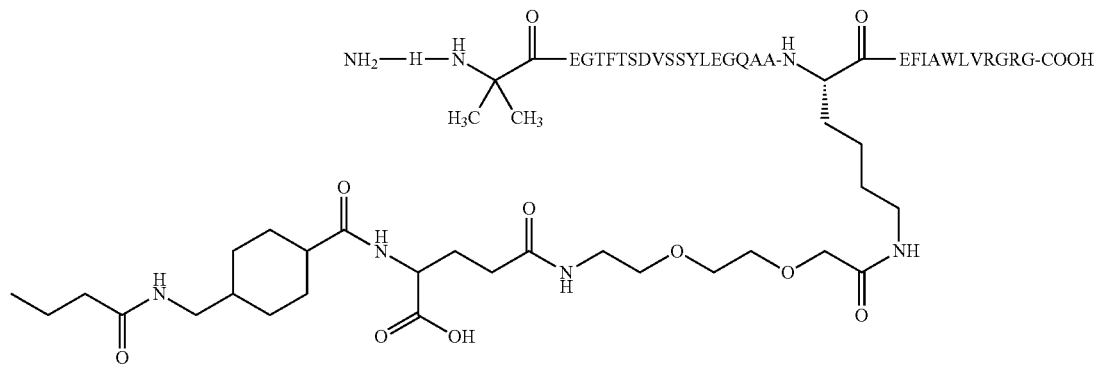

Preparation method: B, and Example 72
The peptide was eluted at 68% acetonitrile.
Structure confirmed by MALDI-MS
Calculated MW=4135.8

Example 19

N-epsilon26-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Arg34]GLP-1-(7-37)-amide

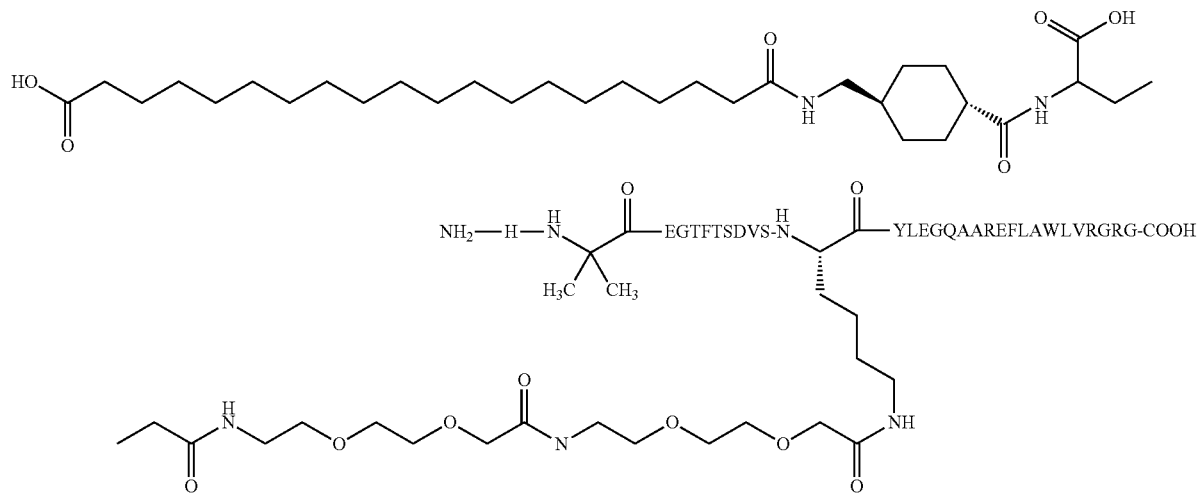

Preparation method: B, and Example 72
The peptide was eluted at 70% acetonitrile.
Structure confirmed by MALDI-MS
Calculated MW=4279.9

Example 20

N-epsilon18-{2-(2-(2-(2-[2-(2-[(S)-4-Carboxy-4-({4-[(19-carboxynonadecanoylamino)methyl]cyclohexanecarbonyl}amino)butanoylamino]ethoxy)ethoxy]acetyl)ethoxy)ethoxy)acetyl}[Aib8,Lys18,Arg26,Arg34]GLP-1(7-37)

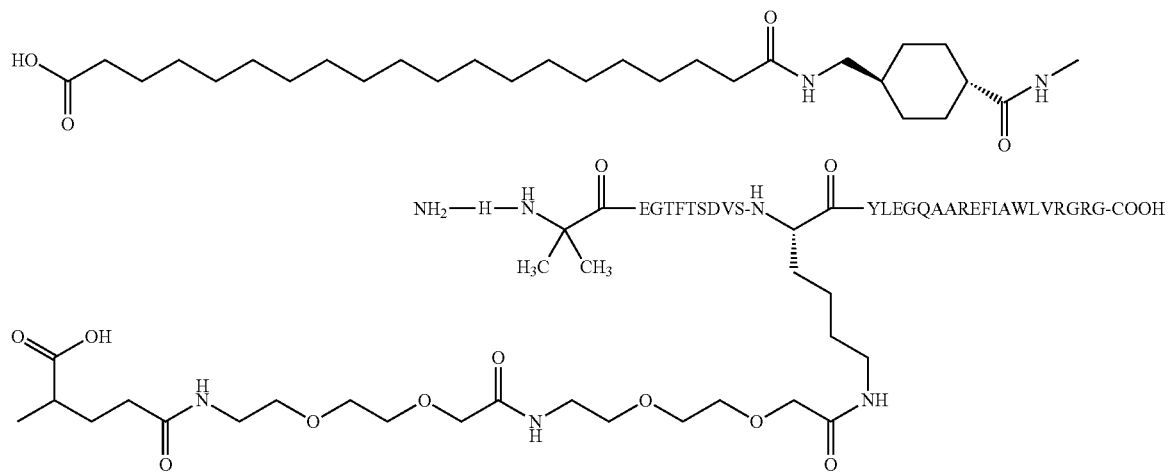

Preparation method: The peptide was prepared on an Apex396 from Advanced Chemtech and the final product was characterized by analytical HPLC and MALDI-MS.

HPLC (method B6):

RT=34.1 min

Example 21
N-ε[20]-[2-(2-[2-(2-[2-(2-((S)-4-[trans-4-([19-Carboxynonadecanoylamino]methyl)cyclohexylcarbonylamino]-4-carboxybutanoylamino)ethoxy)ethoxy]acetylamino)ethoxy]ethoxy)acetyl][desaminoHis[1], Lys[20], Ser(O-benzyl)[33], Ser(O-benzyl)[39]] exendin (1-39)
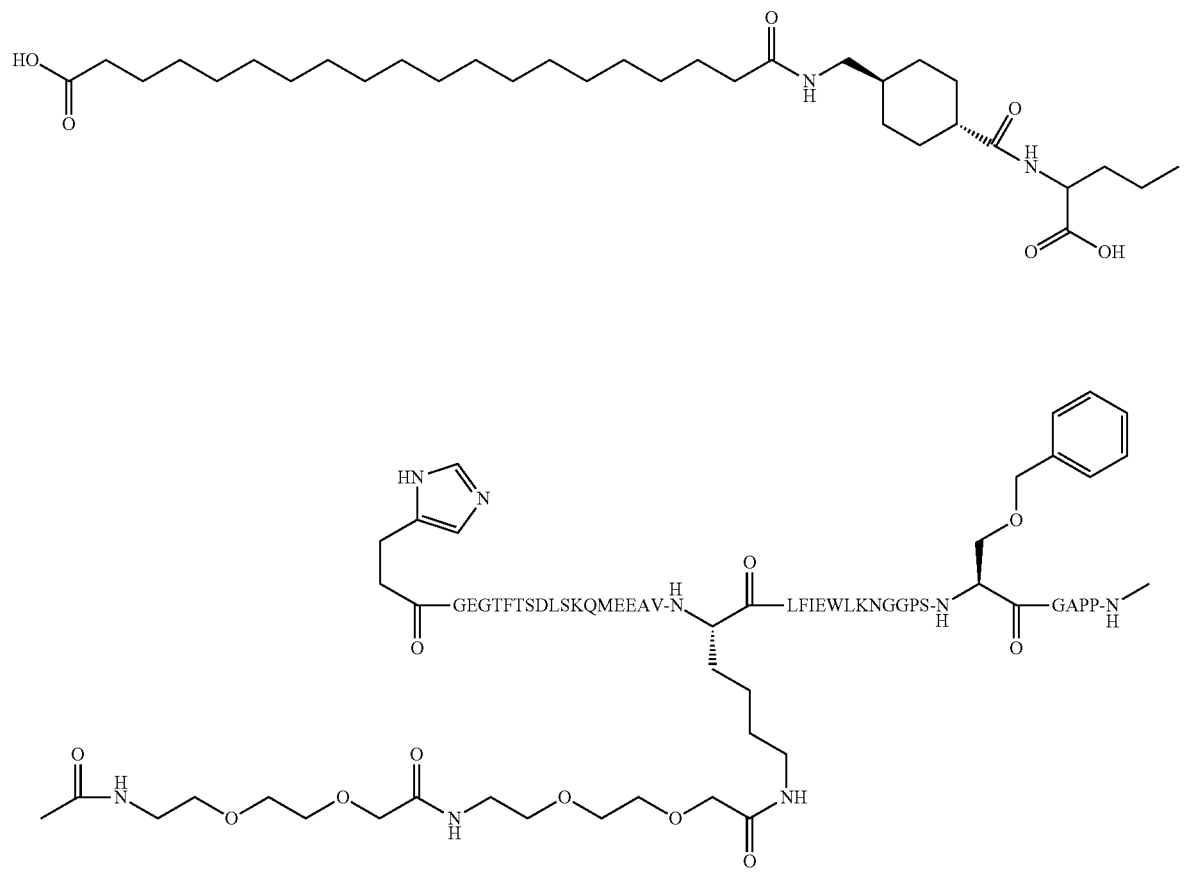
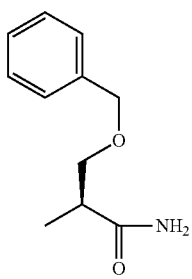
Preparation method: A
HPLC method B6:
RT=39.22 min
LCMS: m/z=1736.9 (M+3H)$^{3+}$
Calculated MW=5207.0

Example 22

[Aib8,Glu22,Arg26,Arg34]GLP-1-(7-37)Lys[2-(2-
[2-(2-[2-(2-((S)-3-[4-([19-Carboxynonadecanoy-
lamino]methyl)cyclohexylcarbonylamino]-3-carbox-
ypropionylamino)ethoxy)ethoxy]acetylamino)
ethoxy]ethoxy)acetyl]amide

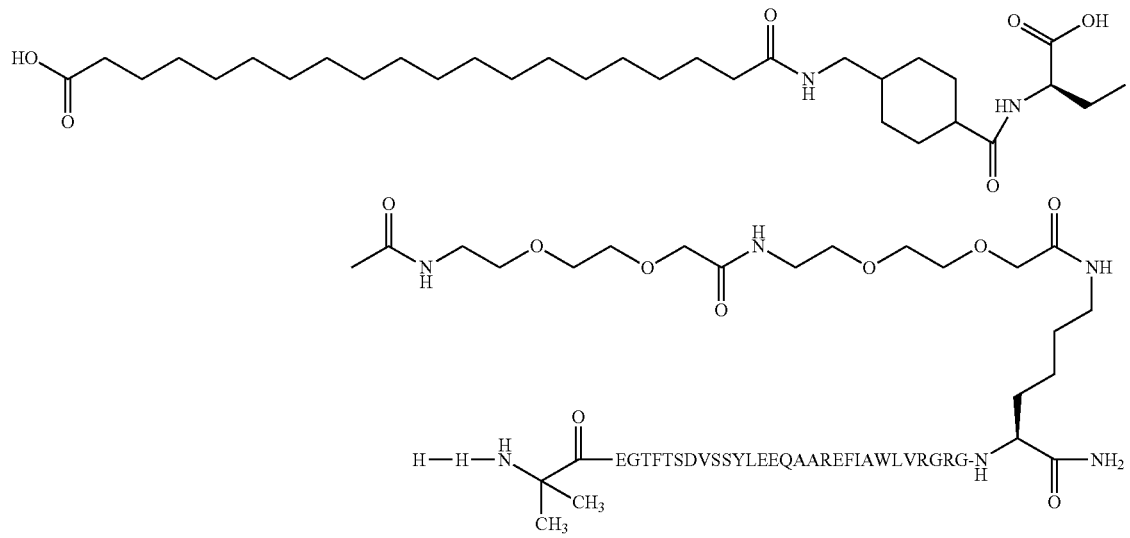

Preparation method: B
The peptide was eluted at 68% acetonitrile.
Structure confirmed by MALDI-MS
Calculated MW=4494.2

Example 23

N-epsilon37-[2-(2-{2-[2-(2-{2-[(S)-4-Carboxy-4-
({trans-4-[(19-carboxy-nonadecanoylamino)methyl]
cyclohexanecarbonyl}amino)butyrylamino]
ethoxy}ethoxy)acetylamino]ethoxy}ethoxy)acetyl]
[Aib8,Glu22,Arg26,Arg34,Lys37]GLP-1-(7-37)
amide

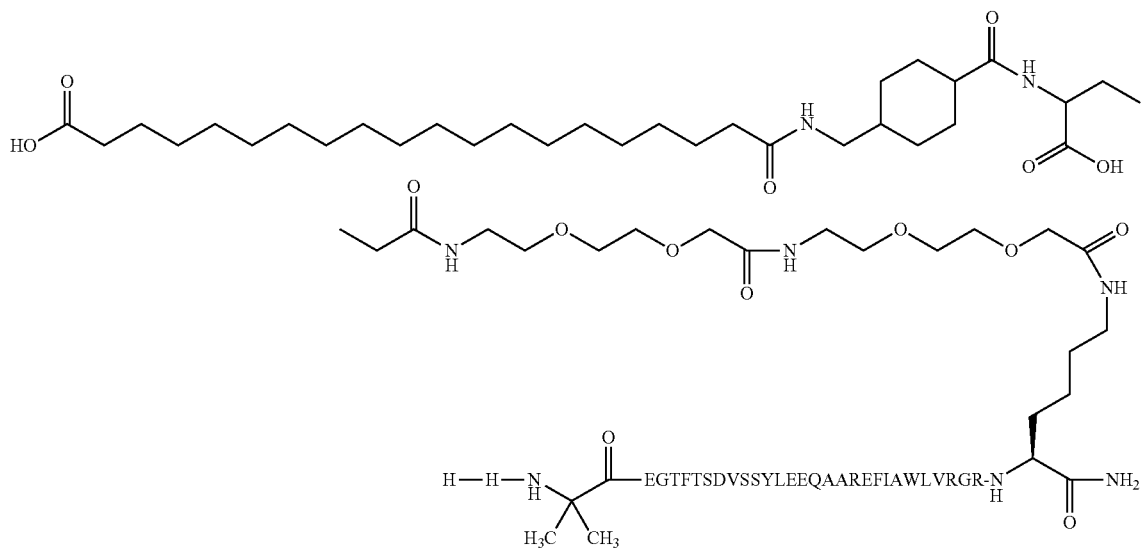

Preparation method: B
The peptide was eluted at 67% acetonitrile.
Structure confirmed by MALDI-MS
Calculated MW=4451.1

Example 24

N-epsilon37-[2-(2-{2-[2-(2-{2-[(S)-4-Carboxy-4-
({trans-4-[(19-carboxy-nonadecanoylamino)methyl]
cyclohexanecarbonyl}amino)butyrylamino]
ethoxy}ethoxy)acetylamino]ethoxy}ethoxy)acetyl]
[DesaminoHis7,Glu22,Arg26,Arg34,Lys37]GLP-1-
(7-37)amide

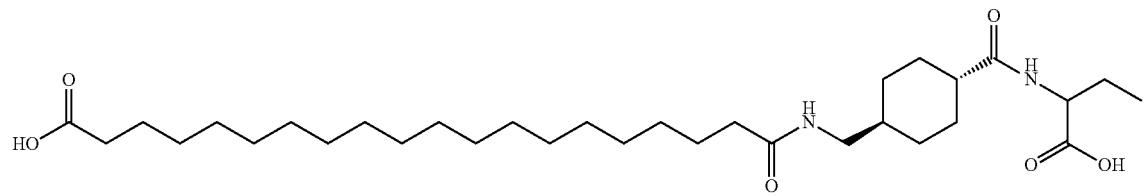

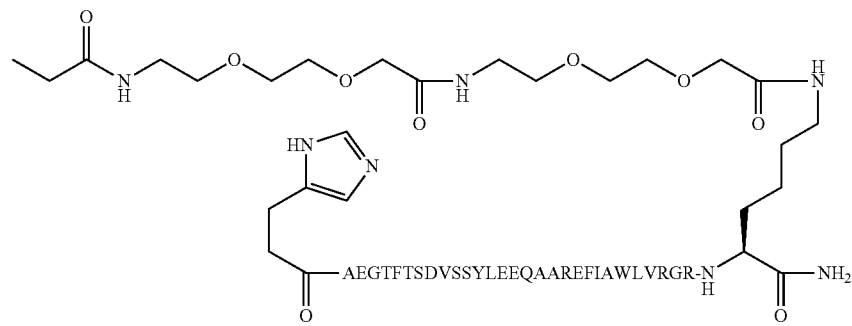

Preparation method: B
The peptide was eluted at 68% acetonitrile.
Structure confirmed by MALDI-MS
Calculated MW=4422.1

Example 25

N-epsilon37-[2-(2-{2-[2-(2-{2-[(S)-4-Carboxy-4-
({4-[(trans-[9-carboxy-nonadecanoylamino)methyl]
cyclohexanecarbonyl}amino)butyrylamino]
ethoxy}ethoxy)acetylamino]ethoxy}ethoxy)acetyl]
[DesaminoHis7,Arg26,Arg34,Lys37]GLP-1-(7-37)
amide

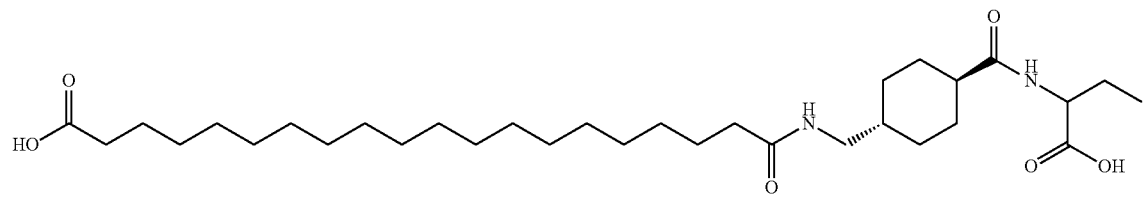

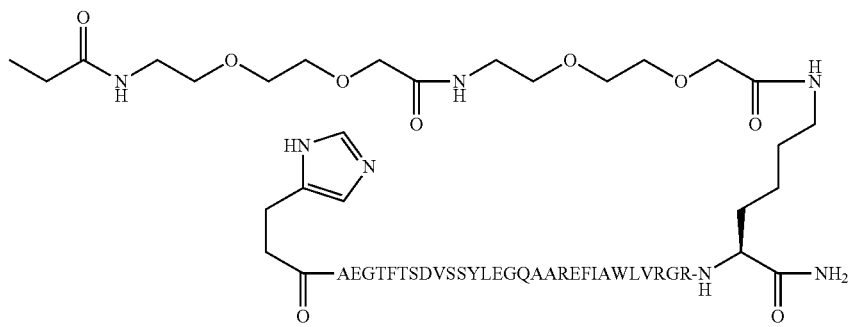

Preparation method: B
The peptide was eluted at 68% acetonitrile.
Structure confirmed by MALDI-MS
Calculated MW=4350.0

Example 26

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37)

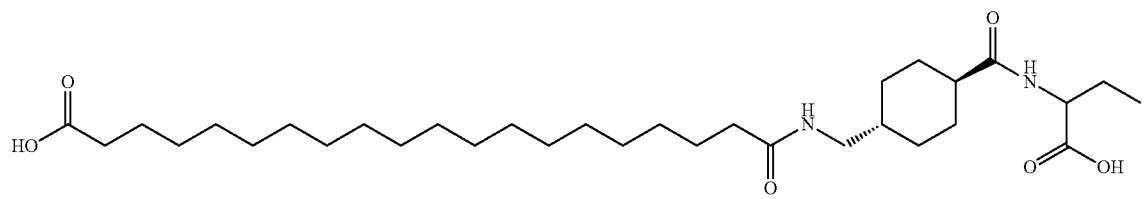

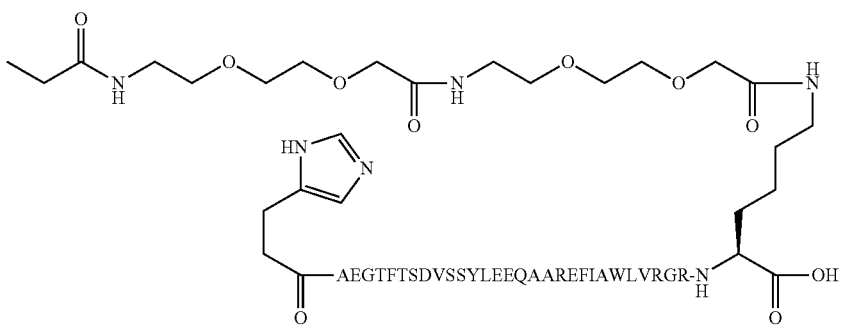

Preparation method: B
The peptide was eluted at 69% acetonitrile.
Structure confirmed by MALDI-MS
Calculated MW=4423.1

Example 27

[DesaminoHis7,Glu22,Arg26,Arg34]GLP-1-(7-37)Lys[2-(2-{2-[2-(2-{2-[4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl]-amide

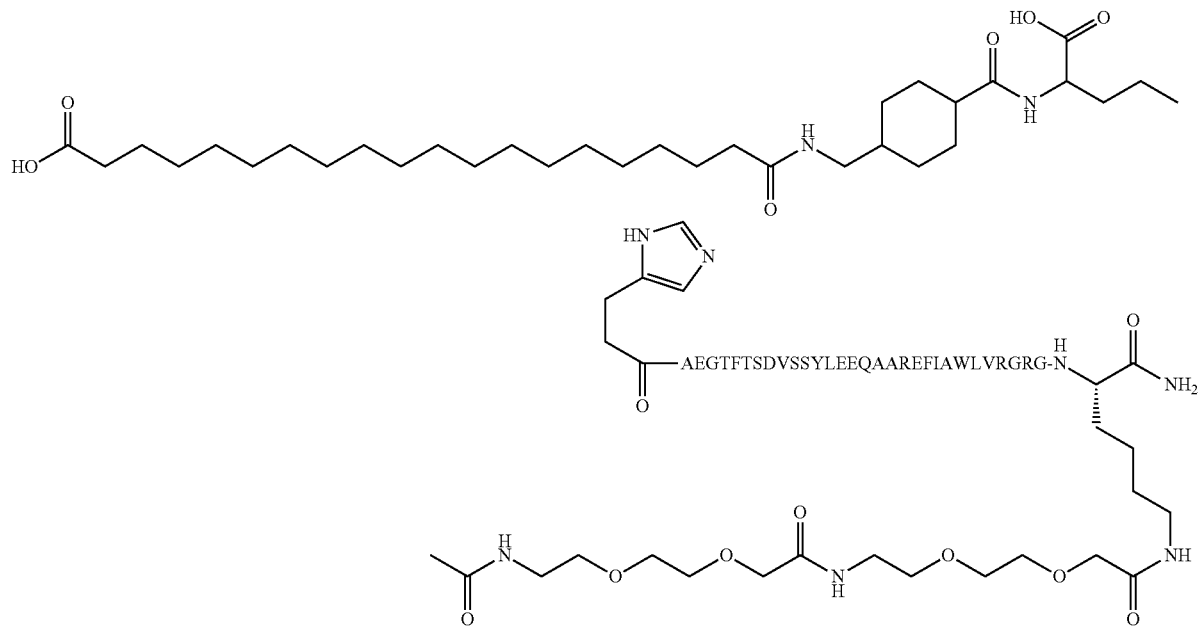

Preparation method: B
The peptide was eluted at 68% acetonitrile.
Structure confirmed by MALDI-MS
Calculated MW=4479.1

Example 28

[desaminoHis$^7$,Arg$^{26}$,Arg$^{34}$]GLP-1-(7-37)Lys[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl]amide

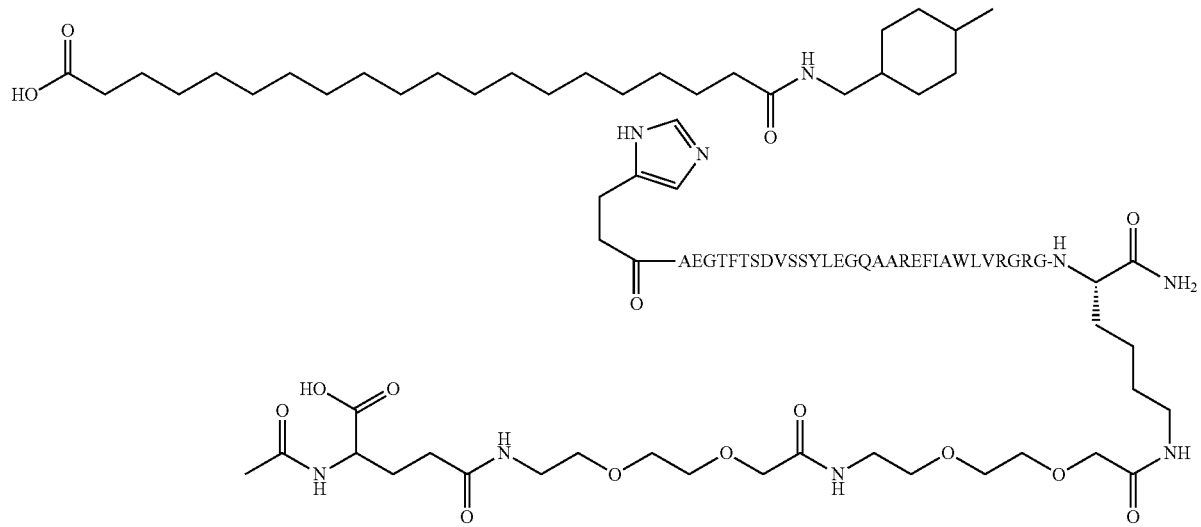

Preparation method: A
HPLC method B6:
RT=35.25 min
LCMS: m/z=1469.0 (M+3H)$^{3+}$
Calculated MW=4407.1
Example 29
N-epsilon26[2-(2-{2-[2-(2-{2-[(S)-4-Carboxy-4-({4-[(19-carboxy-nonadecanoylamino)methyl]cyclohexanecarbonyl}amino)butyrylamino]ethoxy}ethoxy)acetylamino]ethoxy}ethoxy)acetyl [Aib8, Lys 26] GLP-1 (7-37)amide
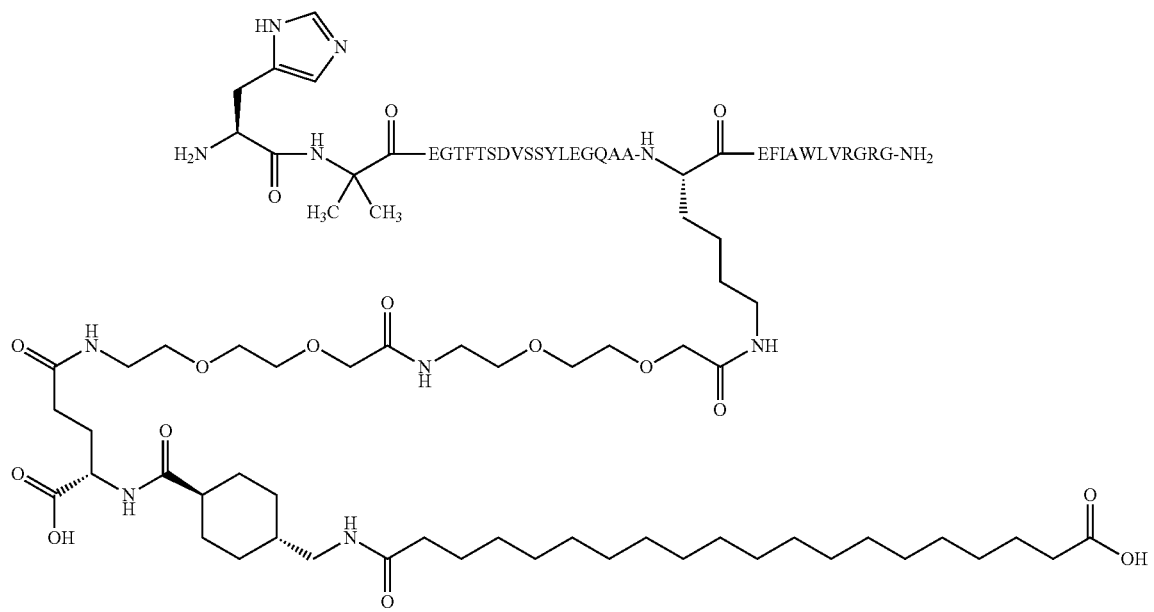
Preparation method: Method C
HPLC method 01_B4_2:
RT=11.26 min
LCMS: m/z=XX (M+4H)$^{4+}$1071
Calculated MW=4279.9

Example 30

N-epsilon26 [2-(2-[2-(2-[2-(2-((S)-2-[trans-4-((9-Carboxynonadecanoylamino]methyl) cyclohexylcarbonylamino]-4-carboxybutanoylamino)ethoxy) ethoxy]acetylamino)ethoxy]ethoxy)acetyl][Aib8, Lys26] GLP-1 (7-37)amide

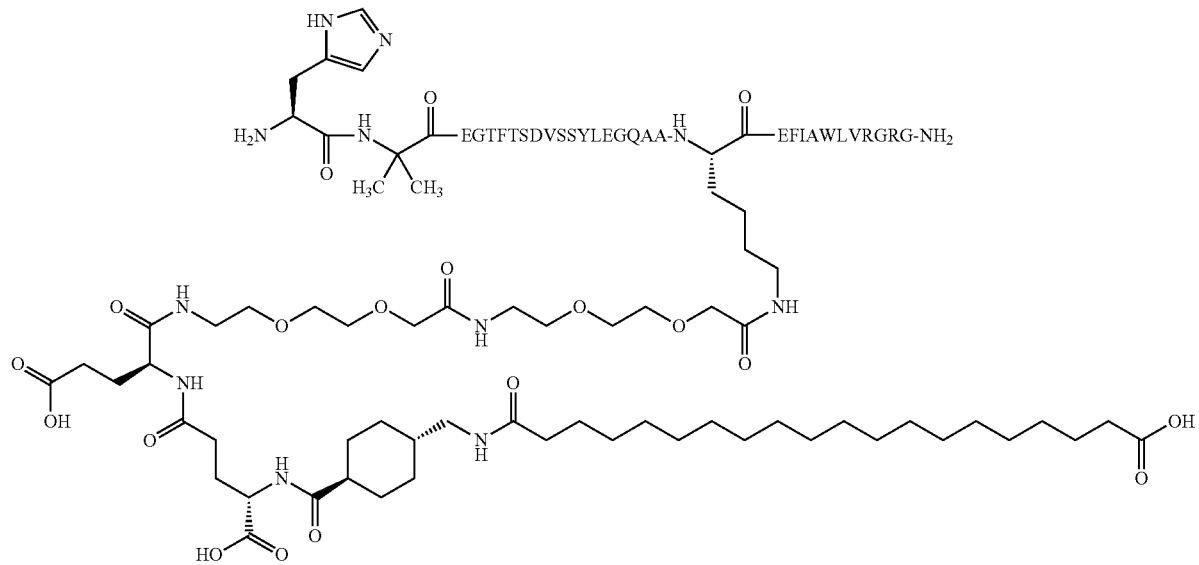

Preparation method: Method C
HPLC method 01_B4_2:
RT=11.11 min
LCMS: m/z=XX (M+4H)$^{4+}$1103
Calculated MW=4409.1

Example 31

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Arg26,Arg34,Lys37]GLP-1-(7-37)

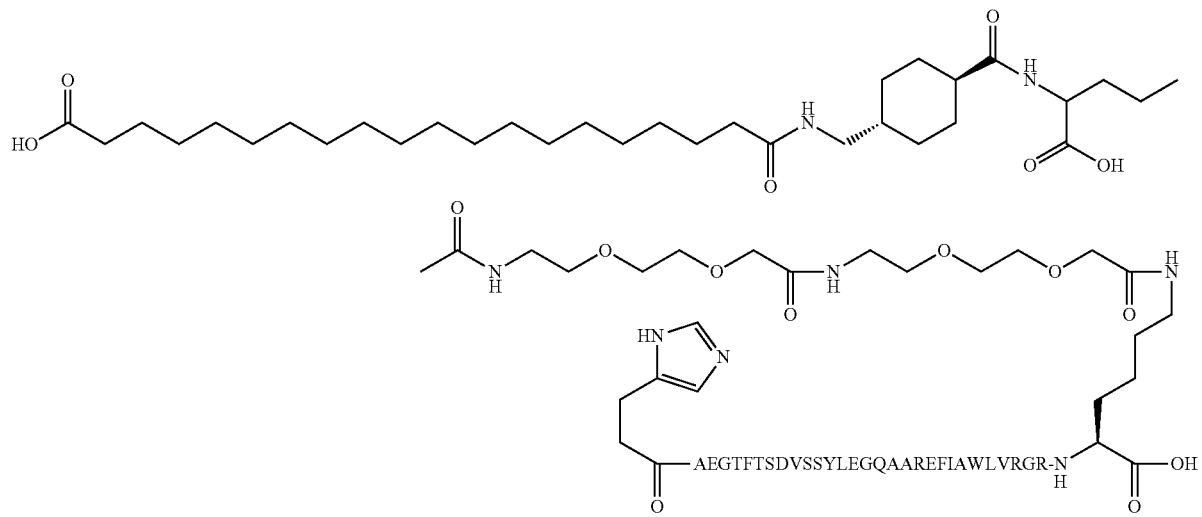

Preparation method: B
The peptide was eluted at 71% acetonitrile.
Structure confirmed by MALDI-MS
Calculated MW=4351.0

Example 32

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Glu30,Arg34,Lys37]GLP-1-(7-37)

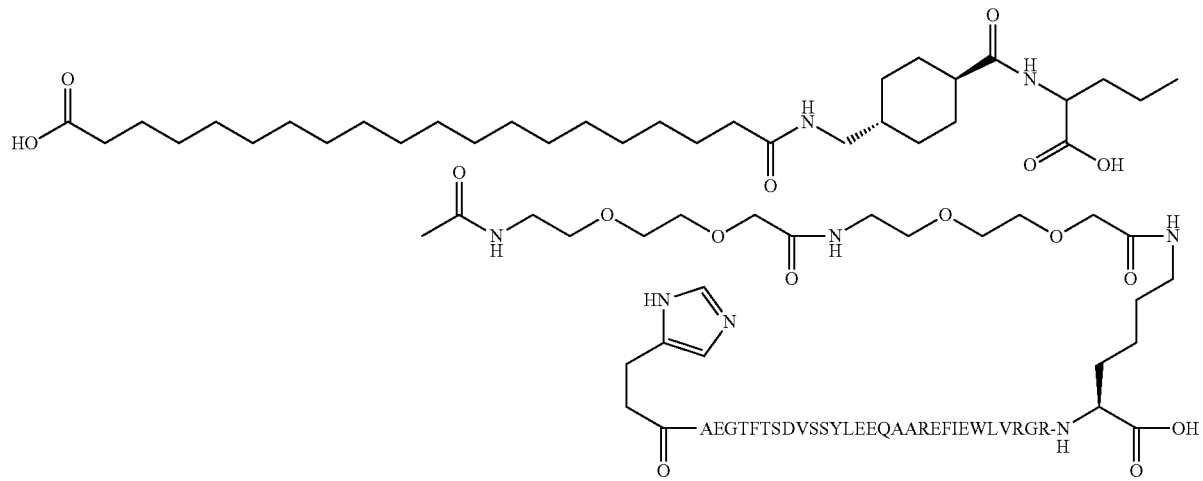

Preparation method: B
The peptide was eluted at 68% acetonitrile.
Structure confirmed by MALDI-MS
Calculated MW=4481.1

Example 33

N-epsilon26-[2-(2-{2-[(S)-4-Carboxy-4-((S)-4-carboxy-4-{4-[4-(16-(1H-tetrazol-5-yl)-hexadecanoyl-sulfamoyl)butyrylamino]-butyrylamino}butyrylamino)butyrylamino]ethoxy}ethoxy)acetyl][Aib8,Arg34]GLP-1-(7-37)

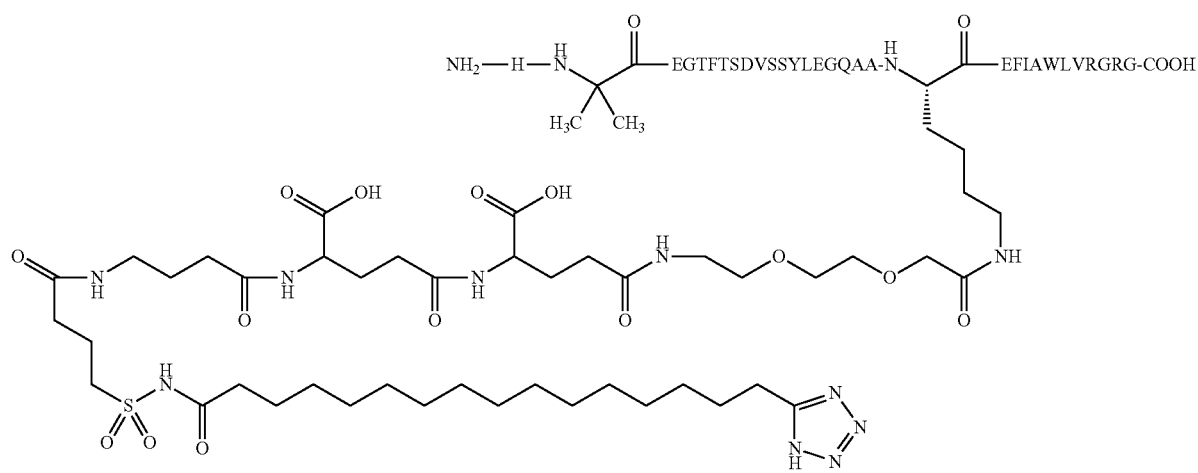

Preparation method: B
The peptide was eluted at 62% acetonitrile.
Structure confirmed by MALDI-MS
Calculated MW=4341.9

Example 34

N-epsilon26-[2-(2-{2-[(S)-4-Carboxy-4-((S)-4-carboxy-4-{12-[4-(16-(1H-tetrazol-5-yl)hexadecanoyl-sulfamoyl)butyrylamino]
dodecanoylamino}butyrylamino)butyrylamino]
ethoxy}ethoxy)acetyl][Aib8,Arg34]GLP-1-(7-37)

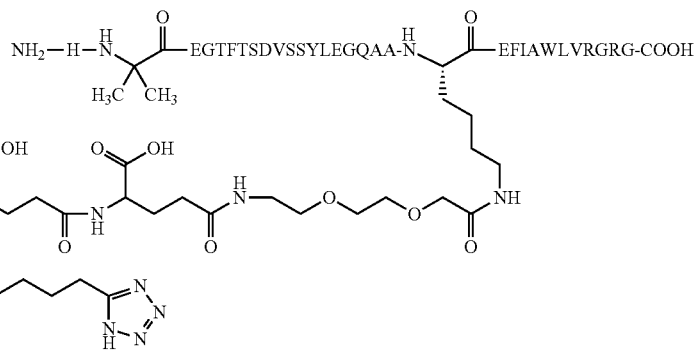

Preparation method: B
The peptide was eluted at 65% acetonitrile.
Structure confirmed by MALDI-MS
Calculated MW=4454.1

Example 35

N-epsilon26-[2-(2-{2-[(S)-4-Carboxy-4-((S)-4-carboxy-4-{6-[4-(16-(1H-tetrazol-5-yl)hexadecanoyl-sulfamoyl)butyrylamino]
hexanoylamino}butyrylamino)butyrylamino]
ethoxy}ethoxy)acetyl][Aib8,Arg34]GLP-1-(7-37)

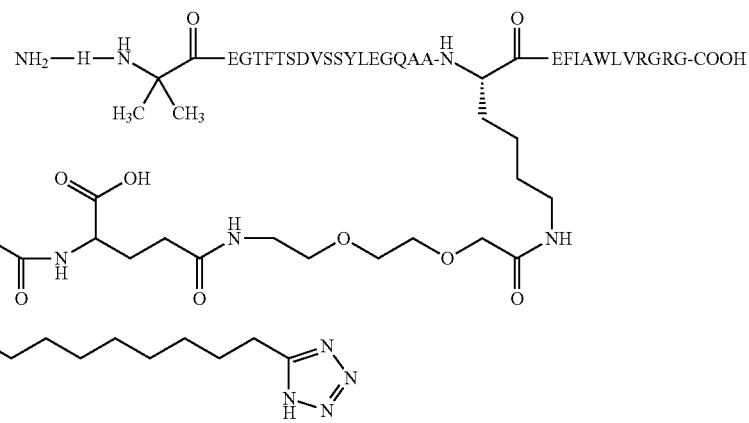

Preparation method: B
The peptide was eluted at 62% acetonitrile.
Structure confirmed by MALDI-MS
Calculated MW=4370.0

Example 36

N-epsilon26-[2-(2-{2-[(S)-4-Carboxy-4-((S)-4-carboxy-4-{4-[4-(16-(1H-tetrazol-5-yl)hexadecanoylsulfamoyl)butyrylamino]butyrylamino}butyrylamino)butyrylamino]ethoxy}ethoxy)acetyl][Aib8,Arg34]GLP-1-(7-34)

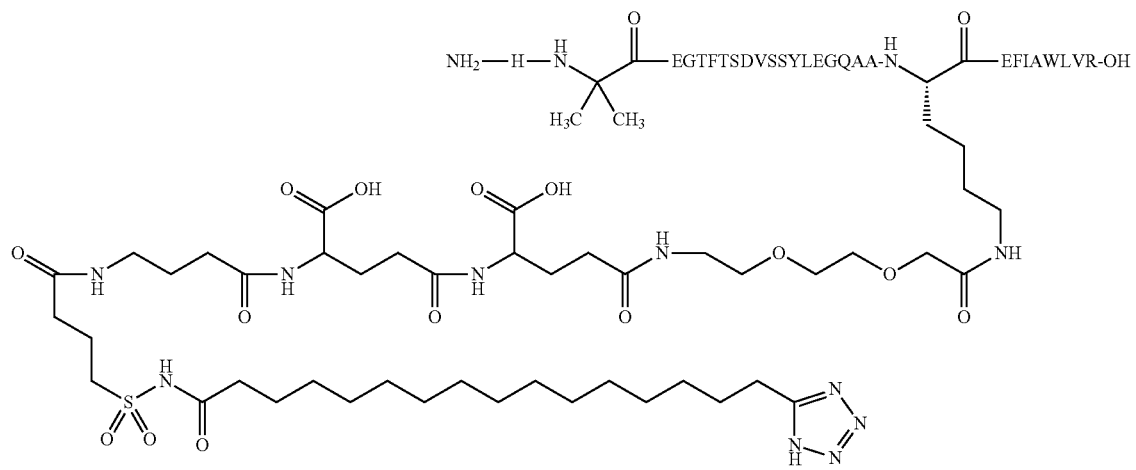

Preparation method: B
The peptide was eluted at 66% acetonitrile.
Structure confirmed by MALDI-MS
Calculated MW=4071.6

Example 37

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]-dodecanoylamino}butyrylamino)butyrylamino]ethoxy}ethoxy)acetyl][Aib8,Arg34]GLP-1-(7-34)

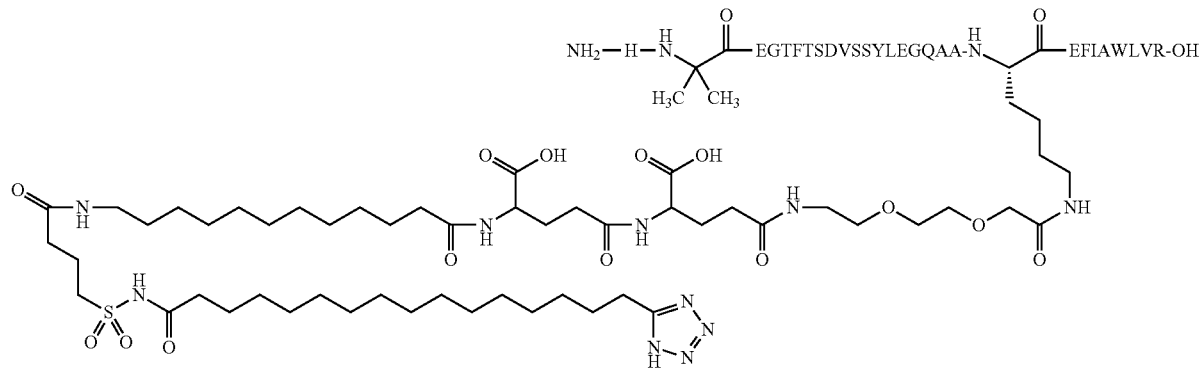

Preparation method: B
The peptide was eluted at 68% acetonitrile.
Structure confirmed by MALDI-MS
Calculated MW=4183.8

Example 38

N-epsilon26-[2-(2-{2-[(S)-4-Carboxy-4-((S)-4-carboxy-4-{6-[4-(16-(1H-tetrazol-5-yl)hexadecanoyl-sulfamoyl)butyrylamino]hexanoylamino}butyrylamino)butyrylamino]ethoxy}ethoxy)acetyl][Aib8,Arg34]GLP-1-(7-34)

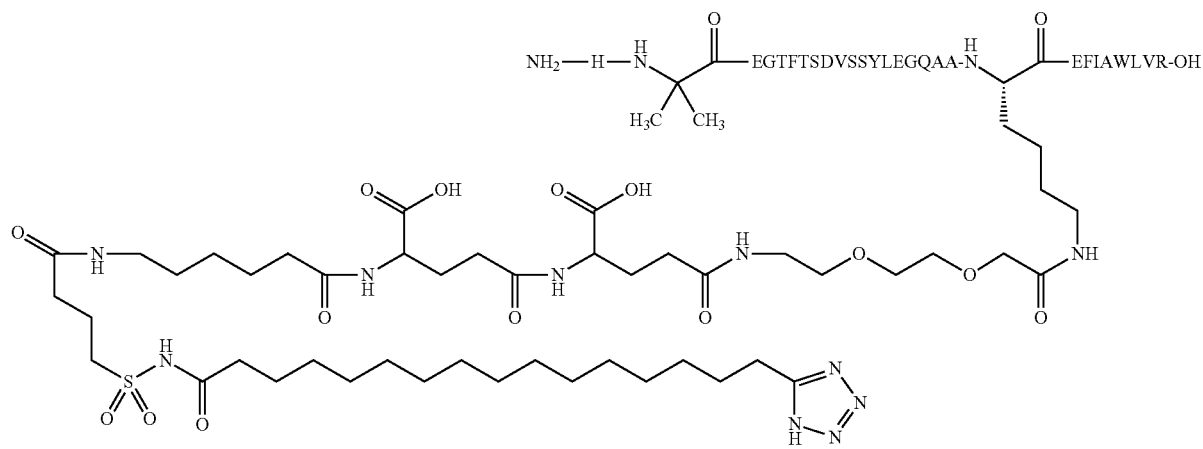

Preparation method: B
The peptide was eluted at 67% acetonitrile.
Structure confirmed by MALDI-MS
Calculated MW=4099.7

Example 39

N-epsilon26-[2-(2-{2-[(S)-4-Carboxy-4-((S)-4-carboxy-4-{12-[4-(16-(1H-tetrazol-5-yl)hexadecanoyl-sulfamoyl)butyrylamino]dodecanoylamino}butyrylamino)butyrylamino]ethoxy}ethoxy)acetyl][Aib8,Arg34]GLP-1-(7-35)

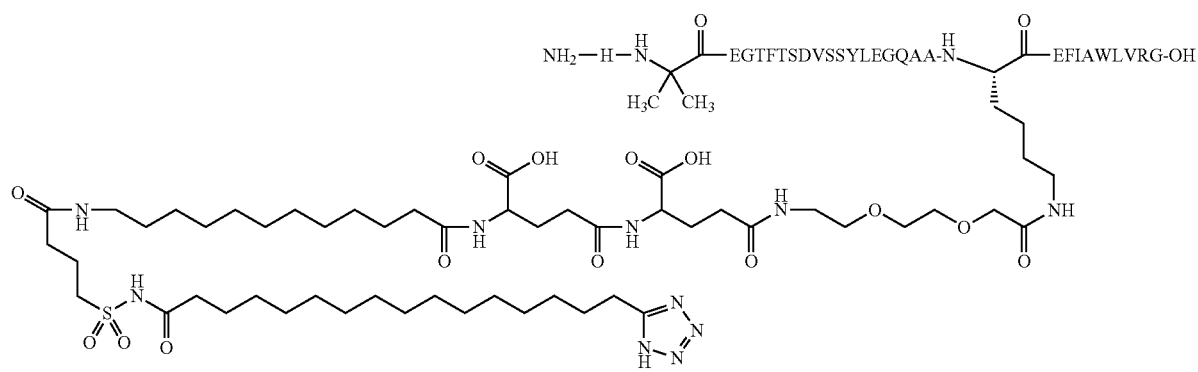

Preparation method: B
The peptide was eluted at 70% acetonitrile.
Structure confirmed by MALDI-MS
Calculated MW=4240.9

Example 40

N-epsilon26-[2-(2-{2-[(S)-4-Carboxy-4-((S)-4-carboxy-4-{6-[4-(16-(1H-tetrazol-5-yl)hexadecanoyl-sulfamoyl)butyrylamino]hexanoylamino}butyrylamino)butyrylamino]ethoxy}ethoxy)acetyl][Aib8,Arg34]GLP-1-(7-35)

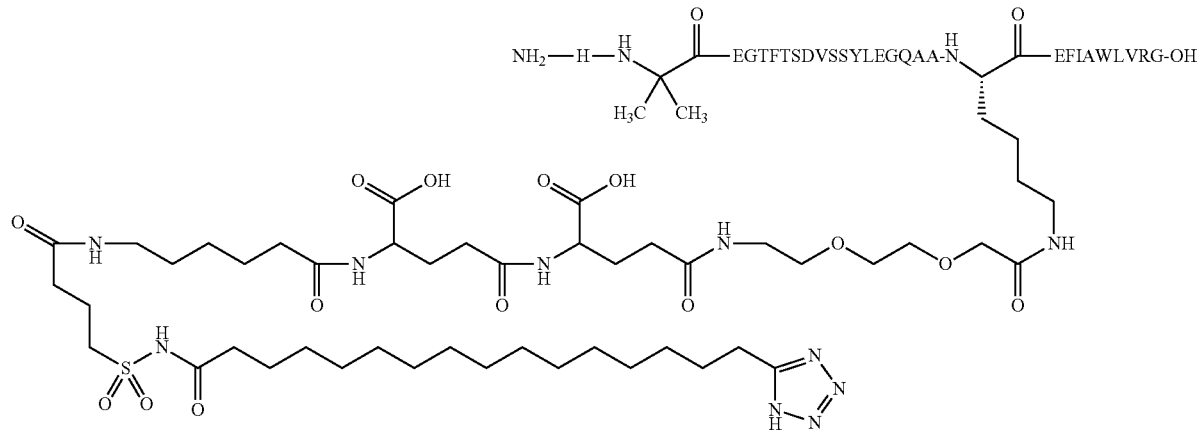

Preparation method: B
The peptide was eluted at 66% acetonitrile.
Structure confirmed by MALDI-MS
Calculated MW=4156.7

Example 41

N-epsilon26-[2-(2-{2-[(S)-4-Carboxy-4-((S)-4-carboxy-4-{6-[4-(16-(1H-tetrazol-5-yl)hexadecanoyl-sulfamoyl)butyrylamino]hexanoylamino}butyrylamino)butyrylamino]ethoxy}ethoxy)acetyl][Aib8,Arg34]GLP-1-(7-36) amide

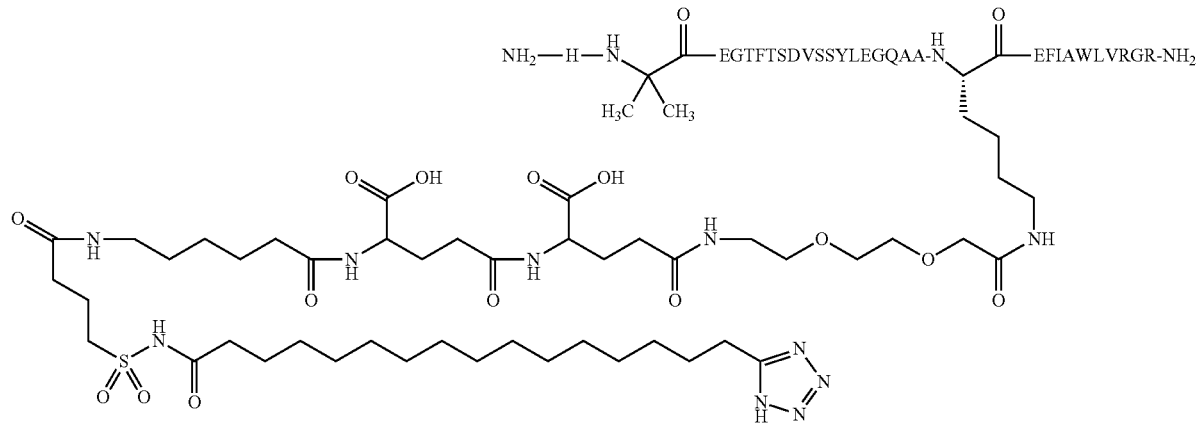

Preparation method: B
The peptide was eluted at 66% acetonitrile.
Structure confirmed by MALDI-MS
Calculated MW=4311.9

Example 42

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35)

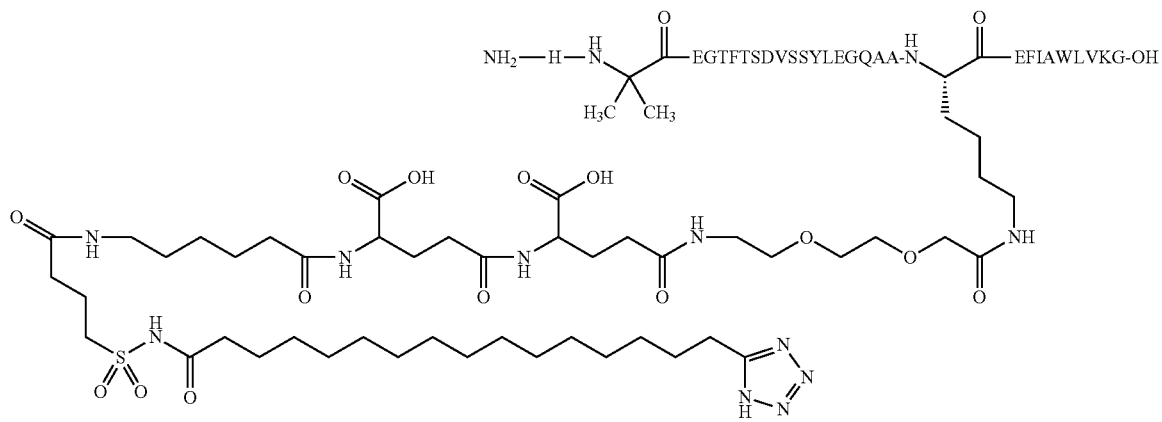

Preparation method: B
The peptide was eluted at 66% acetonitrile.
Structure confirmed by MALDI-MS
Calculated MW=4128.7

Example 43

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys33,Arg34]GLP-1-(7-34)

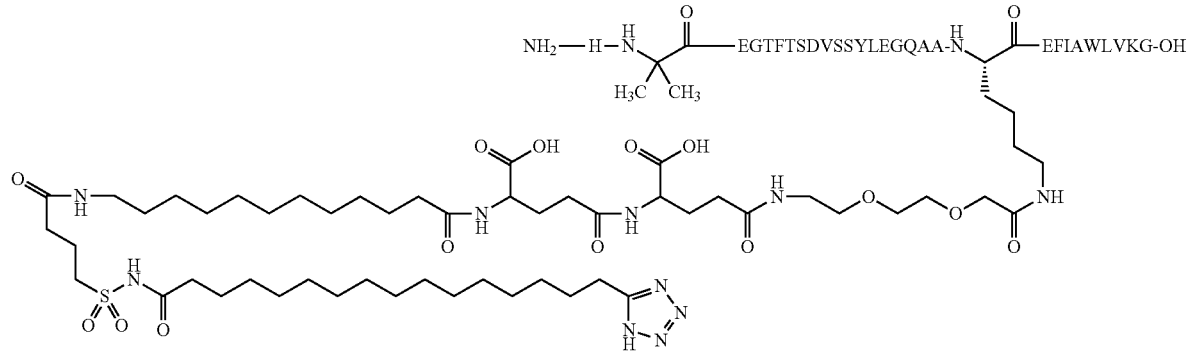

Preparation method: B
The peptide was eluted at 68% acetonitrile.
Structure confirmed by MALDI-MS
Calculated MW=4113.7

Example 44

N-epsilon26-[2-(2-{2-[(S)-4-Carboxy-4-((S)-4-carboxy-4-{12-[4-(16-(1H-tetrazol-5-yl)hexadecanoyl-sulfamoyl)butyrylamino]dodecanoylamino}butyrylamino)butyrylamino]ethoxy}ethoxy)acetyl][Aib8,Arg34]GLP-1-(7-36)amide

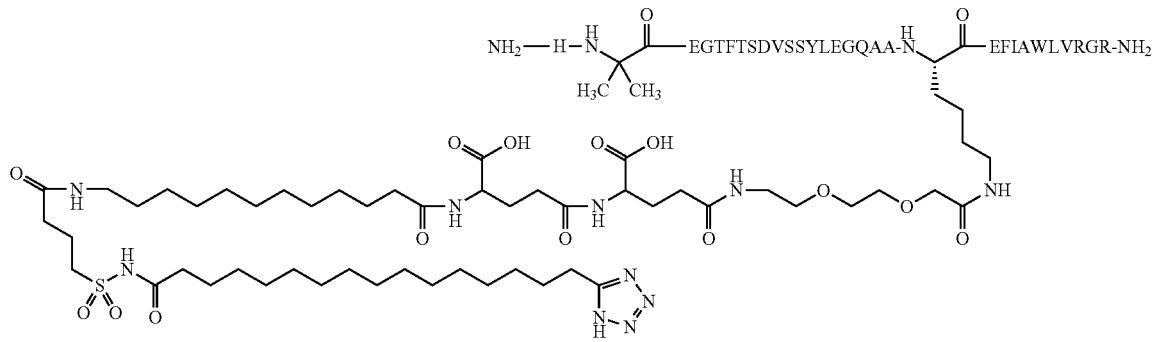

Preparation method: B
The peptide was eluted at 66% acetonitrile.
Structure confirmed by MALDI-MS
Calculated MW=4396.1

Example 45

N-epsilon26-[2-(2-{2-[2-(2-{2-[2-(2-{2-[2-(2-{2-[2-(2-{2-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetylamino]ethoxy}ethoxy)acetylamino]ethoxy}ethoxy)acetylamino]ethoxy}ethoxy)acetylamino]ethoxy}ethoxy)acetylamino]ethoxy}ethoxy)acetyl][Aib8,Lys26,Arg34]GLP-1-(7-36)amide

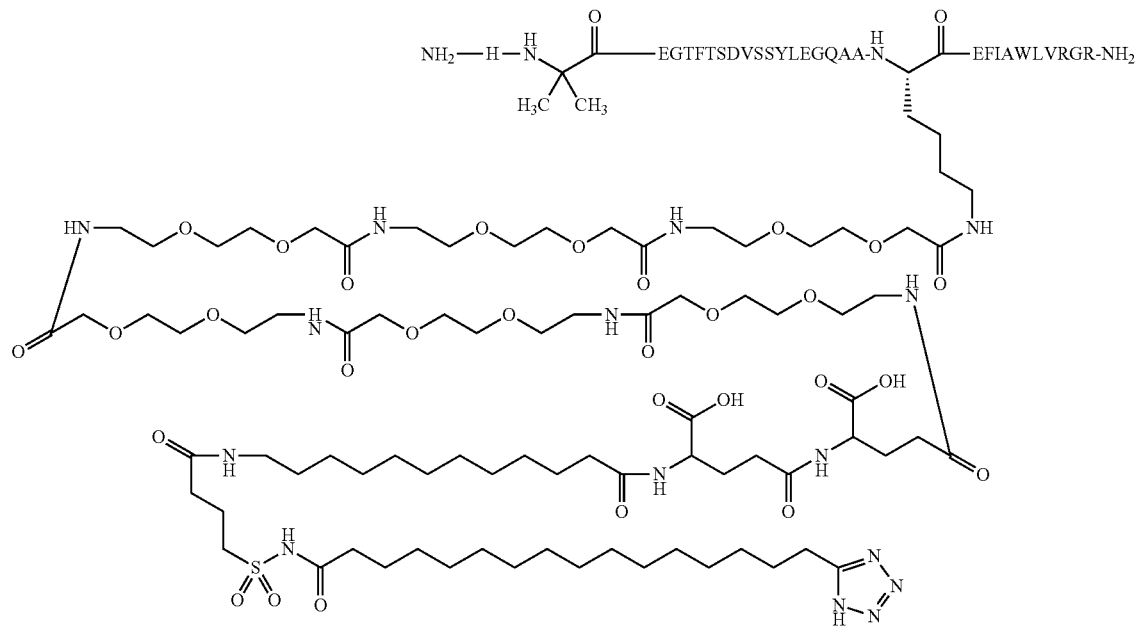

Preparation method: B
The peptide was eluted at 65% acetonitrile.
Structure confirmed by MALDI-MS
Calculated MW=5121.9

Example 46

[Aib8,Glu22,Arg26,Arg34]GLP-1-(7-37)Lys[2-(2-
{2-[(S)-4-Carboxy-4-((S)-4-carboxy-4-{12-[4-(16-
(1H-tetrazol-5-yl)hexadecanoylsulfamoyl)butyry-
lamino]dodecanoylamino}-butyrylamino)
butyrylamino]ethoxy}ethoxy)acetyl]amide

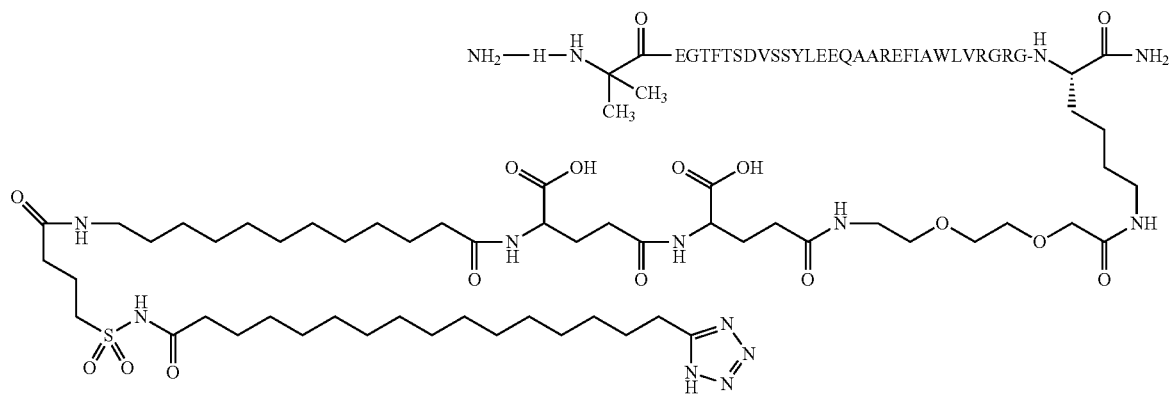

Preparation method: B
The peptide was eluted at 65% acetonitrile.
Structure confirmed by MALDI-MS
Calculated MW=4681.4

Example 47

N-epsilon20-[2-(2-{2-[(S)-4-Carboxy-4-((S)-4-car-
boxy-4-{12-[4-(16-(1H-tetrazol-5-yl)hexadecanoyl-
sulfamoyl)butyrylamino]
dodecanoylamino}butyrylamino)butyrylamino]
ethoxy}ethoxy)acetyl][Aib8,Lys20,Glu22,Arg26,
Glu30,Pro37]GLP-1-(7-37)amide

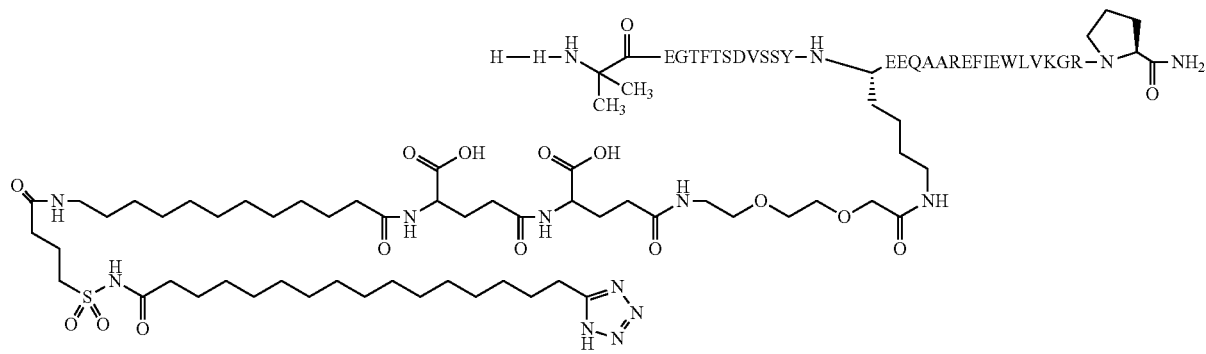

Preparation method: B
The peptide was eluted at 62% acetonitrile.
Structure confirmed by MALDI-MS
Calculated MW=4638.3

Example 48

N-epsilon37-[2-(2-{2-[(S)-4-Carboxy-4-((S)-4-carboxy-4-{12-[4-(16-(1H-tetrazol-5-yl)hexadecanoyl-sulfamoyl)butyrylamino]dodecanoylamino}butyrylamino)butyrylamino]ethoxy}ethoxy)acetyl][Aib8,Glu22,Arg26,Arg34,Lys37]GLP-1-(7-37)amide

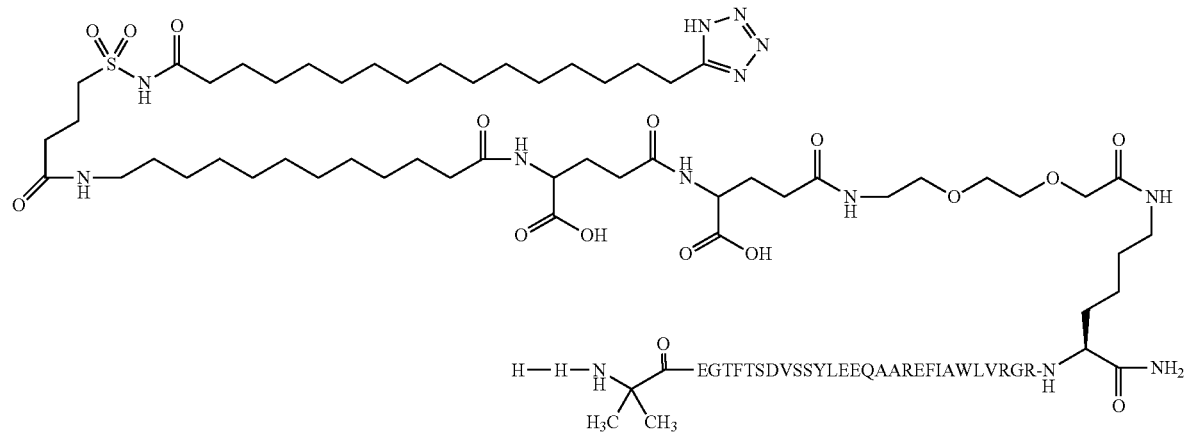

Preparation method: B
The peptide was eluted at 69% acetonitrile.
Structure confirmed by MALDI-MS
Calculated MW=4624.3

Example 49

N-epsilon37-[2-(2-{2-[(S)-4-Carboxy-4-((S)-4-carboxy-4-{12-[4-(16-(1H-tetrazol-5-yl)hexadecanoyl-sulfamoyl)butyrylamino]dodecanoylamino}butyrylamino)butyrylamino]ethoxy}ethoxy)acetyl][DesaminoHis7,Glu22,Arg26,Arg34,Lys37]GLP-1-(7-37)amide

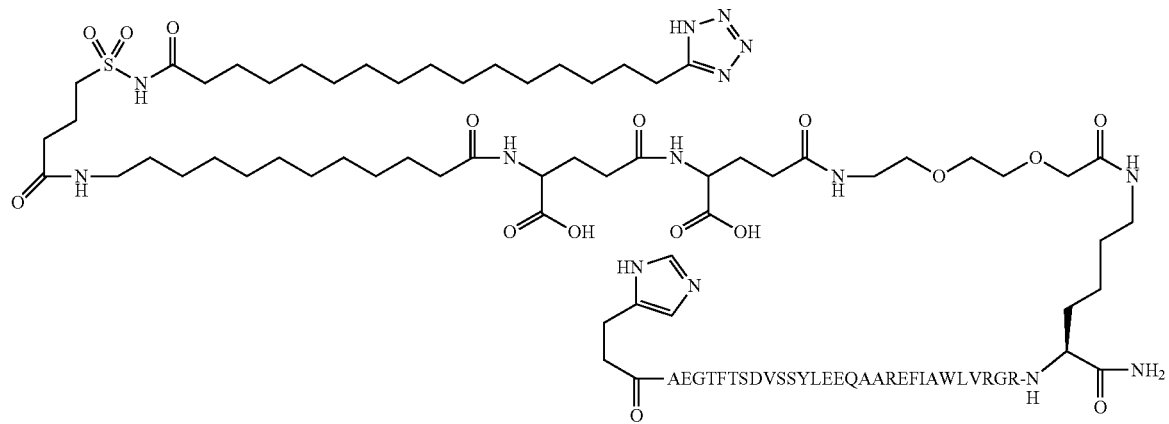

Preparation method: B
The peptide was eluted at 65% acetonitrile.
Structure confirmed by MALDI-MS
Calculated MW=4595.3

Example 50

N-epsilon37-[[2-(2-{2-[(S)-4-Carboxy-4-((S)-4-carboxy-4-{12-[4-(16-(1H-tetrazol-5-yl)hexadecanoyl-sulfamoyl)butyrylamino]
dodecanoylamino}butyrylamino)butyrylamino]
ethoxy}ethoxy)acetyl][DesaminoHis7,Arg26,Arg34,Lys37]GLP-1-(7-37)amide

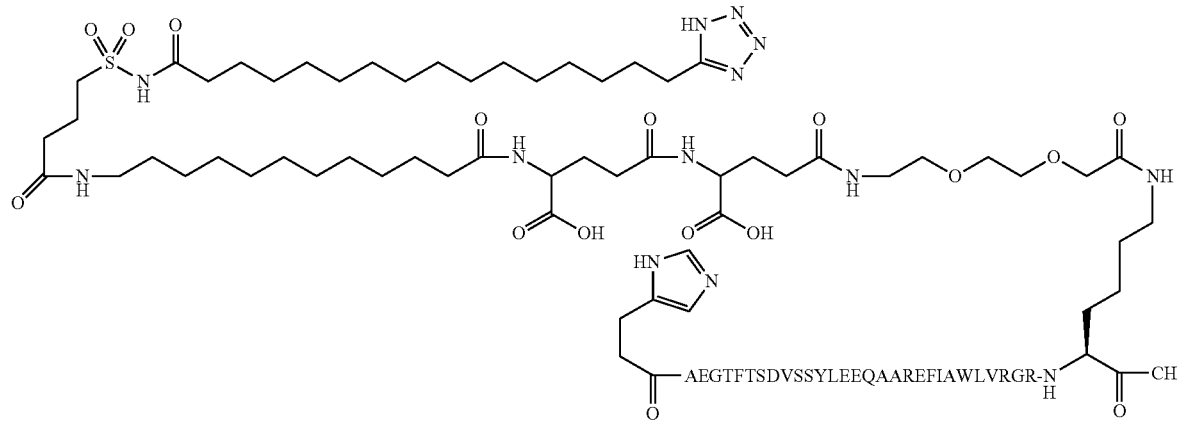

Preparation method: B
The peptide was eluted at 66% acetonitrile.
Structure confirmed by MALDI-MS
Calculated MW=4523.2

Example 51

[Aib8,Glu22,Arg26,Glu30,Pro37]GLP-1-(7-37)Lys
[2-(2-{2-[4-Carboxy-4-(4-carboxy-4-{4-[4-(16-1H-tetrazol-5-yl-hexadecanoylsulfamoyl)butyrylamino]
butyrylamino}butyrylamino)butyrylamino]
ethoxy}ethoxy)acetyl]

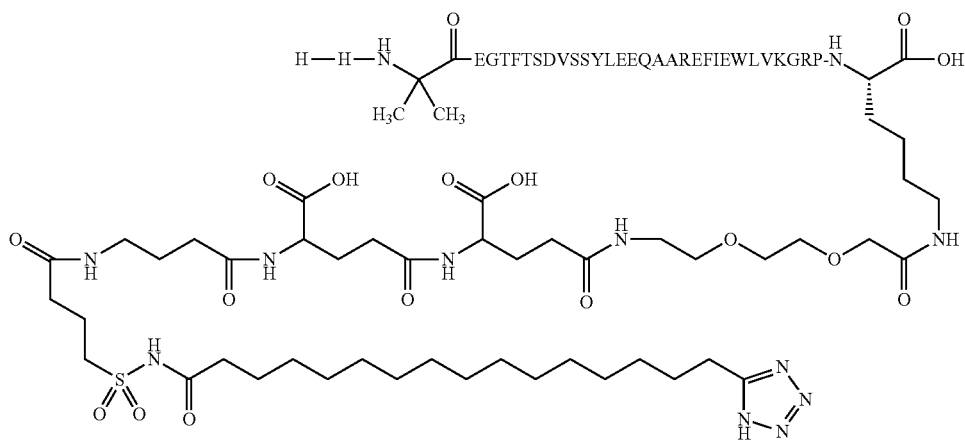

Preparation method: Method A except that the peptide was prepared on an Apex396 from Advanced Chemtech using a molar excess of 8-10 fold amino acid, DIC and HOAt/HOBt (1:1) and the Mtt group was deprotected with hexafluoroisopropanol. Attachment of thioamide linker was achieved in two steps; 4-sulfamoylbutyric acid (3 fold excess) was first coupled the resin using DIC and HOAt/HOBt (1:1). Then, 16-(1H-tetrazol-5-yl)hexadecanoic acid (3 fold excess) mixed with carbonyldiimidazol in NMP was added to the resin followed by addition of DBU.
HPLC method B6:
RT=29.8 min
LCMS: m/z=1161.2 (M+4H)$^{4+}$
Calculated MW=4640.2

Example 52

[Aib8,Glu22,Arg26,Glu30,Pro37]GLP-1-((7-37)Lys
(2-(2-(3-(2-(2-(2-(2-(2-(2-(2-(2-(2-(2-(2-[4-(S)-
carboxy-4-(4-(S)-carboxy-4-(4-{4-[16-(Tetrazol-5-
yl)hexadecanoylsulfamoyl]
butanoylamino}butanoylamino) butyrylamino)
butyrylamino]ethoxy)ethoxy)ethoxy)ethoxy)ethoxy)
ethoxy)ethoxy)ethoxy)ethoxy)ethoxy)
ethoxy) propionylamino)ethoxy)ethoxy) peptide

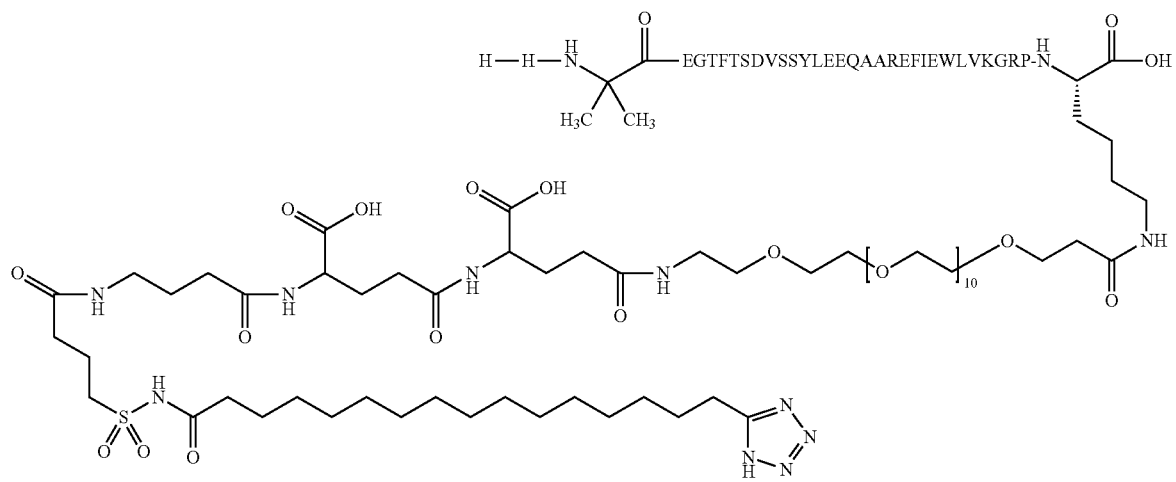

Preparation method: The peptide was prepared on an Apex396 from Advanced Chemtech and attachment of thioamide linker was achieved in two steps. 4-sulfamoylbutyric acid was first coupled the resin using DIC and HOAt/HOBt (1:1). Then, 16-(1H-tetrazol-5-yl)hexadecanoic acid mixed with carbonyldiimidazol in NMP was added to the resin followed by addition of DBU. Otherwise is the same protocol described in the beginning of the example section.

HPLC (method B6):
RT=30 min
LCMS: m/z=XX (M+4H)$^{4+}$: 1274
Calculated (M+H)$^{+}$=5096

Example 53

N-alpha37-[2-(2-{2-[2-(2-{2-[(S)-4-Carboxy-4-
({trans-4-[(19-carboxynonadecanoylamino)methyl]
cyclohexanecarbonyl}amino)butyrylamino]
ethoxy}ethoxy)acetylamino]ethoxy}ethoxy)acetyl]
[DesaminoHis7,Glu22,Arg26,Arg34,epsilon-Lys37]
GLP-1-(7-37)

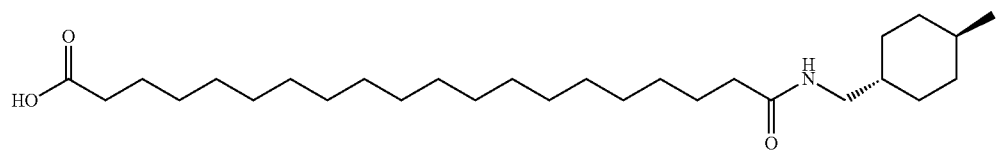

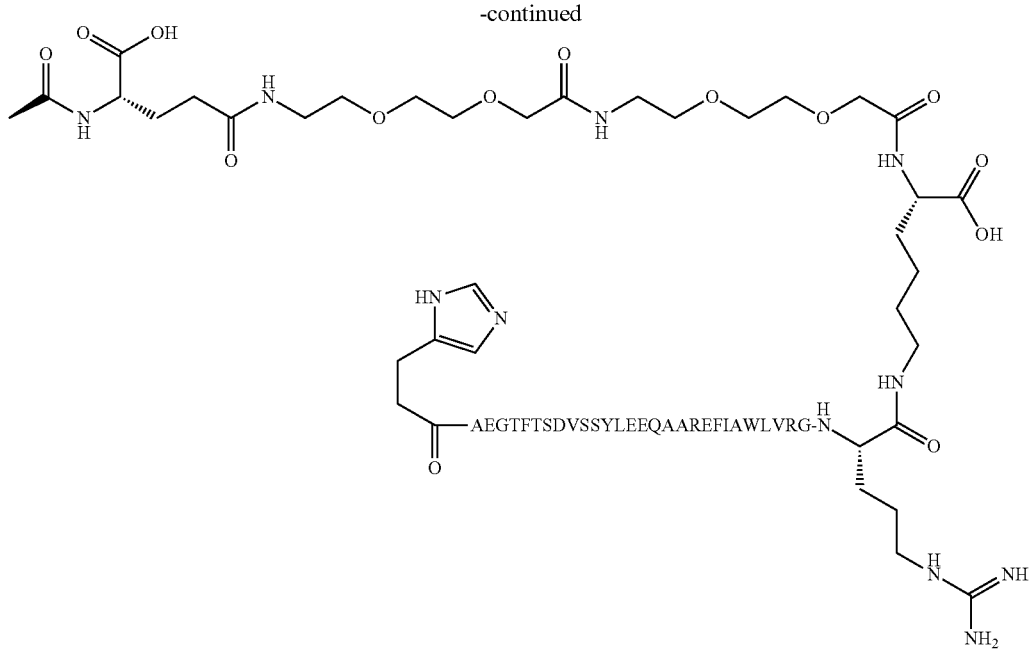

Preparation method: B, in similar fashion as described for example 7.
HPLC method 02_B6__1:
RT=37.05 min
LCMS: m/z=1106.3 $(M+4H)^{4+}$
Calculated (M)=4423.1

Example 54

N-alpha8-[2-(4-imidazolyl)acetyl] N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl] [Glu22,Arg26,Arg34,Lys37]GLP-1-(8-37)

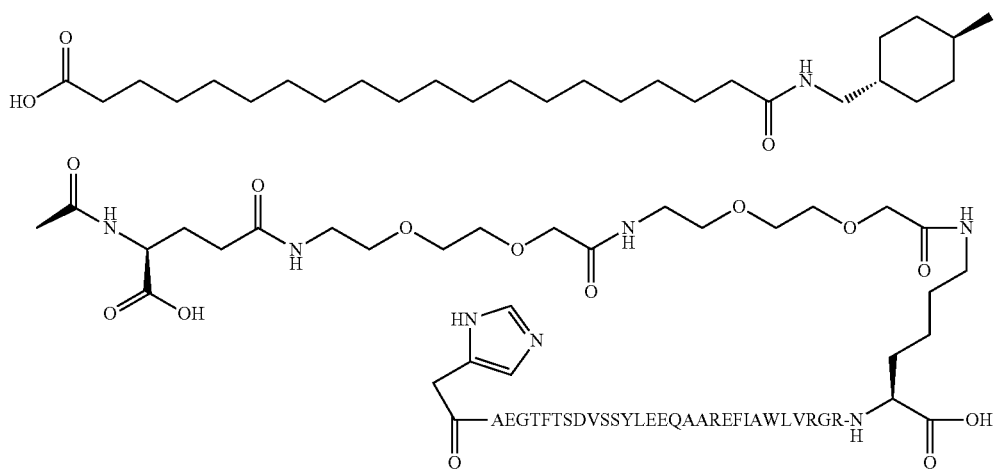

Preparation method: B
The peptide was eluted at 68% acetonitrile.
Structure confirmed by MALDI-MS
Calculated MW=4409.1

Example 55

[DesaminoHis7,Glu22,Arg26,34]-GLP-1 (7-37)-Lys-(2-{2-[2-((S)-4-carboxy-4-{[1-(19-carboxynonadecanoyl)piperidine-4-carbonyl]amino}butyrylamino)ethoxy]ethoxy}acetyl) peptide

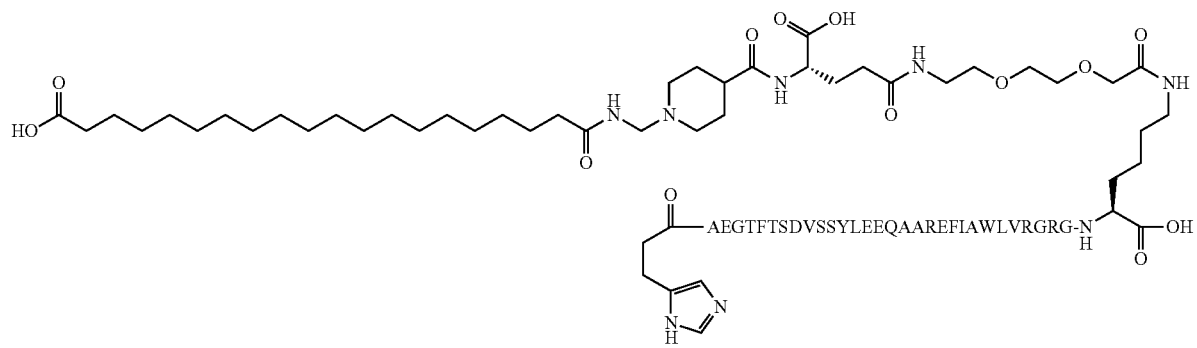

Preparation method: B, in similar fashion as described for example 7.
HPLC method 03_B6__1:
RT=35.58 min
LCMS: m/z=1077.8 $(M+4H)^{4+}$
Calculated (M)=4306.9

Example 56

[DesaminoHis7,Glu22,Arg26,34]-GLP-1 (7-37)-Lys-[2-(2-{2-[2-(2-{2-[4-Carboxy-4-({4-[(19-carboxynonadecanoylamino)methyl]cyclohexanecarbonyl}amino)butyrylamino]ethoxy}ethoxy)acetylamino]ethoxy}ethoxy)acetyl] peptide

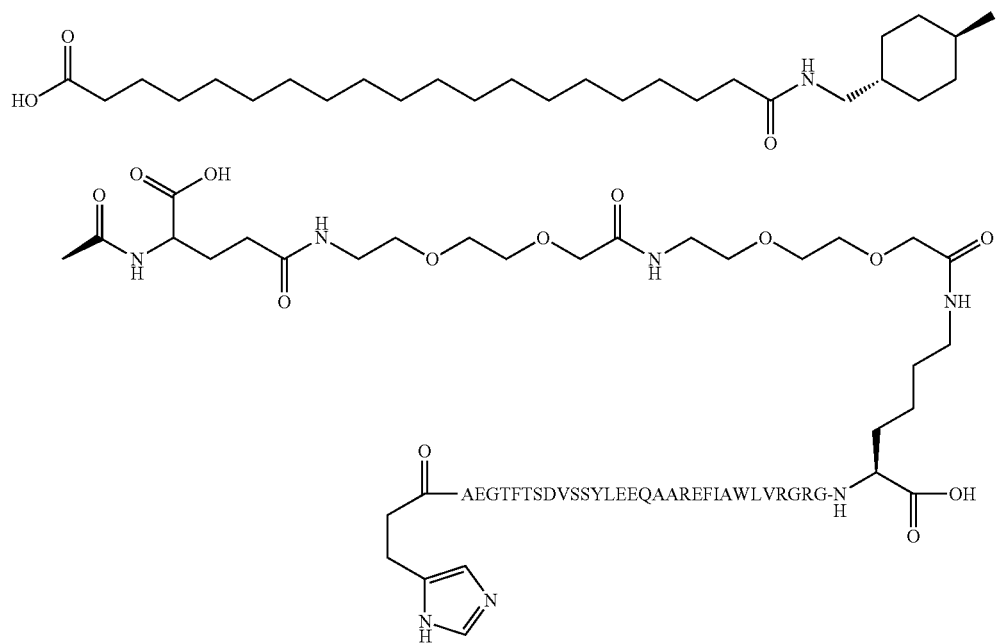

Preparation method: B, in similar fashion as described for example 7.
HPLC method 02_B6_1:
RT=34.40 min
LCMS: m/z=1120.8 (M+4H)$^{4+}$
Calculated (M)=4480.1

Example 57

[DesaminoHis7,Glu22,Arg26,34]-GLP-1 (7-37)-Lys ((S)-4-carboxy-4-(2-{2-[2-((S)-4-carboxy-4-{[1-(19-carboxynonadecanoyl)piperidine-4-carbonyl] amino}butyrylamino)ethoxy]ethoxy}acetylamino) butyryl) peptide

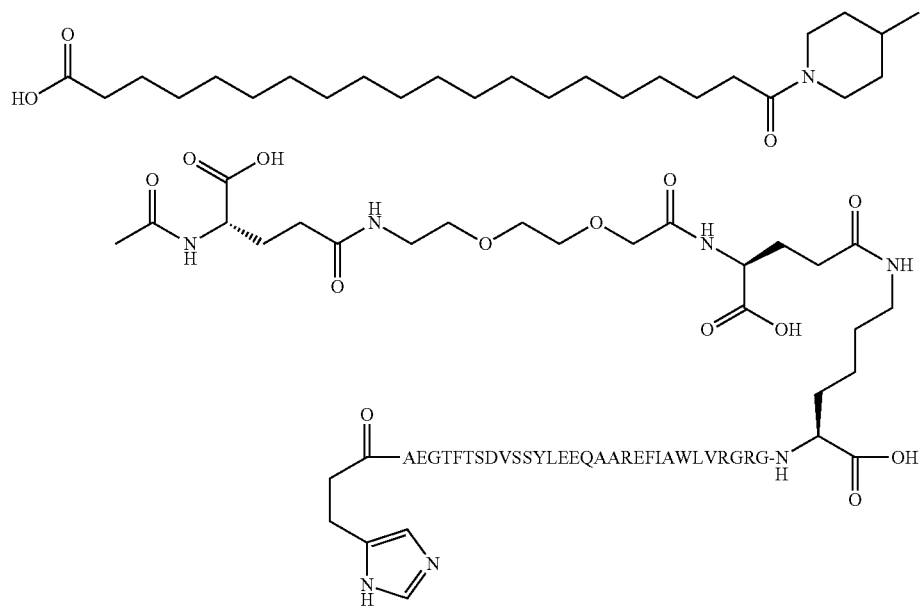

Preparation method: B, in similar fashion as described for example 7.
HPLC method 03_B6_1:
RT=35.14 min
LCMS: m/z=(M+4H)$^{4+}$
Calculated (M)=4436.0

Example 58

[DesaminoHis7,Glu22,Arg26,34]-GLP-1 (7-37)-Lys-(2-(2-{2-[(S)-4-carboxy-4-(2-{2-[2-((S)-4-carboxy-4-{[1-(19-carboxynonadecanoyl)piperidine-4-carbonyl]amino}butyrylamino)ethoxy] ethoxy}acetylamino)butyrylamino]ethoxy}ethoxy) acetyl) peptide

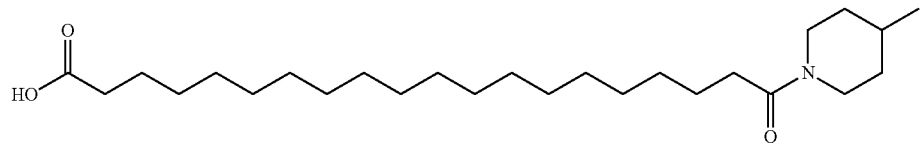

-continued
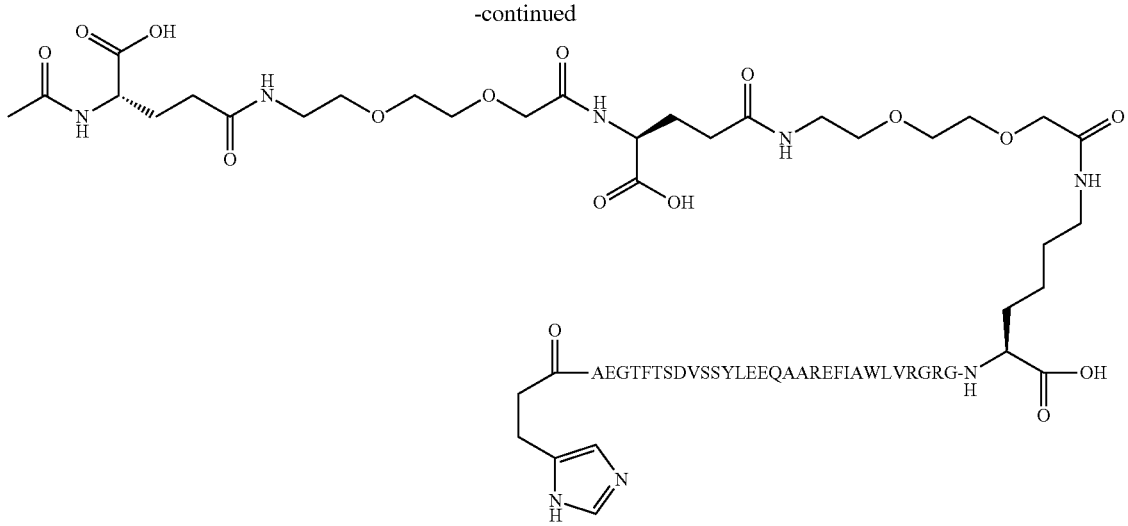
Preparation method: B, in similar fashion as described for example 7.
HPLC method 03_B6_1:
RT=34.92 min
LCMS: m/z=1146.3 (M+4H)$^{4+}$
Calculated (M)=4581.2
Example 59
[DesaminoHis7,Arg26,34]-GLP-1 (7-37)-Lys(2-{2-[2-(2-{2-[2-((S)-4-Carboxy-4-{[1-(19-carboxynona-decanoyl)piperidine-4-carbonyl]amino}butyrylamino)ethoxy]ethoxy}acetylamino)ethoxy]ethoxy}acetyl) peptide
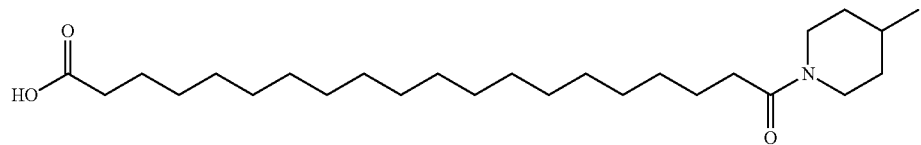
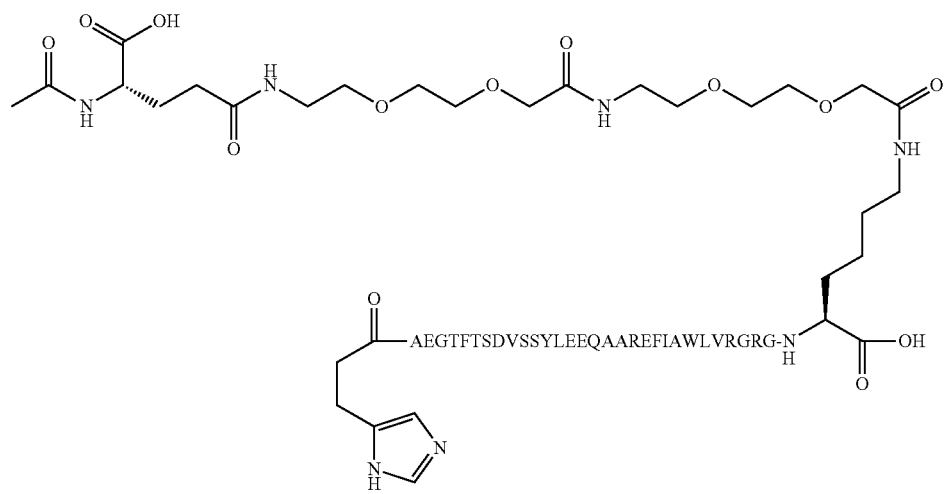

Preparation method: B, in similar fashion as described for example 7.
HPLC method 03_B6_1:
RT=35.39 min
LCMS: m/z=1095.8 (M+4H)$^{4+}$
Calculated (M)=4380.0

Example 60

N-epsilon37-(2-{2-[2-(2-{2-[2-((S)-4-Carboxy-4-{[1-(19-carboxynonadecanoyl)piperidine-4-carbonyl]amino}butyrylamino)ethoxy]ethoxy}acetylamino)ethoxy]ethoxy}acetyl) [DesaminoHis7,Arg26,Arg34,Lys37]GLP-1-(7-37)

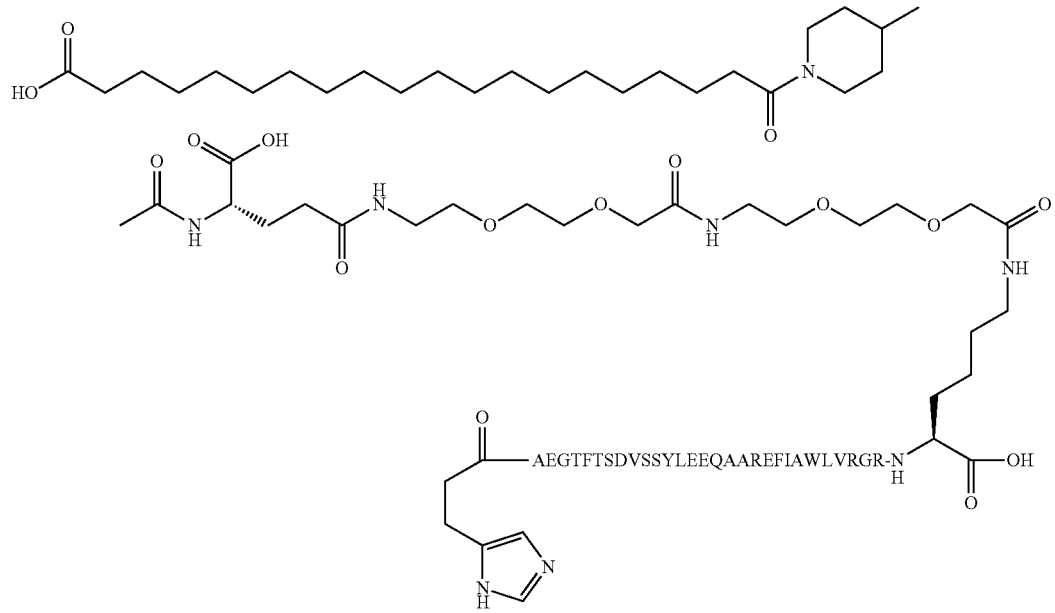

Preparation method: B, in similar fashion as described for example 7.
HPLC method 03_A1_1:
RT=35.73 min
LCMS: m/z=1081.3 (M+4H)$^{4+}$
Calculated (M)=4323.0

Example 61

N-epsilon37-((S)-4-Carboxy-4-{[1-(19-carboxy-nonadecanoyl)-piperidine-4-carbonyl]-amino}-butyryl) [DesaminoHis7,Arg26,Arg34,Lys37]GLP-1-(7-37)

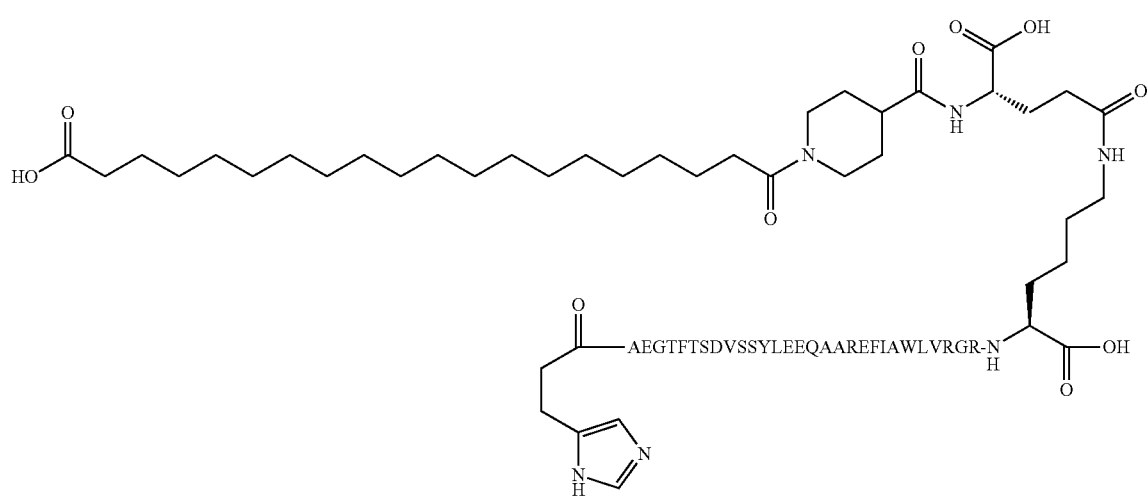

Preparation method: B, in similar fashion as described for example 7.
HPLC method 03_B6_1:
RT=36.28 min
LCMS: m/z=1009.5 $(M+4H)^{4+}$
Calculated (M)=4032.6

Example 62

[DesaminoHis7,Glu22,Arg26,34]-GLP-1 (7-37)-Lys-((S)-4-Carboxy-4-{[1-(19-carboxy-nonadecanoyl)-piperidine-4-carbonyl]-amino}-butyryl) peptide

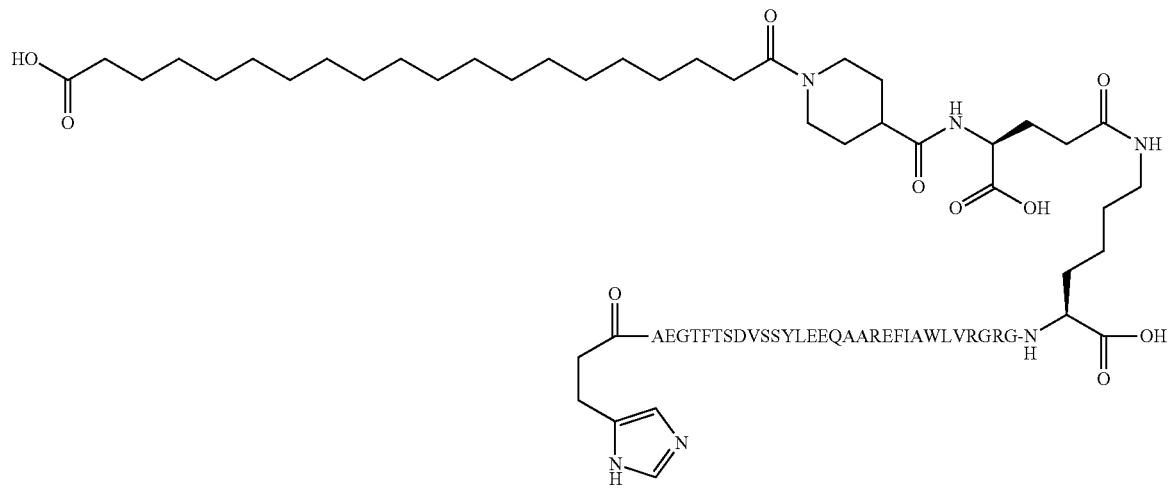

Preparation method: B, in similar fashion as described for example 7.
HPLC method 03_B6_1:
RT=36.06 min
LCMS: m/z=1041.0 $(M+4H)^{4+}$
Calculated (M)=4161.8

Example 63

N-epsilon26-[2-(2-{2-[(R)-4-Carboxy-4-((R)-4-carboxy-4-{12-[4-(16-1H-tetrazol-5-yl-hexadecanoyl-sulfamoyl)butyrylamino]
dodecanoylamino}butyrylamino)butyrylamino]
ethoxy}ethoxy)acetyl]-[Aib8,Arg34]GLP-1 (7-37)

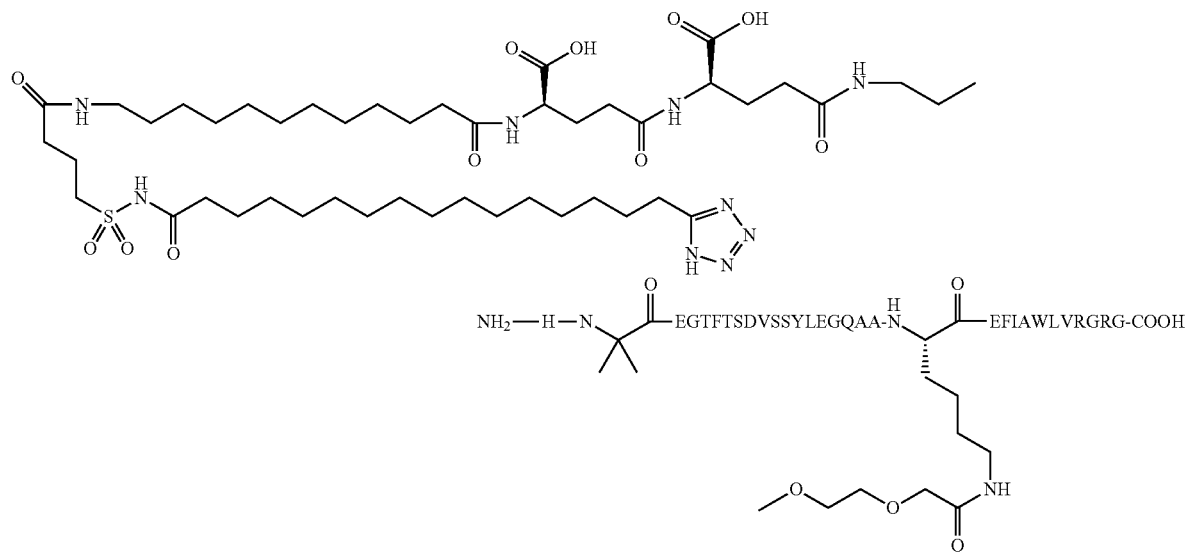

Preparation method B
The peptide was eluted at 70% acetonitrile
Structure confirmed by MALDI-MS
Calculated MW=4454.1

Example 64

N-epsilon37-{2-[2-(2-{(S)-4-[(S)-4-(12-{4-[16-(2-tert-Butyl-2H-tetrazol-5-yl)-hexadecanoylsulfamoyl]butyrylamino}dodecanoylamino)-4-carboxybutyrylamino]-4-carboxybutyrylamino}ethoxy)ethoxy]acetyl}[DesaminoHis7,Glu22,Arg26,Arg34,Lys37] GLP-1 (7-37)

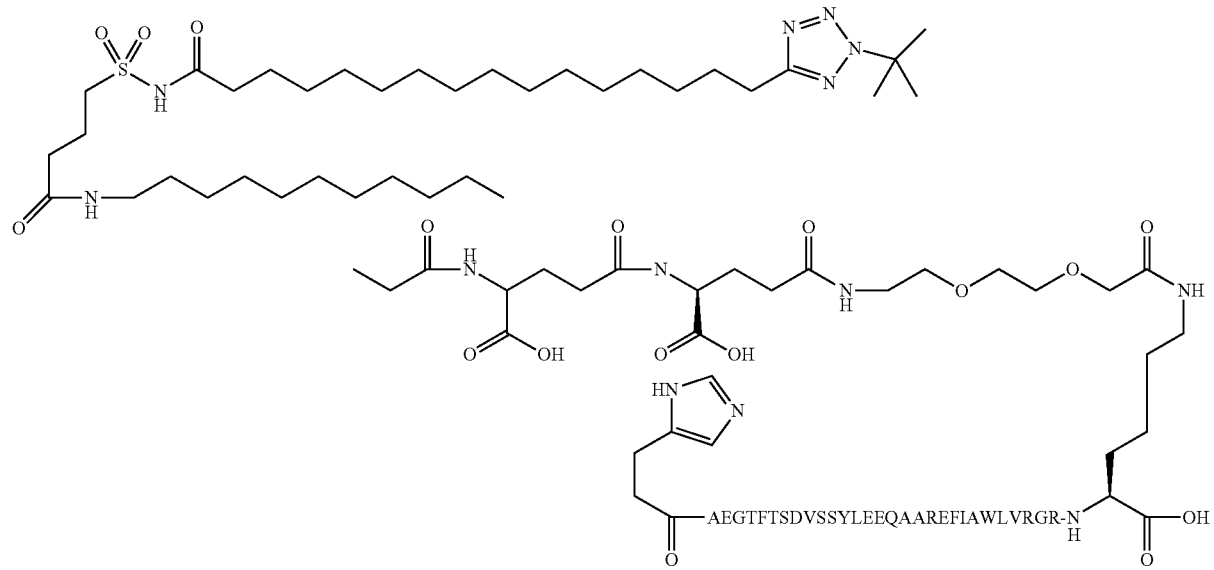

Preparation method B
The peptide was eluted at 74% acetonitrile
Structure confirmed by MALDI-MS
Calculated MW=4652.4

Example 65

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Arg26,Arg34,Lys37]GLP-1-(7-37)

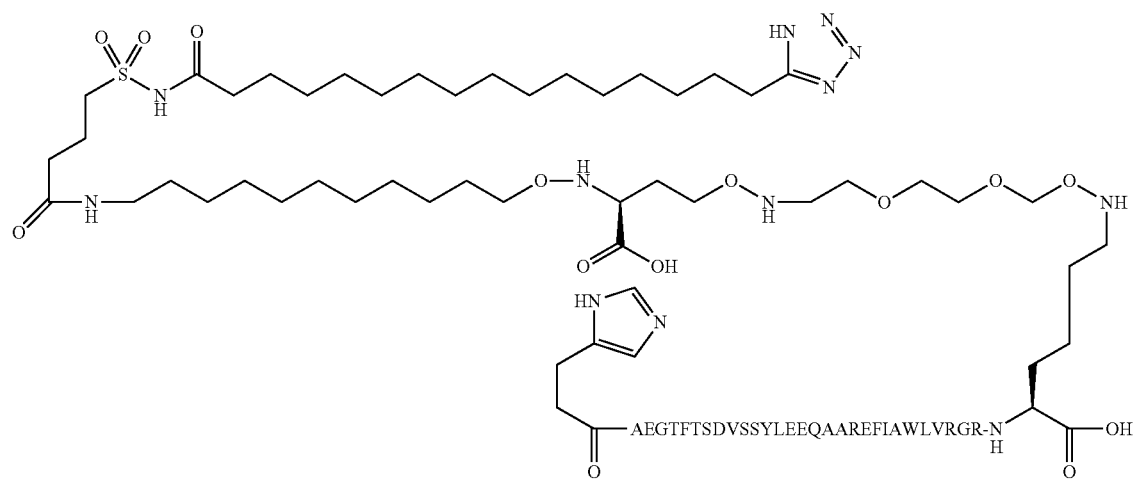

Preparation method B
The peptide was eluted at 65% acetonitrile
Structure confirmed by MALDI-MS
Calculated MW=4524.2

Example 66

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37)

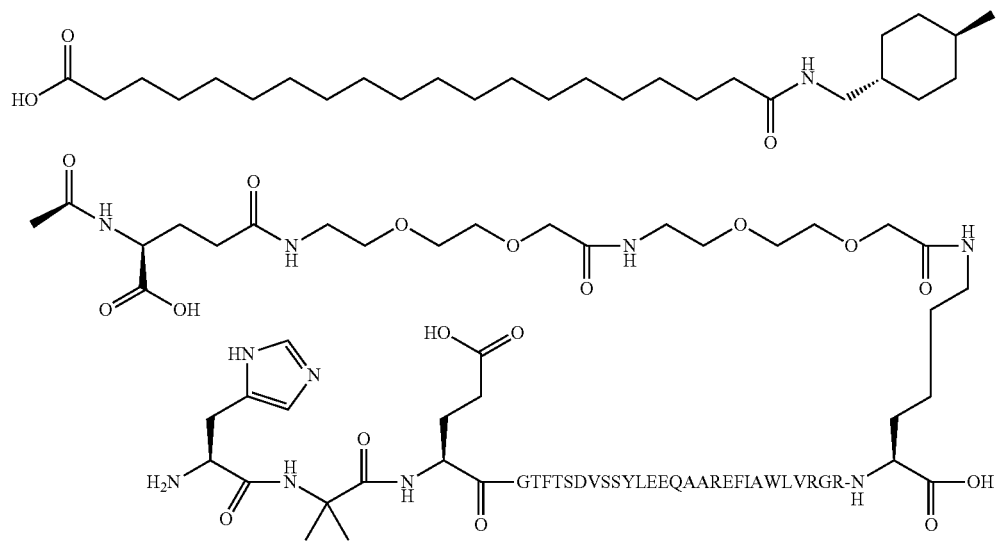

Preparation analogous to SPPS Method B.
HPLC method 02_B6__1:
RT=33.58 min
LCMS: m/z=1114 (M+4H)$^{4+}$
Calculated (M)=4451.1

Example 67

[ImPr$^7$,Arg$^{26,34}$,Glu$^{22}$]GLP-1-(7-37)Lys[2-(2-[2-((S)-4-((S)-4-(12-[4-(16-1H-tetrazol-5-ylhexadecanoylsulfamoyl)butyrylamino]dodecanoylamino)-4-carboxybutyrylamino)-4-carboxybutyrylamino)ethoxy]ethoxy)acetyl]-amid

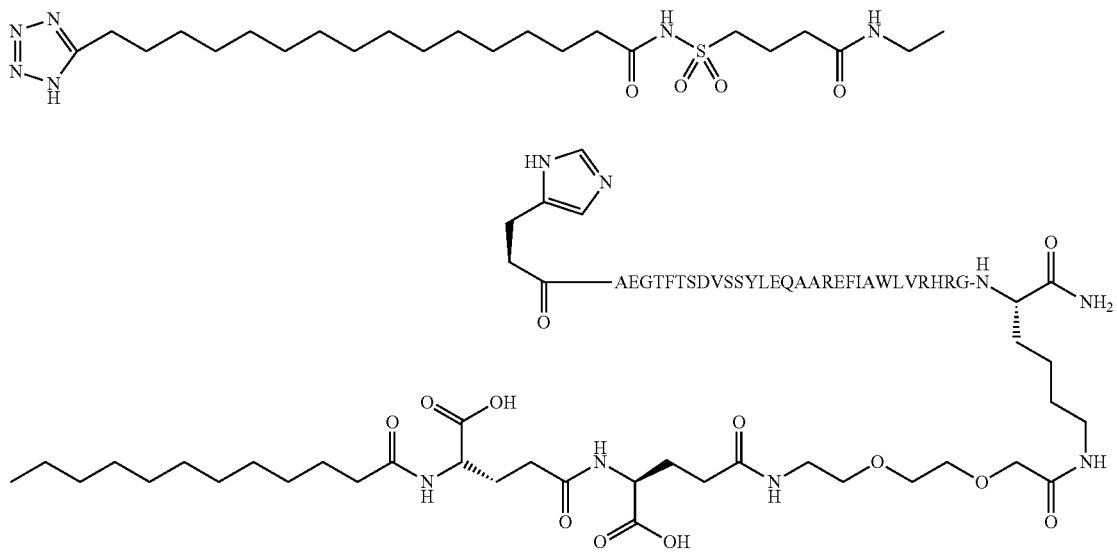

Preparation method A
The peptide was eluted at 61% acetonitrile
Structure confirmed by LC-MS
Calculated MW: (M/3)+1=1550.8 and (M/4)+1=1163.1; (Sciex100 API)
Found MW: (M/3)+1=1551.9 and (M/4)+1=1164.3; (Sciex100 API)

Example 68

N-epsilon36-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Glu22, Gln34]GLP-1-(7-37)

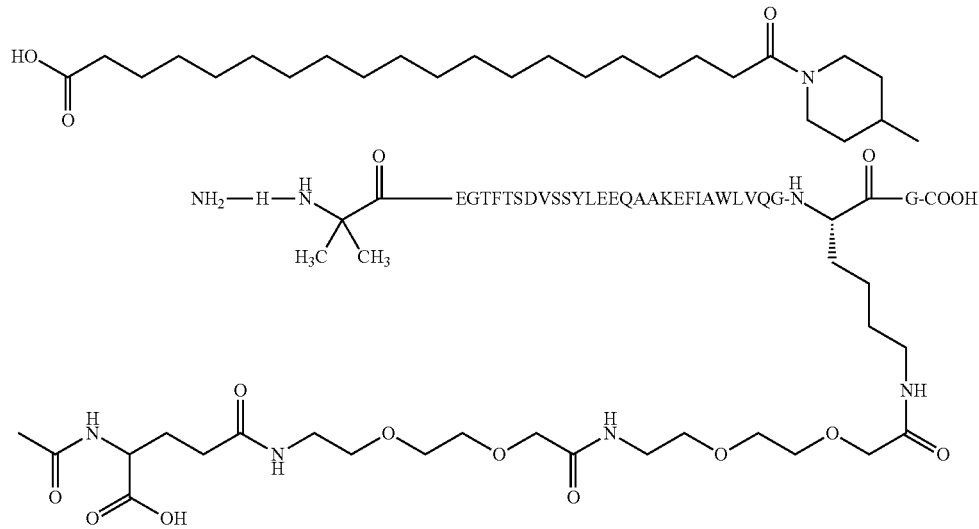

Preparation method: A
HPLC (method B6):
RT=36.8 min
MS-TOF: m/z=4468
Calculated (M+H)$^+$=4469

Example 69

N-epsilon26-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Glu22, Gln34]GLP-1-(7-37)

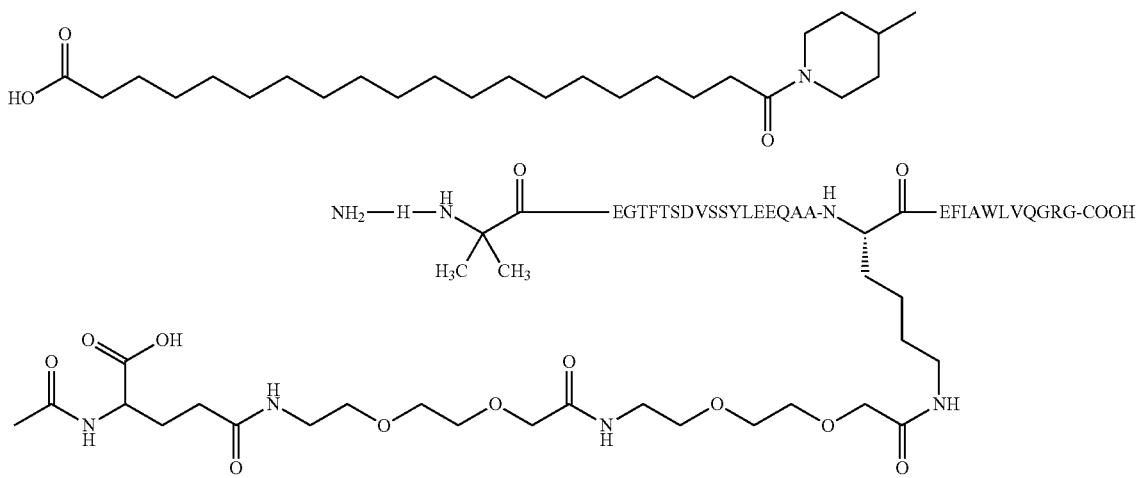

Preparation method: A
HPLC (method B4):
RT=11.4 min
LCMS: m/z=1433 (M+3H)$^{3+}$
Calculated (M+H)$^+$=4296.9

Example 70

N-epsilon18-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, 22,35, Lys18, Arg26,34]GLP-1-(7-37)

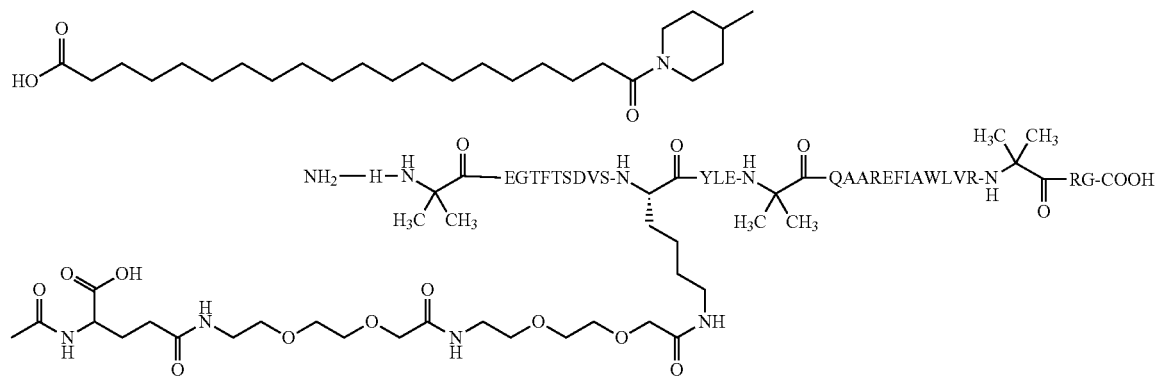

Preparation method: A
HPLC (method B4):
RT=11.0 min
LCMS: m/z=1459 (M+3H)$^{3+}$
Calculated (M+H)$^+$=4378.1

Example 71

N-epsilon18-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Lys18, Glu22, Gln34]GLP-1-(7-37)

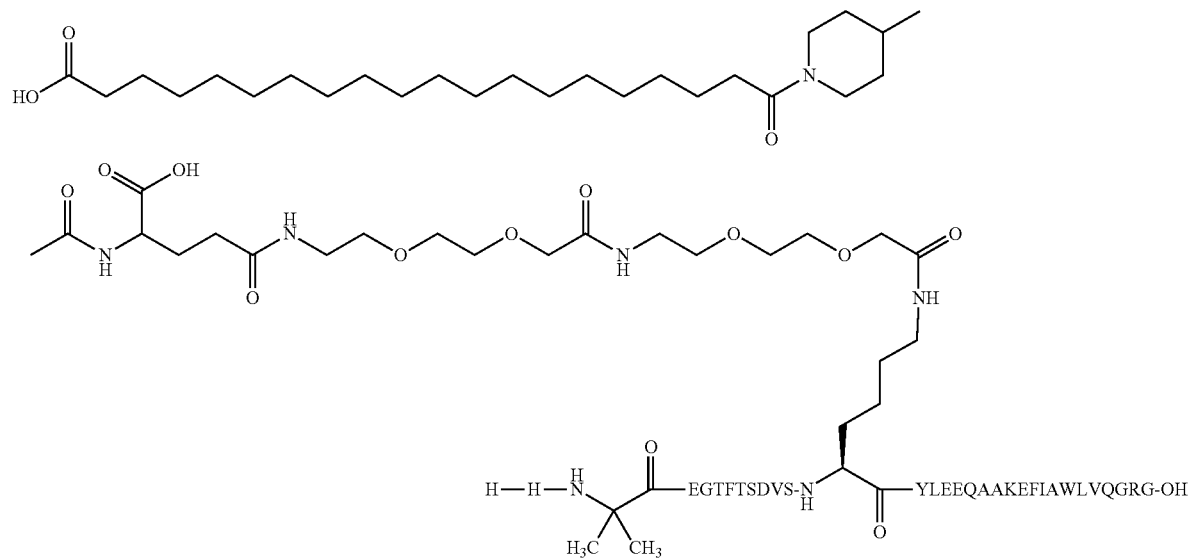

Preparation method: A
HPLC (method B4):
RT=11.4 min
MS-TOF: m/z=4338
Calculated (M+H)$^+$=4338
Microwave-based Liberty peptide synthesizer (CEM Corp., North Carolina 0.125 mMol synthesis of A-B-C-D-derivatized Lys GLP-1 analogues Example 72

Synthesis of Peptide Amides

General notice. The starting resin used for the synthesis of the peptide amides was Rink-Amide resin and either Wang or chlorotrityl resin was used for peptides with a carboxy C-terminal Synthesis of the N-epsilon26-[2-(2-{2-[2-(2-{2-[(S)-4-Carboxy-4-({trans-4-[(19-carboxynonadecanoy-lamino)methyl]cyclohexanecarbonyl}amino)butyry-lamino]ethoxy}ethoxy)acetylamino]ethoxy}ethoxy)acetyl] derivatization in example 19

Step 1

After the peptide sequence was completed, and the mtt protecting was removed from the epsilon amino group of the Lys, a 0.3M solution of FMOC 8-amino-3,6-dioxaoctanic acid/HOAT in NMP (2.5 ml) was added to the resin, followed by addition of a 0.75M solution of DIC in NMP (1 ml). The reaction was heated to 70-75 degrees for 5 min followed by a wash with NMP (4×7 ml).

Step 2

The resin obtained in step 1 was FMOC deprotected using 5% piperidine in NMP (7 ml) heated for 30 sec drained washed with NMP (7 ml) followed by additional 5% piperidine in NMP (7 ml) heated for 3 min at 70-75 degrees followed by washing with NMP (4×7 ml).

A 0.3M solution of FMOC 8-amino-3,6-dioxaoctanic acid/HOAT in NMP (2.5 ml) was added to the resin followed by addition of a 0.75M solution of DIC in NMP (1 ml). The reaction was heated to 70-75 degrees for 5 min followed by a wash with NMP (4×7 ml).

Step 3

The resin obtained in step 2 was FMOC deprotected using 5% piperidine in NMP (7 ml) heated for 30 sec drained washed with NMP (7 ml) followed by additional 5% piperidine in NMP (7 ml) heated for 3 min at 70-75 degrees followed by washing with NMP (4×7 ml).

A 0.3M solution of FMOC-Glu-OTBU/HOAT in NMP (2.5 ml) was added to the resin followed by addition of a 0.75M solution of DIC in NMP (1 ml). The reaction was heated to 70-75 degrees for 5 min followed by a wash with NMP (4×7 ml).

Step 4

The resin obtained in step 3 was FMOC deprotected using 5% piperidine in NMP (7 ml) heated for 30 sec drained washed with NMP (7 ml) followed by additional 5% piperidine in NMP (7 ml) heated for 3 min at 70-75 degrees followed by washing with NMP (4×7 ml).

A 0.3M solution of FMOC-Tranexamic acid/HOAT in NMP (2.5 ml) was added to the resin followed by addition of a 0.75M solution of DIC in NMP (1 ml). The reaction was heated to 70-75 degrees for 5 min followed by a wash with NMP (4×7 ml).

Step 5

The resin obtained in step 4 as FMOC deprotected using 5% piperidine in NMP (7 ml) heated for 30 sec drained washed with NMP (7 ml) followed by additional 5% piperidine in NMP (7 ml) heated for 3 min at 70-75 degrees followed by washing with NMP (4×7 ml).

A 0.3M solution of eicosanedioic acid mono tert.-butyl ester and HOAT in NMP (2.5 ml) was added to the resin followed by addition of a 0.75M solution of DIC in NMP (1 ml). The reaction was heated to 70-75 degrees for 5 min followed by a wash with NMP (4×7 ml).

Step 6

Removal of tert butyl ester protection and cleavage from resin

The resin obtained in step 5 was washed with DCM (4×7 ml) and dried. The dry resin was removed from the Liberty and treated for 2 h with TFA/TIS/water (92.5/5/2.5) cleaving the peptide from the resin and removing the tert. butyl ester protection groups. The resin was filtered off and the peptide was precipitated with diethyl ether, and isolated by centrifugation. The peptide was redissolved in 30% acetic acid or an alternative solvent mixture and purified using one of the described methods.

Synthesis of the [2-(2-[2-(2-[2-(2-((S)-4-[1-[19-Car-boxynonadecanoyl]piperidine-4-carbonylamino]-4-carboxybutyrylamino)ethoxy)ethoxy]acetylamino) ethoxy]ethoxy)acetyl] derivatization in Example 14

Step 7

After the peptide sequence was completed, and the mtt protecting was removed from the epsilon amino group of the Lys, the resin was modified as described in steps 1-3. The resin was FMOC deprotected using 5% piperidine in NMP (7 ml) heated for 30 sec drained washed with NMP (7 ml) followed by additional 5% piperidine in NMP (7 ml) heated for 3 min at 70-75 degrees followed by washing with NMP (4×7 ml).

A 0.3M solution of FMOC-isonipecotic acid/HOAT in NMP (2.5 ml) was added to the resin followed by addition of a 0.75M solution of DIC in NMP (1 ml). The reaction was heated to 70-75 degrees for 5 min followed by a wash with NMP (4×7 ml).

Step 8

The resin obtained in step 7 as FMOC was deprotected using 5% piperidine in NMP (7 ml) heated for 30 sec drained washed with NMP (7 ml) followed by additional 5% piperidine in NMP (7 ml) heated for 3 min at 70-75 degrees followed by washing with NMP (4×7 ml).

A 0.3M solution of eicosanedioic acid mono tert-butyl ester/HOAT in NMP (2.5 ml) was added to the resin followed by addition of a 0.75M solution of DIC in NMP (1 ml). The reaction was heated to 70-75 degrees for 5 min followed by a wash with NMP (4×7 ml) followed by the cleavage procedure described in step 6.

Synthesis of the N-epsilon3'-(2-{2-[2-(2-{2-[2-((S)-3-Carboxy-3-{[1-(19-carboxy-nonadecanoyl)piperi-dine-4-carbonyl]amino}propionylamino)ethoxy] ethoxy}acetylamino)ethoxy]ethoxy}acetyl) derivatization in Example 15

Step 9

The resin obtained in step 2 was FMOC deprotected using 5% piperidine in NMP (7 ml) heated for 30 sec drained washed with NMP (7 ml) followed by additional 5% piperidine in NMP (7 ml) heated for 3 min at 70-75 degrees followed by washing with NMP (4×7 ml).

A 0.3M solution of FMOC-Asp-OTBU/HOAT in NMP (2.5 ml) was added to the resin followed by addition of a 0.75M solution of DIC in NMP (1 ml). The reaction was heated to 70-75 degrees for 5 min followed by a wash with NMP (4×7 ml).

Step 10

The resin obtained in step 9 is followed by Step 7 attaching the FMOC isonipecotic acid followed by step 8 attaching the eicosanedioic acid mono tert.-butyl ester finalising the synthesis by deprotection as described in Step 6

Synthesis of the N-epsilon26-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy) acetyl] derivatization in example 18

Step 11

N-epsilon26-[2-(2-{2-[2-(2-{2-[(S)-4-Carboxy-4-({trans-4-[(19-carboxy-nonadecanoylamino)methyl] cyclohexanecarbonyl}amino)butyrylamino]ethoxy}ethoxy) acetylamino]ethoxy}ethoxy)acetyl] derivatization is obtained following Step 1-3-4-5 and 6

Synthesis of the N-epsilon26-[(S)-4-Carboxy-4-({trans-4-[(19-carboxynonadecanoylamino)methyl] cyclohexanecarbonyl}amino)butyryl] derivatization in example 16

Step 12

A 0.3M solution of FMOC-Glu-OTBU/HOAT in NMP (2.5 ml) was added to the resin after Mtt deprotection followed by addition of a 0.75M solution of DIC in NMP (1 ml). The reaction was heated to 70-75 degrees for 5 min followed by a wash with NMP (4×7 ml), followed by step 4-5 and 6

Step 13

For attachment of described A part of the albumin binder the procedure in step 8 can be used replacing eicosanedioic acid mono tert.-butyl ester with the appropriate A as an acid.

Step 14

For attachment of described B part of the albumin binder the procedure in step 7 can be used replacing the FMOC-Isonipecotic acid with the appropriate B as acid Step 15

For attachment of described C part of the albumin binder the procedure in step 9 can be used replacing the FMOC-Asp-OTBU acid with the appropriate C as an acid.

Step 16

For attachment of described D part of the albumin binder the procedure in step 1 can be used replacing the FMOC 8-amino-3,6-dioxaoctanic acid with the appropriate D as an acid.

Biological Findings

Protraction of GLP-1 Derivatives after i.v. Or s.c. Administration

The protraction of a number GLP-1 derivatives of the invention may be determined by monitoring the concentration thereof in plasma after sc administration to healthy pigs, using the methods described below. For comparison also the concentration in plasma of GLP-1(7-37) after sc. administration may be followed. The protraction of other GLP-1 derivatives of the invention can be determined in the same way.

Example 73

Pharmacokinetic Testing in Minipigs

A number of GLP-1 derivatives of the invention (the compounds of Examples 1, 2, 5, 7, 9, 10, 14, 16, 17, 18, 19, 20, 23, 24, 25, 26, 27, 28, 31, 33, 34, 35, 49, 50, 52, 59, and 63) were subjected to pharmacokinetic testing in minipigs. Liraglutide was included in the test for comparative purposes.

Generally, the test substances are to be dissolved in a vehicle suitable for subcutaneous or intravenous administration. In the present study the test substances were administered subcutaneously. Each animal received a dose of 2 nmol/kg body weight and the concentration was adjusted so the dosing volume was approximately 1 ml, using the following vehicle: 50 mM phosphate buffer with 0.05% w/v Tween 80 (pH approximately 8).

The study was performed in male Göttingen minipigs from Ellegaard Göttingen Minipigs ApS. An acclimatisation period of approximately 6-10 days was allowed before the animals entered the study. At start of the acclimatisation period the minipigs were about 5 months old and in the weight range of 7-10 kg.

The study was conducted in a suitable animal room with a room temperature set at 21-23° C. and the relative humidity to ≥50%. The room was illuminated to give a cycle of 12 hours light and 12 hours darkness. Light was from 06.00 to 18.00 h.

The animals were housed in pens with straw as bedding, six together in each pen.

The animals had free access to domestic quality drinking water during the study, but were fasted from approximately 4 pm the day before dosing until approximately 12 hours after dosing.

The animals were weighed on arrival and on the days of dosing.

The animals received a single subcutaneous injection. The subcutaneous injection was given on the right side of the neck, approximately 5-7 cm from the ear and 7-9 cm from the middle of the neck. The injections were given with a stopper on the needle, allowing 0.5 cm of the needle to be introduced.

Each test substance was given to typically three but in some cases two or more animals. A full plasma concentration-time profile, employing 12-16 sampling points, was obtained from each animal. Blood samples were collected according to the following schedule:

After Intravenous Administration (not Applicable in the Present Study):

Predose (0), 0.17 (10 minutes), 0.5, 1, 2, 4, 6, 8, 12, 24, 48, 72, 96, and 120 hours after injection. In some cases also 168 hours and 240 hours post injection, After Subcutaneous Administration:

Predose (0), 0.5, 1, 2, 4, 6, 8, 12, 24, 48, 72, 96, and 120 hours after injection.

At each sampling time, 1-2 ml of blood was drawn from each animal. The blood samples were taken from a jugular vein. In some cases also 168 hours and 240 hours post injection.

The blood samples were collected into test tubes containing a buffer for stabilisation in order to prevent enzymatic degradation of the GLP-1 derivatives. An example of a suitable buffer is: EDTA (di-natrium) 0.18 M; Aprotinin 15000 KIE/ml, Val-Pyr 0.30 mM and with pH adjusted to 7.4)—or directly into EDTA testtubes (ie Sarstedt Micro tube 1.3 mL K3E). Blood samples were preferably kept on ice for max 20 min. before centrifugation.

Plasma was separated using centrifugation (e.g. at 4 dgC, 10 min., 1500 G) and was immediately transferred to Micronic-tubes. Approximately 200 µl plasma was transferred to each Micronic-tube. The plasma was stored at −20° C. until assayed. The plasma samples were assayed for the content of GLP-1 derivatives using a suitable assay, e.g. an immunoassay, such as ELISA, RIA, RRA, or LCMS assay, as described below.

For the LCMS assay, plasma samples were analysed by LC-MS on an LTQ-Orbitrap mass spectrometer (ThermoFisher Scientific, Bremen) to which Accela HPLC pumps and an autosampler were connected (both from ThermoFisher). The mass spectrometer was equipped with an electrospray interface, which was operated in positive ionisation mode. Analysis was conducted in selected ion monitoring mode with a window of 5 Da and at a resolution of 30000. For quantification purposes, the five most intense isotope peaks were extracted with an accuracy of 5 ppm. Gradient elution was performed on a Jupiter Proteo column (4µ) 90 A (50×2.0 mm ID). Mobile phases consisted of A. 0.1% formic acid and B. 0.1% formic acid in acetonitrile and the flow rate was 0.3 ml/min. Plasma samples were precipitated with organic solvent. For construction of plasma standards, compound was spiked to plasma and the plasma standards were treated as the samples. Quality controls were prepared as the standards, with accept criteria at 20%.

The plasma concentration-time profiles were analysed, e.g. by pharmacokinetic analysis. An example of a suitable analysis tool is (NCA) using WinNonlin Professional 5.0 (Pharsight Inc., Mountain View, Calif., USA). NCA was performed using the individual plasma concentration-time profiles from each animal and terminal half-life (T½) was calculated.

Except for two compounds, all tested GLP-1 derivatives of the invention had a half-life after subcutaneous administration in minipigs in the range of 19-101 hours. And except for three compounds, all tested GLP-1 derivatives of the invention had a half-life after subcutaneous administration in minipigs in the range of 29-101 hours. The half-life of the comparative compound liraglutide was 18 hours.

Selected derivatives of the invention may be tested in Danish Landrace pigs:

Pharmacokinetic Testing of GLP-1 Derivatives in Pigs

Pigs (50% Duroc, 25% Yorkshire, 25% Danish Landrace, app 40 kg) are fasted from the beginning of the experiment. To each pig 0.5 nmol of test derivative per kg body weight is administered in a 50 µM isotonic solution (5 mM phosphate, pH 7.4, 0.02% Tween®-20 (Merck), 45 mg/ml mannitol (pyrogen free, Novo Nordisk). Blood samples are drawn from a catheter in vena jugularis. 5 ml of the blood samples are poured into chilled glasses containing 175 µl of the following solution: 0.18 M EDTA, 15000 KIE/ml aprotinin (Novo Nordisk) and 0.30 mM Valine-Pyrrolidide (Novo Nordisk), pH 7.4. Within 30 min, the samples are centrifuged for 10 min at 5-6000*g. Temperature is kept at 4° C. The supernatant is pipetted into different glasses and kept at minus 20° C. until use.

The plasma concentrations of the peptides are determined in a sandwich ELISA or by RIA using different mono- or polyclonal antibodies. Choice of antibodies depends of the GLP-1 derivatives. The time at which the peak concentration in plasma is achieved varies within wide limits, depending on the particular GLP-1 derivative selected.

General Assay Protocol for Sandwich ELISA in 96-Wells Microtiterplate
Coating buffer (PBS): Phosphate buffered saline, pH7.2
Wash-buffer (PBS-wash): Phosphate buffered saline, 0.05% v/v Tween 20, pH 7.2
Assay-buffer (BSA-buffer): Phosphate buffered saline, 10 g/l Bovin Serum Albumin
   (Fluka 05477), 0.05% v/v Tween 20, pH 7.2
Streptavidin-buffer Phosphate buffered saline, 0.5 M NaCl, 0.05% v/v Tween 20, pH 7.2
Standard: Individual derivatives in a plasma-matrix
A-TNP: Nonsens antibody
AMDEX: Streptavin-horseradish-peroxodase (Amersham RPN4401V)
TMB-substrate: 3,3',5,5tetramethylbenzidine (<0.02%), hydrogen peroxide The assay was carried out as follows (volumen/well):
1.) coat with 100 µl catching antibody 5 µg/ml in PBS-buffer
    incubate o/n, 4° C.
    5×PBS-wash
    blocked with last wash in minimum 30 minute
    then empty the plate
2.) 20 µl sample+100 µl biotinylated detecting antibody 1 µg/ml in BSA-buffer with 10 µg/ml A-TNP
    incubate 2 h, room temperature, on a shaker→5×PBS-wash, then empty the plate
3.) 100 µl AMDEX 1:8000 in Streptavidin-buffer
    incubate 45-60 minute, room temperature, on a shaker
    5×PBS-wash, then empty the plate
4.) 100 µl TMB-substrate
    incubate x minute at room temperature on a shaker
    stop the reaction with 100 µl 4 M $H_3PO_4$
    Read the absorbance at 450 nm with 620 nm as reference
    The concentration in the samples was calculated from standard curves.

General Assay Protocol for RIA
DB-buffer: 80 mM phosphate buffer, 0.1% Human serum albumin, 10 mM EDTA,
   0.6 mM thiomersal, pH 7.5
FAM-buffer: 40 mM phosphate buffer, 0.1% Human Serum Albumin,
   0.6 mM thiomersal, pH 7.5
Charcoal: 40 mM phosphate buffer, 0.6 mM thiomersal, 16.7% bovine plasma, 15 g/l activated carbon, pH 7.5 (mix the suspension minimum 1 h before use at 4° C.)
Standard: Individual derivatives in a plasma-matrix The assay was carried out in minisorp tubes 12×75 mm (volumen/tube) as follows:

|  | Db-buffer | SAM-PLE | Antibody | FAM-buf. | Tracer | Charcoal | $H_2O$ |
|---|---|---|---|---|---|---|---|
| Day 1 | | | | | | | |
| Total | | | | | 100 µL | | |
| NSB | 330 µL | | | 100 µL | 100 µL | | |
| Sample | 300 µL | 30 µL | 100 µL | | 100 µL | | |
| Mix, incubate o/n at 4° C. | | | | | | | |
| Day 2 | | | | | | | |
| Total | | | | | | | 1.5 mL |
| NSB | | | | | | 1.5 mL | |
| Sample | | | | | | 1.5 mL | |

Mix - incubate 30 min at 4° C. - centrifuge at 3000 rpm, 30 min - immediately after transfer supernatants to new tubes, close with stopper and count on gamma-counter for 1 minute. The concentration in the samples was calculated from individual standard curves.

GLP-1 Radio Receptor Assay (RRA):

The method is a radiometric-ligand binding assay using LEADseeker imaging particles. The assay is composed of membrane fragments containing the GLP-1 receptor, unlabeled GLP-1 analogues, human GLP-1 labelled with $^{125}$I and PS LEADseeker particles coated with wheat germ agglutinin (WGA). Cold and $^{125}$I-labelled GLP-1 will compete for the binding to the receptor. When the LEADseeker particles are added they will bind to carbohydrates residues on the membrane fragments via the WGA-residues. The proximity between the $^{125}$I-molecules and the LEADseeker particles causes light emission from the particles. The LEADseeker will image the emitted light and it will be reversibly correlated to the amount of GLP-1 analogue present in the sample.

Reagents & Materials:

Pre treatment of animal plasma: Animal plasma was heat treated for 4 hrs at 56° C. and centrifuged at 10.000 rpm for 10 minutes. Afterwards, Val-Pyr (10 µM) and aprotenin (500 KIE/mL) was added and stored at <−18° C. until use.

GLP-1 analogues calibrators: GLP-1 analogues were spiked into heat-treated plasma to produce dilution lines ranging from approximately 1 µM to 1 µM.

GLP-1 RRA assay buffer: 25 mM Na-HEPES (pH=7.5), 2.5 mM $CaCl_2$, 1 mM $MgCl_2$, 50 mM NaCl, 0.1% ovalbumin, 0.003% tween 20, 0.005% bacitracin, 0.05% $NaN_3$.

GLP-1 receptor suspension: GLP-1 receptor membrane fragments were purified from baby hamster kidney (BHK) cells stably expressing the human pancreatic GLP-1 receptor. Stored <−80° C. until use.

WGA-coupled polystyrene LEADseeker imaging beads (RPNQ0260, Amersham): The beads were reconstituted with GLP-1 RRA assay buffer to a concentration of 13.3 mg/mL. The GLP-1 receptor membrane suspension was then added and incubated cold (2-8° C.) at end-over-end for at least 1 hr prior to use.

[$^{125}$I]-GLP-1(7-36)amide (Novo Nordisk A/S). Stored <−18° C. until use.

Ethanol 99.9% vol (De Dansk Spritfabrikker A/S): Stored <−18° C. until use.

MultiScreen® Solvinert 0.45 µm hydrophobic PTFE plates (MSRPN0450, Millipore Corp.)

Poly propylene plates (cat. no. 650201, Greiner Bio-One)

White polystyrene 384-well plates (cat. no. 781075, Greiner Bio-One)

Apparatus:

Horizontal plate mixer

Centrifuge with a standard swinging-bucket microtitre plate rotor assembly

UltraVap—Drydown Sample Concentrator (Porvair)

LEADseeker™ Multimodality Imaging System (Amersham)

Assay Procedure:

Sample Preparation:

Mount the MultiScreen® Solvinert filter plate on a chemical-comparable receiver plate (i.e. poly propylene plates) to collect the filtrate.

Add 150 µL ice-cold ethanol 99.9% into the empty wells of the MultiScreen® Solvinert filter plate followed by 50 µL calibrator or plasma sample. Place the storage lid on the filter plate.

Incubate 15 minutes at 18-22° C. on a horizontal plate mixer.

Place the assembled filter and receiver plate, with the lid, into a standard swinging-bucket microtitre plate rotor assembly. The filtrate is then collected in the empty wells of the receiver plate at 1500 rpm for 2 minutes.

Dry down the filtrate by using the UltraVap with heated (40° C.) $N_2$ for duration of 15 minutes. Reconstitute the dry material by adding 100 µL GLP-1 RRA assay buffer into each well. Incubate for 5 minutes on a horizontal mixer.

GLP-1 Radio Receptor Assay:

Use the following pipetting scheme and white polystyrene 384-well plates:

35 µL GLP-1 RRA assay buffer

5 µL reconstituted filtrate.

10 µL [$^{125}$I]GLP-1(7-36)amide. The stock solution was diluted in GLP-1 RRA assay buffer to 20.000 cpm/well prior to use.

15 µL GLP-1 receptor membrane fragments (≈0.5 µg/well) pre-coated to WGA-polystyrene LEADseeker imaging beads (0.2 mg/well)

Seal the plates and incubate over night at 18-22° C.

The light emission from each wells are detected by using the LEADseeker™ Multimodality Imaging System for duration of 10 minutes.

Example 74

Stimulation of cAMP Formation in a Cell Line Expressing the Cloned Human GLP-1 Receptor The potencies of a number of GLP-1 derivatives of the invention (the compounds of Examples 1-28, 31-37, and 39-71) were determined as described below, i.e. as the stimulation of the formation of cyclic AMP (cAMP) in a medium containing the human GLP-1 receptor. For comparison, the potency of liraglutide was also determined.

Purified plasma membranes from a stable transfected cell line, BHK467-12A (tk-ts13), expressing the human GLP-1 receptor was stimulated with the GLP-1 derivative in question, and the potency of cAMP production was measured using the AlphaScreen™ cAMP Assay Kit from Perkin Elmer Life Sciences.

A stable transfected cell line has been prepared at NN A/S, Denmark, and a high expressing clone was selected for screening. The cells were grown at 5% $CO_2$ in DMEM, 5% FCS, 1% Pen/Strep (Pencillin/Streptomycin) and 0.5 mg/ml of the selection marker G418.

Cells at approximate 80% confluence were washed 2× with PBS (Phosphate Buffered Saline) and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenized by the Ultrathurax for 20-30 sec. in 10 ml of Buffer 1 (20 mM Na-HEPES, 10 mM EDTA, pH=7.4), centrifuged 15 min at 20.000 rpm and the pellet resuspended in 10 ml of Buffer 2 (20 mM Na-HEPES, 0.1 mM EDTA, pH=7.4). The suspension was homogenized for 20-30 sec and centrifuged 15 min at 20.000 rpm. Suspension in Buffer 2, homogenization and centrifugation was repeated once and the membranes were resuspended in Buffer 2 and ready for further analysis or stored at −80° C.

The functional receptor assay was carried out by measuring the peptide induced cAMP production by The AlphaScreen Technology. The basic principle of The AlphaScreen Technology is a competition between endogenous cAMP and exogenously added biotin-cAMP. The capture of cAMP is achieved by using a specific antibody conjugated to acceptor beads. Formed cAMP was counted and measured at a AlphaFusion Microplate Analyzer. The $EC_{50}$ values were calculated using the Graph-Pad Prisme software (version 5).

Except for six compounds, all tested GLP-1 derivatives of the invention were found to have potencies ($EC_{50}$) below 4.00.

Example 75

Affinity to the GLP-1 Receptor at High Vs. Low Albumin

The binding affinity of GLP-1 peptides to the human GLP-1 receptor was measured by way of its displacement of $^{125}$I-GLP-1 from the receptor.

In order to test the binding of the peptides to albumin, the assay was performed with a low concentration of albumin (0.005%—corresponding to the residual amount thereof in the tracer), as well as with a high concentration of albumin (2.0% added).

A shift in the binding affinity, $IC_{50}$, is an indication that the peptide in question binds to albumin, and thereby a prediction of a potential protracted pharmacokinetic profile of the peptide in question in animal models.
Conditions
Species (in vitro): Hamster
Biological End Point: Receptor Binding
Assay Method: SPA
Receptor: GLP-1 receptor
Cell Line: BHK tk-ts13
Membrane Purification:

The cells (approx. 80% confluence) were washed twice in PBS and harvested (PBS+EDTA or Versene), following which they were separated by centrifugation at 1000 rpm for 5 min. The cells/cell pellet must be kept on ice to the extent possible in the subsequent steps. The cell pellet was homogenised with Ultrathurrax for 20-30 seconds in a suitable amount of Buffer 1 (depending on the amount of cells, but e.g. 10 ml). The homogenate as centrifuged at 20000 rpm for 15 minutes. The pellet was resuspended (homogenised) in 10 ml Buffer 2 and re-centrifuged. This step was repeated once more. The resulting pellet was resuspended in Buffer 2, and the protein concentration was determined. The membranes were stored at −80° C.
Buffer 1: 20 mM Na-HEPES+10 mM EDTA, pH 7.4
Buffer 2: 20 mM Na-HEPES+0.1 mM EDTA, pH 7.4
Binding Assay:
SPA:

Test compounds/peptides, membranes, SPA-particles and [$^{125}$I] are diluted in assay buffer. 25 ul (micro liter) of test compounds/peptides are added to Optiplate. HSA ("high albumin" experiment), or buffer ("low albumin" experiment), is added (50 ul). Add 5-10 ug protein/sample (50 ul) corresponding to 0.1-0.2 mg protein/ml (to be preferably optimised for each membrane preparation). Add SPA-particles (Wheatgerm agglutinin SPA beads) RPNQ 0001) 0.5 mg/well (50 ul). Start the incubation with [I$^{125}$]-GLP-1 (final concentration 0.05 nM corresponding to 49.880 DPM, 25 ul). The plates are sealed with PlateSealer. Incubate for 120 minutes at 30° C. while shaking. The plates are centrifuged (1500 rpm, 10 min) and counted in Topcounter.
Assay buffer: 50 mM HEPES
5 mM EGTA
5 mM MgCl2
0.005% Tween 20
pH 7.4
HSA was SIGMA A1653.

The $IC_{50}$ value is read from the curve as the concentration which displaces 50% of $^{125}$I-GLP-1 from the receptor, and the ratio of [($IC_{50}$/nM) high HSA]/[($IC_{50}$/nM) ultralow HSA] was determined. Twenty-one of the tested GLP-1 derivatives had a ratio below 10, twelve in the range of 10-30, twelve in the range of 30-50, and fourteen in the range of 50-100.

Example 76

Albumin Binding Affinity

The affinities of a number of GLP-1 derivatives of the invention (the compounds of Examples 1-2, 4-16, 22-28, 31, and 33-71) for human serum albumin (HSA) were measured by a competition scintillation proximity assay (SPA) as described in the following.

Streptavidin-SPA beads (GE Healthcare RPNQ0009) were incubated with biotinylated HSA for 5 hours. The beads were washed with buffer to remove unbound HSA. The beads were mixed with a $^{125}$I-labeled acylated GLP-1 analogue (N-epsilon37-[2-(2-[2-((S)-4-((S)-4-(12-[4-(16-(1H-tetrazol-5-yl)hexadecanoylsulfamoyl)butyrylamino]dodecanoylamino)-4-carboxybutyrylamino)-4-carboxybutyrylamino)ethoxy]ethoxy)acetyl][Aib8,$^{125}$I-Tyr19,Glu22,Arg26,Arg34,Lys37] GLP-1(7-37)-NH$_2$) in a buffer containing 100 mM Hepes, 100 mM NaCl, 10 mM MgSO$_4$, 0.025% Tween-20, pH 7.4. The mixture was pipetted into the wells of a Perkin Elmer Optiplate-96 6005290 (100 µl per well) and 100 µl of a dilution series of the GLP-1 derivative to be measured was added in the same buffer. After 20 hours of gentle rocking at room temperature the plates were centrifuged and counted on a TopCounter. Bound cpm was plotted as a function of GLP-1 derivative concentration and the $EC_{50}$ value of the competition curve was used as a measure of the affinity of the derivative for HSA.

The albumin binding affinities ($EC_{50}$, in nM) of various GLP-1 derivatives of the invention are shown in Table 1 below.

TABLE 1

| Albumin binding affinity | |
| --- | --- |
| Compound of Example No. | Albumin binding affinity ($EC_{50}$/nM) |
| 63, 44, 50, 47, 53, 67, 37, 46, 43, 42, 65, 68, 64, 34, 66, 38, 39 | 1-100 |
| 33, 49, 69, 57, 35, 45, 36, 10, 58 | 100-150 |
| 51, 55, 41, 40, 56, 15, 22, 54, 9, 13 | 150-300 |
| 62, 12, 7, 60, 4, 52, 2, 5, 8, 31, 16, 14, 1 | 300-800 |
| 70, 26, 71, 48, 61, 11, 23, 24, 27, 6 | 800-2000 |
| 59, 28, 25 | above 2000 |

As it is apparent from Table 1, several of the GLP-1 derivatives of the invention have a high albumin binding affinity corresponding to an $EC_{50}$ of below 2000 nM (the lower the $EC_{50}$, the higher the albumin binding affinity).

Example 77

Dose-Response Study in db/db Mice

A number of GLP-1 derivatives of the invention (the compounds of Examples 1, 7, 14, 16, 22, 23, 24, 26, 27, 28. 31, 33, 46, 47, 48, 49, 50, 53, and 59) were tested in a dose-response study in an obese, diabetic mouse model (db/db mice) as described in the following.

Fifty db/db mice (Taconic, Denmark), 10-12 weeks of age, were housed according to standard animal welfare rules of Novo Nordisk and were given free access to standard chow (e.g. Altromin 1324, Brogaarden, Gentofte, Denmark) and tap water and kept at 24° C. After 1 week of acclimatisation, the basal blood glucose was assessed twice. Based on the mean blood glucose values, 42 mice were selected for further experimentation and allocated to 7 groups (n=6) with matching blood glucose levels. The mice were used in experiments of 3-6 days' duration for up to 4 times, following which they were euthanized.

The seven groups received treatment as follows:
1: Vehicle, s.c.
2: GLP-1 derivative, 0.3 nmol/kg, s.c.
3: GLP-1 derivative, 1 nmol/kg, s.c.
4: GLP-1 derivative, 3 nmol/kg, s.c.
5: GLP-1 derivative, 10 nmol/kg, s.c.
6: GLP-1 derivative, 30 nmol/kg, s.c.
7: GLP-1 derivative, 100 nmol/kg, s.c.

Vehicle: 50 mM phosphate, 0.05% tween 80, pH 8. The GLP-1 derivative was dissolved in the vehicle, e.g. to concentrations of 0.05, 0.17, 0.5, 1.7, 5 and 17 nmol/ml and 300 microliter were administered s.c. per mouse weighing 50 g (6 ml/kg).

On the day of dosing, the compound in question was dosed at approximately 9 am (time 0). At time −½ h (8.30 am) blood glucose was assessed, following which the mice were weighed. Blood glucose was assessed several times on the day of dosing, usually at time 1, 3 and 6 h (10 am, 12 am and 3 pm).

On the following days, the blood glucose was assessed at time 24, 48, 72, and 96 h after dosing (i.e. at 9 am on day 2, 3, 4, 5), followed by weighing. In some studies, blood glucose and body weight was furthermore assessed 120 h (day 6) after dosing.

The mice were weighed individually on a digital weight.

Samples for the measurement of blood glucose were obtained from the tail tip capillary of conscious mice. Blood, 10 µl, was collected into heparinised capillaries and transferred to 500 µl glucose buffer (EBIO buffer solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

The half-lives (T½) were calculated according to the following mathematical model: Assuming that
(1) the disappearance of the compounds from plasma is monoexponential;
(2) the effect on blood glucose (deltaBG) can be described by a standard sigmoidal dose-response curve;
(3) the first 6 hours of absorption and distribution are ignored and only the return of the glucose from the bottom to the baseline (minimum to 0) is fitted;
then the glucose response (Y) (for example deltaBG) can be described by the following equation:

$$Y = \text{Bottom} + (\text{Top} - \text{Bottom})/(1 + \text{Dose} * \exp(-\ln 2 * t/T\frac{1}{2})/ED50),$$

where the variables ED50 and T½ are defined as follows:
ED50 is the dose giving rise to half maximal effect on BG (in nmol/kg)
T½ is the half-life (in hours); and the following are global Constants:
Top (the response after return to baseline glucose), and Bottom (the response at maximal glucose fall); and the following is a constant for each data set (each dose):
Dose (the administered dose (in nmol/kg)).

All data sets are fitted simultaneously.

All compounds tested had a half-life (T½) in the range of 12-35 hours.

The invention claimed is:

1. A peptide derivative comprising a peptide wherein at least one amino acid residue is derivatized with A-B-C-D- wherein (i) A- is

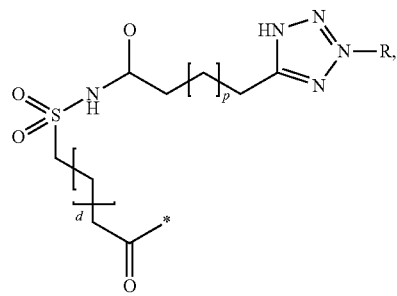

wherein R is lower linear or branched alkyl, p is selected from the group consisting of 10, 11, 12, 13 and 14, and d is selected from the group consisting of 0, 1, 2, 3, 4 and 5, and B- is selected from the group consisting of

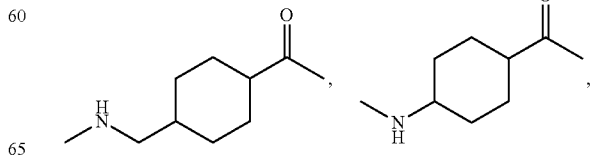

-continued

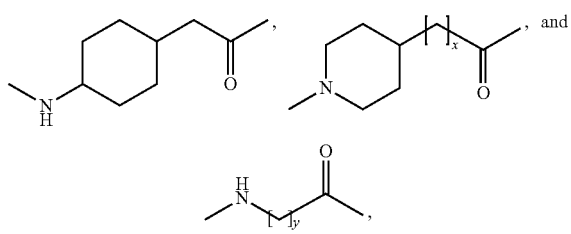

wherein x is selected from the group consisting of 0, 1, 2, 3 and 4, and y is selected from the group consisting of 1, 2, 3, 4, 5, 6, 7, 8, 9, 10, 11 and 12, or (ii) A is

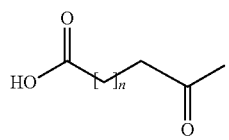

wherein n is selected from the group consisting of 14, 15, 16 17, 18 and 19, and B is selected from the group consisting of

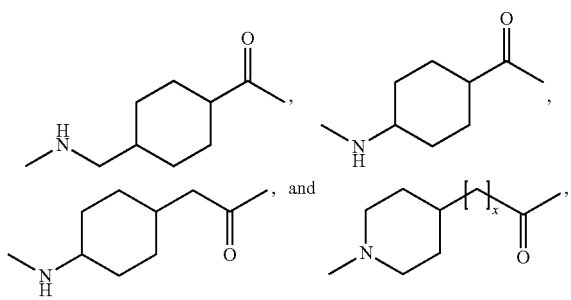

wherein x is selected from the group consisting of 0, 1, 2, 3 and 4, and together with either (i) or (ii)

-C- is selected from the group consisting of

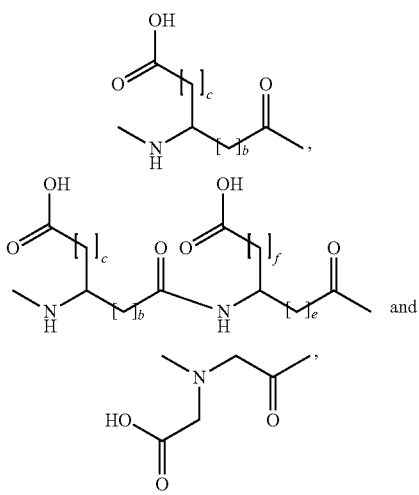

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker, represents a bond, or is absent.

2. The derivative according to claim 1, wherein at least one amino acid residue is derivatized with A-B-C-.

3. The derivative according to claim 1, wherein said peptide is a GLP-1 peptide selected from GLP-1(7-37) and an analogue of GLP-1(7-37), wherein, in said peptide, at least one amino acid residue is derivatised with A-B-C-, or A-B-C-D-.

4. The derivative according to claim 3, wherein the derivatised amino acid residue comprises an amino group.

5. The derivative according to claim 4, wherein the derivatised amino acid residue is lysine.

6. The derivative according to claim 5, wherein the linker comprises at least 5 non-hydrogen atoms, 30-50% of which are either N or O.

7. The derivative according to claim 6, wherein D is selected from the group consisting of

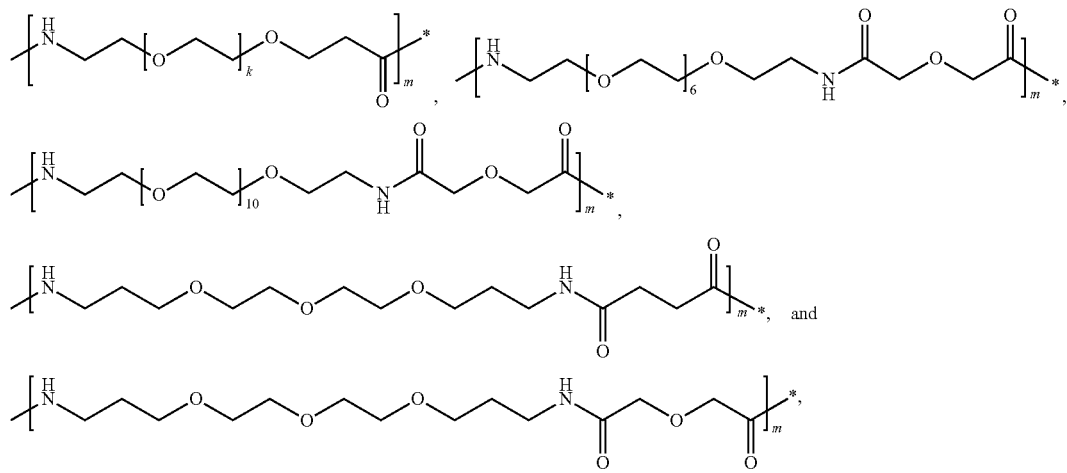

wherein k is selected from the group consisting of 0, 1, 2, 3, 4, 5, 11 and 27, and m is selected from the group consisting of 0, 1, 2, 3, 4, 5 and 6, and D is attached to the amino acid residue in the end depicted with *.

8. The derivative according to claim 1, wherein said GLP-1 analogue comprises an amino acid sequence according to formula (I):

Formula (I) (SEQ ID No: 2)
$Xaa_7$-$Xaa_8$-Glu-Gly-Thr-Phe-Thr-Ser-Asp-$Xaa_{16}$-

Ser-$Xaa_{18}$-$Xaa_{19}$-$Xaa_{20}$-Glu-$Xaa_{22}$-$Xaa_{23}$-Ala- $Xaa_{25}$-$Xaa_{26}$-$Xaa_{27}$-Phe-Ile-$Xaa_{30}$-Trp-Leu- $Xaa_{33}$-$Xaa_{34}$-$Xaa_{35}$-$Xaa_{36}$-$Xaa_{37}$-$Xaa_{38}$-$Xaa_{39}$-

$Xaa_{40}$-$Xaa_{41}$-$Xaa_{42}$-$Xaa_{43}$-$Xaa_{44}$-$Xaa_{45}$-$Xaa_{46}$ wherein
$Xaa_7$ is L-histidine, D-histidine, desamino-histidine, 2-amino-histidine, β-hydroxy-histidine, homohistidine, Nα-acetyl-histidine, α-fluoromethyl-histidine, α-methyl-histidine, 2(3H-imidazol-4-yl)acetyl, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{16}$ is Val, or Leu;
$Xaa_{18}$ is Ser, Lys, or Arg;
$Xaa_{19}$ is Tyr, or Gln;
$Xaa_{20}$ is Leu, Met, or Lys;
$Xaa_{22}$ is Gly, Glu, or Aib;
$Xaa_{23}$ is Gln, Glu, Lys, or Arg;
$Xaa_{25}$ is Ala, or Val;
$Xaa_{26}$ is Lys, Glu, or Arg;
$Xaa_{27}$ is Glu, or Leu;
$Xaa_{30}$ is Ala, Glu, Lys, or Arg;
$Xaa_{33}$ is Val, Thr(O-benzyl), or Lys;
$Xaa_{34}$ is Lys, Glu, Gln, Asn, or Arg;
$Xaa_{35}$ is Gly, Aib, or absent;
$Xaa_{36}$ is Arg, Gly, Lys, or absent;
$Xaa_{37}$ is Gly, Ala, Glu, Pro, Lys, epsilon-amino-Lys, amide or is absent;
$Xaa_{38}$ is Lys, Ser, amide, or is absent;
$Xaa_{39}$ is Ser, Lys, amide, or is absent;
$Xaa_{40}$ is Gly, amide, or is absent;
$Xaa_{41}$ is Ala, amide, or is absent;
$Xaa_{42}$ is Pro, amide, or is absent;
$Xaa_{43}$ is Pro, amide, or is absent;
$Xaa_{44}$ is Pro, amide, or is absent;
$Xaa_{45}$ is Ser, amide, or is absent;
$Xaa_{46}$ is amide, or is absent;
provided that if $Xaa_{38}$, $Xaa_{39}$, $Xaa_{40}$, $Xaa_{41}$, $Xaa_{42}$, $Xaa_{43}$, $Xaa_{44}$, $Xaa_{45}$ or $Xaa_{46}$ is absent then each amino acid residue downstream is also absent.

9. The derivative according to claim 1, wherein said GLP-1 analogue comprises an amino acid sequence according to formula (II):

Formula (II) (SEQ ID No: 3)
$Xaa_7$-$Xaa_8$-Glu-Gly-Thr-Phe-Thr-Ser-Asp-Val-Ser- $Xaa_{18}$-Tyr-Leu-Glu-$Xaa_{22}$-$Xaa_{23}$-Ala-Ala-$Xaa_{26}$-

Glu-Phe-Ile-$Xaa_{30}$-Trp-Leu-Val-$Xaa_{34}$-$Xaa_{35}$-

$Xaa_{36}$-$Xaa_{37}$-$Xaa_{38}$ wherein
$Xaa_7$ is L-histidine, D-histidine, desamino-histidine, 2-amino-histidine, β-hydroxy-histidine, homohistidine, Nα-acetyl-histidine, α-fluoromethyl-histidine, α-methyl-histidine, 2(3H-imidazol-4-yl)acetyl, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{18}$ is Ser, Lys, or Arg;
$Xaa_{22}$ is Gly, Glu, or Aib;
$Xaa_{23}$ is Gln, Glu, Lys, or Arg;
$Xaa_{26}$ is Lys, Glu, or Arg;
$Xaa_{30}$ is Ala, Glu, Lys, or Arg;
$Xaa_{34}$ is Lys, Glu, Gln, or Arg;
$Xaa_{35}$ is Gly, Aib, or absent;
$Xaa_{36}$ is Arg, Lys, or absent;
$Xaa_{37}$ is Gly, Ala, Glu, Pro, Lys, or epsilon-amino-Lys;
$Xaa_{38}$ is Lys, amide, or is absent.

10. The derivative according to claim 1, wherein said GLP-1 analogue comprises an amino acid sequence according to formula (III) which is derivatised in position 18, 23, 26, 30, 31, 34, 36, 37 or 38:

Formula (III) (SEQ ID No: 6)
$Xaa_7$-$Xaa_8$-$Xaa_9$-Gly-Thr-Phe-Thr-Ser-Asp-$Xaa_{16}$-

Ser-$Xaa_{18}$-Tyr-Leu-Glu-Glu-$Xaa_{23}$-Ala-$Xaa_{25}$-

Arg-$Xaa_{27}$-Phe-Ile-$Xaa_{30}$-Trp-Leu-$Xaa_{33}$-$Xaa_{34}$-

$Xaa_{35}$-$Xaa_{36}$-$Xaa_{37}$-$Xaa_{38}$-$Xaa_{39}$ wherein
$Xaa_7$- $Xaa_8$ is 2(3H-imidazol-4-yl)acetyl-alanine, L-histidine-Aib, desamino-histidine-alanine, or desamino-histidine-Aib;
$Xaa_9$ is Glu or a Glu derivative such as alpha, alpha dimethyl-Glu;
$Xaa_{16}$ is Val, or Leu;
$Xaa_{18}$ is Ser, Lys, or Arg;
$Xaa_{19}$ is Tyr, or Gln;
$Xaa_{23}$ is Gln, Glu, Lys, or Arg;
$Xaa_{25}$ is Ala, or Val;
$Xaa_{27}$ is Glu, or Leu;
$Xaa_{30}$ is Ala, Glu, Lys, Arg, or absent;
$Xaa_{33}$ is Val, Thr(O-benzyl), or Lys;
$Xaa_{34}$ is Lys, Glu, Gln, Asn, or Arg;
$Xaa_{35}$ is Gly, Aib, or absent;
$Xaa_{36}$ is Arg, Lys, or absent;
$Xaa_{37}$ is Gly, Aib, Pro, epsilon-amino-Lys, or absent
$Xaa_{38}$ is Lys, Glu, or absent
$Xaa_{39}$ is amide, or is absent;
provided that if $Xaa_{37}$ is absent then $Xaa_{38}$ is also absent.

11. The derivative according to claim 1, wherein the GLP-1 peptide comprises an amino acid sequence according to formula (IV) which is derivatised with an albumin binding residue in position 18, 23, 26, 30, 31, 34, 36, 37, or 38:

Formula (IV) (SEQ ID No: 7)
Xaa$_7$-Xaa$_8$-Glu-Gly-Thr-Phe-Thr-Ser-Asp-Val-Ser-
Xaa$_{18}$-Tyr-Leu-Glu-Glu-Gln-Ala-Ala-Arg-Glu-Phe-
Ile-Xaa$_{30}$-Trp-Leu-Xaa$_{33}$-Xaa$_{34}$-Xaa$_{35}$-Xaa$_{36}$-Xaa$_{37}$-
Xaa$_{38}$-Xaa$_{39}$ wherein
Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 2(3H-imidazol-4-yl)acetyl, 3-pyridylalanine, 2-pyridylalanine or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{18}$ is Ser, Lys or Arg;
Xaa$_{30}$ is Ala, Glu, Lys or Arg;
Xaa$_{33}$ is Val or Lys;
Xaa$_{34}$ is Lys, Glu, Gln, or Arg;
Xaa$_{35}$ is Gly, Aib, or absent;
Xaa$_{36}$ is Arg, Lys, or absent;
Xaa$_{37}$ is Gly, Aib, Pro, epsilon-amino-Lys, or absent;
Xaa$_{38}$ is Lys, or absent; and
Xaa$_{39}$ is amide or is absent.

12. The derivative according to claim 11, wherein Xaa$_{38}$ is absent.

13. The derivative according to claim 11, wherein Xaa$_{37}$ and Xaa$_{38}$ are both absent.

14. The derivative according to claim 11, wherein Xaa$_7$ is desamino-histidine.

15. The derivative according to claim 11, wherein Xaa$_8$ is Aib.

16. The derivative according to claim 1, which is selected from the following:
N-ε$^{37}${2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis$^7$,Glu$^{22}$,Arg$^{26}$,Arg$^{34}$,Lys$^{37}$]GLP-1(7-37)amide;
N-ε$^{20}$-{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib$^2$,Leu$^{14}$,Lys$^{20}$,Gln$^{28}$,Ser(O-benzyl)$^{39}$] exendin-4 (1-39)amide;
N-ε$^{26}${2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis$^7$,Arg$^{34}$]GLP-1-(7-37);
N-epsilon37{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Arg34,Lys37]GLP-1-(7-37)amide;
N-epsilon23-[2-(2-[2-(2-[2-(2-((R)-3-[1-(17-Carboxyheptadecanoylamino)piperidin-4-ylcarbonylamino]-3-(carboxypropionylamino)ethoxy)ethoxy]acetylamino)ethoxy])acetyl][Aib8,Arg26,Arg 34]GLP-1-(7-37);
N-epsilon37-[2-(2-[2-(2-[2-(2-((R)-3-[1-(17-Carboxyheptadecanoyl)piperidin-4-ylcarbonylamino]3-carboxypropionylamino)ethoxy)ethoxy]acetylamino)ethoxy]ethoxy)acetyl][DesaminoHis7, Glu22 Arg26, Arg 34, Phe(m-CF3)28]GLP-1-(7-37)amide;
[DesaminoHis7,Glu22,Arg26,Arg34]GLP-1-(7-37)-Lys (2-{2-[2-(2-{2-[2-((S)-4-Carboxy-4-{[1-(19-carboxynonadecanoyl)piperidine-4-carbonyl]amino}butyrylamino)ethoxy]ethoxy}acetylamino)ethoxy]ethoxy}acetyl);
N-ε$^{20}$({2-[2-(2-{2-[2-((R)-3-carboxy-3-{[1-(17-carboxyheptadecanoyl)piperidine-4-carbonyl]amino}propionylamino)ethoxy]ethoxy}acetyl) [Aib$^8$,Lys$^{20}$,Arg$^{26}$,Glu$^{30}$,Thr(O-benzyl)$^{33}$]GLP-1-(7-37)amide;
N-epsilon30{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Lys30]GLP-1-(7-37);
N-epsilon31{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8, Glu22, Arg26,Lys 31]GLP-1-(7-37);
N-ε$^{20}$({2-[2-(2-{2-[2-((R)-3-carboxy-3-{[1-(17-carboxyheptadecanoyl)piperidine-4-carbon yl]amino}propionylamino)ethoxy]ethoxy}acetylamino)ethoxy]ethoxy}acetyl) [Aib$^8$, Lys$^{20}$,Arg$^{26}$,2-Naphtylalanine$^{28}$, Glu$^{30}$]GLP-1 (7-37) amide;
[Aib8, Glu22, Arg26, Arg34]GLP-1-(7-37)Lys[2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl]amide;
N-ε$^{20}$({2-[2-(2-{2-[2-((R)-3-carboxy-3-{[1-(17-carboxyheptadecanoyl)piperidine-4-carbon yl]amino}propionylamino)ethoxy]ethoxy}acetylamino)ethoxy]ethoxy}acetyl) [Aib$^8$, Lys$^{20}$,Arg$^{26}$, 2-Naphtylalanine$^{12}$, Glu$^{30}$]GLP-1-(7-37) amide;
[DesaminoHis7,Glu22,Arg26,Arg34]GLP-1-(7-37)Lys [2-(2-[2-(2-[2-(2-((S)-4-[1-[19-Carboxynonadecanoyl]piperidine-4-carbonylamino]-4-carboxybutyrylamino)ethoxy)ethoxy]acetylamino)ethoxy]ethoxy)acetyl] amide
N-epsilon31-(2-{2-[2-(2-{2-[2-((S)-3-Carboxy-3-{[1-(19-carboxy-nonadecanoyl)piperidine-4-carbonyl]amino}propionylamino)ethoxy]ethoxy}acetylamino)ethoxy]ethoxy}acetyl)[Aib8,Glu22,Arg26,Lys31, Arg34]GLP-1-(7-37);
N-epsilon26-[(S)-4-Carboxy-4-({trans-4-[(19-carboxynonadecanoylamino)methyl]cyclohexanecarbonyl}amino)butyryl][Aib8,Arg34]GLP-1-(7-37);
N-epsilon26-{4-[(S)-4-Carboxy-4-({trans-4-[(19-carboxynonadecanoylamino)methyl]cyclohexanecarbonyl}amino)butyrylamino]butyryl}[Aib 8,Arg34]GLP-1-(7-37);
N-epsilon26-[2-(2-{2-[(S)-4-Carboxy-4-({trans-4-[(19-carboxy-nonadecanoylamino)methyl]cyclohexanecarbonyl}amino)butyrylamino]ethoxy}ethoxy) acetyl][Aib8,Arg34]GLP-1-(7-37);
N-epsilon26-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl] [Aib8,Arg34]GLP-1-(7-37)-amide;

N-epsilon18-{2-(2-(2-(2-[2-(2-[(S)-4-Carboxy-4-({4-[(19-carboxynonadecanoylamino)methyl]cyclohexanecarbonyl}amino)butanoylamino]ethoxy)ethoxy]acetyl]ethoxy)ethoxy)acetyl}[Aib8,Lys18,Arg26,Arg34]GLP-1(7-37)

N-ε²⁰-[2-(2-[2-(2-[2-(2-((S)-4-[trans-4-([19-Carboxynonadecanoylamino]methyl)cyclohexylcarbonylamino]-4-carboxybutanoylamino)ethoxy)ethoxy]acetylamino)ethoxy]ethoxy)acetyl][desaminoHis¹, Lys²⁰, Ser(O-benzyl)³³, Ser(O-benzyl)³⁹] exendin (1-39);

[Aib8,Glu22,Arg26,Arg34]GLP-1-(7-37)Lys[2-(2-[2-(2-[2-(2-((S)-3-[4-([19-Carboxynonadecanoylamino]methyl)cyclohexylcarbonylamino]-3-carboxypropionylamino)ethoxy)ethoxy]acetylamino)ethoxy]ethoxy)acetyl]amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37)amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37)amide;

N-epsilon37-[2-(2-{2-[2-(2-{2-[(S)-4-Carboxy-4-({4-[(trans-19-carboxy-nonadecanoylamino)methyl]cyclohexanecarbonyl}amino)butyrylamino]ethoxy}ethoxy)acetylamino]ethoxy}ethoxy)acetyl][DesaminoHis7,Arg26,Arg34,Lys37]GLP-1-(7-37)amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37);

[DesaminoHis7,Glu22,Arg26,Arg34]GLP-1-(7-37)Lys[2-(2-{2-[2-(2-{2-[4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl]-amide;

[desaminoHis⁷,Arg²⁶,Arg³⁴]GLP-1-(7-37)Lys[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl]amide;

N-epsilon26[2-(2-{2-[2-(2-{2-[(S)-4-Carboxy-4-({4-[(19-carboxy-nonadecanoylamino)methyl]cyclohexanecarbonyl}amino)butyrylamino]ethoxy}ethoxy)acetylamino]ethoxy}ethoxy)acetyl [Aib8, Lys 26] GLP-1 (7-37)amide;

N-epsilon26 [2-(2-[2-(2-[2-(2-((S)-2-[trans-4-((9-Carboxynonadecanoylamino]methyl)cyclohexylcarbonylamino]-4-carboxybutanoylamino)ethoxy)ethoxy]acetylamino)ethoxy]ethoxy)acetyl][Aib8, Lys26] GLP-1 (7-37)amide;

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Arg26,Arg34,Lys37]GLP-1-(7-37);

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Glu30,Arg34,Lys37]GLP-1-(7-37);

N-epsilon26-[2-(2-{2-[(S)-4-Carboxy-4-((S)-4-carboxy-4-{4-[4-(16-(1H-tetrazol-5-yl)-hexadecanoylsulfamoyl)butyrylamino]-butyrylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-37);

N-epsilon26-[2-(2-{2-[(S)-4-Carboxy-4-((S)-4-carboxy-4-{4-[4-(16-(1H-tetrazol-5-yl)hexadecanoylsulfamoyl)butyrylamino]butyrylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]-dodecanoylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-36)amide;

N-epsilon26-[2-(2-{2-[(S)-4-Carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys33,Arg34]GLP-1-(7-34);

N-epsilon26-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-36)amide;

N-epsilon26-[2-(2-{2-[2-(2-{2-[2-(2-{2-[2-(2-{2-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetylamino]ethoxy}ethoxy)acetylamino]ethoxy}ethoxy)acetylamino]ethoxy}ethoxy)acetylamino]ethoxy}ethoxy)acetyl][Aib8,Lys26,Arg34]GLP-1-(7-36)amide;

[Aib8,Glu22,Arg26,Arg34]GLP-1-(7-37)Lys[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}-butyrylamino)butyrylamino]ethoxy}ethoxy)acetyl]amide;

N-epsilon20-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys20,Glu22,Arg26,Glu30,Pro37]GLP-1-(7-37)amide;

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Glu22,Arg26,Arg34,Lys37]GLP-1-(7-37)amide;

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Glu22,Arg26,Arg34,Lys37]GLP-1-(7-37)amide;

N-epsilon37-[[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Arg26,Arg34,Lys37]GLP-1-(7-37)amide;

[Aib8,Glu22,Arg26,Glu30,Pro37]GLP-1-(7-37)Lys [2-(2-{2-[4-Carboxy-4-(4-carboxy-4-{4-[4-(16-1H-tetrazol-5-yl-hexadecanoylsulfamoyl)butyrylamino]butyrylamino}butyrylamino)butyrylamino]ethoxy}ethoxy)acetyl];

[Aib8,Glu22,Arg26,Glu30,Pro37]GLP-1-((7-37)Lys (2-(2-(3-(2-(2-(2-(2-(2-(2-(2-(2-(2-(2-[4-(S)-carboxy-4-(4-(S)-carboxy-4-(4-{4-[16-(Tetrazol-5-yl)hexadecanoylsulfamoyl]butanoylamino}butanoylamino)butyrylamino)butyrylamino]ethoxy)ethoxy)ethoxy)ethoxy)ethoxy)ethoxy)ethoxy)ethoxy)ethoxy) propionylamino)ethoxy)ethoxy) peptide;

N-alpha37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,epsilon-Lys37]GLP-1-(7-37);

N-alpha8-[2-(4-imidazolyl)acetyl] N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][Glu22,Arg26,Arg34,Lys37]GLP-1-(8-37);

[DesaminoHis7,Glu22,Arg26,34]-GLP-1 (7-37)-Lys-(2-{2-[2-((S)-4-carboxy-4-{[1-(19-carboxynonadecanoyl)piperidine-4-carbonyl]amino}butyrylamino)ethoxy]ethoxy}acetyl) peptide;

[DesaminoHis7,Glu22,Arg26,34]-GLP-1 (7-37)-Lys-[2-(2-{2-[2-(2-{2-[4-Carboxy-4-({4-[(19-carboxynonadecanoylamino)methyl]cyclohexanecarbonyl}amino)butyrylamino]ethoxy}ethoxy)acetylamino]ethoxy}ethoxy)acetyl] peptide;

[DesaminoHis7,Glu22,Arg26,34]-GLP-1 (7-37)-Lys((S)-4-carboxy-4-(2-{2-[2-((S)-4-carboxy-4-{[1-(19-carboxynonadecanoyl)piperidine-4-carbonyl]amino}butyrylamino)ethoxy]ethoxy}acetylamino)butyryl) peptide;

[DesaminoHis7,Glu22,Arg26,34]-GLP-1 (7-37)-Lys-(2-(2-{2-[(S)-4-carboxy-4-(2-{2-[2-((S)-4-carboxy-4-{[1-(19-carboxynonadecanoyl)piperidine-4-carbonyl]amino}butyrylamino)ethoxy]ethoxy}acetylamino)butyrylamino]ethoxy}ethoxy)acetyl) peptide;

[DesaminoHis7,Arg26,34]-GLP-1 (7-37)-Lys(2-{2-[2-(2-{2-[2-((S)-4-Carboxy-4-{[1-(19-carboxynonadecanoyl)piperidine-4-carbonyl]amino}butyrylamino)ethoxy]ethoxy}acetylamino)ethoxy]ethoxy}acetyl) peptide;

N-epsilon37-(2-{2-[2-(2-{2-[2-((S)-4-Carboxy-4-{[1-(19-carboxynonadecanoyl)piperidine-4-carbonyl]amino}butyrylamino)ethoxy]ethoxy}acetylamino)ethoxy]ethoxy}acetyl) [DesaminoHis7,Arg26,Arg34,Lys37]GLP-1-(7-37);

N-epsilon37-((S)-4-Carboxy-4-{[1-(19-carboxy-nonadecanoyl)-piperidine-4-carbonyl]-amino}-butyryl) [DesaminoHis7,Arg26,Arg34,Lys37]GLP-1-(7-37);

[DesaminoHis7,Glu22,Arg26,34]-GLP-1 (7-37)-Lys-((S)-4-Carboxy-4-{[1-(19-carboxy-nonadecanoyl)-piperidine-4-carbonyl]-amino}-butyryl) peptide;

N-epsilon26-[2-(2-{2-[(R)-4-Carboxy-4-((R)-4-carboxy-4-{12-[4-(16-1H-tetrazol-5-yl-hexadecanoylsulfamoyl)butyrylamino]dodecanoylamino}butyrylamino)butyrylamino]ethoxy}ethoxy)acetyl]-[Aib8,Arg34]GLP-1 (7-37);

N-epsilon37-{2-[2-(2-{(S)-4-[(S)-4-(12-{4-[16-(2-tert-Butyl-2H-tetrazol-5-yl)-hexadecanoylsulfamoyl]butyrylamino}dodecanoylamino)-4-carboxybutyrylamino]-4-carboxybutyrylamino}ethoxy)ethoxy]acetyl}[DesaminoHis7,Glu22,Arg26,Arg34,Lys37]GLP-1 (7-37);

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Arg26,Arg34,Lys37]GLP-1-(7-37);

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37);

[ImPr7,Arg26,34,Glu22]GLP-1-(7-37)Lys[2-(2-[2-((S)-4-((S)-4-(12-[4-(16-1H-tetrazol-5-ylhexadecanoylsulfamoyl)butyrylamino]dodecanoylamino)-4-carboxybutyrylamino)-4-carboxybutyrylamino)ethoxy]ethoxy)acetyl]-amid;

N-epsilon36-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Glu22, Gln34]GLP-1-(7-37);

N-epsilon26-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Glu22, Gln34]GLP-1-(7-37);

N-epsilon18-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, 22,35, Lys18, Arg26,34]GLP-1-(7-37); and N-epsilon18-[2-(2-[2-(2-[2-(2-((R)-3-[trans-4-((9-Carboxynonadecanoylamino]methyl)cyclohexylcarbonylamino]3-carboxypropionylamino)ethoxy)ethoxy]acetylamino)ethoxy]ethoxy)acetyl][Aib8, Lys18, Glu22, Gln34]GLP-1-(7-37).

17. A pharmaceutical composition comprising a derivative according to claim 1 or a pharmaceutically acceptable salt, amide, alkyl, or ester thereof, and a pharmaceutically acceptable excipient.

18. A method of treating hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers in a subject in need of such treatment, the method comprising administering to the subject a therapeutically effective amount of a pharmaceutical composition according to claim 17.

19. The derivative according to claim 3, wherein A is

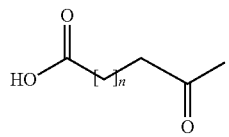

wherein n is selected from the group consisting of 14, 15, 16 17, 18 and 19, and B is selected from the group consisting of

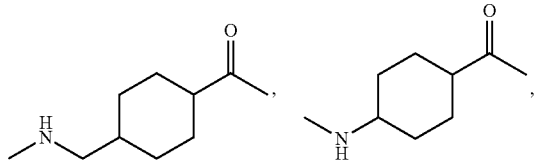

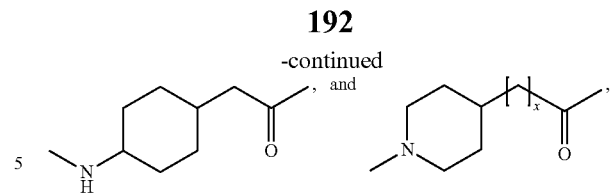

wherein x is selected from the group consisting of 0, 1, 2, 3 and 4.

20. The derivative according to claim 8, wherein A is

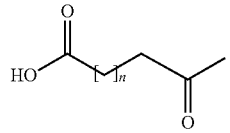

wherein n is selected from the group consisting of 14, 15, 16, 17, 18 and 19, and B is selected from the group consisting of

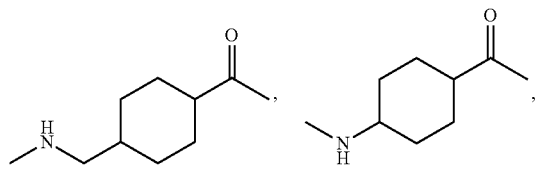

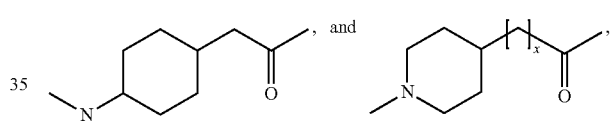

wherein x is selected from the group consisting of 0, 1, 2, 3 and 4.

21. The derivative according to claim 19, wherein A-B-C-D- is selected and combined from

-A-

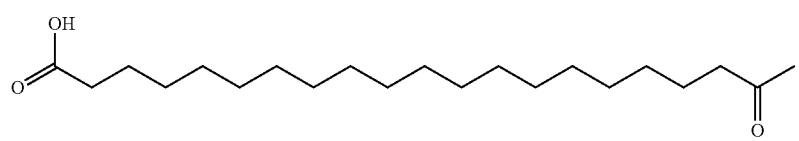

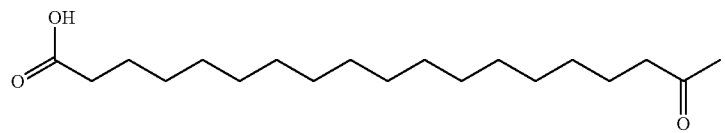

-B-

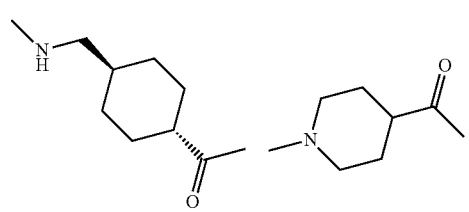

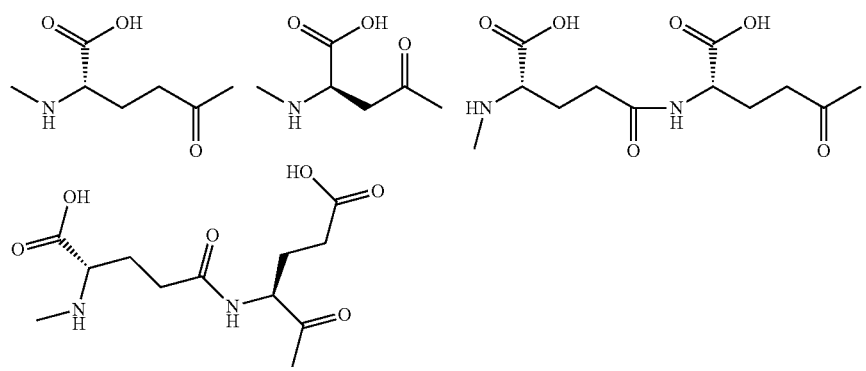
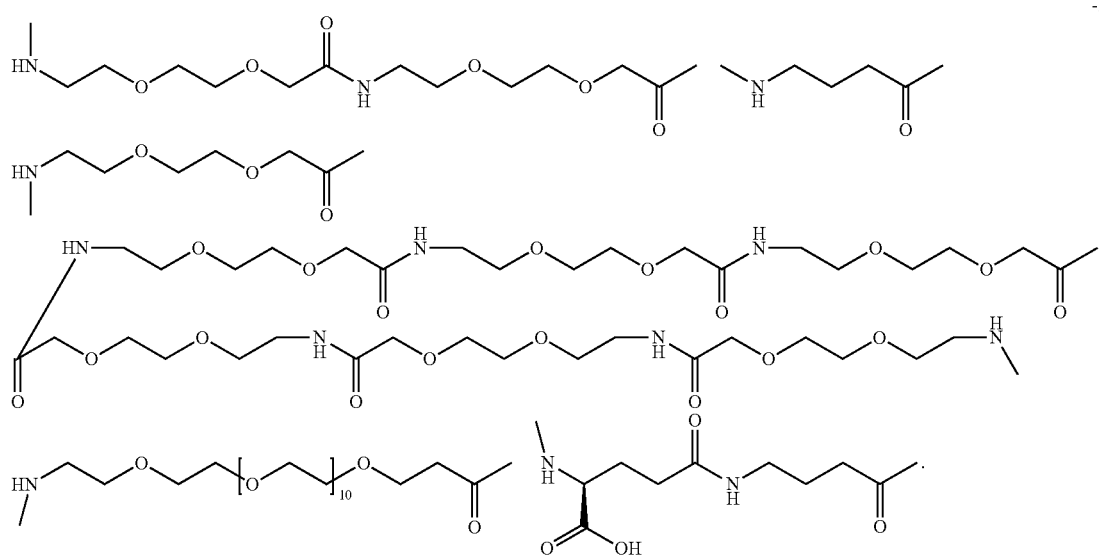
22. The derivative according to claim 20, wherein A-B-C-D- is selected and combined from
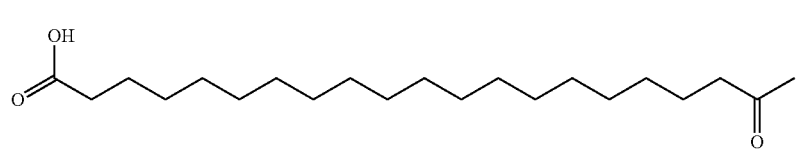
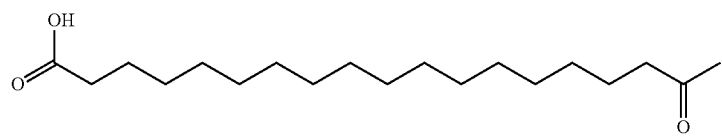
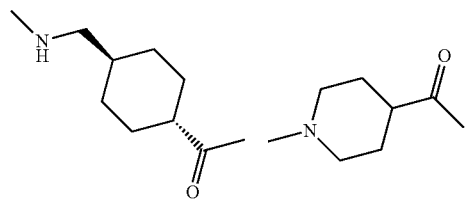

-continued
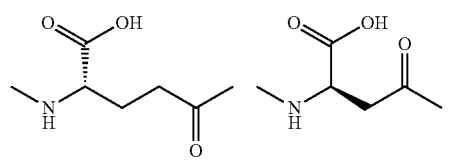
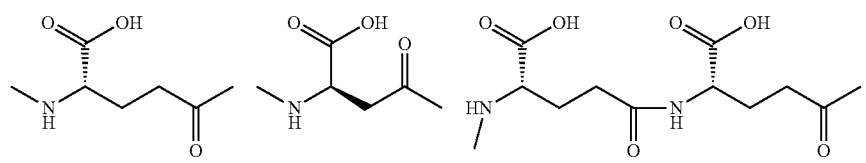
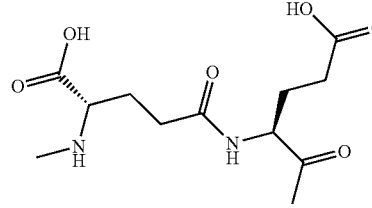
-C-
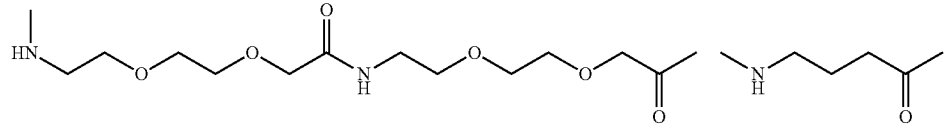
-D-
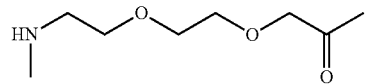
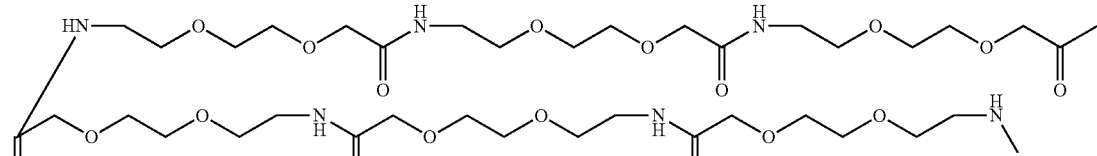
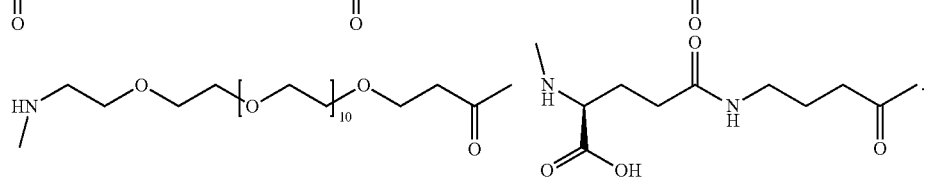
* * * * *